US012660500B2

(12) United States Patent
Lee et al.

(10) Patent No.: US 12,660,500 B2
(45) Date of Patent: Jun. 16, 2026

(54) COMPOSITION FOR ORGANIC LIGHT EMITTING DEVICE AND ORGANIC LIGHT EMITTING DEVICE COMPRISING SAME

(71) Applicant: LT MATERIALS CO., LTD., Yongin-City (KR)

(72) Inventors: Young-Jin Lee, Yongin-City (KR); Jun-Tae Mo, Yongin-City (KR); Yu-Jin Heo, Yongin-City (KR); Yong-Hui Lee, Yongin-City (KR); Seung-Woo Lee, Yongin-City (KR); Dong-Jun Kim, Yongin-City (KR); Dae-Hyuk Choi, Yongin-City (KR)

(73) Assignee: LT MATERIALS CO., LTD., Yongin-si (KR)

( * ) Notice: Subject to any disclaimer, the term of this patent is extended or adjusted under 35 U.S.C. 154(b) by 385 days.

(21) Appl. No.: 18/509,471

(22) Filed: Nov. 15, 2023

(65) Prior Publication Data

US 2024/0237515 A1 Jul. 11, 2024

(30) Foreign Application Priority Data

Nov. 29, 2022 (KR) ........................ 10-2022-0163046

(51) Int. Cl.
*H10K 85/60* (2023.01)
*C07D 405/04* (2006.01)
(Continued)

(52) U.S. Cl.
CPC ......... *H10K 85/636* (2023.02); *C07D 405/04* (2013.01); *C07D 405/14* (2013.01); *C09K 11/06* (2013.01); *H10K 85/615* (2023.02); *H10K 85/626* (2023.02); *H10K 85/654* (2023.02); *H10K 85/6574* (2023.02);
(Continued)

(58) Field of Classification Search
CPC .. H10K 85/636; H10K 85/615; H10K 85/626; H10K 85/654; H10K 85/6574; H10K 50/12; H10K 2101/90; H10K 2101/10; H10K 50/00; H10K 50/11; H10K 85/657; H10K 85/6572; H10K 85/6576; C07D 405/04; C07D 405/14; C09K 11/06; C09K 2211/1018; C07B 2200/05
See application file for complete search history.

(56) References Cited

U.S. PATENT DOCUMENTS

| | | | | |
|---|---|---|---|---|
| 4,356,429 | A | 10/1982 | Tang | |
| 10,862,037 | B2 * | 12/2020 | Diev | C08G 61/12 |

(Continued)

FOREIGN PATENT DOCUMENTS

| | | | |
|---|---|---|---|
| EP | 4 227 301 | A1 | 8/2023 |
| KR | 10-2021-0146113 | A | 12/2021 |

(Continued)

OTHER PUBLICATIONS

Korean Office Action for application No. 10-2022-0163046 mailed Aug. 4, 2023.

(Continued)

*Primary Examiner* — Ibrahim A Khan
(74) *Attorney, Agent, or Firm* — Birch, Stewart, Kolasch & Birch, LLP

(57) ABSTRACT

The present specification provides a composition for an organic light emitting device and an organic light emitting device including the same.

13 Claims, 2 Drawing Sheets

(51) Int. Cl.

| | |
|---|---|
| ***C07D 405/14*** | (2006.01) |
| ***C09K 11/06*** | (2006.01) |
| *H10K 50/12* | (2023.01) |
| *H10K 101/00* | (2023.01) |

(52) U.S. Cl.

CPC .. *C07B 2200/05* (2013.01); *C09K 2211/1018* (2013.01); *H10K 50/12* (2023.02); *H10K 2101/90* (2023.02)

(56) References Cited

U.S. PATENT DOCUMENTS

| | | | | |
|---|---|---|---|---|
| 11,985,889 | B2 * | 5/2024 | Lee | H10K 85/341 |
| 12,048,238 | B2 * | 7/2024 | Shin | H10K 85/361 |
| 12,069,947 | B2 * | 8/2024 | Seo | H10K 85/6572 |
| 12,274,160 | B2 * | 4/2025 | Kim | H10K 85/657 |
| 12,473,256 | B2 * | 11/2025 | Kim | H10K 85/654 |
| 12,520,714 | B2 * | 1/2026 | Shin | H10K 85/346 |
| 2015/0162538 | A1 * | 6/2015 | Zeng | H10K 85/6572 548/440 |
| 2015/0318501 | A1 * | 11/2015 | Watanabe | H10K 85/626 556/404 |
| 2016/0372683 | A1 * | 12/2016 | Tanimoto | C09K 11/06 |
| 2017/0271598 | A1 * | 9/2017 | Zeng | H10K 50/18 |
| 2020/0119286 | A1 * | 4/2020 | Liaptsis | H10K 85/40 |
| 2020/0203623 | A1 * | 6/2020 | Lee | C07D 409/10 |
| 2020/0203631 | A1 * | 6/2020 | Gao | H10K 85/6574 |
| 2020/0317646 | A1 * | 10/2020 | He | C09K 11/06 |
| 2022/0255012 | A1 * | 8/2022 | Kim | H10K 85/615 |
| 2022/0289693 | A1 * | 9/2022 | Lee | C07D 401/10 |
| 2022/0328775 | A1 * | 10/2022 | Shin | C07F 15/0086 |
| 2023/0025656 | A1 * | 1/2023 | Liu | C07D 405/14 |
| 2023/0083073 | A1 | 3/2023 | Lee et al. | |
| 2023/0090185 | A1 | 3/2023 | Park et al. | |
| 2023/0123928 | A1 * | 4/2023 | Park | H10K 50/125 257/40 |
| 2023/0124167 | A1 * | 4/2023 | Song | H10K 85/342 257/40 |
| 2023/0132589 | A1 * | 5/2023 | Moon | C07F 15/0033 257/40 |
| 2023/0171978 | A1 * | 6/2023 | Choung | H10K 85/615 257/40 |
| 2023/0171979 | A1 * | 6/2023 | Park | H10K 85/654 257/40 |
| 2023/0171981 | A1 * | 6/2023 | Park | H10K 85/6576 257/40 |
| 2023/0189645 | A1 | 6/2023 | Lee et al. | |
| 2023/0217667 | A1 * | 7/2023 | Yang | H10K 85/658 257/40 |
| 2023/0268467 | A1 * | 8/2023 | Jun | H10K 50/121 257/79 |
| 2023/0292601 | A1 | 9/2023 | Mo et al. | |
| 2024/0381756 | A1 * | 11/2024 | Choung | H10K 85/624 |

FOREIGN PATENT DOCUMENTS

| | | | |
|---|---|---|---|
| KR | 10-2334762 | B1 | 12/2021 |
| KR | 10-2022-0022339 | A | 2/2022 |
| KR | 10-2022-0047429 | A | 4/2022 |
| KR | 10-2022-0082362 | A | 7/2022 |
| KR | 10-2020-0077371 | A | 2/2026 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Material, 1994, vol. 6, No. 9, pp. 677-679.

* cited by examiner

[Figure 1]
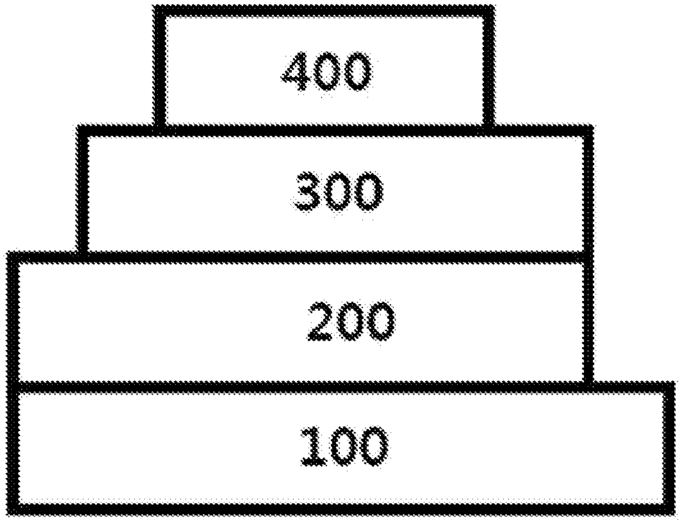
[Figure 2]
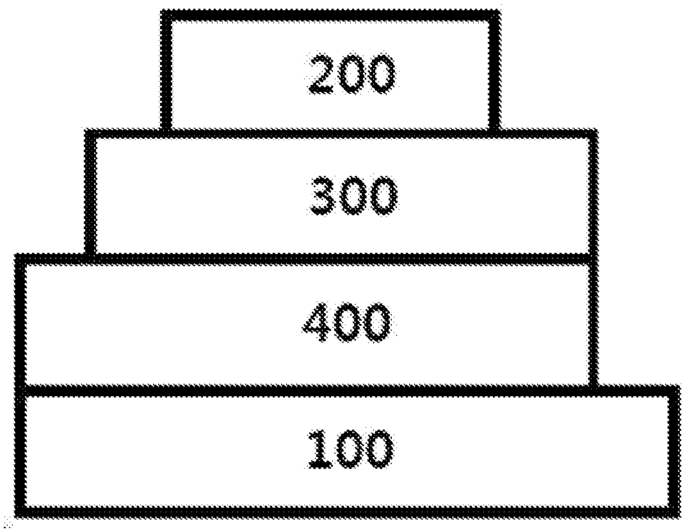

[Figure 3]
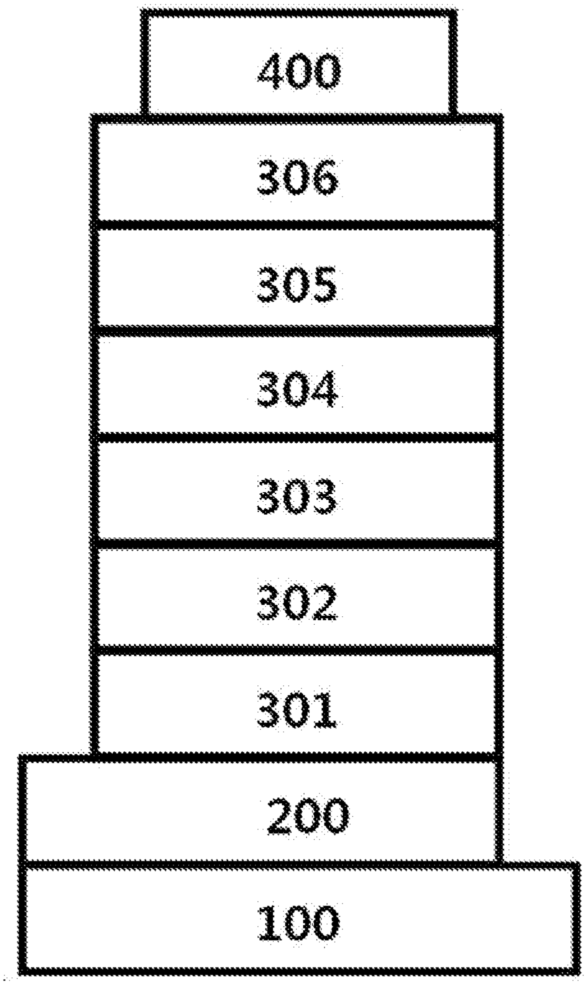

COMPOSITION FOR ORGANIC LIGHT EMITTING DEVICE AND ORGANIC LIGHT EMITTING DEVICE COMPRISING SAME

CROSS-REFERENCE TO RELATED APPLICATIONS

This application claims priority to and the benefit of Korean Patent Application No. 10-2022-0163046 filed in the Korean Intellectual Property Office on Nov. 29, 2022, the entire contents of which are incorporated herein by reference.

TECHNICAL FIELD

The present invention relates to a composition for an organic light emitting device and an organic light emitting device including the same.

BACKGROUND ART

An electroluminescence device is a kind of self-emitting type display device, and has an advantage in that the viewing angle is wide, the contrast is excellent, and the response speed is fast.

An organic light emitting device is composed of a structure in which an organic thin film is disposed between two electrodes. When a voltage is applied to an organic light emitting device having such a structure, electrons and holes injected from the two electrodes are combined with each other in the organic thin film to make a pair, and then, the paired electrons and holes emit light while being annihilated. The organic thin film may be composed of a single layer or multiple layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, efficiency and service life of the organic light emitting device, there is a continuous need for developing a material for an organic 238

RELATED ART DOCUMENTS

[Patent Document] (Patent Document 1) U.S. Pat. No. 4,356,429

DISCLOSURE

Technical Problem

The present invention has been made in an effort to provide a composition for an organic light emitting device and an organic light emitting device including the same.

Technical Solution

In an exemplary embodiment of the present application, provided is a composition for an organic light emitting device, including a heterocyclic compound represented by the following Chemical Formula A, a heterocyclic compound represented by the following Chemical Formula B, and a heterocyclic compound represented by the following Chemical Formula C.

[Chemical Formula A]

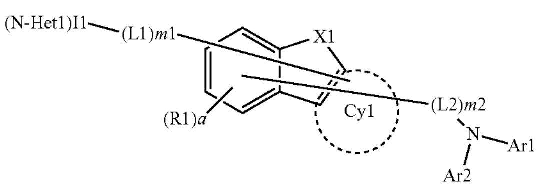

[Chemical Formula B]

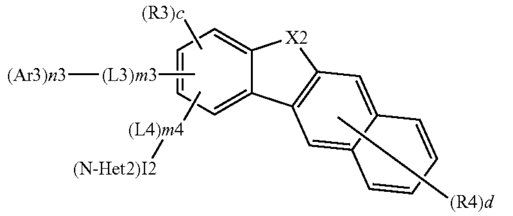

[Chemical Formula C]

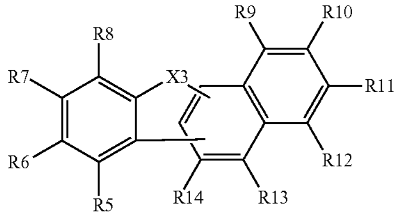

In Chemical Formulae A, B and C,

X1 to X3 are the same as or different from each other, and are each independently O; or S, Cy1 is a substituted or unsubstituted benzene ring; or a substituted or unsubstituted naphthalene ring, R1, R3, and R4 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', any one of R5 to R14 is -(L5)m5-(Ar4)n4, the other one is -(L6)m6-(N-Het3)l3, and the others are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', R, R', and R" are the same as or different from each other, and are each independently hydrogen; deuterium; —CN; a substituted or unsubstituted C1 to C60 alkyl group; a substituted or unsubstituted C2 to C60 cycloalkyl group; a substituted or unsubstituted C6 to C60 aryl group; or a substituted or unsubstituted C2 to C60 heteroaryl group, L1 to L6 are the same as or different from each other, and are each independently a direct bond; a substituted or unsubstituted C6 to C60 arylene group; or a substituted or unsubstituted C2 to C60 heteroarylene group, Ar1 to Ar4 are the same as or different from each other, and are each independently a substituted or unsubstituted C6 to C60 aryl group; a substituted or unsubstituted C2 to C60 heteroaryl group; or a combination thereof, N-Het1, N-Het2, and N-Het3 are the same as or different from each other, and are each independently represented by the following Structural Formula D,

[Structural Formula D]

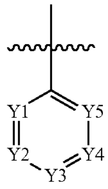

in Structural Formula D,

means a moiety linked to another structure,

Y1 to Y5 are the same as or different from each other, and are each independently CRa or N, and at least one is N, Ra is a substituted or unsubstituted C6 to C60 aryl group; or a substituted or unsubstituted C2 to C60 heteroaryl group, or two or more adjacent Ra groups are bonded to each other to form a ring, a is an integer from 0 to 4, c is an integer from 0 to 2, d is an integer from 0 to 6, l1 to l3, m1 to m6, n3, and n4 are the same as or different from each other, and are each independently an integer from 0 to 4, and when each of a, c, d, l1 to l3, m1 to m6, n3, and n4 is 2 or higher, substituents in the parenthesis are the same as or different from each other.

Further, an exemplary embodiment of the present application provides an organic light emitting device including: a first electrode; a second electrode provided to face the first electrode; and an organic material layer having one or more layers provided between the first electrode and the second electrode, in which one or more layers of the organic material layer include the above-described composition for an organic light emitting device.

Advantageous Effects

A composition for an organic light emitting device according to an exemplary embodiment of the present application can be used as a material for an organic material layer of an organic light emitting device. The composition for an organic light emitting device can be used as a material for a hole injection layer, a hole transport layer, a light emitting layer, an electron transport layer, an electron injection layer, a charge generation layer, and the like in an organic light emitting device. In particular, the composition for an organic light emitting device includes a heterocyclic compound represented by Chemical Formula A as a bipolar p-host, a heterocyclic compound represented by Chemical Formula B as a unipolar p-host for improving service life, and a heterocyclic compound represented by Chemical Formula C as a unipolar n-host for improving efficiency, and has an effect of improving device characteristics compared to existing single and premixed materials.

Whereby, when the composition for an organic light emitting device is used for an organic light emitting device, the driving voltage of the device can be lowered, the light efficiency of the device can be improved, and the service life characteristics of the device can be improved due to the thermal stability of the compound.

DESCRIPTION OF DRAWINGS

FIGS. 1 to 3 are views each schematically illustrating a stacking structure of an organic light emitting device according to an exemplary embodiment of the present application.

MODE FOR INVENTION

Hereinafter, the present specification will be described in more detail.

When one part "includes" one constituent element in the present specification, unless otherwise specifically described, this does not mean that another constituent element is excluded, but means that another constituent element may be further included.

In the present specification,

of a chemical formula means a position to which a constituent element is bonded.

In the present specification, n of Cn means the number of carbon atoms. That is, for example, C6 to C60 means 6 to 60 carbon atoms.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more substituents are substituted, the two or more substituents may be the same as or different from each other.

In the present specification, "substituted or unsubstituted" means being unsubstituted or substituted with one or more substituents selected from the group consisting of deuterium; a halogen group; —CN; a C1 to C60 alkyl group; a C2 to C60 alkenyl group; a C2 to C60 alkynyl group; a C1 to C60 haloalkyl group; a C1 to C60 alkoxy group; a C6 to C60 aryloxy group; a C1 to C60 alkylthioxy group; a C6 to C60 arylthioxy group; a C1 to C60 alkylsulfoxy group; a C6 to C60 arylsulfoxy group; a C3 to C60 cycloalkyl group; a C2 to C60 heterocycloalkyl group; a C6 to C60 aryl group; a C2 to C60 heteroaryl group; —SiRR'R"; —P(=O)RR'; and —NRR', or a substituent to which two or more substituents selected among the exemplified substituents are linked, and R, R' and R" are each independently a substituent composed of at least one of hydrogen; deuterium; a halogen group; an alkyl group; an alkenyl group; an alkoxy group; a cycloalkyl group; a heterocycloalkyl group; an aryl group; and a heteroaryl group.

In the present specification, "when a substituent is not indicated in the structure of a chemical formula or compound" means that a hydrogen atom is bonded to a carbon atom. However, since deuterium ($^2H$) is an isotope of hydrogen, some hydrogen atoms may be deuterium.

In an exemplary embodiment of the present application, "when a substituent is not indicated in the structure of a chemical formula or compound" may mean that all the positions that may be reached by the substituent are hydrogen or deuterium. That is, deuterium is an isotope of hydrogen, and some hydrogen atoms may be deuterium which is an isotope, and in this case, the content of deuterium may be 0% to 100%.

In an exemplary embodiment of the present application, in "the case where a substituent is not indicated in the structure of a chemical formula or compound", when the content of deuterium is 0%, the content of hydrogen is 100%, and all the substituents do not explicitly exclude deuterium such as hydrogen, hydrogen and deuterium may be mixed and used in the compound.

In an exemplary embodiment of the present application, deuterium is one of the isotopes of hydrogen, is an element that has a deuteron composed of one proton and one neutron as a nucleus, and may be represented by hydrogen-2, and the element symbol may also be expressed as D or $^2H$.

In an exemplary embodiment of the present application, the isotope means an atom with the same atomic number (Z), but different mass numbers (A), and the isotope may also be interpreted as an element which has the same number of protons, but different number of neutrons.

In an exemplary embodiment of the present application, when the total number of substituents of a basic compound is defined as T1 and the number of specific substituents among the substituents is defined as T2, the content T % of the specific substituent may be defined as T2/T1×100=T %.

That is, in an example, the deuterium content of 20% in a phenyl group represented by

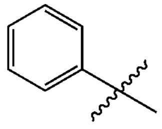 [SMILES: *c1ccccc1]

may be represented by 20% when the total number of substituents that the phenyl group can have is 5 (T1 in the formula) and the number of deuteriums among the substituents is 1 (T2 in the formula). That is, a deuterium content of 20% in the phenyl group may be represented by the following structural formula.

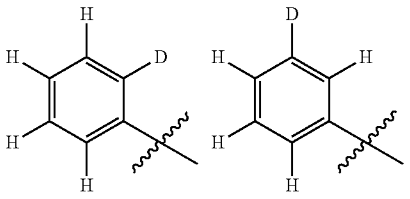

-continued

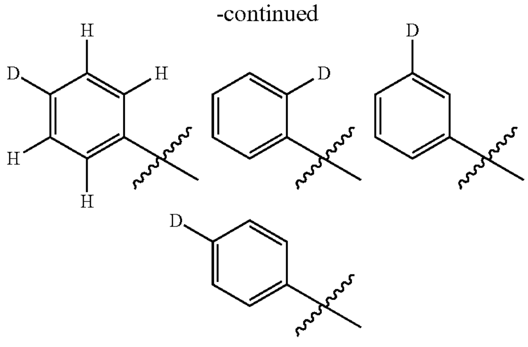

Further, in an exemplary embodiment of the present application, "a phenyl group having a deuterium content of 0%" may mean a phenyl group that does not include a deuterium atom, that is, has five hydrogen atoms.

In the present specification, the halogen may be fluorine, chlorine, bromine or iodine.

In the present specification, an alkyl group includes a straight-chain or branched-chain having 1 to 60 carbon atoms, and may be additionally substituted with another substituent. The number of carbon atoms of the alkyl group may be 1 to 60, specifically 1 to 40, and more specifically 1 to 20. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, an alkenyl group includes a straight-chain or branched-chain having 2 to 60 carbon atoms, and may be additionally substituted with another substituent. The number of carbon atoms of the alkenyl group may be 2 to 60, specifically 2 to 40, and more specifically 2 to 20. Specific examples thereof include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, an alkynyl group includes a straight-chain or branched-chain having 2 to 60 carbon atoms, and may be additionally substituted with another substituent. The number of carbon atoms of the alkynyl group may be 2 to 60, specifically 2 to 40, and more specifically 2 to 20.

In the present specification, a haloalkyl group means an alkyl group substituted with a halogen group, and specific examples thereof include $—CF_3$, $—CF_2CF_3$, and the like, but are not limited thereto.

In the present specification, an alkoxy group is represented by —O(R101), and the above-described examples of the alkyl group may be applied to R101.

In the present specification, an aryloxy group is represented by —O(R102), and the above-described examples of the aryl group may be applied to R102.

In the present specification, an alkylthioxy group is represented by —S(R103), and the above-described examples of the alkyl group may be applied to R103.

In the present specification, an arylthioxy group is represented by —S(R104), and the above-described examples of the aryl group may be applied to R104.

In the present specification, an alkylsulfoxy group is represented by $—S(=O)_2(R105)$, and the above-described examples of the alkyl group may be applied to R105.

In the present specification, an arylsulfoxy group is represented by $—S(=O)_2(R106)$, and the above-described examples of the aryl group may be applied to R106.

In the present specification, a cycloalkyl group includes a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, a heterocycloalkyl group includes 0, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, an aryl group includes a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group includes a spiro group. The number of carbon atoms of the aryl group may be 6 to 60, specifically 6 to 40, and more specifically 6 to 25. Specific examples of the aryl group include a phenyl group, a biphenyl group, a terphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the terphenyl group may be selected from the following structures.

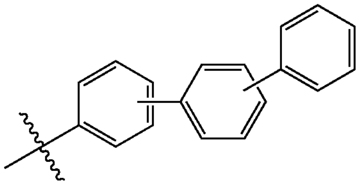

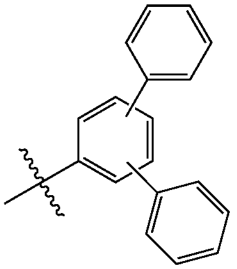

In the present specification, the fluorenyl group may be substituted, and adjacent substituents may be bonded to each other to form a ring.

When the fluorenyl group is substituted, the substituent may be any one of the following structures, but is not limited thereto.

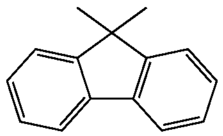
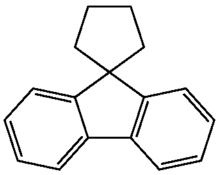
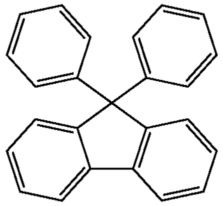
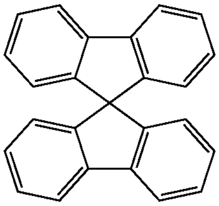
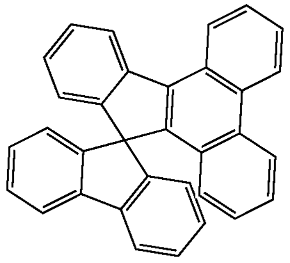
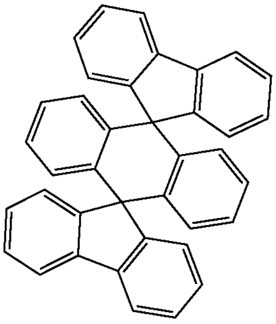

In the present specification, a heteroaryl group includes S, O, Se, N, or Si as a heteroatom, includes a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group include a pyridine group, a pyrrole group, a pyrimidine group, a pyridazine group, a furan group, a thiophene group, an imidazole group, a pyrazole group, an oxazole group, an isoxazole group, a thiazole group, an isothiazole group, a triazole group, a furazan group, an oxadiazole group, a thiadiazole group, a dithiazole group, a tetrazolyl group, a pyran group, a thiopyran group, a diazine group, an oxazine group, a thiazine group, a dioxin group, a triazine group, a tetrazine group, a quinoline group, an isoquinoline group, a quinazoline group, an isoquinazoline group, a quinozoline group, a naphthyridine group, an acridine group, a phenanthridine group, an imidazopyridine group, a diazanaphthalene group, a triazaindene group, an indole group, an indolizine group, a benzothiazole group, a benzoxazole group, a benzimidazole group, a benzothiophene group, a benzofuran group, a dibenzothiophene group, a dibenzofuran group, a carbazole group, a benzocarbazole group, a dibenzocarbazole group, a phenazine group, a dibenzosilole group, spirobi(dibenzosilole), a dihydrophenazine group, a phenoxazine group, a phenanthridine group, a thienyl group, an indolo[2,3-a] carbazole group, an indolo[2,3-b] carbazole group, an indoline group, a 10,11-dihydrodibenzo[b,f]azepine group, a 9,10-dihydroacridine group, a phenanthrazine group, a phenothiazine group, a phthalazine group, a phenanthroline group, a naphthobenzofuran group, a naphthobenzothiophene group, a benzo[c][1,2,5]thiadiazole group, a 2,3-dihydrobenzo[b]thiophene group, a 2,3-dihydrobenzofuran group, a 5,10-dihydrodibenzo[b,e][1,4]azasiline group, a pyrazolo[1,5-c]quinazoline group, a pyrido[1,2-b]indazole group, a pyrido[1,2-a]imidazo[1,2-e]indoline group, a 5,11-dihydroindeno[1,2-b]carbazole group, and the like, but are not limited thereto.

In the present specification, when the substituent is a carbazole group, it means being bonded to nitrogen or carbon of carbazole.

In the present specification, when a carbazole group is substituted, an additional substituent may be substituted with the nitrogen or carbon of the carbazole.

In the present specification, a benzocarbazole group may be any one of the following structures.

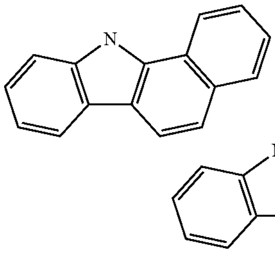
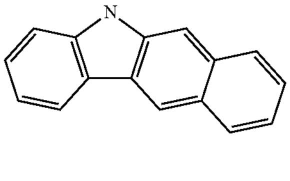
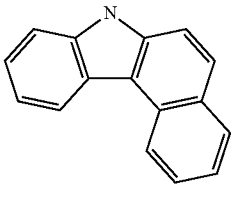

In the present specification, a dibenzocarbazole group may be any one of the following structures.

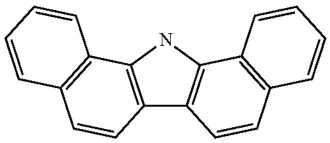
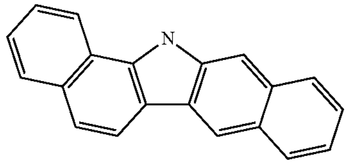
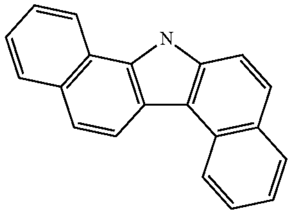
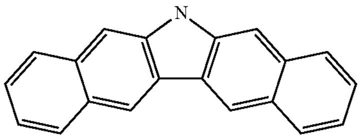
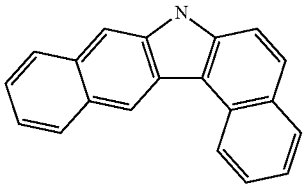
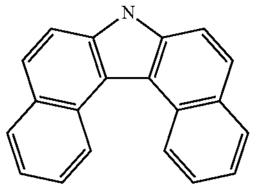

In the present specification, a naphthobenzofuran group may be any one of the following structures.

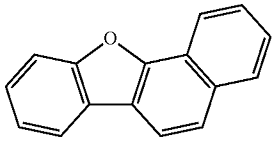
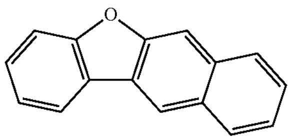
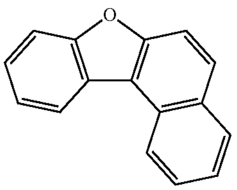

In the present specification, a naphthobenzothiophene group may be any one of the following structures.

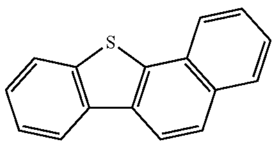
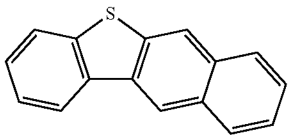

-continued

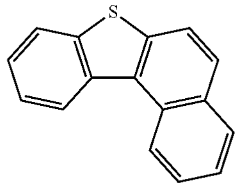

In the present specification, a silyl group includes Si and is a substituent to which the Si atom is directly linked as a radical, and is represented by —Si(R107) (R108) (R109), and R107 to R109 are the same as or different from each other, and may be each independently a substituent composed of at least one of hydrogen; deuterium; a halogen group; an alkyl group; an alkenyl group; an alkoxy group; a cycloalkyl group; a heterocycloalkyl group; an aryl group; and a heteroaryl group.

Specific examples of the silyl group include

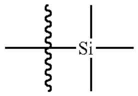 [SMILES: *[Si](C)(C)C]

(a trimethylsilyl group),

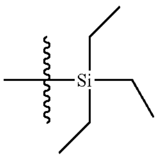 [SMILES: *[Si](CC)(CC)CC]

(a triethylsilyl group),

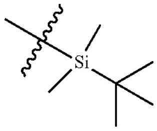 [SMILES: *[Si](C)(C)C(C)(C)C]

(a t-butyldimethylsilyl group),

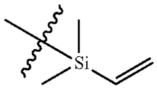

(a vinyldimethylsilyl group),

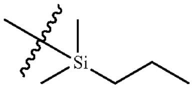 [SMILES: *[Si](C)(C)CCC]

(a propyldimethylsilyl group),

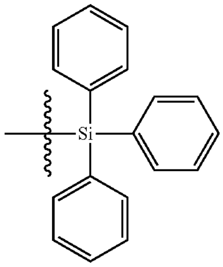 [SMILES: *[Si](c1ccccc1)(c1ccccc1)c1ccccc1]

(a triphenylsilyl group),

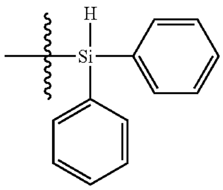 [SMILES: *[SiH](c1ccccc1)c1ccccc1]

(a diphenylsilyl group),

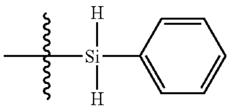 [SMILES: *[SiH2]c1ccccc1]

(a phenylsilyl group) and the like, but are not limited thereto.

In the present specification, a phosphine oxide group is represented by —P(═O) (R110) (R111), and R110 and R111 are the same as or different from each other, and may be each independently a substituent composed of at least one of hydrogen; deuterium; a halogen group; an alkyl group; an alkenyl group; an alkoxy group; a cycloalkyl group; a heterocycloalkyl group; an aryl group; and a heteroaryl group. Specifically, the phosphine oxide group may be substituted with an alkyl group or an aryl group, and the above-described example may be applied to the alkyl group and the aryl group. Examples of the phosphine oxide group include a dimethylphosphine oxide group, a diphenylphosphine oxide group, dinaphthylphosphine oxide, and the like, but are not limited thereto.

In the present specification, an amine group is represented by —N(R112) (R113), and R112 and R113 are the same as or different from each other, and may be each independently a substituent composed of at least one of hydrogen; deuterium; a halogen group; an alkyl group; an alkenyl group; an alkoxy group; a cycloalkyl group; a heterocycloalkyl group; an aryl group; and a heteroaryl group. The amine group may be selected from the group consisting of —$NH_2$; a monoalkylamine group; a monoarylamine group; a monoheteroarylamine group; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, the above-described examples of the aryl group may be applied to an arylene group except for a divalent arylene group.

In the present specification, the above-described examples of the heteroaryl group may be applied to a heteroarylene group except for a divalent heteroarylene group.

In the present specification, the "adjacent" group may mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted at the same carbon in an aliphatic ring may be interpreted as groups which are "adjacent" to each other.

Hydrocarbon rings and hetero rings that adjacent groups may form include an aliphatic hydrocarbon ring, an aromatic hydrocarbon ring, an aliphatic hetero ring and an aromatic hetero ring, and structures exemplified by the above-described cycloalkyl group, aryl group, heterocycloalkyl group and heteroaryl group may be each applied to the rings, except for those that are not monovalent groups.

In an exemplary embodiment of the present application, provided is a composition for an organic light emitting device, including a heterocyclic compound represented by the following Chemical Formula A, a heterocyclic compound represented by the following Chemical Formula B, and a heterocyclic compound represented by the following Chemical Formula C.

[Chemical Formula A]

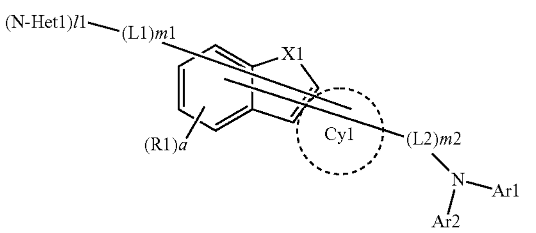

[Chemical Formula B]

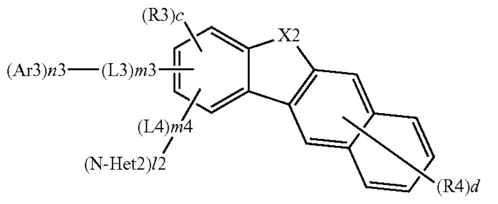

-continued

[Chemical Formula C]

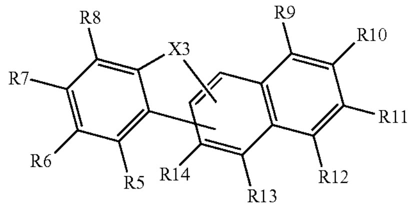

In Chemical Formulae A, B and C,

X1 to X3 are the same as or different from each other, and are each independently O; or S, Cy1 is a substituted or unsubstituted benzene ring; or a substituted or unsubstituted naphthalene ring, R1, R3, and R4 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', any one of R5 to R14 is -(L5)m5-(Ar4)n4, the other one is -(L6)m6-(N-Het3)l3, and the others are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', R, R', and R" are the same as or different from each other, and are each independently hydrogen; deuterium; —CN; a substituted or unsubstituted C1 to C60 alkyl group; a substituted or unsubstituted C2 to C60 cycloalkyl group; a substituted or unsubstituted C6 to C60 aryl group; or a substituted or unsubstituted C2 to C60 heteroaryl group, L1 to L6 are the same as or different from each other, and are each independently a direct bond; a substituted or unsubstituted C6 to C60 arylene group; or a substituted or unsubstituted C2 to C60 heteroarylene group, Ar1 to Ar4 are the same as or different from each other, and are each independently a substituted or unsubstituted C6 to C60 aryl group; a substituted or unsubstituted C2 to C60 heteroaryl group; or a combination thereof, N-Het1, N-Het2, and N-Het3 are the same as or different from each other, and are each independently represented by the following Structural Formula D,

[Structural Formula D]

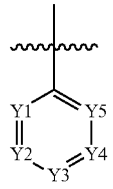

in Structural Formula D,

means a moiety linked to another structure,

Y1 to Y5 are the same as or different from each other, and are each independently CRa or N, and at least one is N, Ra is a substituted or unsubstituted C6 to C60 aryl group; or a substituted or unsubstituted C2 to C60 heteroaryl group, or two or more adjacent Ra groups are bonded to each other to form a ring, a is an integer from 0 to 4, c is an integer from 0 to 2, d is an integer from 0 to 6, l1 to l3, m1 to m6, n3, and n4 are the same as or different from each other, and are each independently an integer from 0 to 4, and when each of a, c, d, l1 to l3, m1 to m6, n3, and n4 is 2 or higher, substituents in the parenthesis are the same as or different from each other.

The heterocyclic compound represented by Chemical Formula A is an O- or S-containing tricyclic or more heterocyclic compound, and includes an azine and an amine substituent. The heterocyclic compound includes the amine substituent to exhibit a fast hole mobility tendency, and thus acts as a bipolar p-host. In addition, there is an effect of improving driving voltage and efficiency by increasing the moving speed of holes and reducing hole traps.

In addition, the heterocyclic compound represented by the Chemical Formula B is an O- or S-containing tetracyclic heterocyclic compound, and is a unipolar n-host which is composed of naphthobenzofuran in a sterically planar or linear form, and thus, has a strong EOD tendency. Furthermore, the heterocyclic compound is composed of a planar or linear form, and has the characteristics of significantly improving the service life due to an increase in the stability of the conjugation molecular structure and vapor deposition structure.

Further, the heterocyclic compound represented by Chemical Formula C is an O- or S-containing tetracyclic heterocyclic compound, in which an azine is substituted with a non-linear naphthobenzofuran in a non-planar form, resulting in a decrease in conjugation scalability, and thus, the tendency of electron mobility is weakened. Accordingly, the heterocyclic compound represented by Chemical Formula C may serve to confine electrons in the light emitting layer, thereby increasing the overall efficiency. However, since the aforementioned characteristics may weaken the structural stability, and thus, reduce the service life, it is desirable to use the compound in a limited ratio to 25% or less.

Through this, when a composition for an organic light emitting device, which includes the heterocyclic compound represented by Chemical Formula A, the heterocyclic compound represented by Chemical Formula B, and the heterocyclic compound represented by Chemical Formula C, is used for an organic light emitting device, it is possible to manufacture an organic light emitting device with excellent device driving, efficiency, and/or service life. Specifically, the heterocyclic compound represented by Chemical Formula A is characterized by low voltage, high efficiency, and long service life. Accordingly, it could be confirmed that when the three types of the heterocyclic compound represented by Chemical Formula A, the heterocyclic compound represented by Chemical Formula B, which is characterized by a relatively longer service life, and the heterocyclic compound represented by Chemical Formula C, which is characterized by a relatively higher efficiency, are mixed at an appropriate ratio, the voltage, efficiency, and service life effects were additionally improved.

In an exemplary embodiment of the present application, a group not represented by a substituent; or a group represented by hydrogen may mean being all substitutable with deuterium. That is, it may be shown that hydrogen; or deuterium can be substituted with each other.

In an exemplary embodiment of the present application, the deuterium content of the heterocyclic compounds represented by Chemical Formulae A, B, and C may be the same or different from each other, and may be each independently 0% to 100%.

In an exemplary embodiment of the present application, the deuterium content of the heterocyclic compounds represented by Chemical Formulae A, B, and C may be the same or different from each other, and may be each independently 10% to 100%.

In an exemplary embodiment of the present application, the deuterium content of the heterocyclic compounds represented by Chemical Formulae A, B, and C may be the same or different from each other, and may be each independently 20% to 100%.

In an exemplary embodiment of the present application, the deuterium content of the heterocyclic compounds represented by Chemical Formulae A, B, and C may be the same or different from each other, and may be each independently 30% to 100%.

In an exemplary embodiment of the present application, the deuterium content of the heterocyclic compounds represented by Chemical Formulae A, B, and C may be the same or different from each other, and may be each independently 40% to 100%.

In an exemplary embodiment of the present application, the deuterium content of the heterocyclic compounds represented by Chemical Formulae A, B, and C may be the same or different from each other, and may be each independently 50% to 100%.

In an exemplary embodiment of the present application, the deuterium content of the heterocyclic compounds represented by Chemical Formulae A, B, and C may be the same or different from each other, and may be each independently 60% to 100%.

In an exemplary embodiment of the present application, the deuterium content of the heterocyclic compounds represented by Chemical Formulae A, B, and C may be the same or different from each other, and may be each independently 70% to 100%.

In an exemplary embodiment of the present application, the deuterium content of the heterocyclic compounds represented by Chemical Formulae A, B, and C may be the same or different from each other, and may be each independently 80% to 100%.

In an exemplary embodiment of the present application, the deuterium content of the heterocyclic compounds represented by Chemical Formulae A, B, and C may be the same or different from each other, and may be each independently 90% to 100%.

In general, compounds bonded with hydrogen and compounds substituted with deuterium exhibit a difference in thermodynamic behavior. The reason for this is that the mass of a deuterium atom is 2-fold higher than that of hydrogen, but due to the difference in the mass of atoms, deuterium is characterized by having even lower vibration energy. In addition, the bond length of carbon and deuterium is shorter than that of a bond with hydrogen, and a dissociation energy used to break the bond is also stronger than that of the bond with hydrogen. This may occur because the van der Waals radius of deuterium is smaller than that of hydrogen, and thus the extension amplitude of a bond between carbon and deuterium becomes even narrower.

The deuterium-substituted compound in the heterocyclic compounds represented by Chemical Formulae A, B, and C of the present invention is characterized in that the energy in the ground state is further lower than that of the hydrogen-substituted compound, and the shorter the bond length between carbon and deuterium is, the smaller the molecular hardcore volume is. Accordingly, the electrical polarizability may be reduced and the intermolecular interaction can be weakened, so that the volume of the device thin film may be increased. These characteristics induce an effect of lowering the crystallinity by creating the amorphous state of a thin film. Therefore, the deuterium-substituted compound in the heterocyclic compounds represented by Chemical Formulae A, B, and C may further improve the heat resistance of an organic light emitting diode (OLED) device, thereby further improving the service life and driving characteristics.

In the present specification, the term 'OLED device' may be expressed by 'organic light emitting diode, 'organic light emitting diodes (OLEDs)', 'organic light emitting device', and 'organic electroluminescence device', and the like.

In another exemplary embodiment of the present application, R1, R3, and R4 are the same as or different from each other, and may be each independently selected from the group consisting of hydrogen; deuterium; a halogen; a substituted or unsubstituted C1 to C40 alkyl group; a substituted or unsubstituted C2 to C40 alkenyl group; a substituted or unsubstituted C2 to C40 alkynyl group; a substituted or unsubstituted C1 to C40 alkoxy group; a substituted or unsubstituted C3 to C40 cycloalkyl group; a substituted or unsubstituted C2 to C40 heterocycloalkyl group; a substituted or unsubstituted C6 to C40 aryl group; a substituted or unsubstituted C2 to C40 heteroaryl group; —SiRR'R"; and —P(=O)RR'.

In still another exemplary embodiment of the present application, R1, R3, and R4 are the same as or different from each other, and may be each independently selected from the group consisting of hydrogen; deuterium; a halogen; a substituted or unsubstituted C1 to C20 alkyl group; a substituted or unsubstituted C2 to C20 alkenyl group; a substituted or unsubstituted C2 to C20 alkynyl group; a substituted or unsubstituted C1 to C20 alkoxy group; a substituted or unsubstituted C3 to C20 cycloalkyl group; a substituted or unsubstituted C2 to C20 heterocycloalkyl group; a substituted or unsubstituted C6 to C20 aryl group; a substituted or unsubstituted C2 to C20 heteroaryl group; —SiRR'R"; and —P(=O)RR'.

In yet another exemplary embodiment of the present application, R1, R3, and R4 are the same as or different from each other, and may be each independently selected from the group consisting of hydrogen; deuterium; a halogen; a substituted or unsubstituted C1 to C20 alkyl group; a substituted or unsubstituted C6 to C20 aryl group; and a substituted or unsubstituted C2 to C20 heteroaryl group.

In still yet another exemplary embodiment of the present application, R1, R3, and R4 are the same as or different from each other, and may be each independently selected from the group consisting of hydrogen; deuterium; a halogen; a C1 to C20 alkyl group unsubstituted or substituted with deuterium; a C6 to C20 aryl group unsubstituted or substituted with deuterium; and a C2 to C20 heteroaryl group unsubstituted or substituted with deuterium.

In a further exemplary embodiment of the present application, R1, R3, and R4 are the same as or different from each other, and may be each independently hydrogen; or deuterium.

In another further exemplary embodiment of the present application, any one of R5 to R14 is -(L5)m5-(Ar4)n4, the other one is -(L6)m6-(N-Het3)l3, and the others are the same as or different from each other, and may be each independently selected from the group consisting of hydrogen; deuterium; a halogen; a substituted or unsubstituted C1 to C40 alkyl group; a substituted or unsubstituted C2 to C40 alkenyl group; a substituted or unsubstituted C2 to C40 alkynyl group; a substituted or unsubstituted C1 to C40 alkoxy group; a substituted or unsubstituted C3 to C40 cycloalkyl group; a substituted or unsubstituted C2 to C40 heterocycloalkyl group; a substituted or unsubstituted C6 to C40 aryl group; a substituted or unsubstituted C2 to C40 heteroaryl group; —SiRR'R"; and —P(=O)RR'.

In still another further exemplary embodiment of the present application, any one of R5 to R14 is -(L5)m5-(Ar4)n4, the other one is -(L6)m6-(N-Het3)l3, and the others are the same as or different from each other, and may be each independently selected from the group consisting of hydrogen; deuterium; a halogen; a substituted or unsubstituted C1 to C20 alkyl group; a substituted or unsubstituted C2 to C20 alkenyl group; a substituted or unsubstituted C2 to C20 alkynyl group; a substituted or unsubstituted C1 to C20 alkoxy group; a substituted or unsubstituted C3 to C20 cycloalkyl group; a substituted or unsubstituted C2 to C20 heterocycloalkyl group; a substituted or unsubstituted C6 to C20 aryl group; a substituted or unsubstituted C2 to C20 heteroaryl group; —SiRR'R"; and —P(=O)RR'.

In yet another further exemplary embodiment of the present application, any one of R5 to R14 is -(L5)m5-(Ar4)n4, the other one is -(L6)m6-(N-Het3)l3, and the others are the same as or different from each other, and may be each independently selected from the group consisting of hydrogen; deuterium; a halogen; a substituted or unsubstituted C1 to C20 alkyl group; a substituted or unsubstituted C6 to C20 aryl group; and a substituted or unsubstituted C2 to C20 heteroaryl group.

In still yet another further exemplary embodiment of the present application, any one of R5 to R14 is -(L5)m5-(Ar4)n4, the other one is -(L6)m6-(N-Het3)l3, and the others are the same as or different from each other, and may be each independently selected from the group consisting of hydrogen; deuterium; a halogen; a C1 to C20 alkyl group unsubstituted or substituted with deuterium; a C6 to C20 aryl group unsubstituted or substituted with deuterium; and a C2 to C20 heteroaryl group unsubstituted or substituted with deuterium.

In a still further exemplary embodiment of the present application, any one of R5 to R14 is -(L5)m5-(Ar4)n4, the other one is -(L6)m6-(N-Het3)l3, and the others are the same as or different from each other, and may be each independently hydrogen; or deuterium.

In a yet still further exemplary embodiment of the present application, R, R', and R" are the same as or different from each other, and may be each independently hydrogen; deuterium; —CN; a substituted or unsubstituted C1 to C40 alkyl group; a substituted or unsubstituted C2 to C40 cycloalkyl group; a substituted or unsubstituted C6 to C40 aryl group; or a substituted or unsubstituted C2 to C40 heteroaryl group.

In another exemplary embodiment of the present application, R, R, and R" are the same as or different from each other, and may be each independently hydrogen; deuterium; —CN; a substituted or unsubstituted C1 to C20 alkyl group; a substituted or unsubstituted C2 to C20 cycloalkyl group; a substituted or unsubstituted C6 to C20 aryl group; or a substituted or unsubstituted C2 to C20 heteroaryl group.

In still another exemplary embodiment of the present application, L1 to L6 are the same as or different from each other, and may be each independently a direct bond; a substituted or unsubstituted C6 to C40 arylene group; or a substituted or unsubstituted C2 to C40 heteroarylene group.

In yet another exemplary embodiment of the present application, L1 to L6 are the same as or different from each other, and may be each independently a direct bond; a substituted or unsubstituted C6 to C20 arylene group; or a substituted or unsubstituted C2 to C20 heteroarylene group.

In still yet another exemplary embodiment of the present application, L1 to L6 are the same as or different from each other, and may be each independently a direct bond; or a substituted or unsubstituted C6 to C20 arylene group.

In a further exemplary embodiment of the present application, L1 to L6 are the same as or different from each other, and may be each independently a direct bond; or a C6 to C20 arylene group unsubstituted or substituted with deuterium.

In another further exemplary embodiment of the present application, L1 to L6 are the same as or different from each other, and may be each independently a direct bond; a substituted or unsubstituted phenylene group; a substituted or unsubstituted biphenylene group; or a naphthylene group unsubstituted or substituted with deuterium.

In still another exemplary embodiment of the present application, L1 to L6 are the same as or different from each other, and may be each independently a direct bond; a phenylene group unsubstituted or substituted with deuterium; a biphenylene group unsubstituted or substituted with deuterium; or a naphthylene group unsubstituted or substituted with deuterium.

In yet another further exemplary embodiment of the present application, L1 may be each a direct bond; a phenylene group unsubstituted or substituted with deuterium; or a naphthylene group unsubstituted or substituted with deuterium.

In still yet another further exemplary embodiment of the present application, L2 may be each independently a direct bond; a phenylene group unsubstituted or substituted with deuterium; or a naphthylene group unsubstituted or substituted with deuterium.

In a still further exemplary embodiment of the present application, L3 may be each a direct bond; a phenylene group unsubstituted or substituted with deuterium; a biphenylene group unsubstituted or substituted with deuterium; or a naphthylene group unsubstituted or substituted with deuterium.

In a yet still further exemplary embodiment of the present application, L4 may be each a direct bond; a phenylene group unsubstituted or substituted with deuterium; or a naphthylene group unsubstituted or substituted with deuterium.

In another exemplary embodiment of the present application, L5 may be each a direct bond; a phenylene group unsubstituted or substituted with deuterium; a biphenylene group unsubstituted or substituted with deuterium; or a naphthylene group unsubstituted or substituted with deuterium.

In still another exemplary embodiment of the present application, L6 may be each a direct bond.

In yet another exemplary embodiment of the present application, Ar1 to Ar4 are the same as or different from each other, and may be each independently a substituted or unsubstituted C6 to C40 aryl group; a substituted or unsubstituted C2 to C40 heteroaryl group; or a combination thereof.

In still yet another exemplary embodiment of the present application, Ar1 to Ar4 are the same as or different from each other, and may be each independently a substituted or unsubstituted C6 to C20 aryl group; a substituted or unsubstituted C2 to C20 heteroaryl group; or a combination thereof.

In a further exemplary embodiment of the present application, Ar1 to Ar4 are the same as or different from each other, and may be each independently a substituted or unsubstituted C6 to C20 aryl group; a C2 to C20 heteroaryl group unsubstituted or substituted with deuterium; or a combination thereof, and the heteroaryl group may include a heteroatom of O or S.

In another further exemplary embodiment of the present application, Ar1 to Ar4 are the same as or different from each other, and may be each independently a C6 to C20 aryl group unsubstituted or substituted with deuterium, a halogen, or a substituted or unsubstituted C2 to C20 aryl group; a C2 to C20 heteroaryl group unsubstituted or substituted with deuterium; or a combination thereof, and the heteroaryl group may include a heteroatom of O or S.

In still another further exemplary embodiment of the present application, Ar1 and Ar2 are the same as or different from each other, and may be each independently a phenyl group; a biphenyl group; a terphenyl group; a naphthyl group; a dibenzofuranyl group; a dibenzothiophene group; or a combination thereof, and may be unsubstituted or substituted with deuterium, a phenyl group, a naphthyl group, or a biphenyl group.

In yet another further exemplary embodiment of the present application, Ar3 may be a phenyl group; a biphenyl group; a terphenyl group; a naphthyl group; a dibenzofuranyl group; a dibenzothiophene group; or a combination thereof, and may be unsubstituted or substituted with deuterium, a halogen (particularly, —F), a phenyl group, a naphthyl group, or a biphenyl group.

In still yet another further exemplary embodiment of the present application, Ar4 may be a phenyl group; a biphenyl group; a terphenyl group; a naphthyl group; a chrysenyl group; a dibenzofuranyl group; a dibenzothiophene group; or a combination thereof, and may be unsubstituted or substituted with deuterium, a phenyl group, a naphthyl group, or a biphenyl group.

In an exemplary embodiment of the present application, N-Het1, N-Het2, and N-Het3 are the same as or different from each other, and are each independently represented by the following Structural Formula D.

[Structural Formula D]

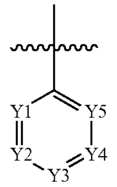

In another exemplary embodiment of the present application, Y1 to Y5 are the same as or different from each other, and are each independently CRa or N, and any one among them may be N.

In still another exemplary embodiment of the present application, Y1 to Y5 are the same as or different from each other, and are each independently CRa or N, and two or more among them may be N.

In yet another exemplary embodiment of the present application, Y1 to Y5 are the same as or different from each other, and are each independently CRa or N, and three or more among them may be N.

In still yet another exemplary embodiment of the present application, Ra is a substituted or unsubstituted C6 to C40 aryl group; or a substituted or unsubstituted C2 to C40 heteroaryl group, or two or more adjacent Ra groups may be bonded to each other to form a substituted or unsubstituted C2 to C40 aliphatic ring or a substituted or unsubstituted C2 to C40 aromatic ring.

In a further exemplary embodiment of the present application, Ra is a substituted or unsubstituted C6 to C20 aryl group; or a substituted or unsubstituted C2 to C20 heteroaryl group, or two or more adjacent Ra groups may be bonded to each other to form a substituted or unsubstituted C2 to C20 aliphatic ring or a substituted or unsubstituted C2 to C20 aromatic ring.

In another further exemplary embodiment of the present application, Ra is a substituted or unsubstituted C6 to C20 aryl group; or a substituted or unsubstituted C2 to C20 heteroaryl group, or two or more adjacent Ra groups may be bonded to each other to form a substituted or unsubstituted C2 to C20 aromatic hydrocarbon ring or a substituted or unsubstituted C2 to C20 aromatic hetero ring.

In still another further exemplary embodiment of the present application, Ra may be a phenyl group; a biphenyl group; a terphenyl group; a naphthyl group; a dibenzofuranyl group; or a dibenzothiophene group, and may be unsubstituted or substituted with deuterium, a halogen (particularly, —F), a methyl group, or a tert-butyl group, a phenyl group, a biphenyl group, or a naphthyl group. Alternatively, two or more adjacent Ra groups may be bonded to each other to form a benzene ring, a benzofuran ring, or a benzothiophene ring.

In yet another further exemplary embodiment of the present application, a may be an integer of 0, 1, 2, 3, or 4.

In still yet another further exemplary embodiment of the present application, c may be an integer of 0, 1, or 2.

In a still further exemplary embodiment of the present application, d may be an integer of 0, 1, 2, 3, 4, 5, or 6.

In a yet still further exemplary embodiment of the present application, l1 to l3, m1 to m6, n3 and n4 may be an integer of 0, 1, 2, 3, or 4.

In an exemplary embodiment of the present application, provided is a composition for an organic light emitting device, in which Chemical Formula A is represented by any one of the following Chemical Formulae A-1 to A-3.

[Chemical Formula A-1]

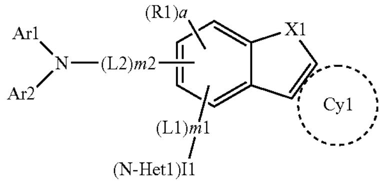

[Chemical Formula A-2]

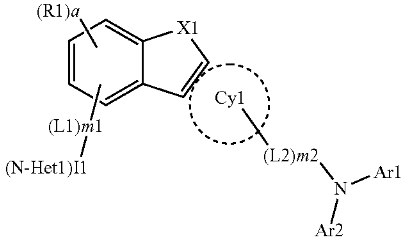

[Chemical Formula A-3]

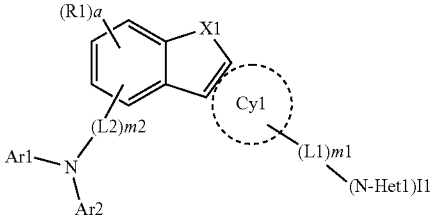

[Chemical Formula A-4]

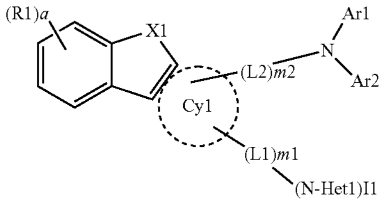

In Chemical Formulae A-1 to A-4, the definitions of X1, Cy1, R1, L1, L2, N-Het1, Ar1, Ar2, a, l1, m1, and m2 are the same as those described in Chemical Formula A. In addition, the specific description on the substituent is the same as described above.

In another exemplary embodiment of the present application, provided is a composition for an organic light emitting device, in which Chemical Formula A-1 is represented by any one of the following Chemical Formulae A-101 to A-108.

[Chemical Formula A-101]

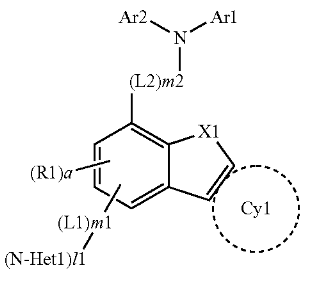

-continued

[Chemical Formula A-102]

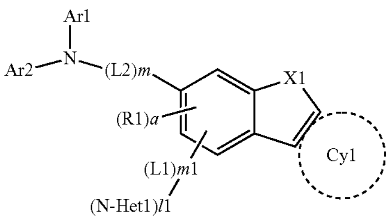

[Chemical Formula A-103]

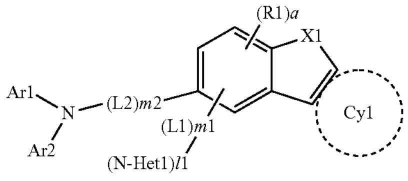

[Chemical Formula A-104]

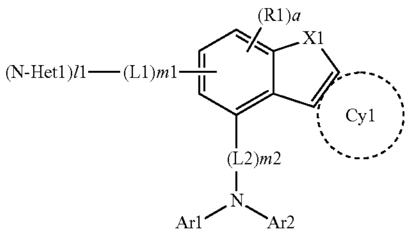

[Chemical Formula A-105]

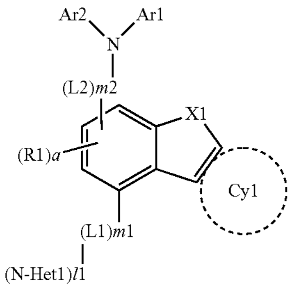

[Chemical Formula A-106]

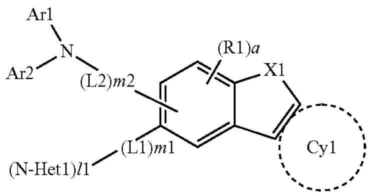

[Chemical Formula A-107]

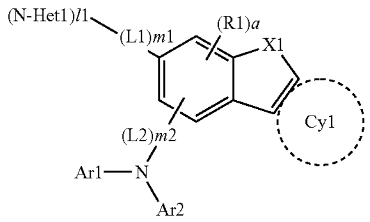

-continued

[Chemical Formula A-108]

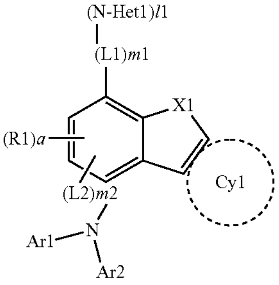

In Chemical Formulae A-101 to A-108, the definitions of X1, R1, L1, L2, N-Het1, Ar1, Ar2, Cy1, a, l1, m1, and m2 are the same as those described in Chemical Formula A. Furthermore, the specific description on the substituent is the same as described above.

In an exemplary embodiment of the present invention, provided is a composition for an organic light emitting device, in which Chemical Formula A is represented by any one of the following Chemical Formulae Aa to Ad.

[Chemical Formula Aa]

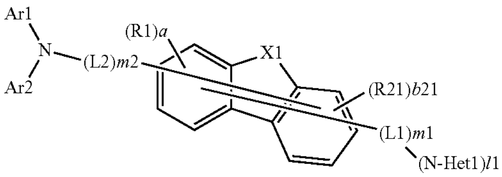

[Chemical Formula Ab]

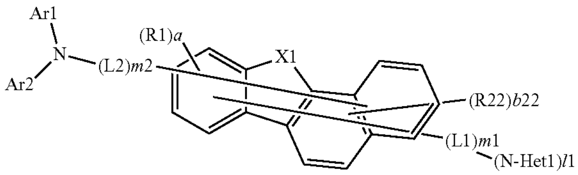

[Chemical Formula Ac]

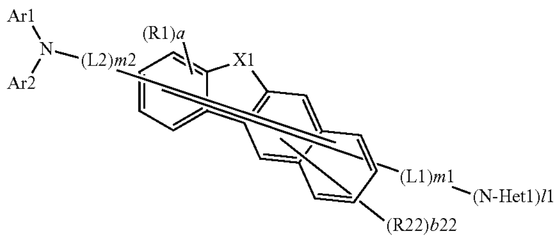

[Chemical Formula Ad]

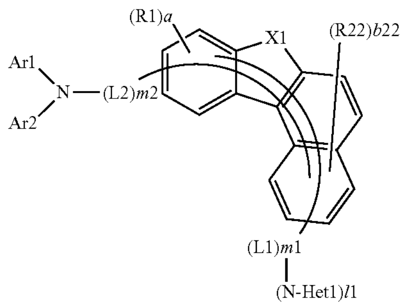

In Chemical Formulae Aa, Ab, Ac, and Ad, the definitions of X1, R1, L1, L2, N-Het1, Ar1, Ar2, a, l1, m1, and m2 are the same as those described in Chemical Formula A, R21 and R22 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', b21 is an integer from 0 to 4, b22 is an integer from 0 to 6, and when each of b21 and b22 is 2 or higher, substituents in the parenthesis are the same as or different from each other.

In another exemplary embodiment of the present invention, b21 may be an integer of 0, 1, 2, 3, or 4.

In still another exemplary embodiment of the present invention, b22 may be an integer of 0, 1, 2, 3, 4, 5, or 6.

In yet another exemplary embodiment of the present application, Chemical Formula A-2 may be represented by any one of the following Chemical Formulae A-201 to A-238.

[Chemical Formula A-201]

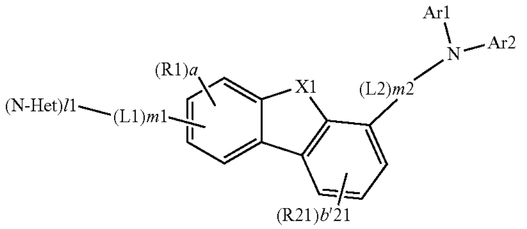

[Chemical Formula A-202]

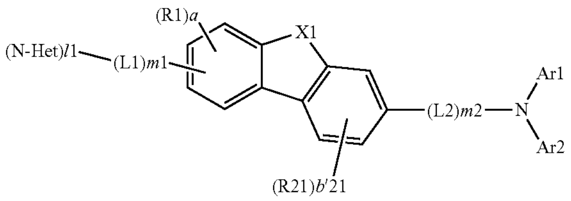

[Chemical Formula A-203

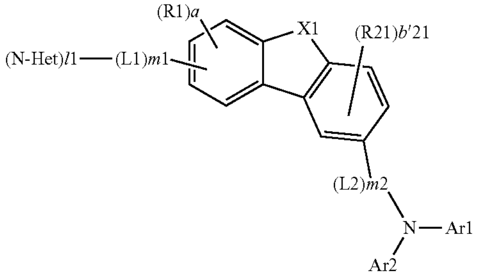

-continued

[Chemical Formula A-204

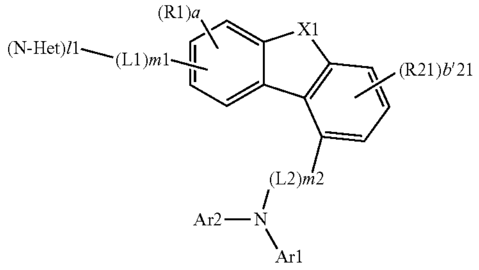

[Chemical Formula A-205]

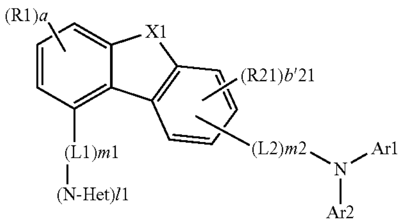

[Chemical Formula A-206]

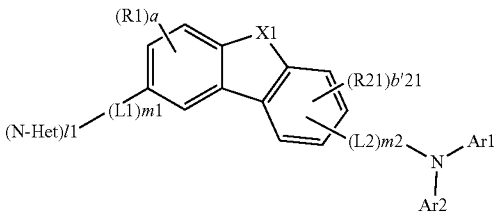

[Chemical Formula A-207]

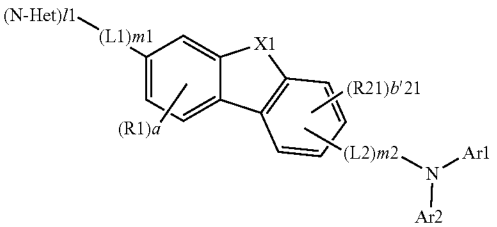

[Chemical Formula A-208]

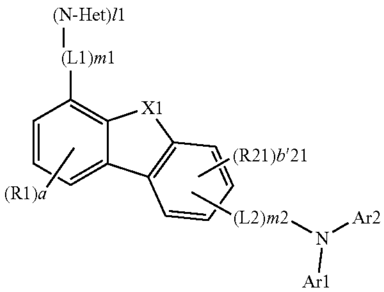

[Chemical Formula A-209]

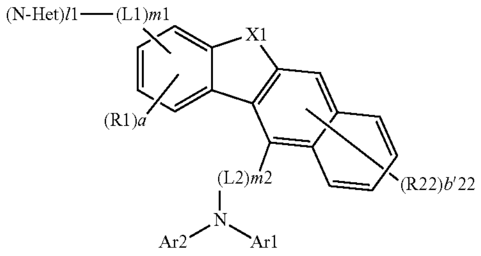

-continued
[Chemical Formula A-210]
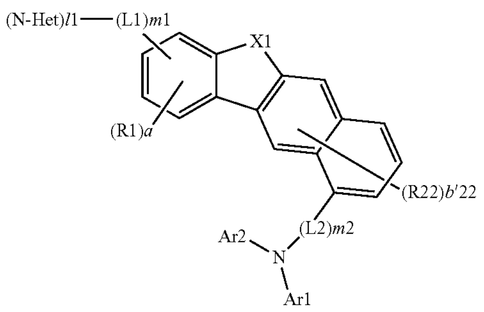
[Chemical Formula A-211]
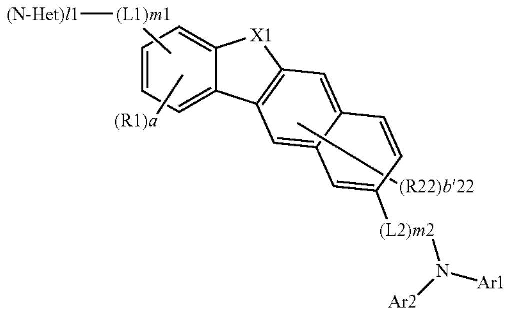
[Chemical Formula A-212]
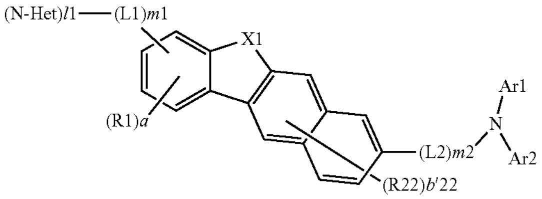
[Chemical Formula A-213]
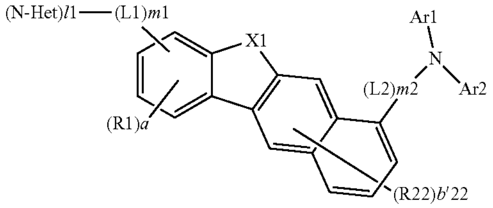
[Chemical Formula A-214]
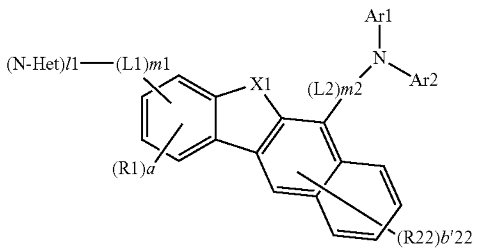
-continued
[Chemical Formula A-215]
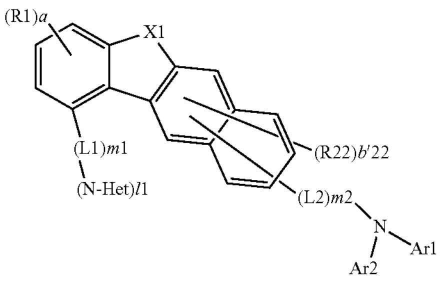
[Chemical Formula A-216]
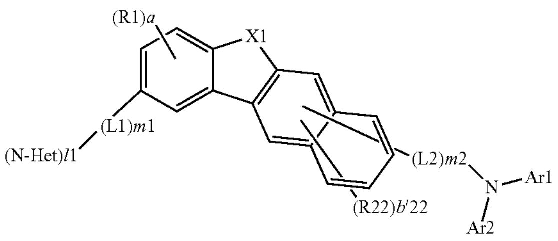
[Chemical Formula A-217]
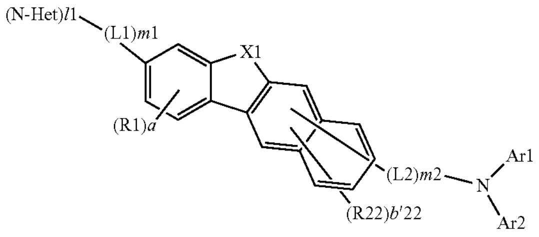
[Chemical Formula A-218]
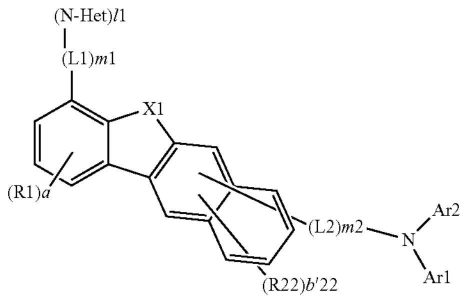
[Chemical Formula A-219]
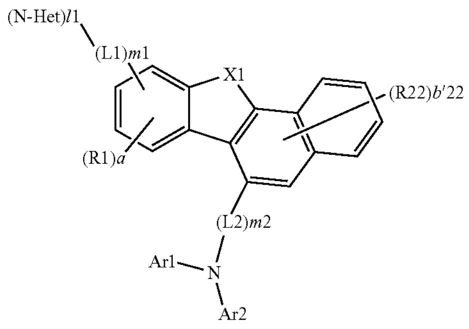

[Chemical Formula A-221]
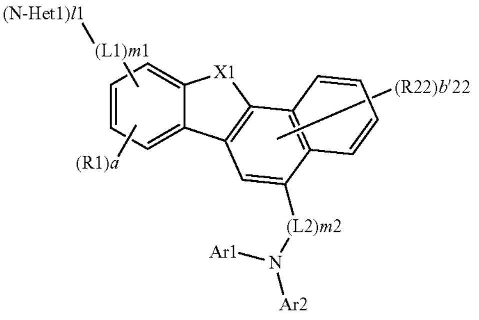
[Chemical Formula A-222]
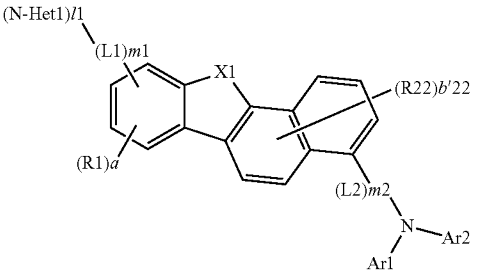
[Chemical Formula A-223]
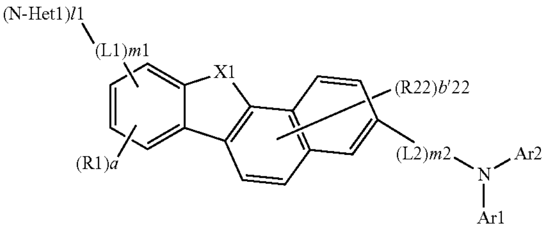
[Chemical Formula A-224]
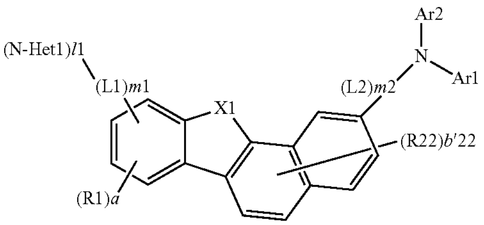
[Chemical Formula A-225]
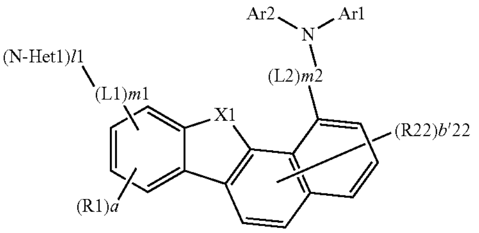
-continued
[Chemical Formula A-226]
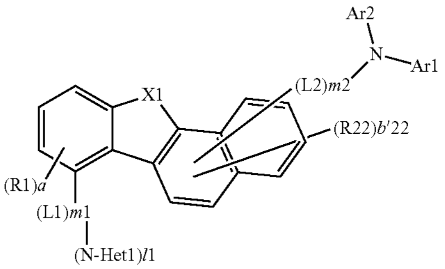
[Chemical Formula A-227]
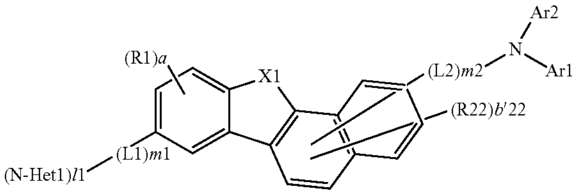
[Chemical Formula A-228]
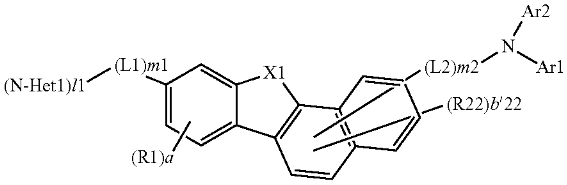
[Chemical Formula A-229]
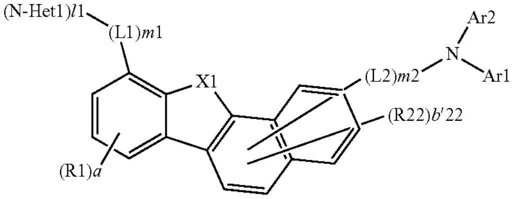
[Chemical Formula A-230]
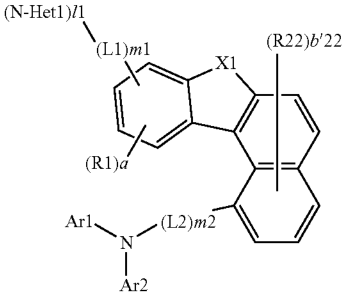

-continued

[Chemical Formula A-231]

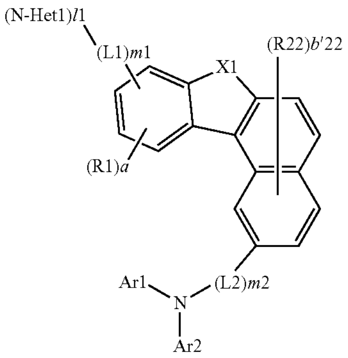

[Chemical Formula A-232]

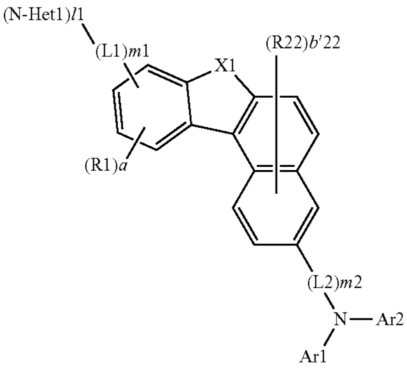

[Chemical Formula A-233]

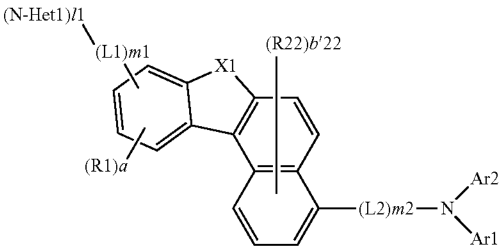

[Chemical Formula A-234]

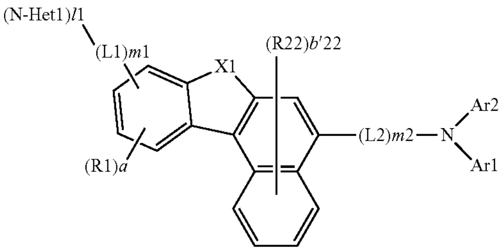

[Chemical Formula A-235]

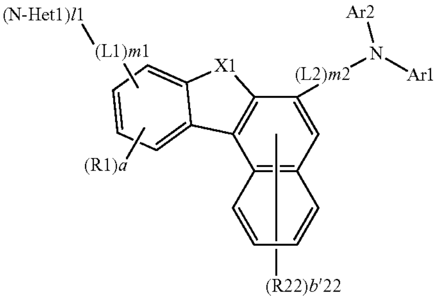

-continued

[Chemical Formula A-236]

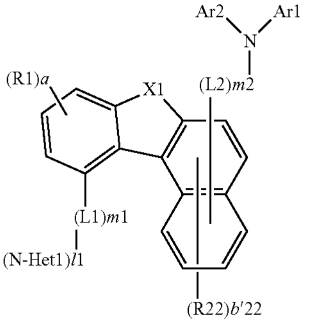

[Chemical Formula A-237]

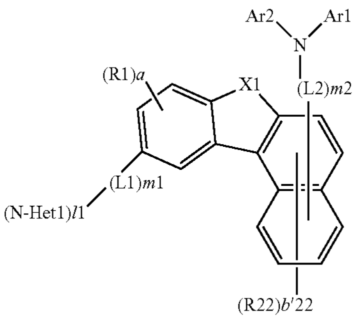

[Chemical Formula A-238]

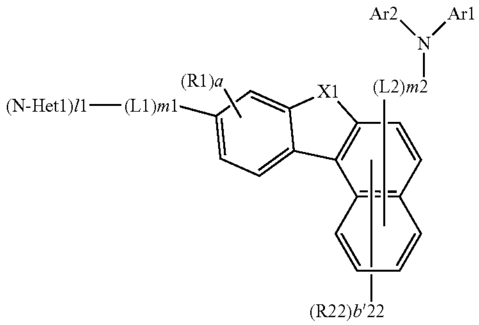

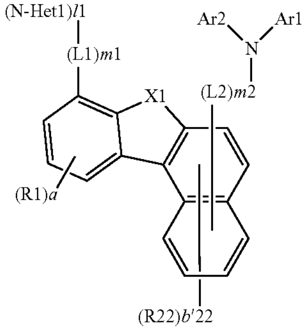

In Chemical Formulae A-201 to A-238, the definitions of X1, R1, L1, L2, N-Het1, Ar1, Ar2, a, l1, m1, and m2 are the same as those described in Chemical Formula A, R21 and R22 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', and b'21 is an integer from 0 to 4, b'22 is an integer from 0 to 6, and when each of b'21 and b'22 is 2 or higher, substituents in the parenthesis are the same as or different from each other. Furthermore, the specific description on the substituent is the same as described above.

In still yet another exemplary embodiment of the present application, provided is a composition for an organic light emitting device, in which Chemical Formula A-3 is represented by any one of the following Chemical Formulae A-301 to A-338.

[Chemical Formula A-301]

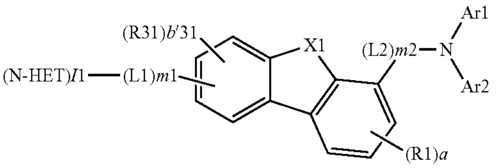

[Chemical Formula A-302]

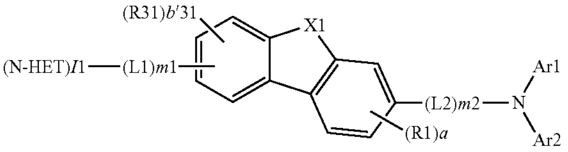

[Chemical Formula A-303]

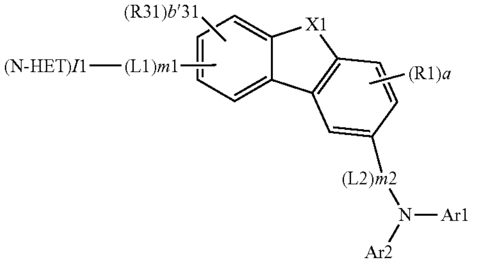

[Chemical Formula A-304]

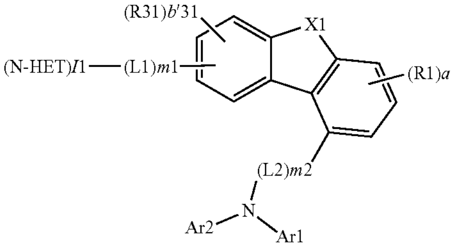

{Chemical Formula A-305]

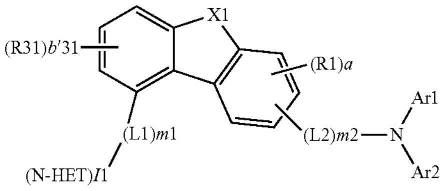

-continued

[Chemical Formula A-306]

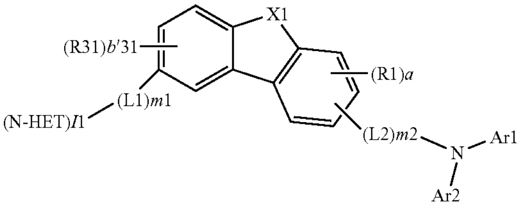

[Chemical Formula A-307]

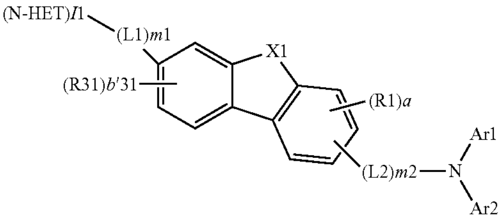

[Chemical Formula A-308]

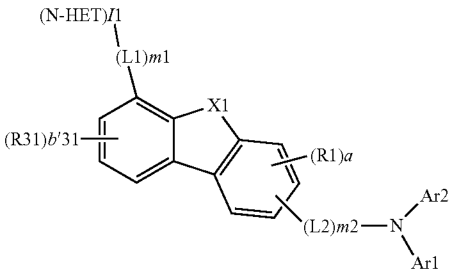

[Chemical Formula A-309]

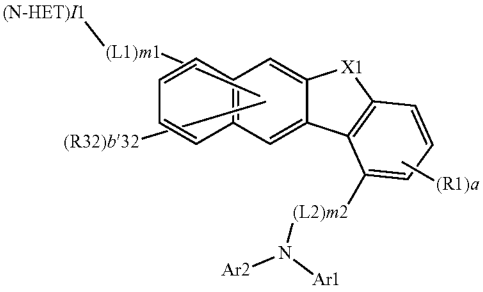

[Chemical Formula A-310]

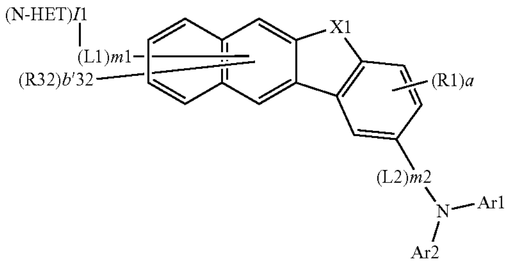

[Chemical Formula A-311]

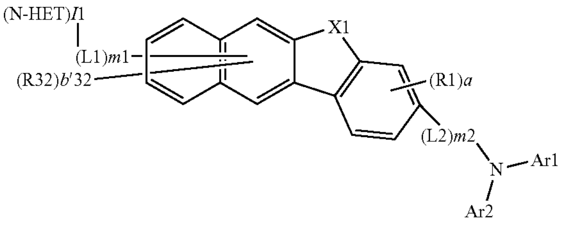

-continued
[Chemical Formula A-312]
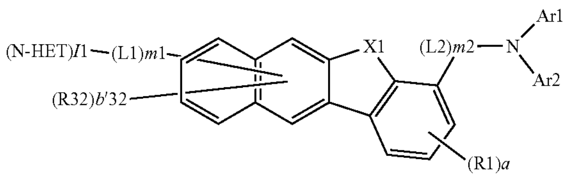
[Chemical Formuls A-313]
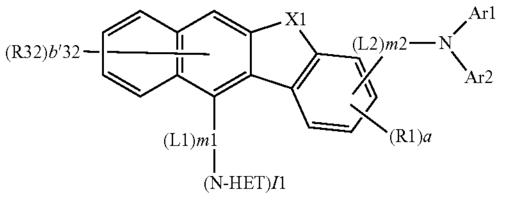
[Chemical Formula A-314]
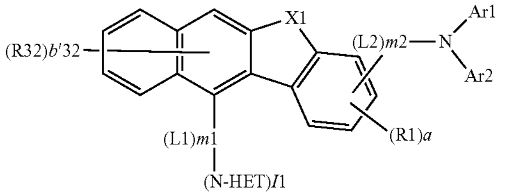
[Chemical Formula 3-15]
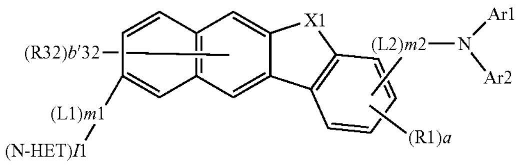
[Chemical Formula A-316]
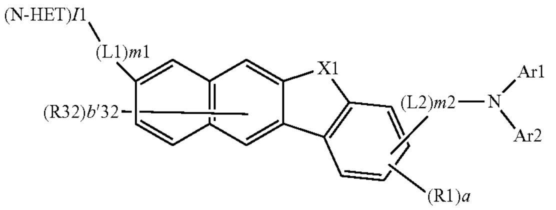
[Chemical Formula A-317]
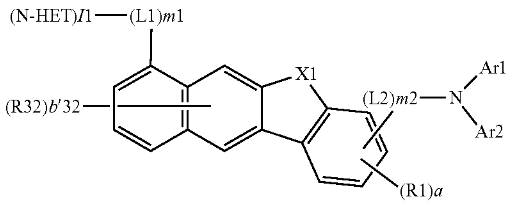
[Chemical Formula A-318]
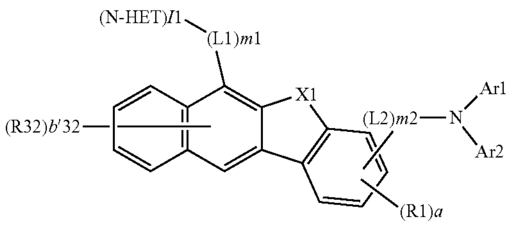
-continued
[Chemical Formula A-319]
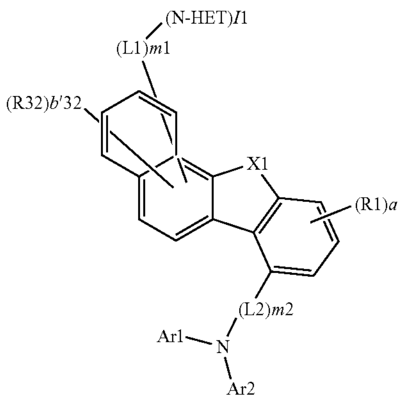
[Chemical Formula A-320]
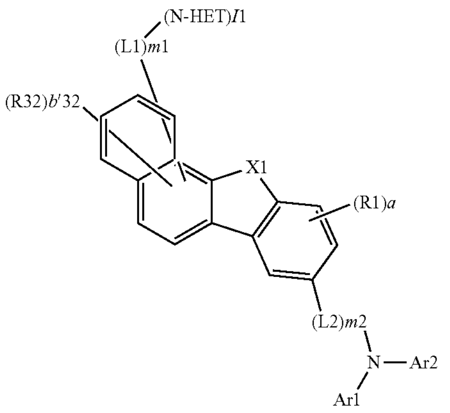
[Chemical Formula A-321]
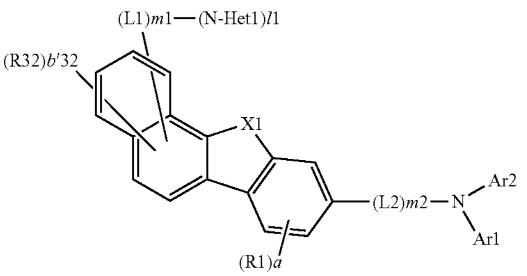
[Chemical Formula A-322]
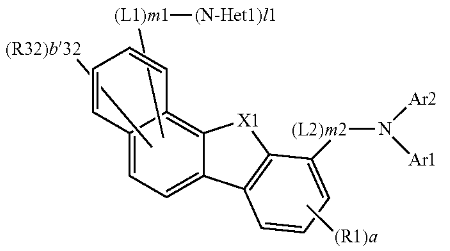

-continued
[Chemical Formula A-323]
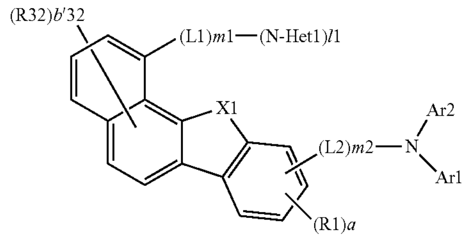
[Chemical Formula A-324]
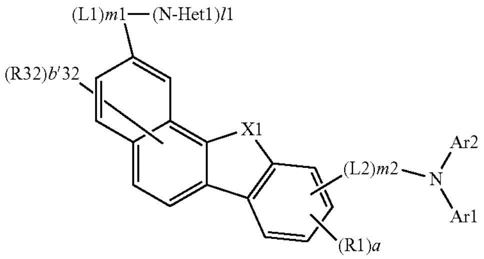
[Chemical Formula A-325]
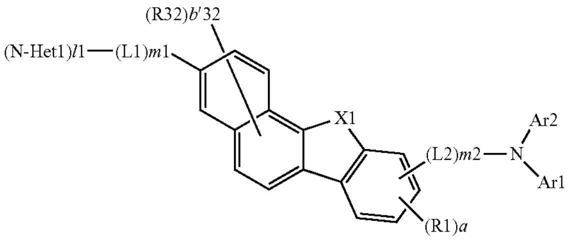
[Chemical Formula A-326]
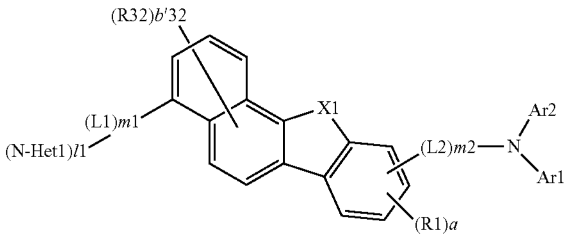
[Chemical Formula A-327]
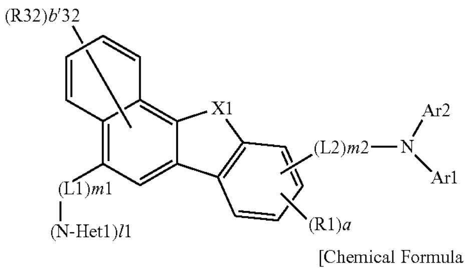
[Chemical Formula A-328]
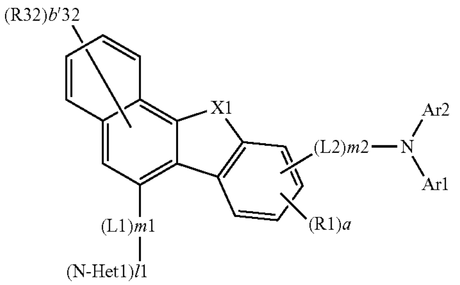
-continued
[Chemical Formula A-329]
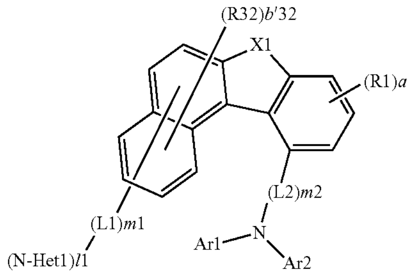
[Chemical Formula A-330]
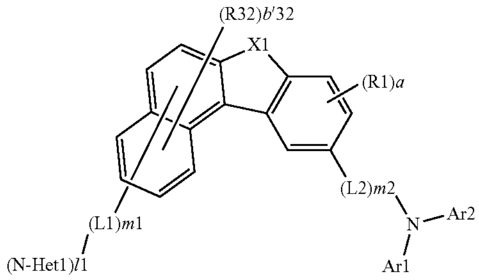
[Chemical Formula A-331]
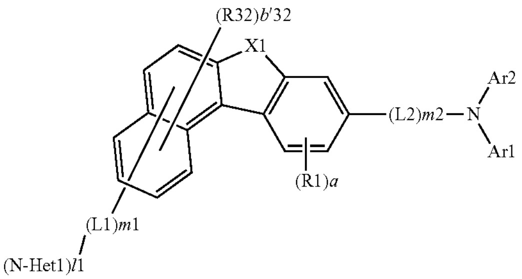
[Chemical Formula A-332]
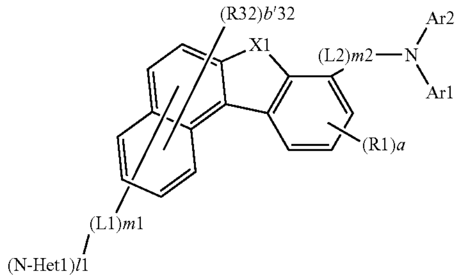
[Chemical Formula A-333]
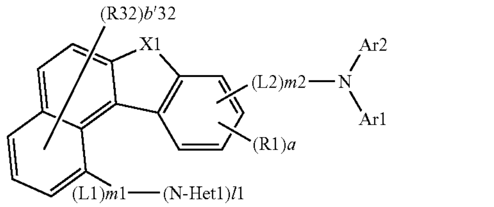

-continued

[Chemical Formula A-334]

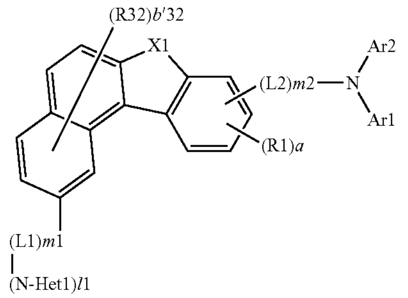

[Chemical Formula A-335]

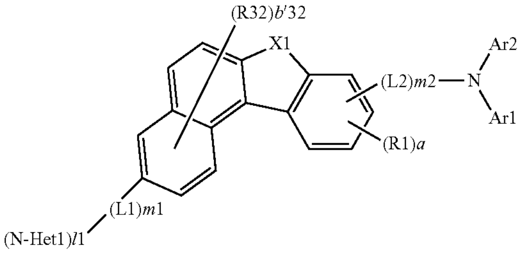

[Chemical Formula A-336]

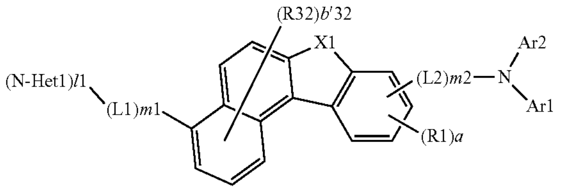

[Chemical Formula A-337]

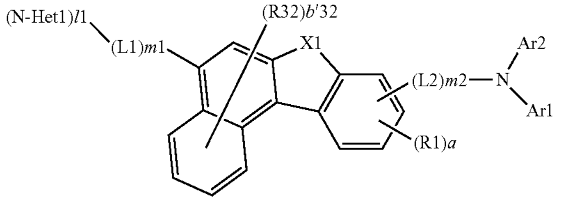

[Chemical Formula A-338]

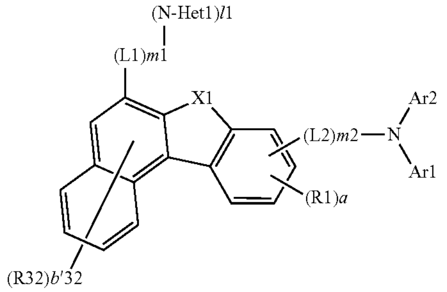

In Chemical Formulae A-301 to A-338, the definitions of X1, R1, L1, L2, N-Het1, Ar1, Ar2, a, l1, m1, and m2 are the same as those described in Chemical Formula A, R31 and R32 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', and b'31 is an integer from 0 to 3, b'32 is an integer from 0 to 5, and when each of b'31 and b'32 is 2 or higher, substituents in the parenthesis are the same as or different from each other. Further, the specific description on the substituent is the same as described above.

In a further exemplary embodiment of the present invention, R31 and R32 are the same as or different from each other, and may be each independently selected from the group consisting of hydrogen; deuterium; a halogen; a substituted or unsubstituted C1 to C40 alkyl group; a substituted or unsubstituted C2 to C40 alkenyl group; a substituted or unsubstituted C2 to C40 alkynyl group; a substituted or unsubstituted C1 to C40 alkoxy group; a substituted or unsubstituted C3 to C40 cycloalkyl group; a substituted or unsubstituted C2 to C40 heterocycloalkyl group; a substituted or unsubstituted C6 to C40 aryl group; a substituted or unsubstituted C2 to C40 heteroaryl group; —SiRR'R"; and —P(═O)RR'.

In another further exemplary embodiment of the present invention, R31 and R32 are the same as or different from each other, and may be each independently selected from the group consisting of hydrogen; deuterium; a halogen; a substituted or unsubstituted C1 to C20 alkyl group; a substituted or unsubstituted C2 to C20 alkenyl group; a substituted or unsubstituted C2 to C20 alkynyl group; a substituted or unsubstituted C1 to C20 alkoxy group; a substituted or unsubstituted C3 to C20 cycloalkyl group; a substituted or unsubstituted C2 to C20 heterocycloalkyl group; a substituted or unsubstituted C6 to C20 aryl group; a substituted or unsubstituted C2 to C20 heteroaryl group; —SiRR'R"; and —P(═O)RR'.

In still another further exemplary embodiment of the present invention, R31 and R32 are the same as or different from each other, and may be each independently selected from the group consisting of hydrogen; deuterium; a halogen; a substituted or unsubstituted C1 to C20 alkyl group; a substituted or unsubstituted C6 to C20 aryl group; and a substituted or unsubstituted C2 to C20 heteroaryl group.

In yet another further exemplary embodiment of the present invention, R31 and R32 are the same as or different from each other, and may be each independently selected from the group consisting of hydrogen; deuterium; a C6 to C20 aryl group unsubstituted or substituted with deuterium; and a C2 to C20 heteroaryl group unsubstituted or substituted with deuterium.

In still yet another further exemplary embodiment of the present invention, R31 and R32 are the same as or different from each other, and may be each independently hydrogen; or deuterium.

In a still further exemplary embodiment of the present invention, b'31 may be an integer of 0, 1, 2, or 3.

In yet still further exemplary embodiment of the present invention, b'32 may be an integer of 0, 1, 2, 3, 4, or 5.

In another exemplary embodiment of the present application, provided is a composition for an organic light emitting device, in which

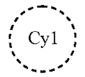

of Chemical Formula A-4 is represented by any one of the following Chemical Formulae A-401 to A-408.

[Chemical Formula A-401]

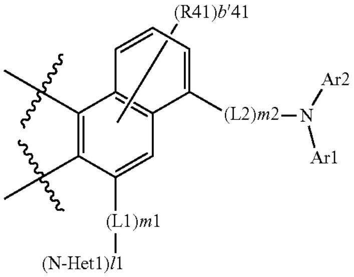

[Chemical Formula A-402]

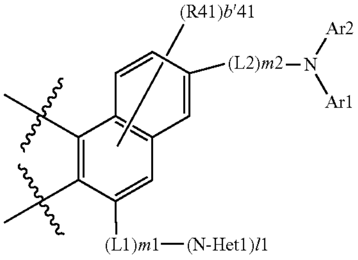

[Chemical Formula A-403]

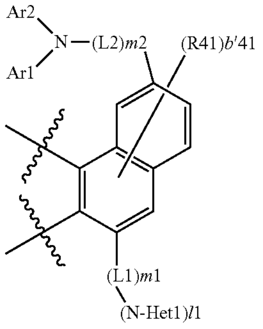

[Chemical Formula A-404]

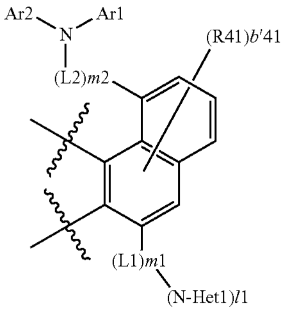

[Chemical Formula A-405]

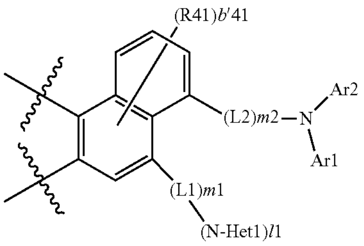

-continued

[Chemical Formula A-406]

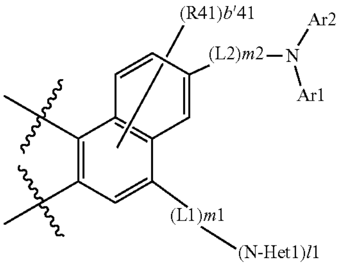

[Chemical Formula A-407]

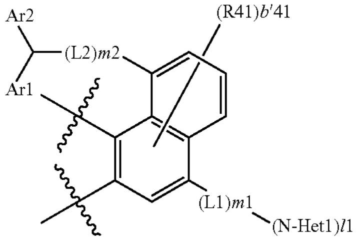

[Chemical Formula A-408]

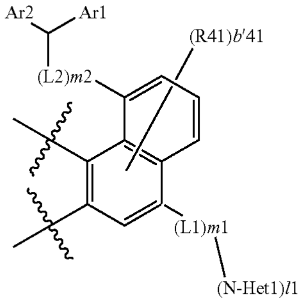

In Chemical Formulae A-401 to A-408,

means a moiety linked to another structure, the definitions of L1, L2, N-Het1, Ar1, Ar2, l1, m1, and m2 are the same as those described in Chemical Formula A, R41 is selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', and b'41 is an integer from 0 to 4. Further, the specific description on the substituent is the same as described above.

In still another exemplary embodiment of the present invention, R41 may be selected from the group consisting of hydrogen; deuterium; a halogen; a substituted or unsubstituted C1 to C40 alkyl group; a substituted or unsubstituted C2 to C40 alkenyl group; a substituted or unsubstituted C2 to C40 alkynyl group; a substituted or unsubstituted C1 to C40 alkoxy group; a substituted or unsubstituted C3 to C40 cycloalkyl group; a substituted or unsubstituted C2 to C40 heterocycloalkyl group; a substituted or unsubstituted C6 to C40 aryl group; a substituted or unsubstituted C2 to C40 heteroaryl group; —SiRR'R"; and —P(═O)RR'.

In yet another exemplary embodiment of the present invention, R41 may be selected from the group consisting of hydrogen; deuterium; a halogen; a substituted or unsubstituted C1 to C20 alkyl group; a substituted or unsubstituted C2 to C20 alkenyl group; a substituted or unsubstituted C2 to C20 alkynyl group; a substituted or unsubstituted C1 to C20 alkoxy group; a substituted or unsubstituted C3 to C20 cycloalkyl group; a substituted or unsubstituted C2 to C20 heterocycloalkyl group; a substituted or unsubstituted C6 to C20 aryl group; a substituted or unsubstituted C2 to C20 heteroaryl group; —SiRR'R"; and —P(═O)RR'.

In still yet another exemplary embodiment of the present invention, R41 may be selected from the group consisting of hydrogen; deuterium; a halogen; a substituted or unsubstituted C1 to C20 alkyl group; a substituted or unsubstituted C6 to C20 aryl group; and a substituted or unsubstituted C2 to C20 heteroaryl group.

In a further exemplary embodiment of the present invention, R41 may be selected from the group consisting of hydrogen; deuterium; a C6 to C20 aryl group unsubstituted or substituted with deuterium; and a C2 to C20 heteroaryl group unsubstituted or substituted with deuterium.

In another further exemplary embodiment of the present invention, R41 may be hydrogen; or deuterium.

In still another further exemplary embodiment of the present invention, b'41 may be an integer of 0, 1, 2, 3, or 4.

In an exemplary embodiment of the present invention, Chemical Formula B may include a heterocyclic compound represented by any one of the following Chemical Formulae B-1 to B-6.

[Chemical Formula B-1]

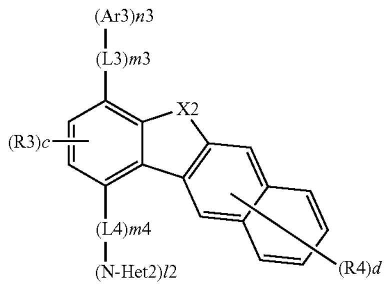

[Chemical Formula B-2]

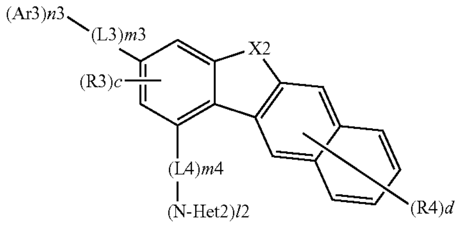

-continued

[Chemical Formula B-3]

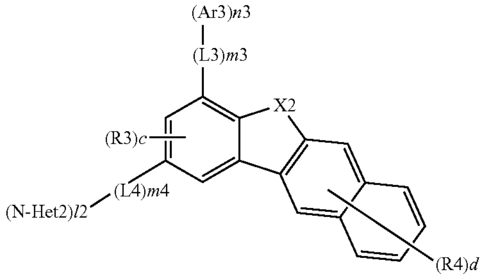

[Chemical Formula B-4]

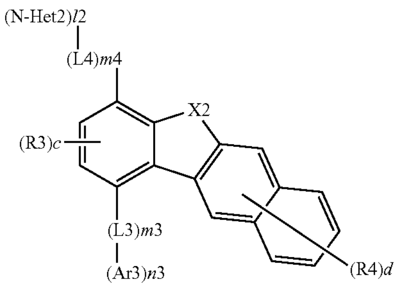

[Chemical Formula B-5]

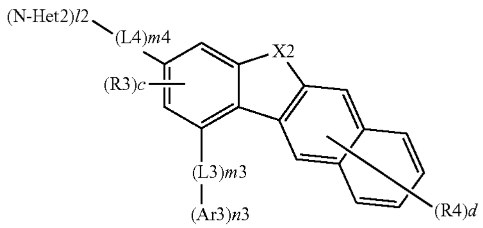

[Chemical Formula B-6]

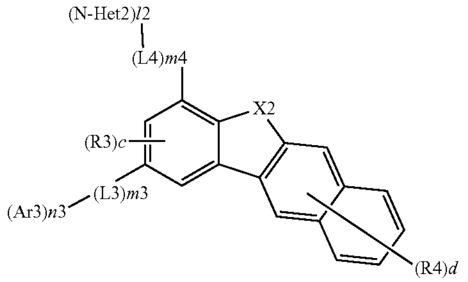

In Chemical Formulae B-1 to B-6, the definitions of X2, R3, R4, L3, L4, N-Het2, Ar3, c, d, 12, m3, m4, and n3 are the same as those described in Chemical Formula B.

In an exemplary embodiment of the present invention, provided is a composition for an organic light emitting device, in which Chemical Formula C is represented by the following Chemical Formula Ca or Cb.

[Chemical Formula Ca]

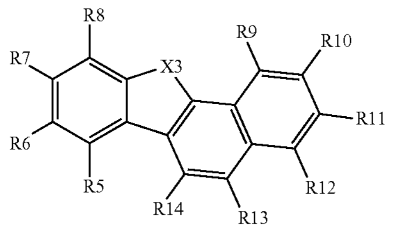

[Chemical Formula Cb]

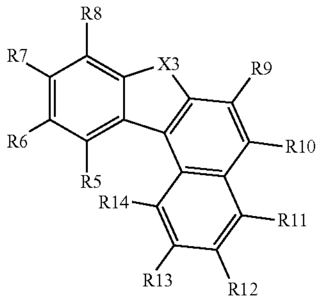

In Chemical Formulae Ca and Cb, the definitions of X3 and R5 to R14 are the same as those described in Chemical Formula C.

In an exemplary embodiment of the present invention, any one of R5 to R8 is -(L5)m5-(Ar4)n4, any one of R9 to R14 is -(L6)m6-(N-Het3)l3, and the others are the same as or different from each other, and may be each independently hydrogen, or deuterium.

In an exemplary embodiment of the present invention, any one of R9 to R14 is -(L5)m5-(Ar4)n4, any one of R5 to R8 is -(L6)m6-(N-Het3)l3, and the others are the same as or different from each other, and may be each independently hydrogen, or deuterium.

In addition, the specific description on the substituent is the same as described above.

In an exemplary embodiment of the present invention, Chemical Formula A may include any one of the following compounds.

A1

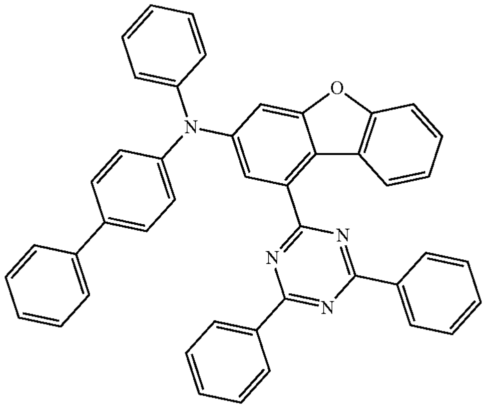

-continued

A2

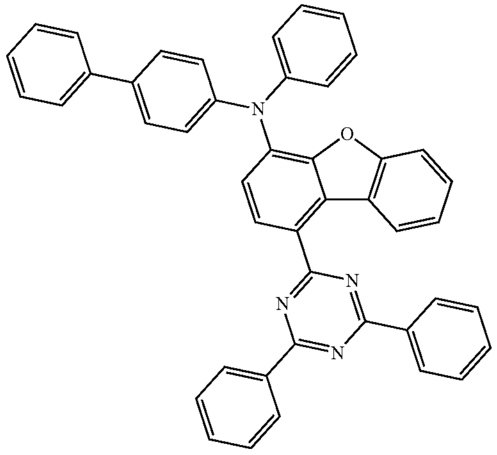

A3

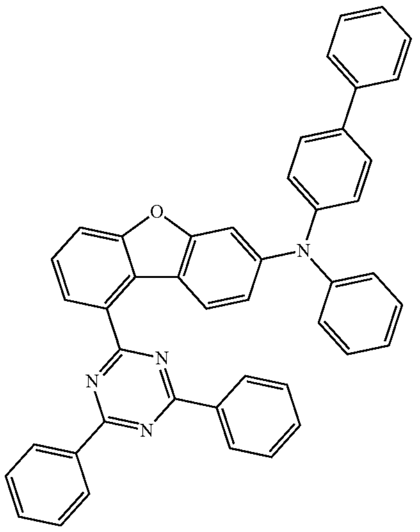

A4

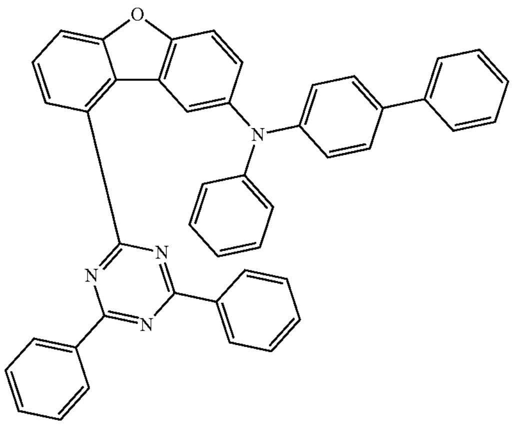

-continued
A5
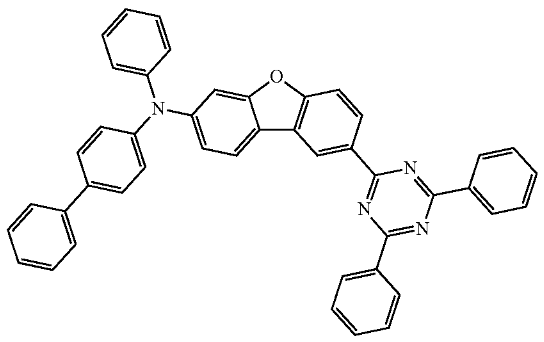
A6
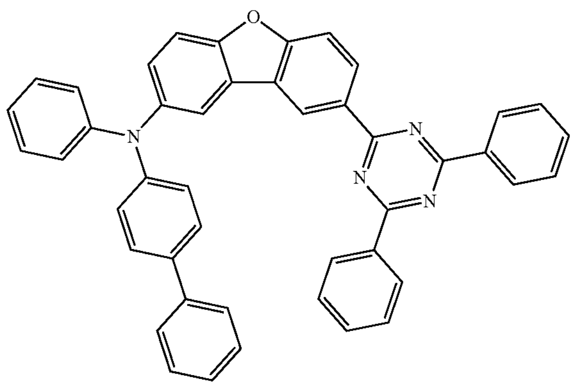
A7
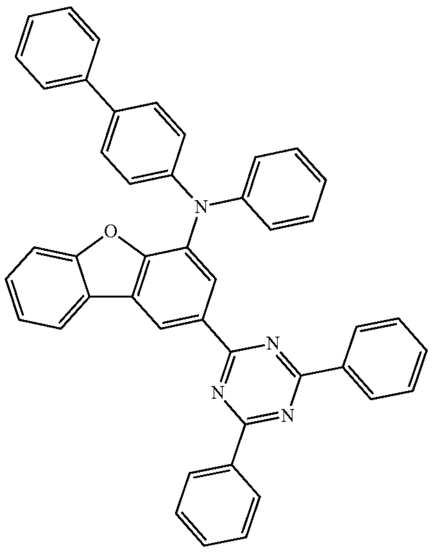
-continued
A8
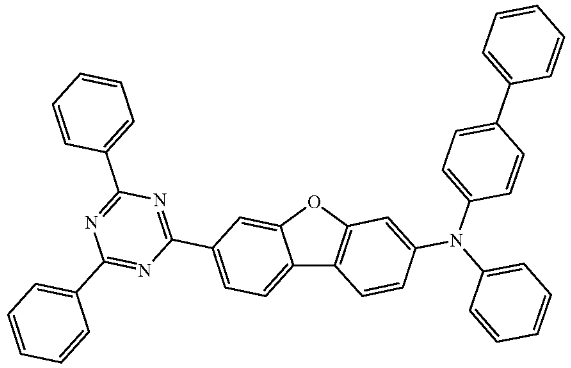
A9
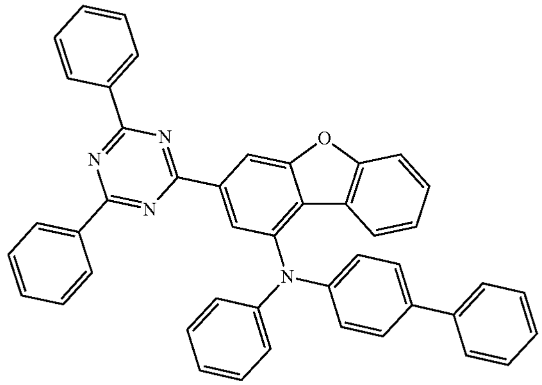
A10
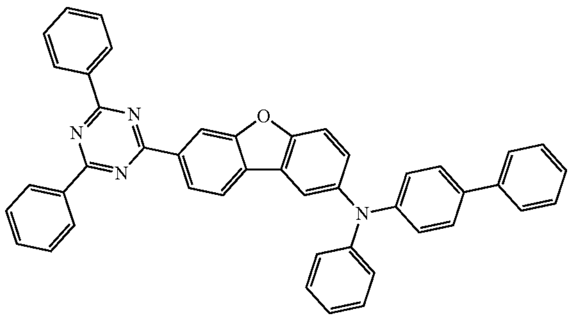
A11
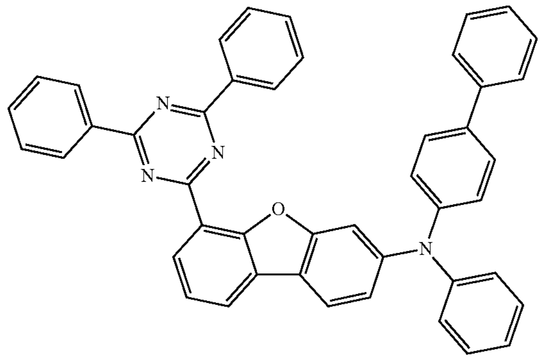

-continued
A12
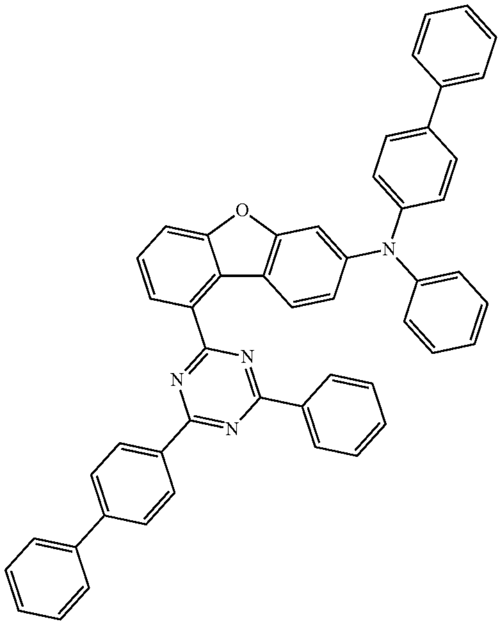
A13
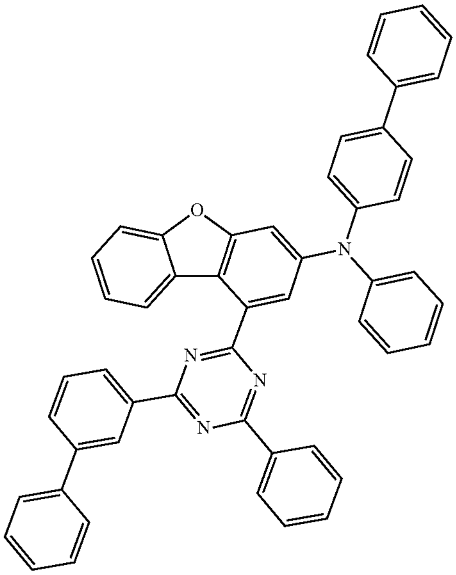
-continued
A14
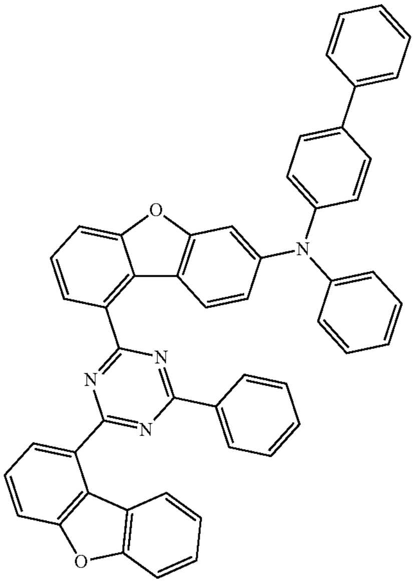
A15
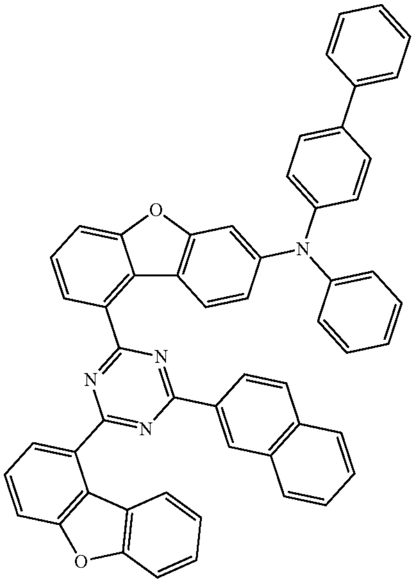

-continued
A16
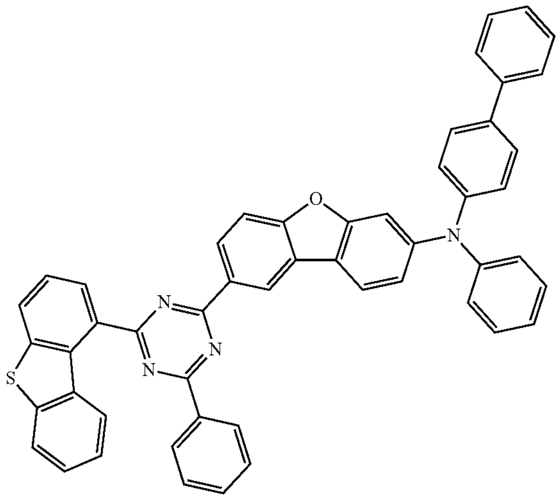
A17
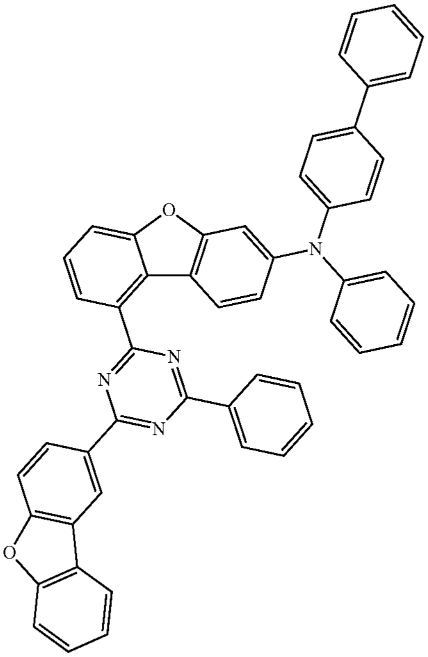
-continued
A18
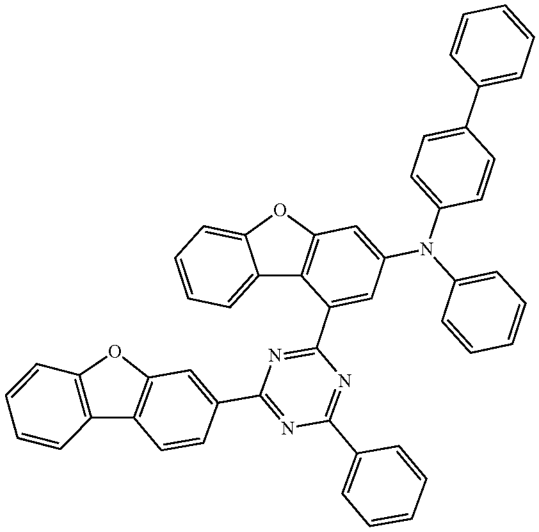
A19
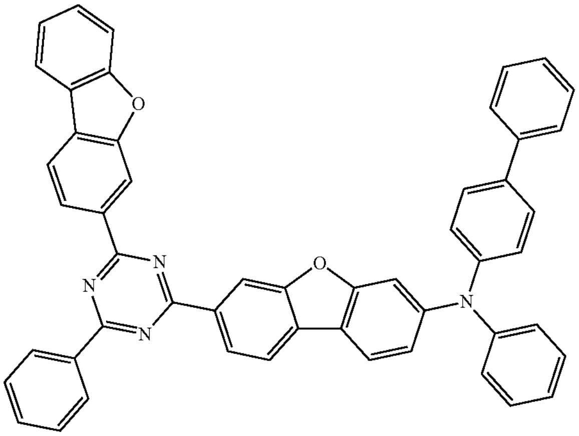
A20
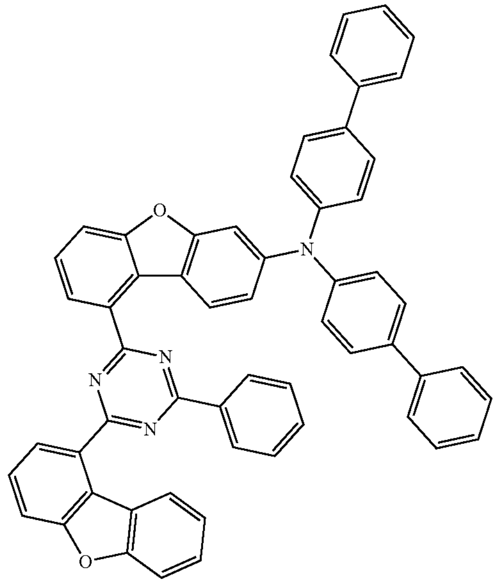

-continued
A21
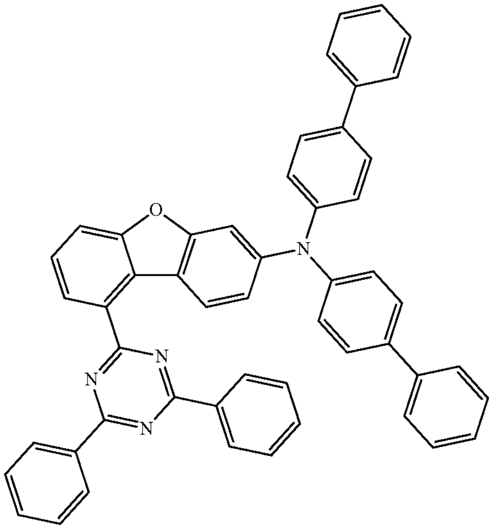
A22
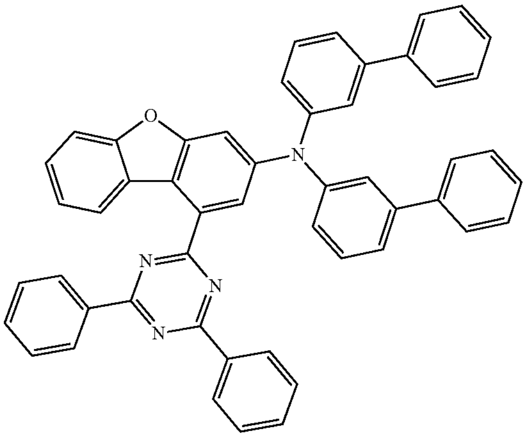
A23
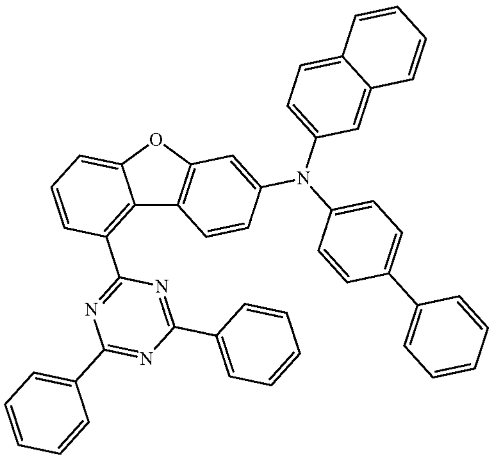
-continued
A24
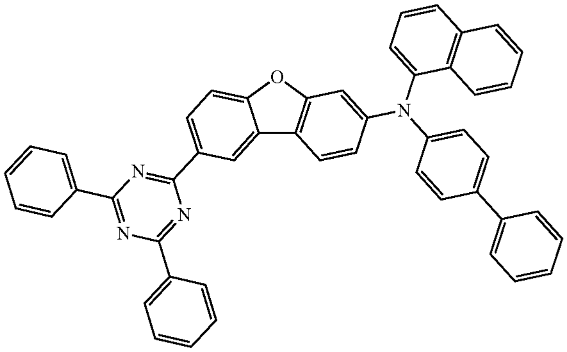
A25
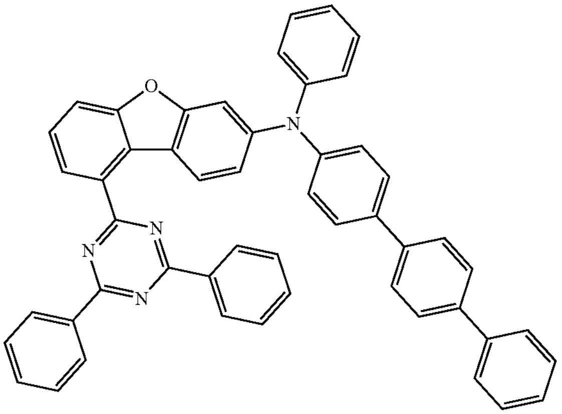
A26
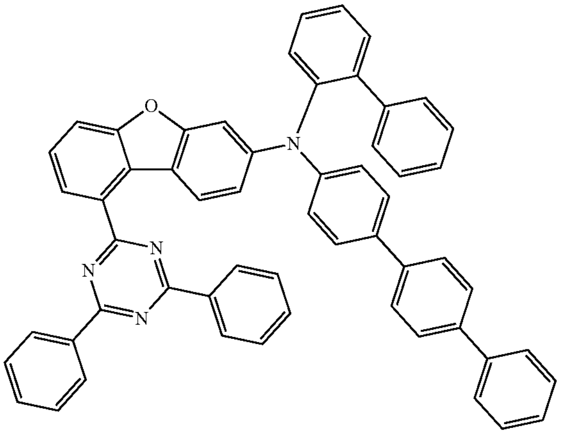

A27
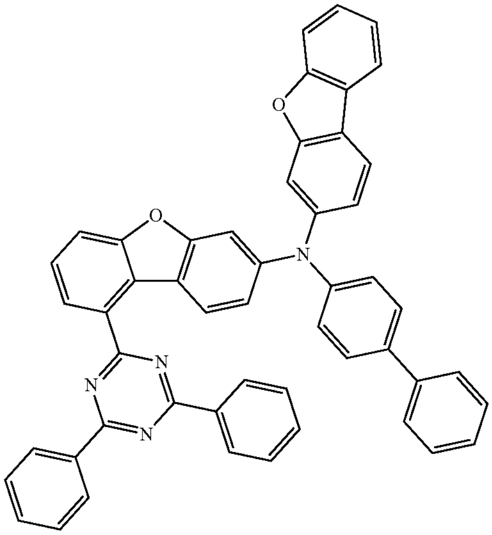
A28
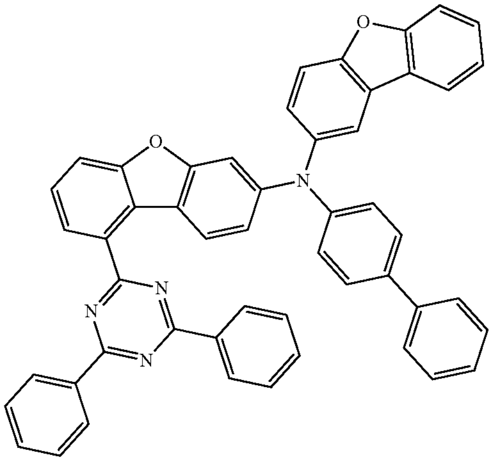
A29
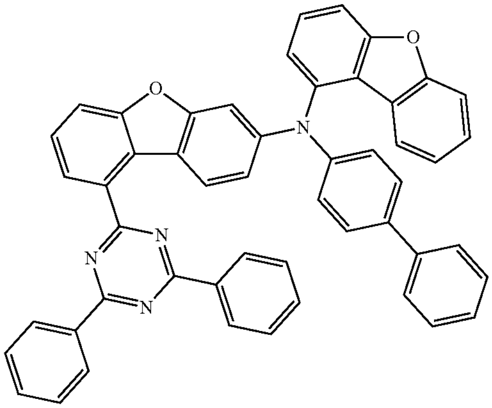
A30
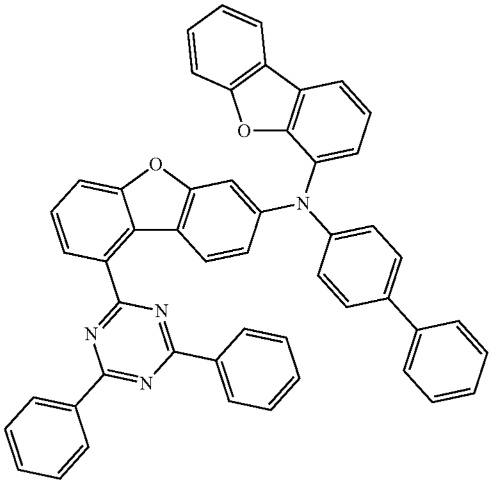
A31
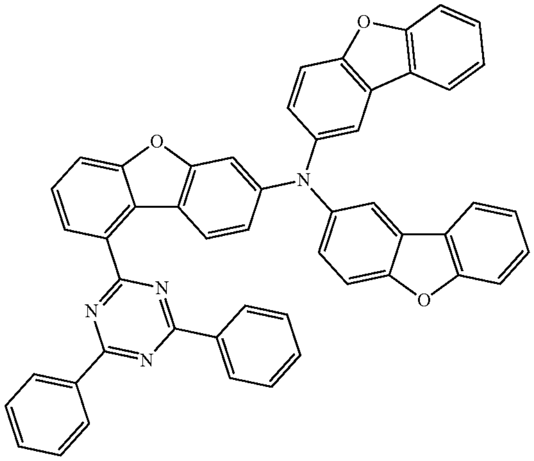
A32
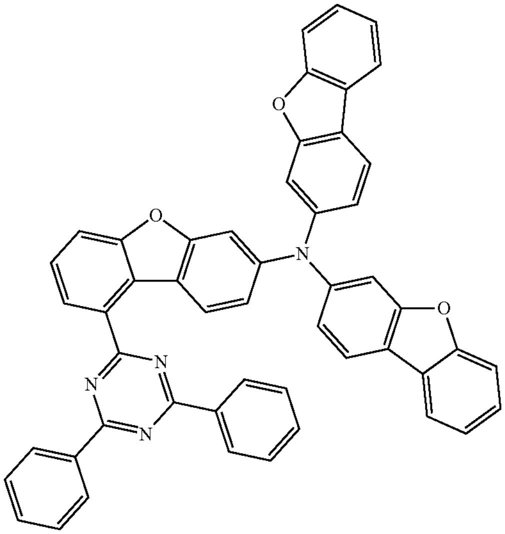

-continued
A33
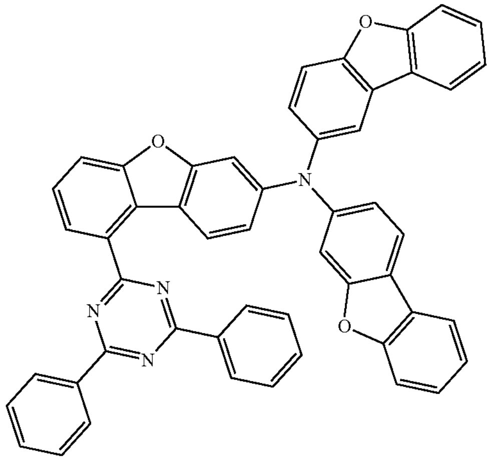
A34
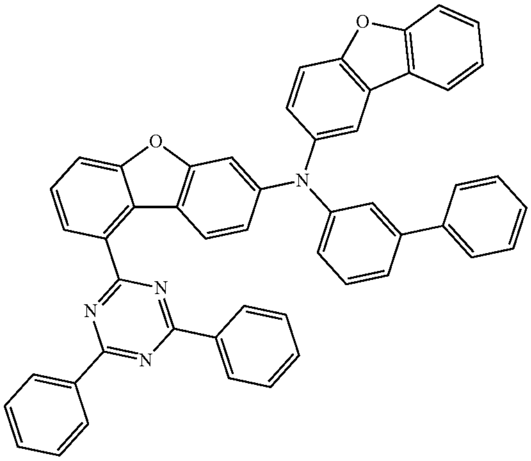
A35
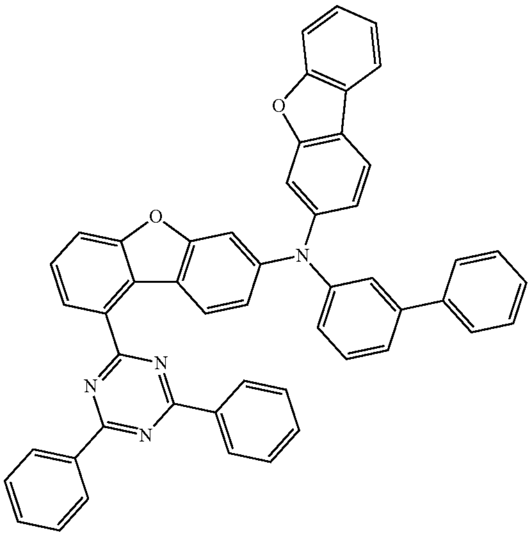
-continued
A36
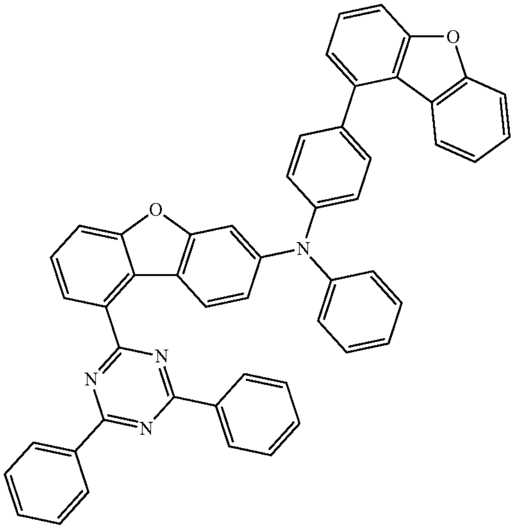
A37
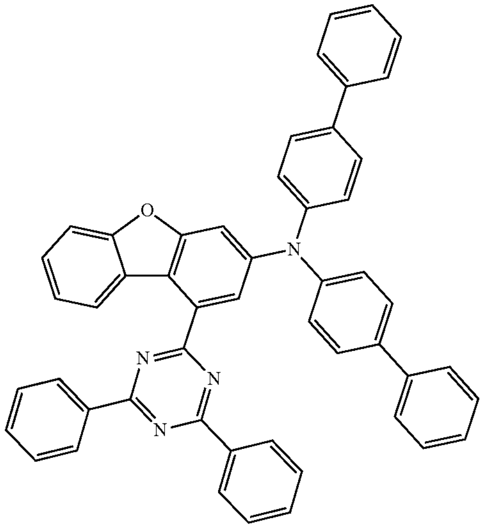
A38
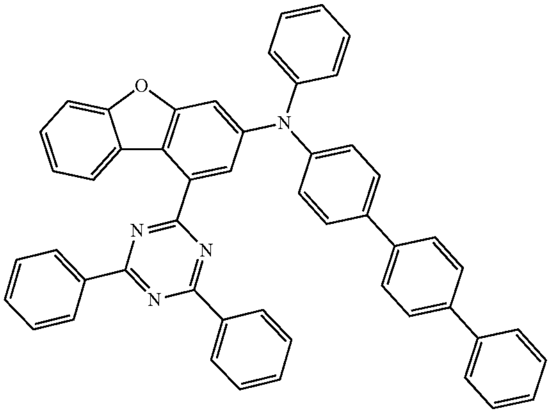

A39
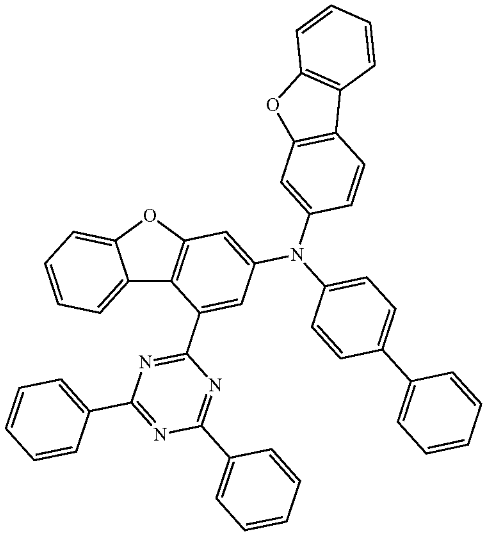
A40
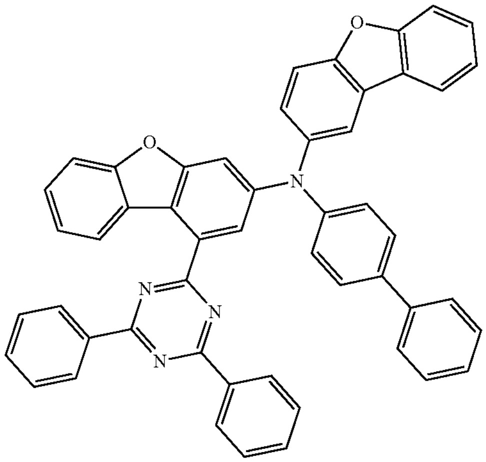
A41
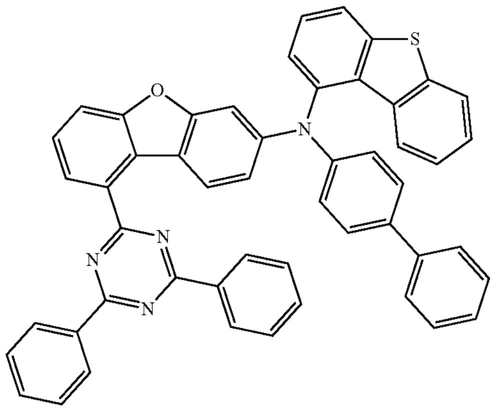
A42
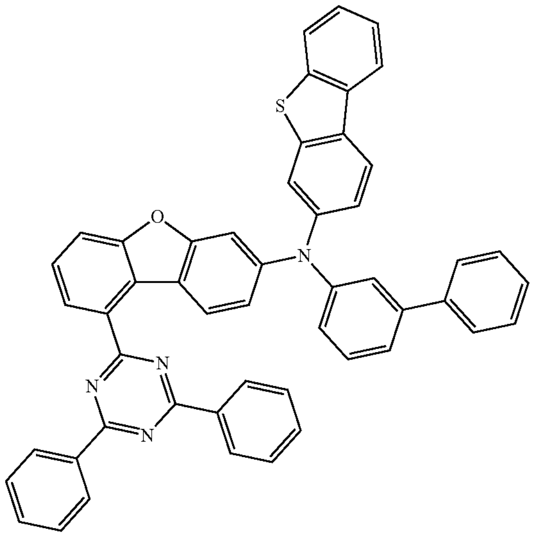
A43
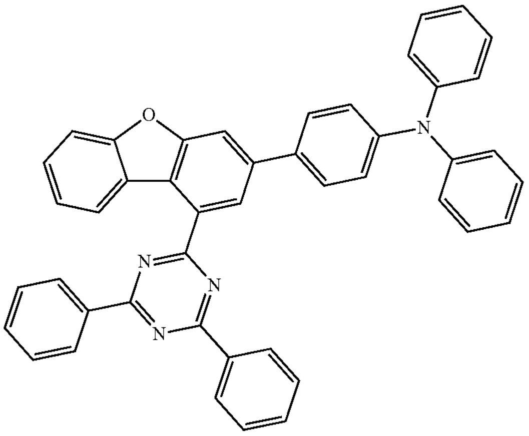
A44
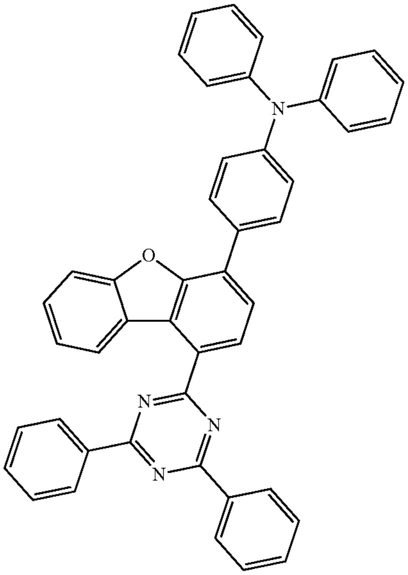

-continued
A45
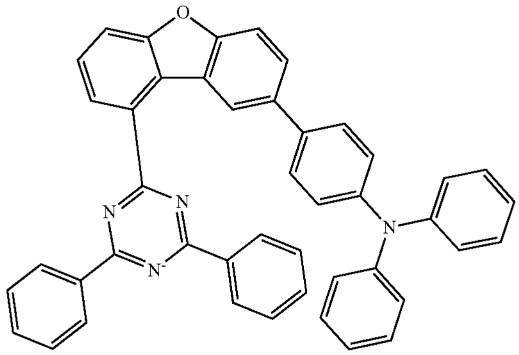
A46
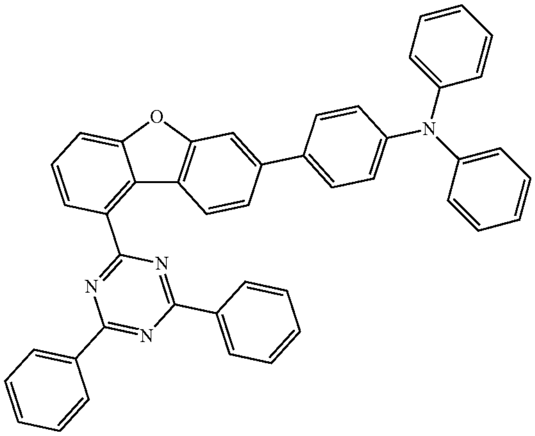
A47
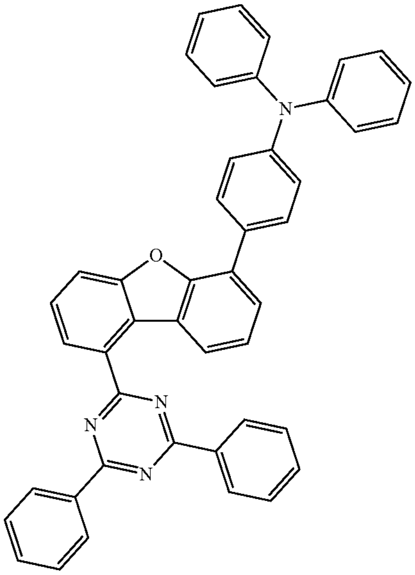
-continued
A48
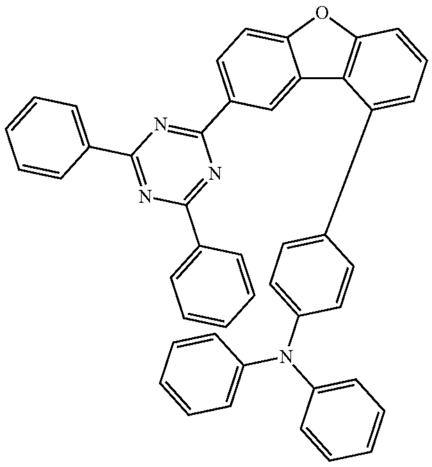
A49
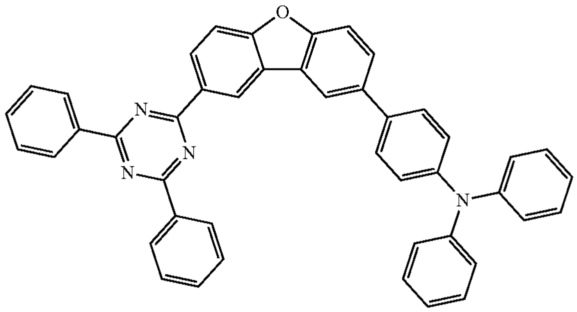
A50
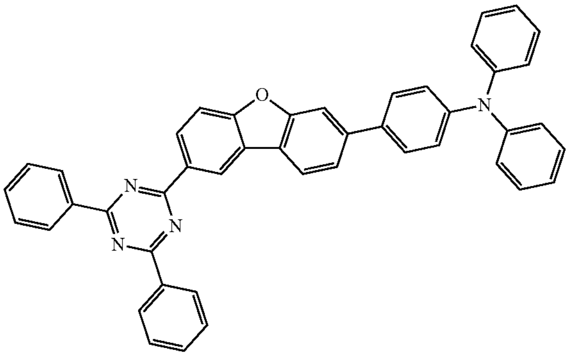

-continued
A51
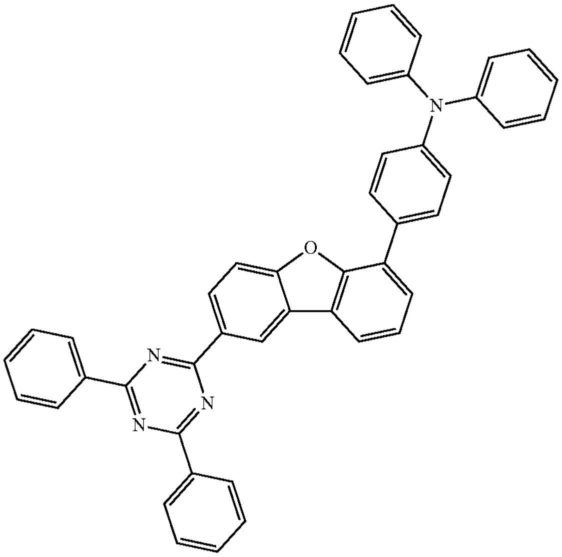
A52
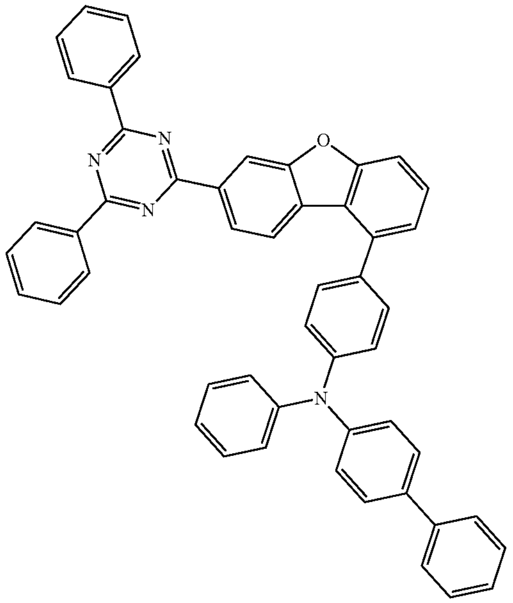
A53
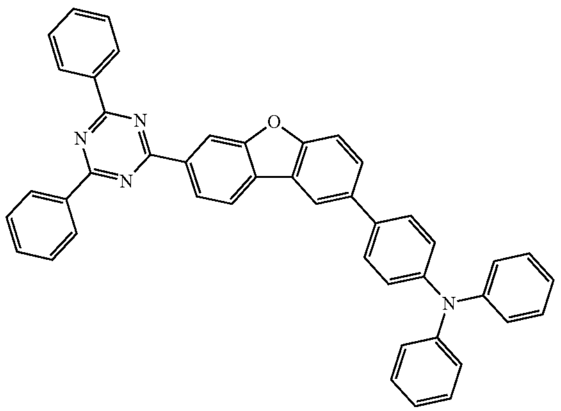
-continued
A54
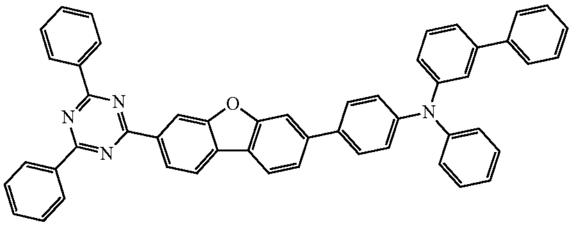
A55
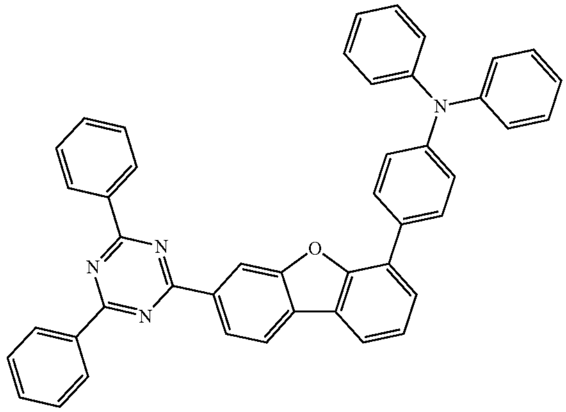
A56
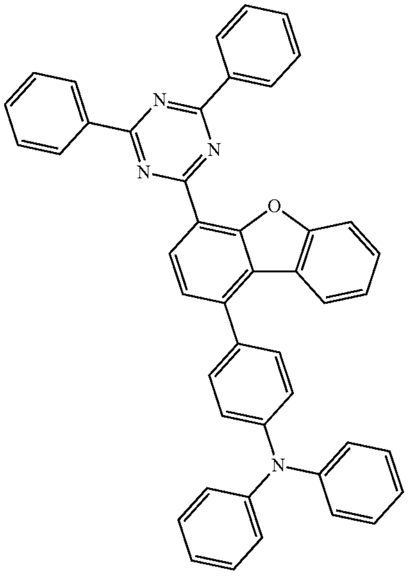

-continued
A57
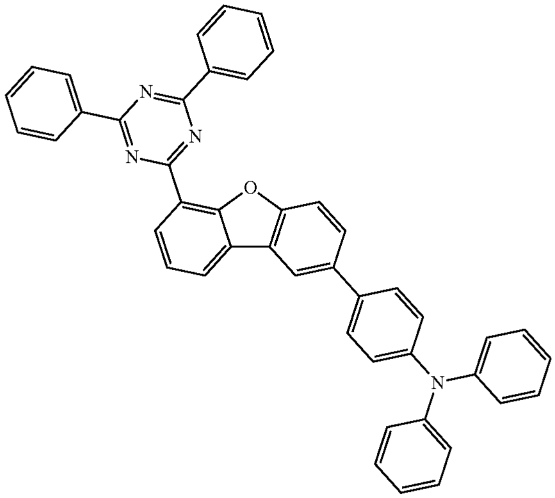
A58
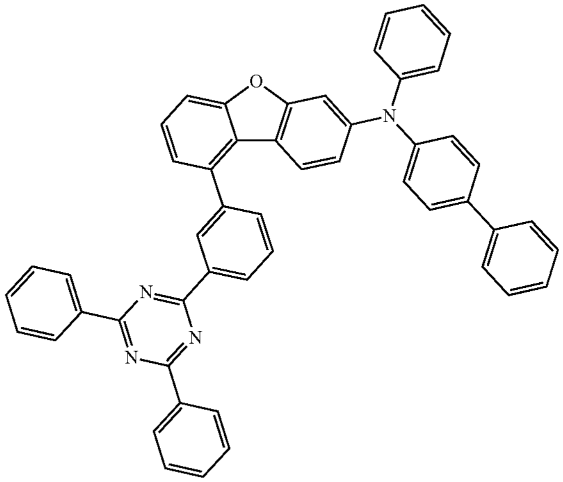
A59
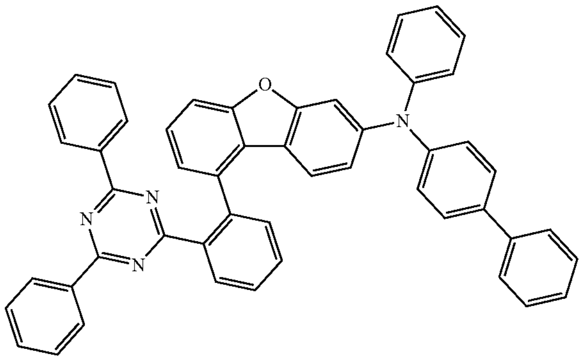
-continued
A60
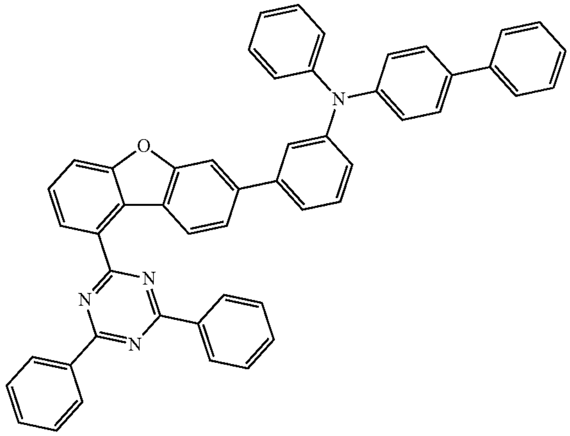
A61
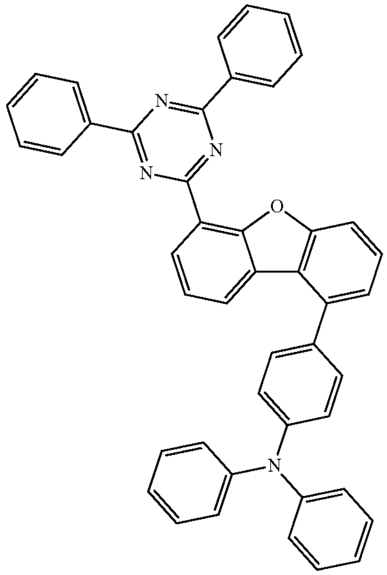
A62
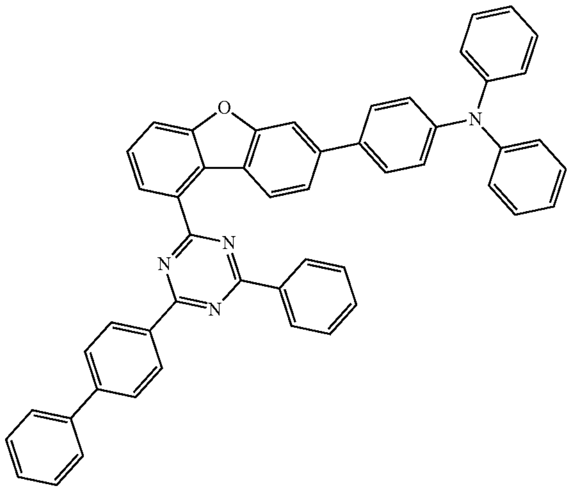

-continued
A63
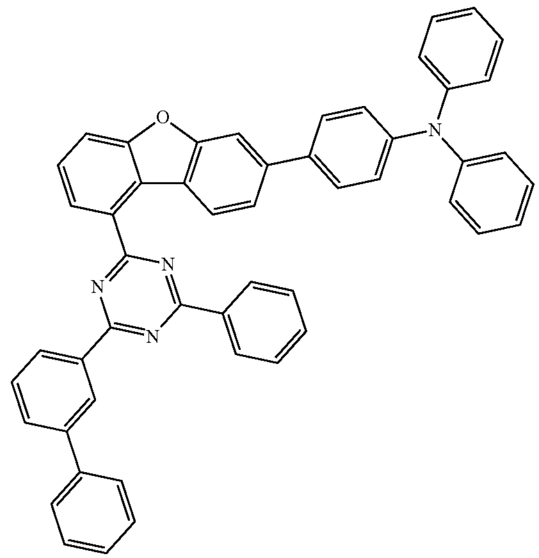
A64
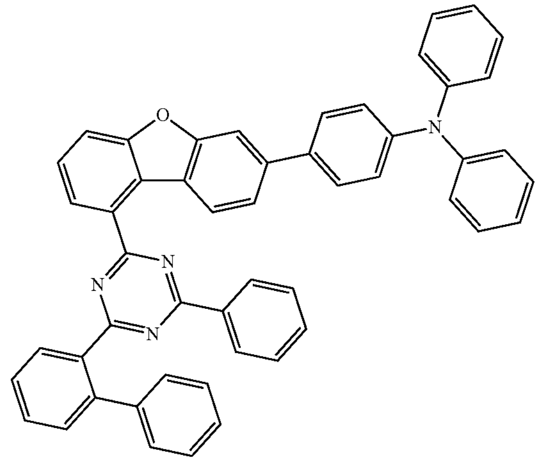
A65
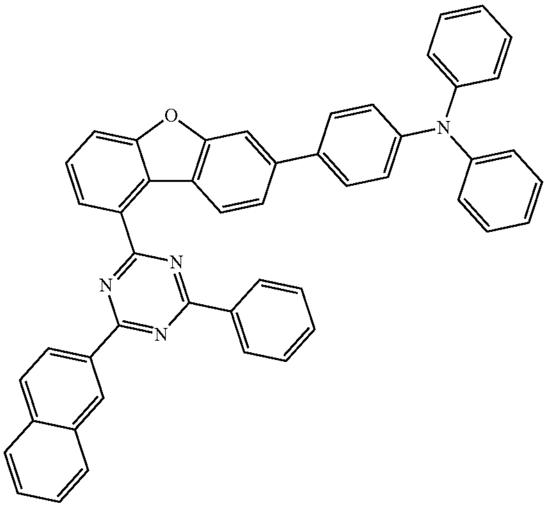
-continued
A66
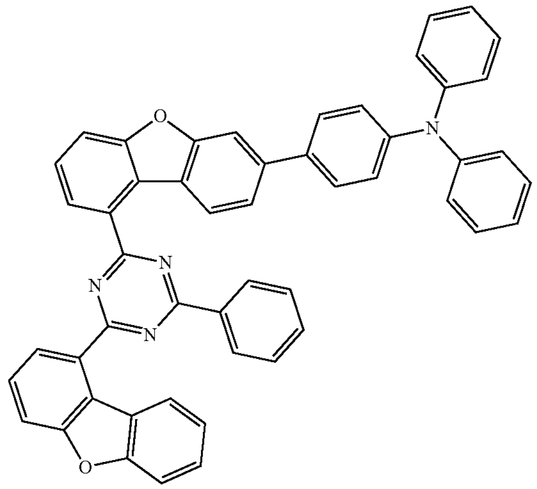
A67
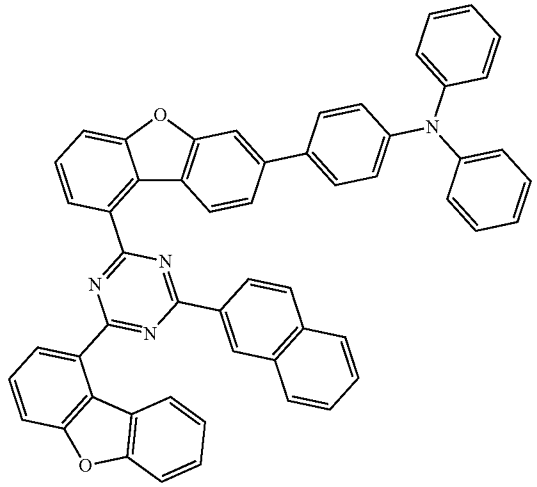
A68
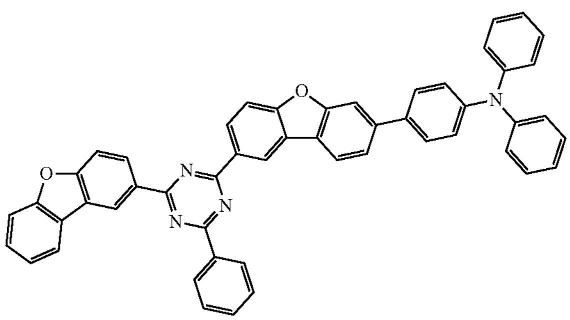

-continued
A69
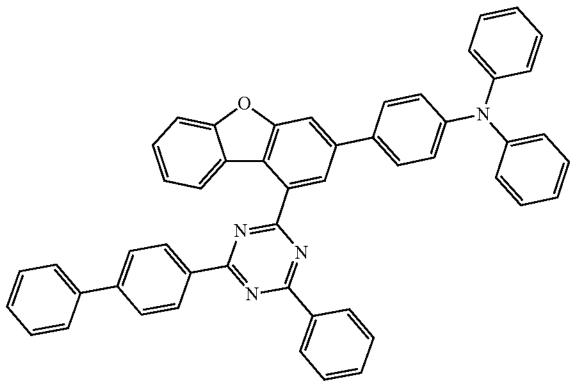
A70
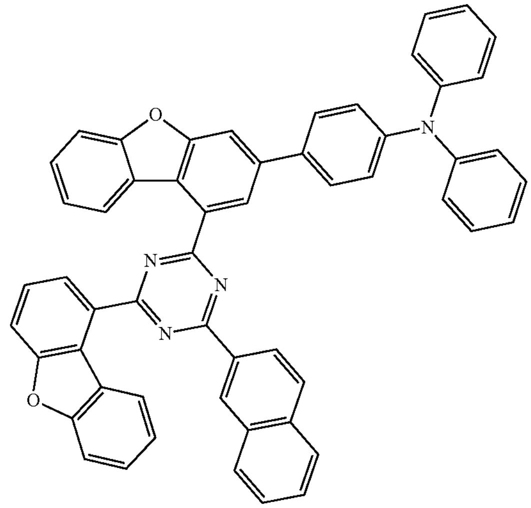
A71
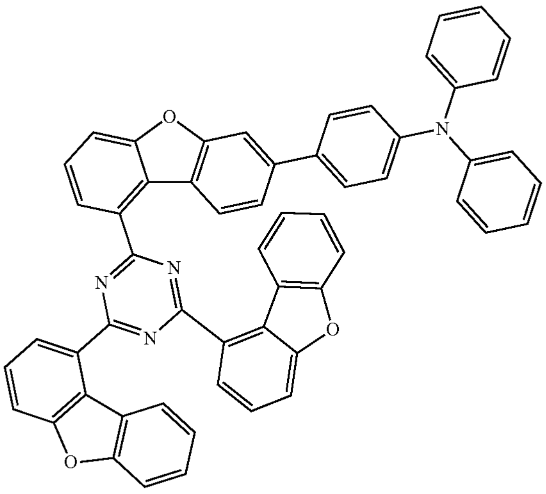
-continued
A72
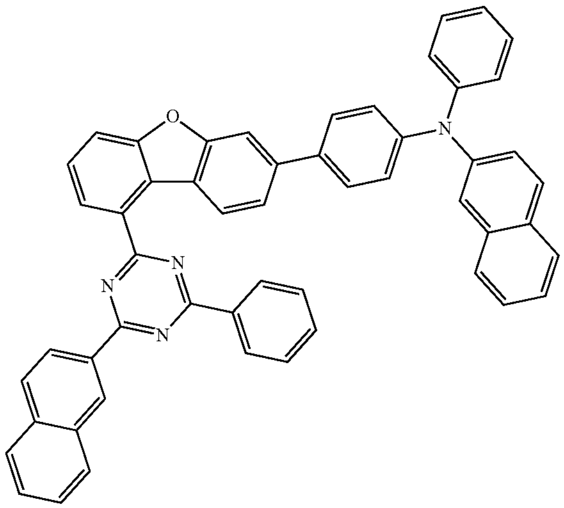
A73
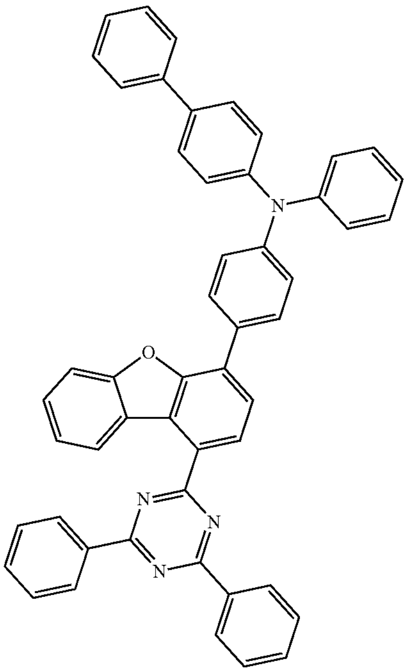
A74
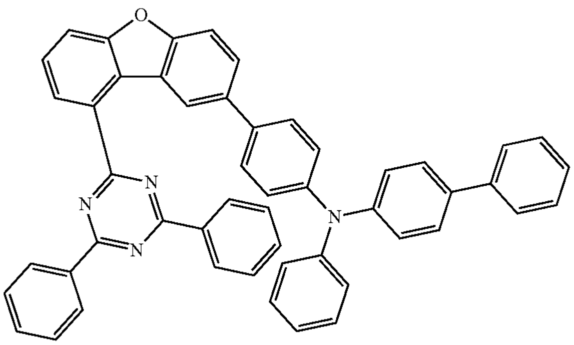

-continued
A75
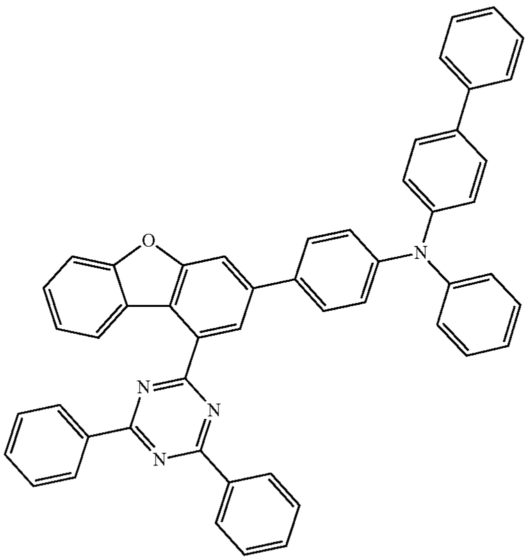
A76
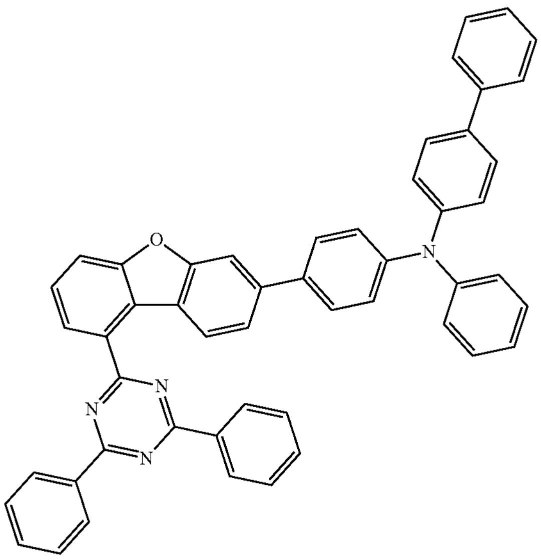
-continued
A77
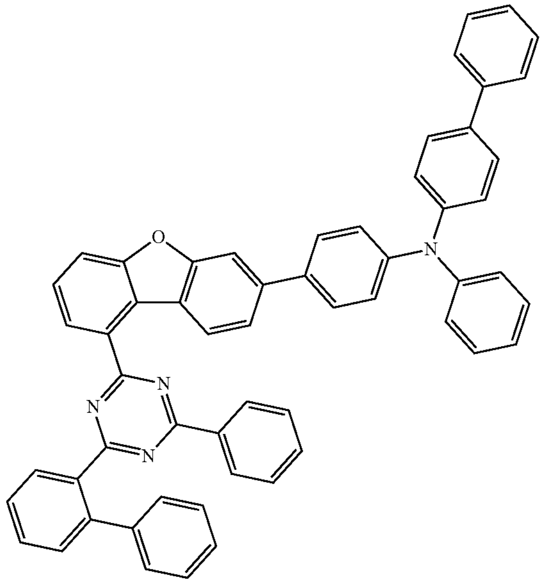
A78
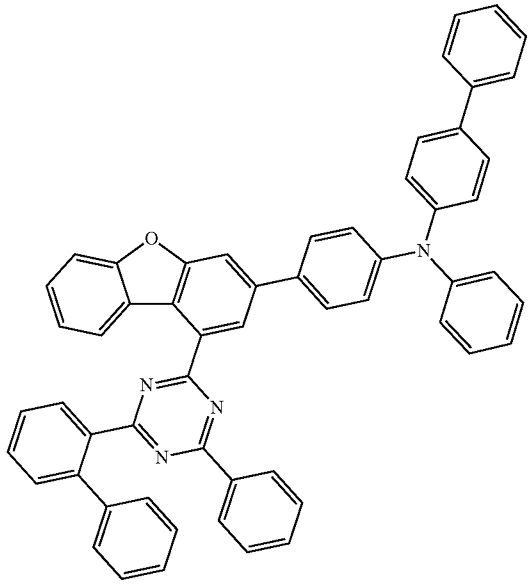
A79
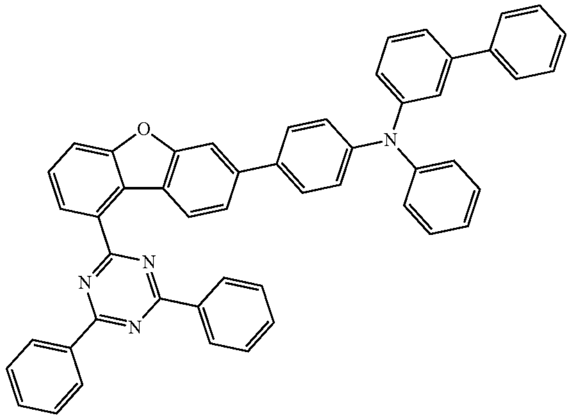

-continued
A80
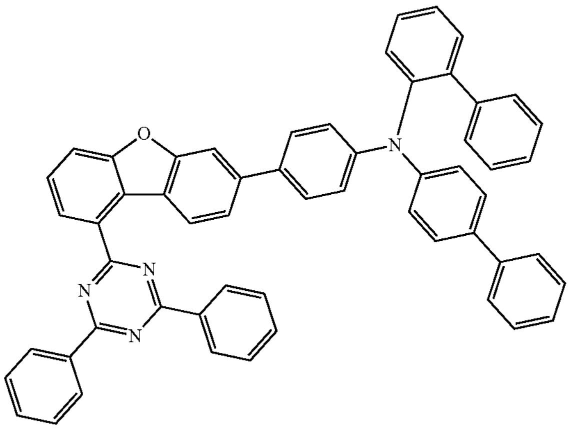
A81
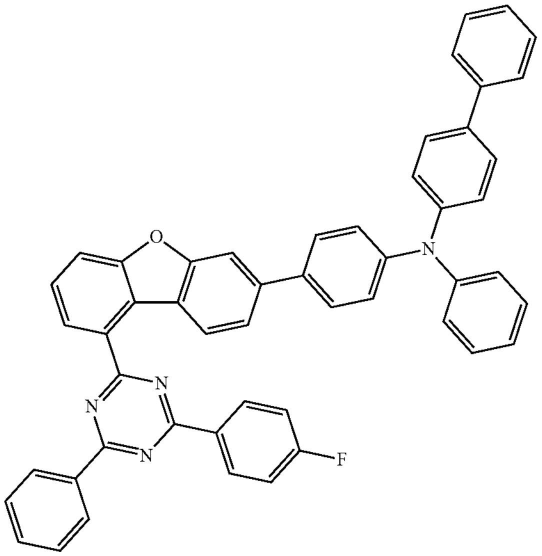
A82
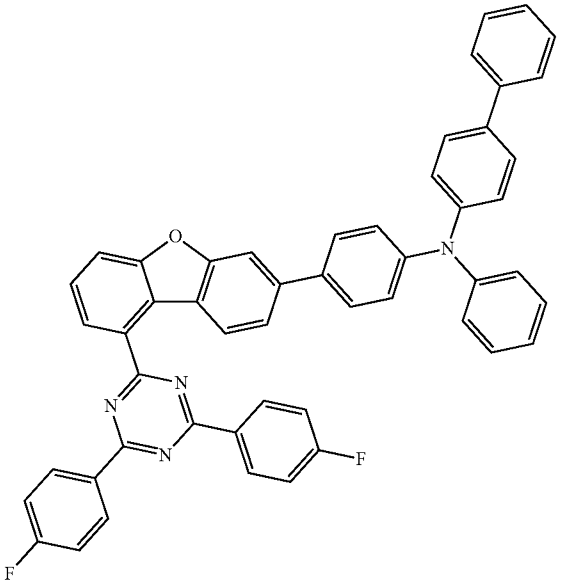
-continued
A83
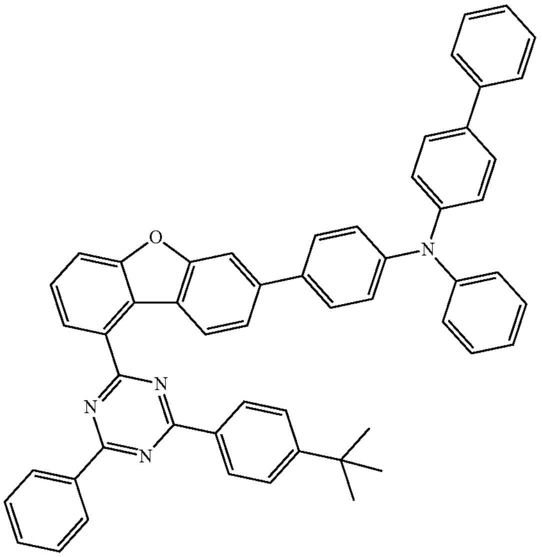
A84
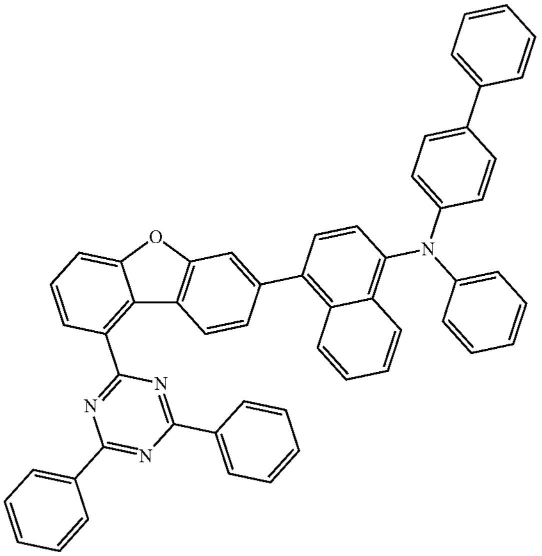

-continued
A85
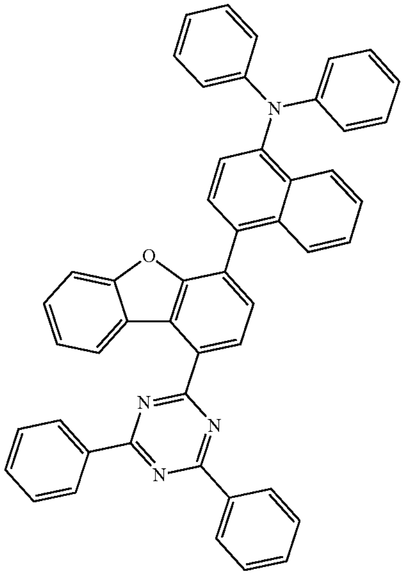
A86
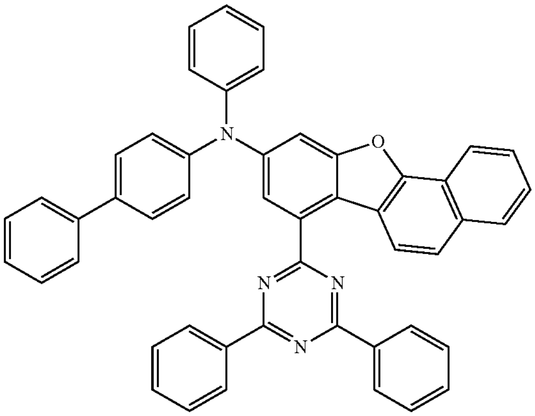
A87
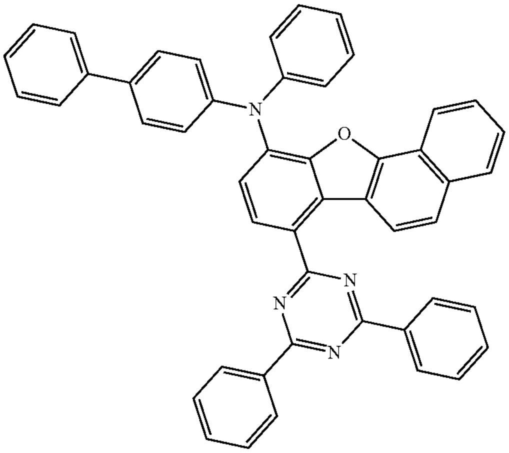
-continued
A88
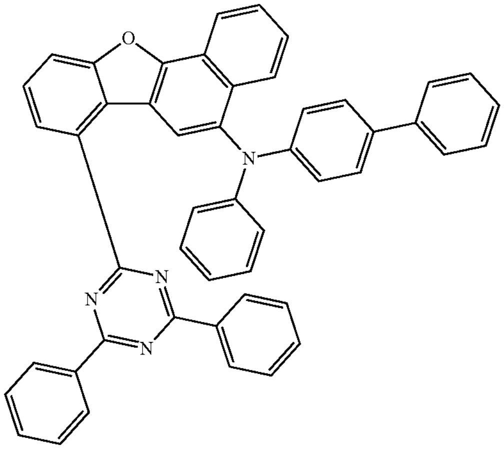
A89
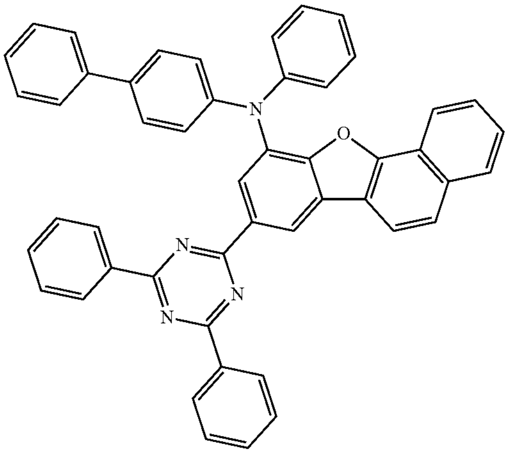
A90
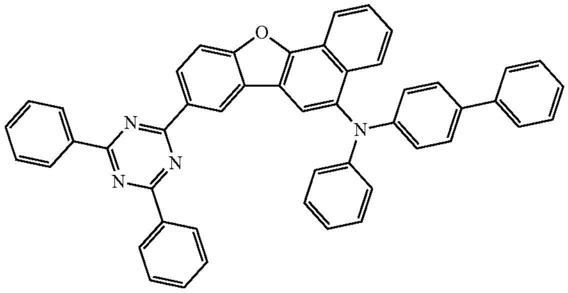

-continued
A91
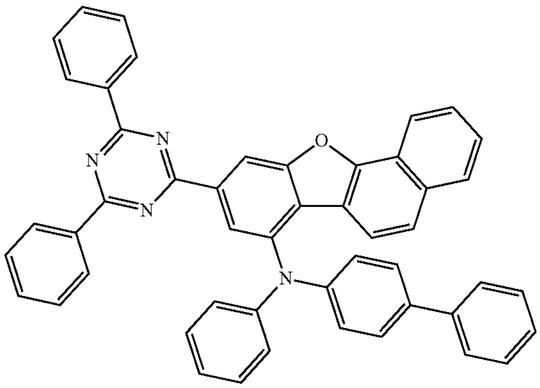
A92
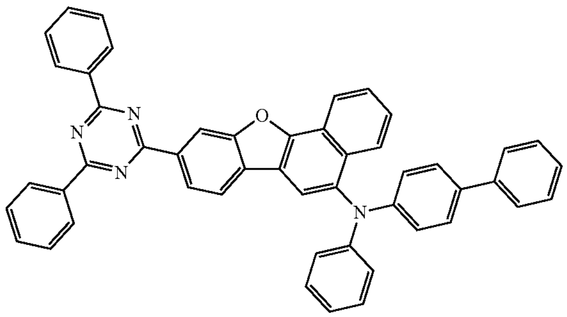
A93
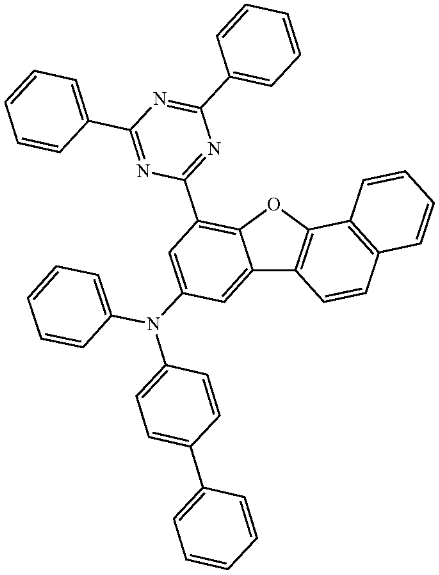
-continued
A94
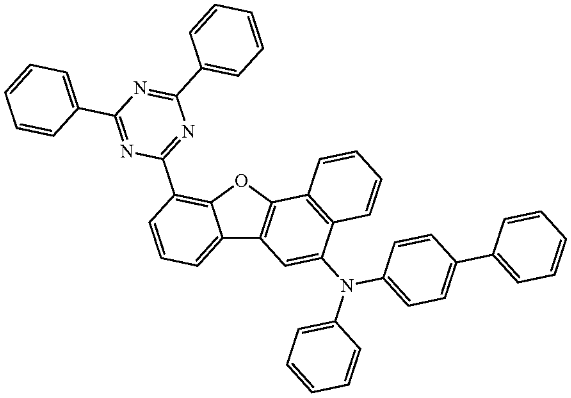
A95
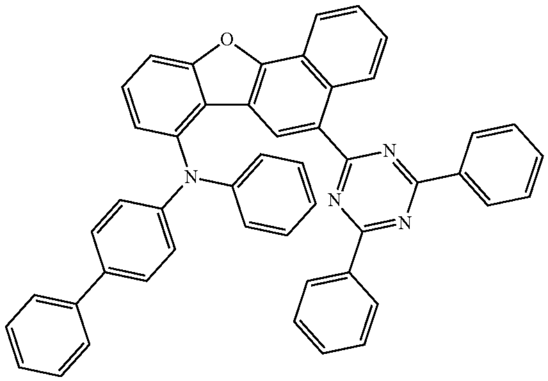
A96
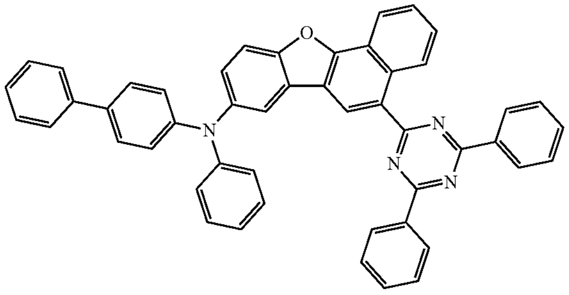

-continued
A97
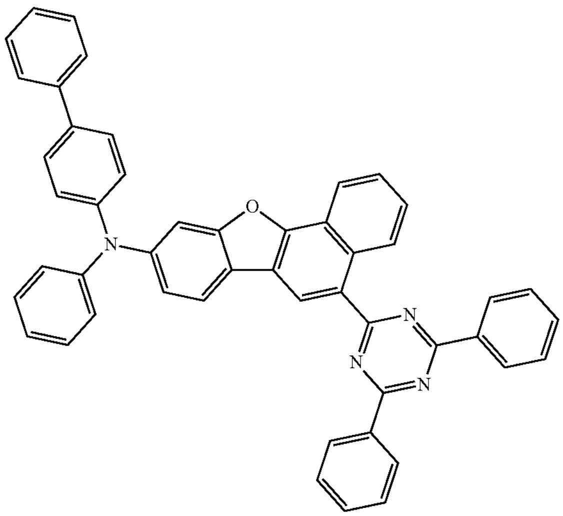
A98
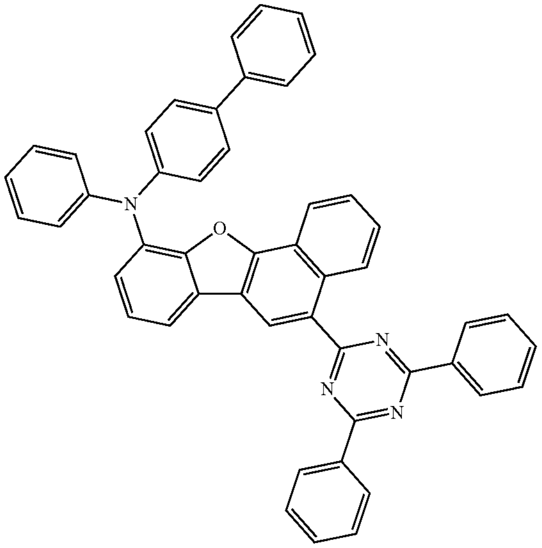
A99
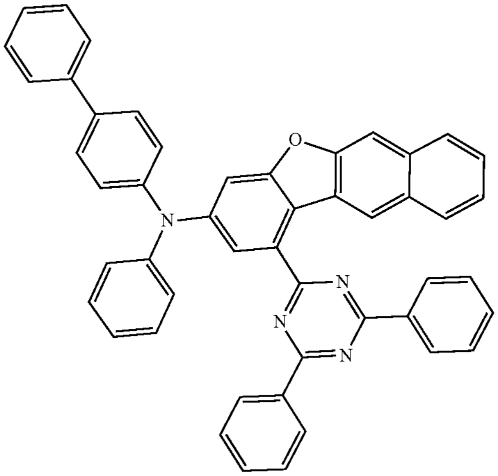
-continued
A100
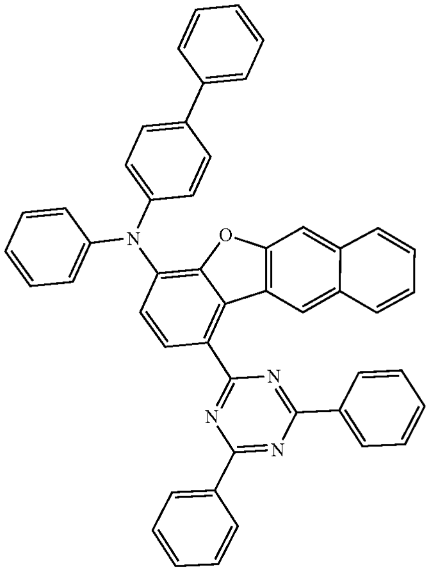
A101
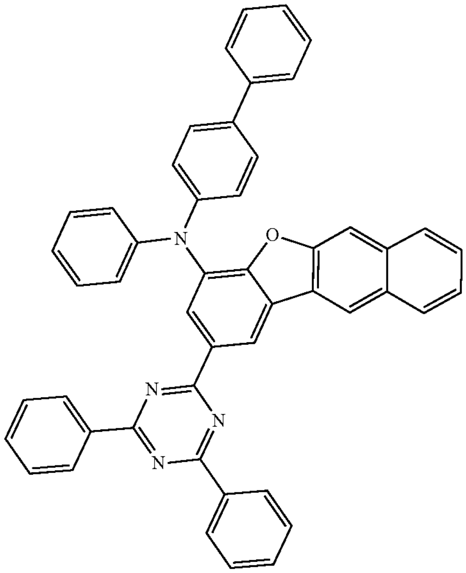
A102
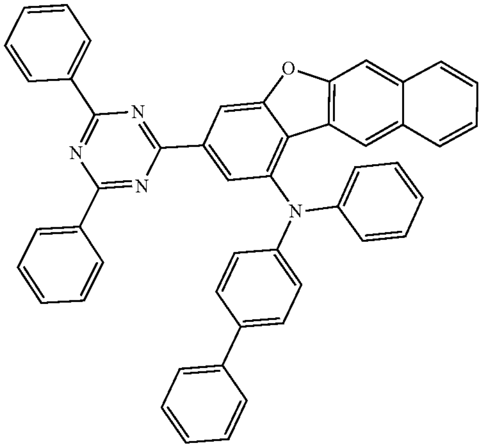

-continued
A103
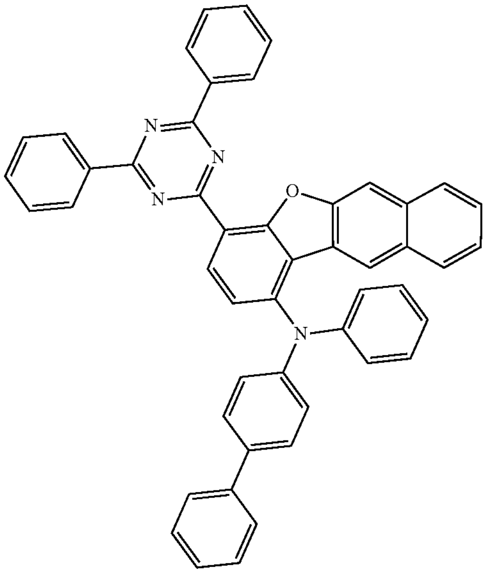
A104
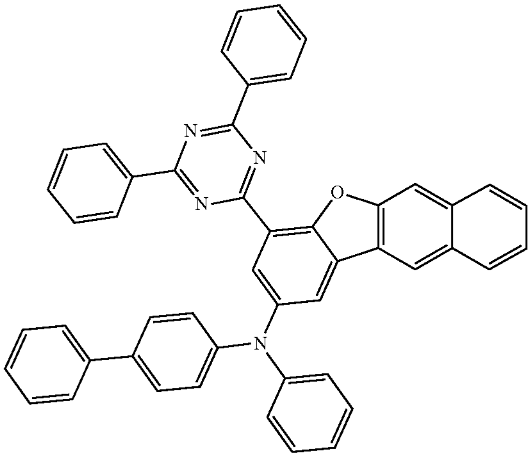
A105
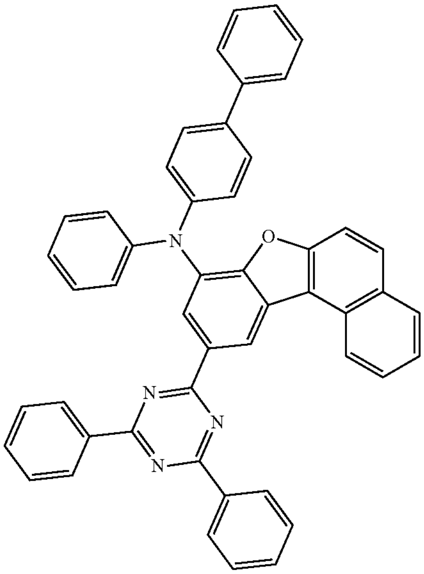
-continued
A106
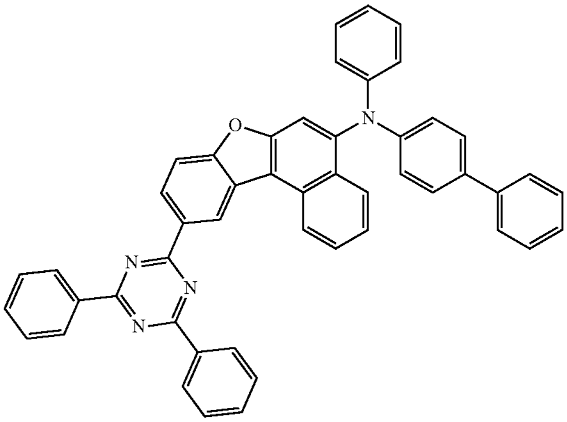
A107
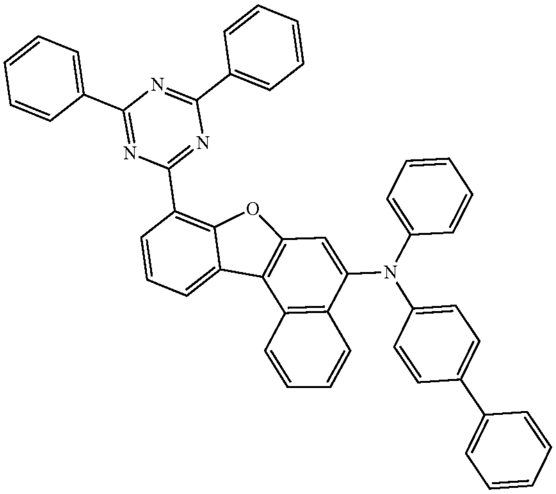
A108
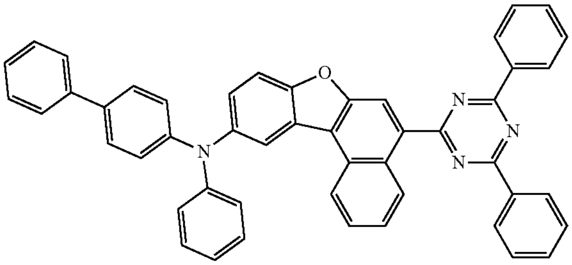

-continued
A109
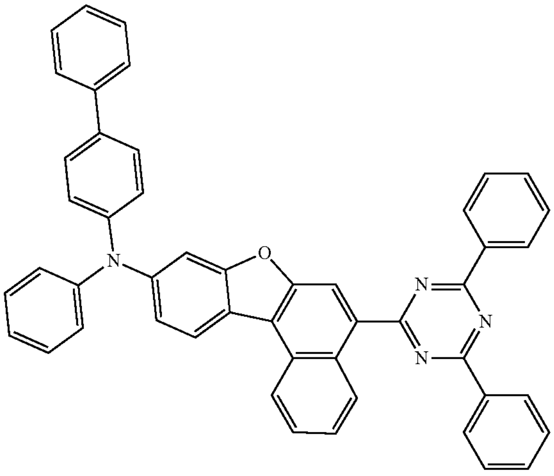
A110
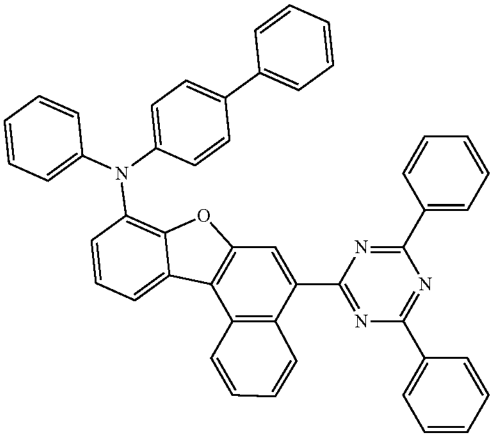
A111
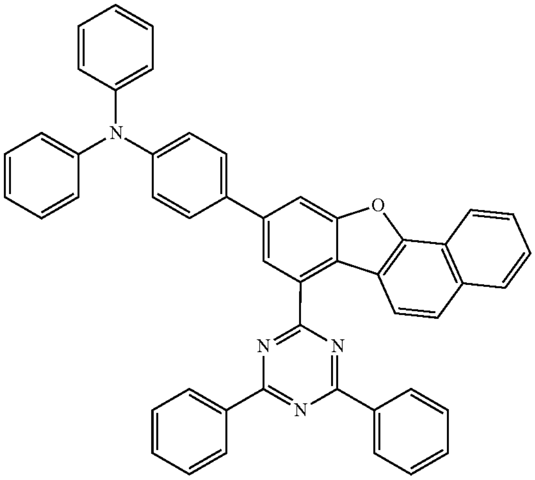
-continued
A112
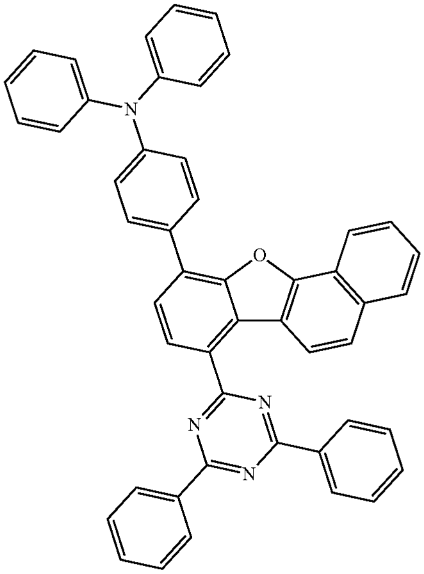
A113
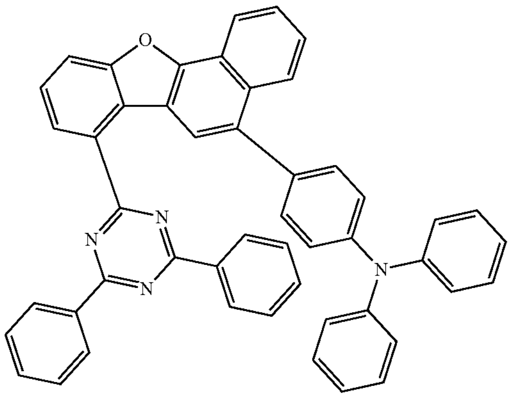
A114
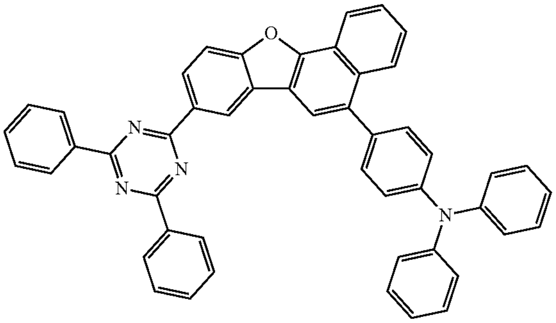

-continued
A115
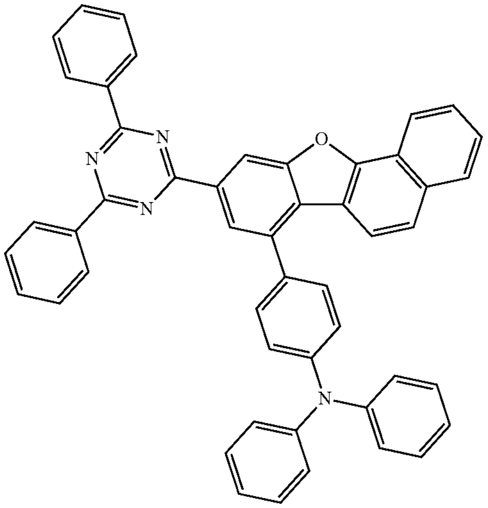
A116
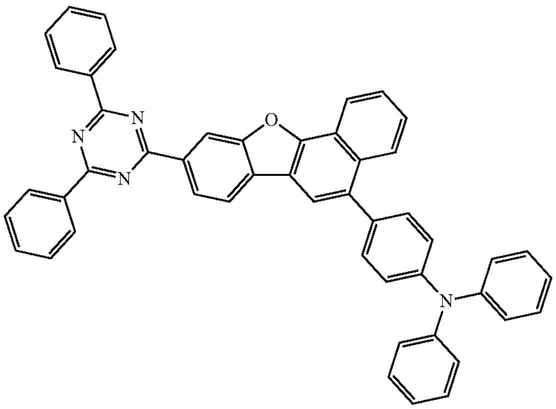
A117
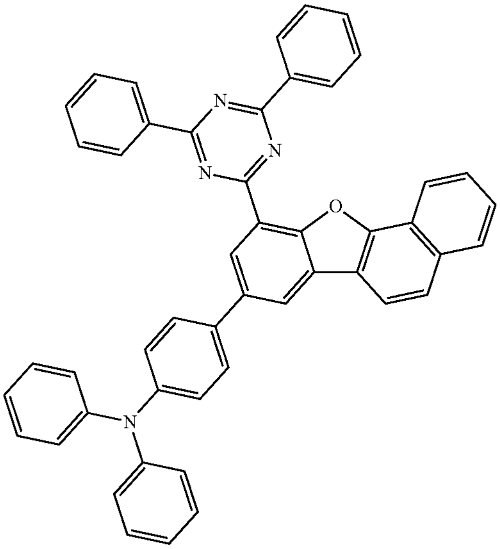
-continued
A118
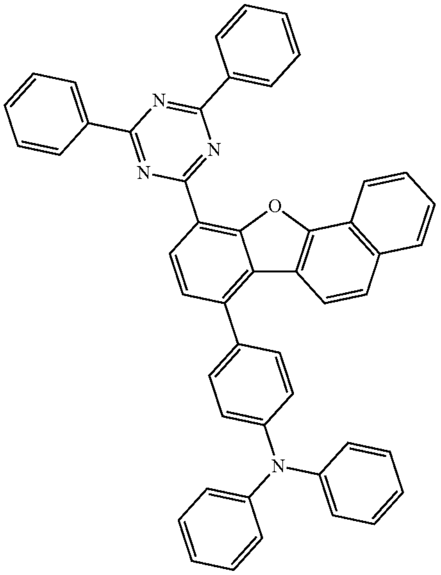
A119
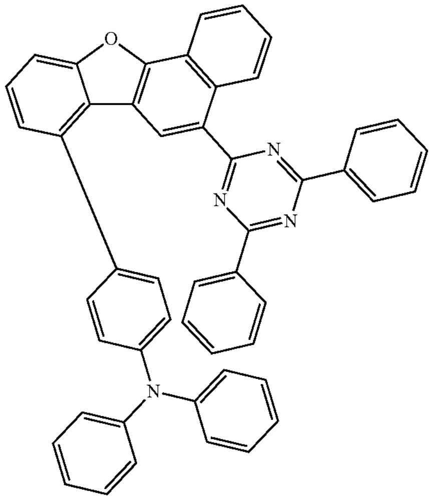
A120
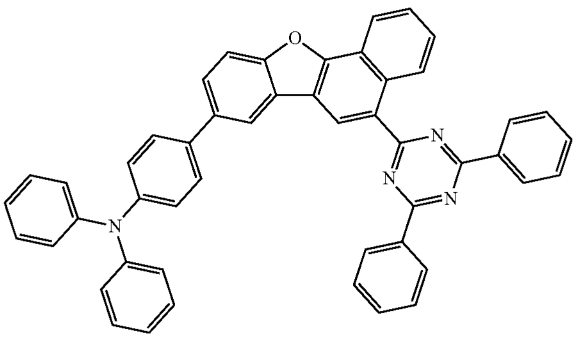

-continued
A121
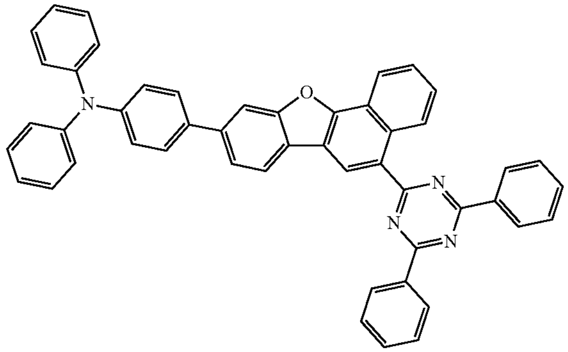
A122
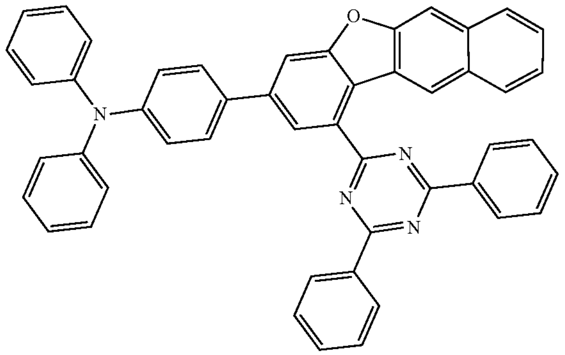
A123
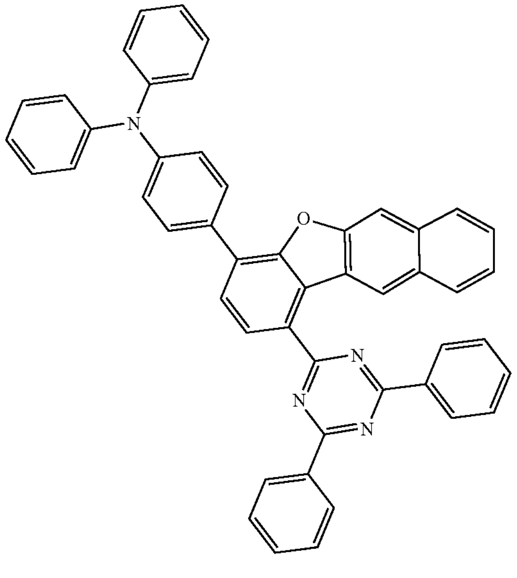
-continued
A124
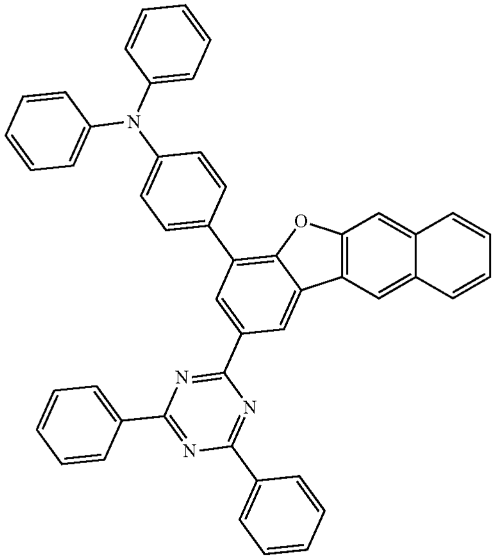
A125
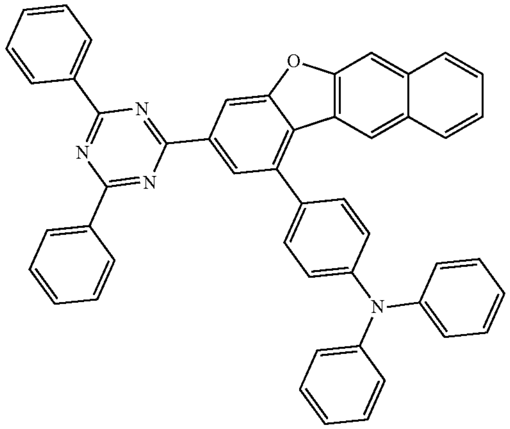
A126
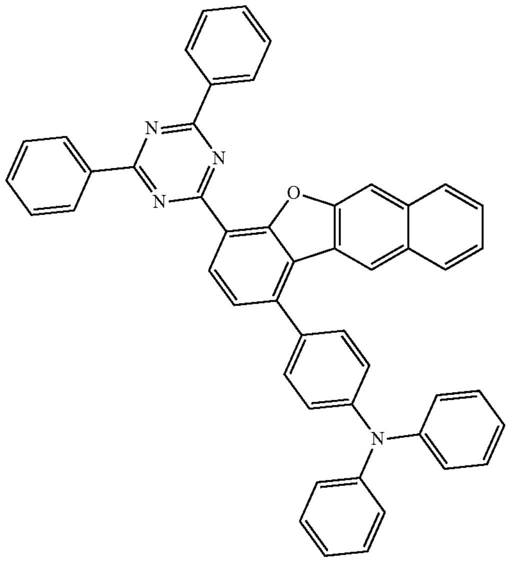

-continued
A127
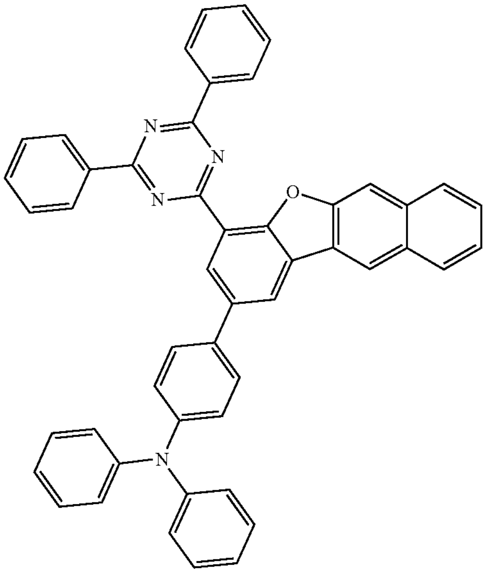
A128
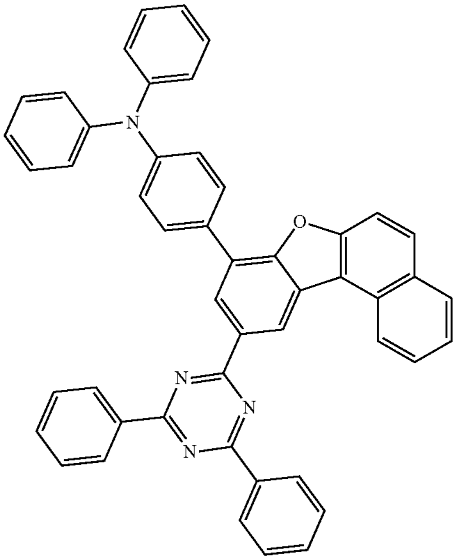
A129
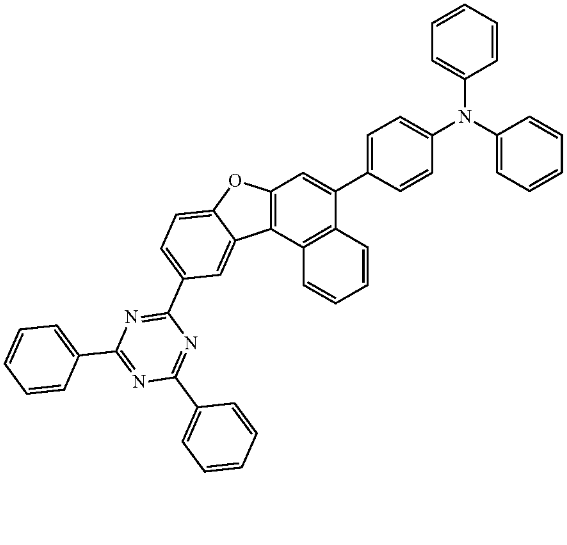
-continued
A130
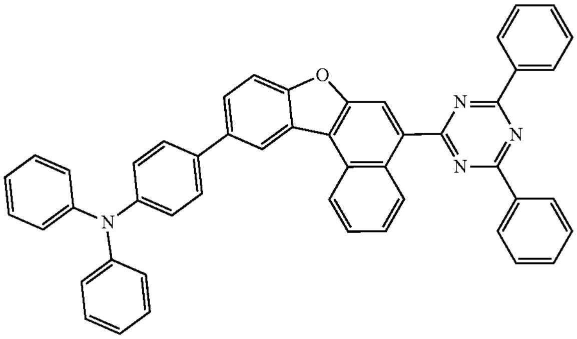
A131
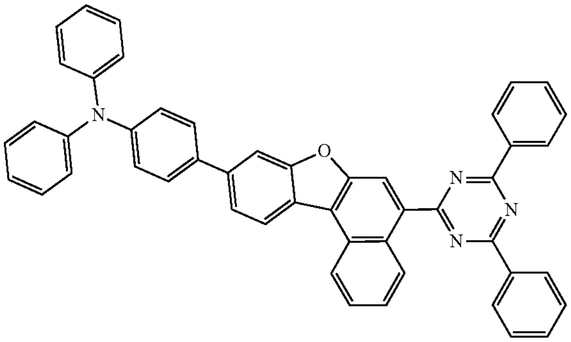
A132
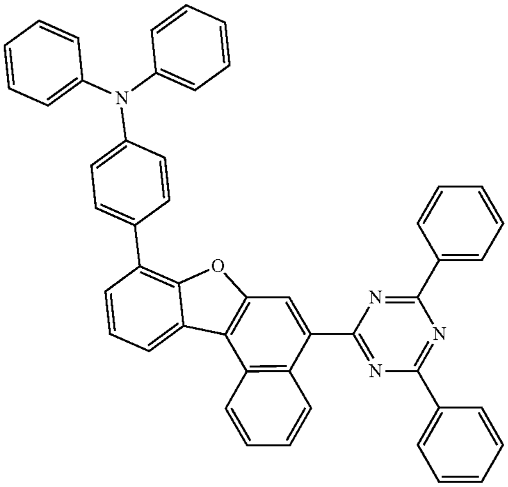

-continued
A133
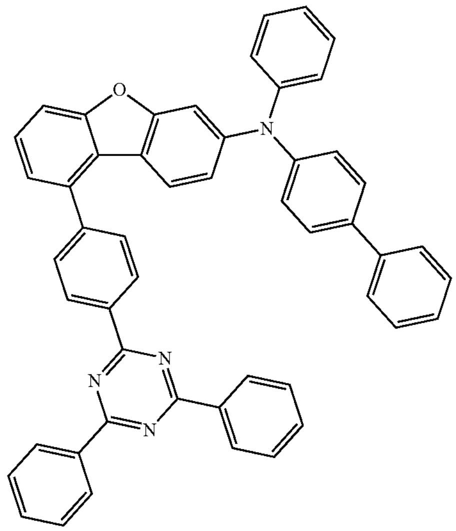
A134
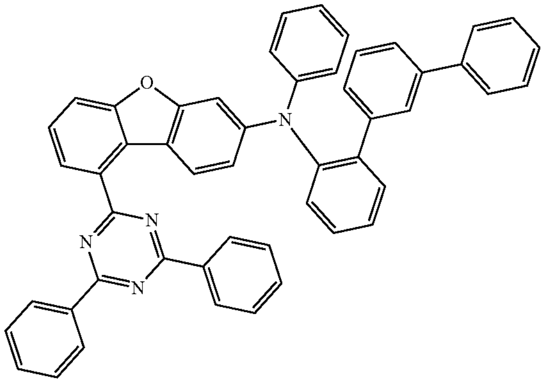
A135
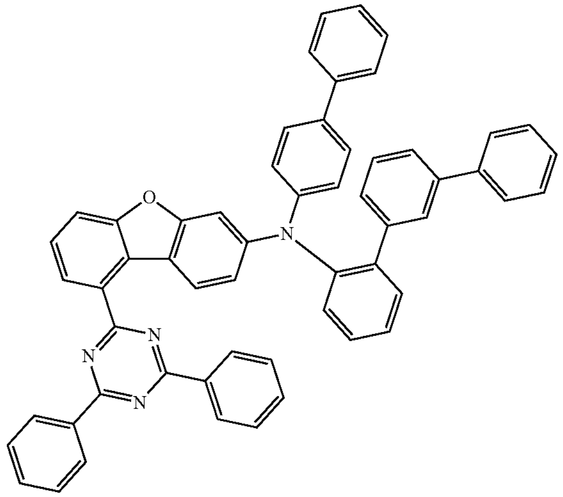
-continued
A136
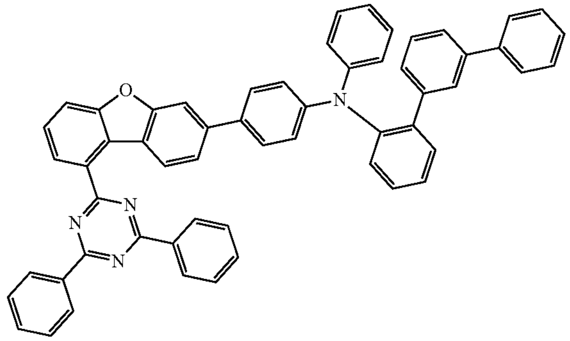
A137
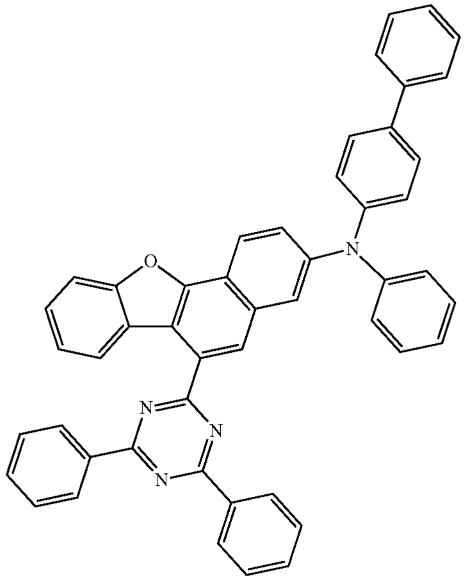
A138
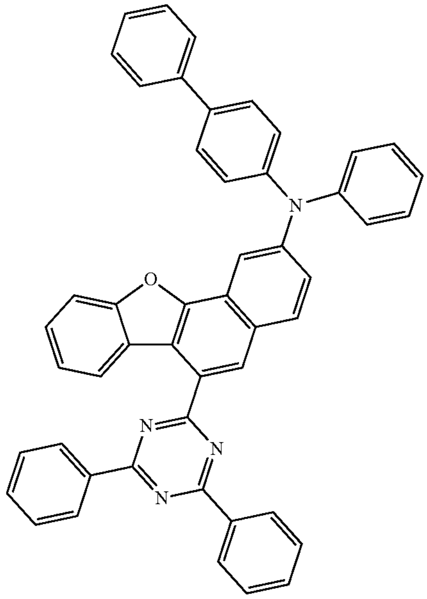

-continued
A139
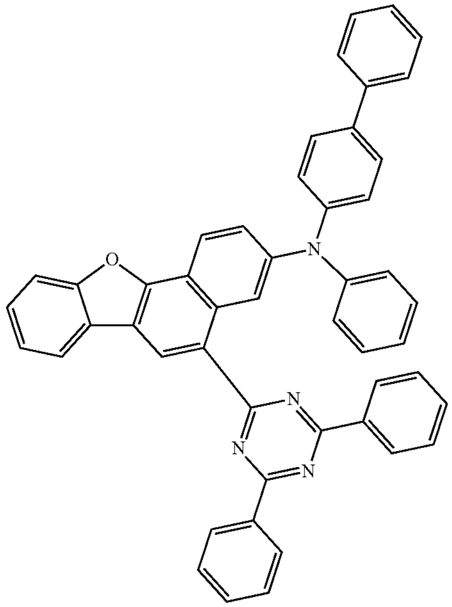
A140
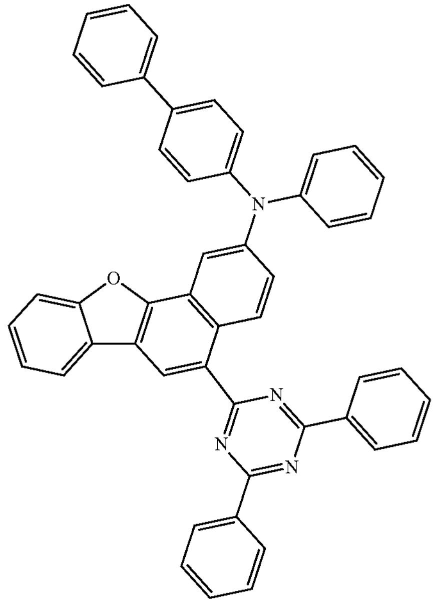
A141
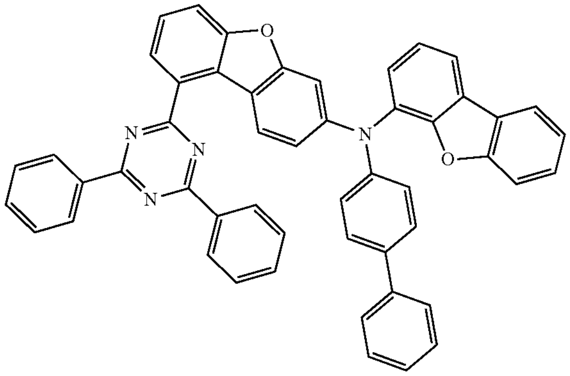
-continued
A142
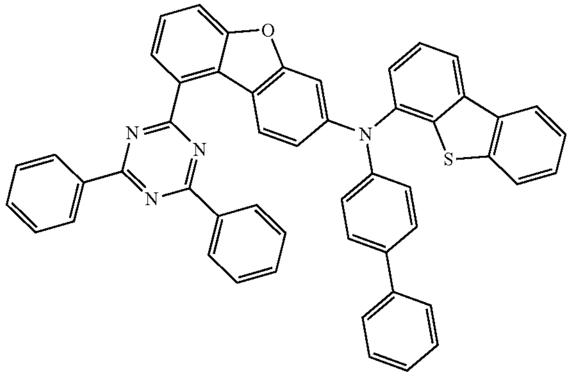
A143
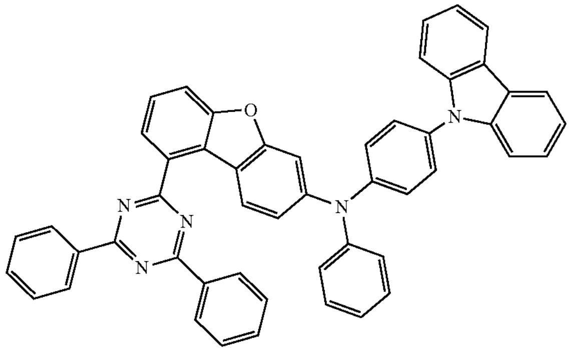
A144
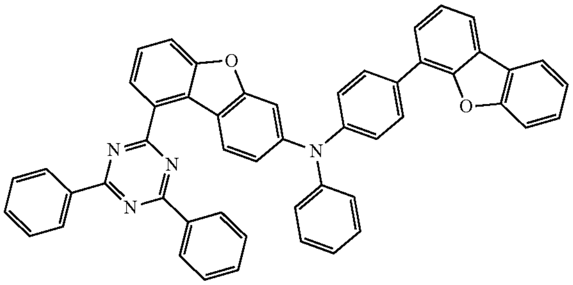
A145
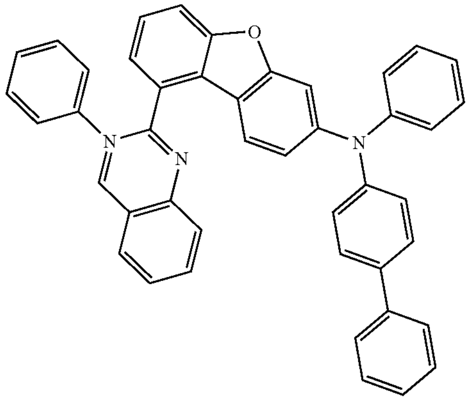

-continued
A146
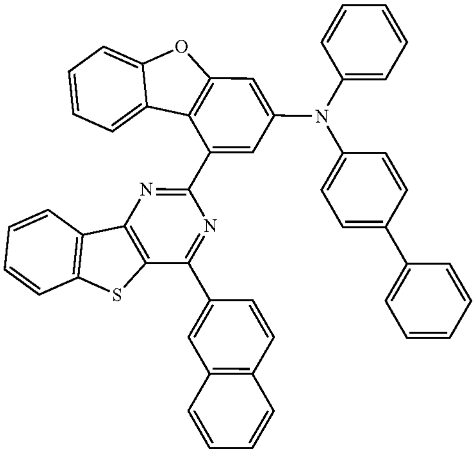
A147
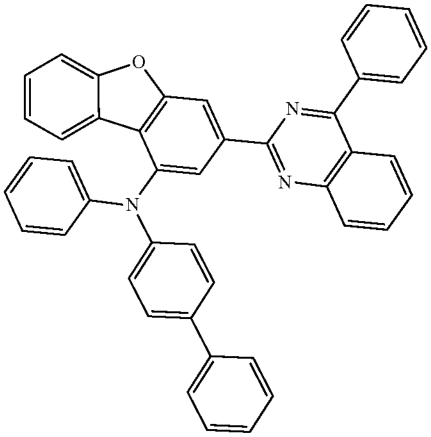
A148
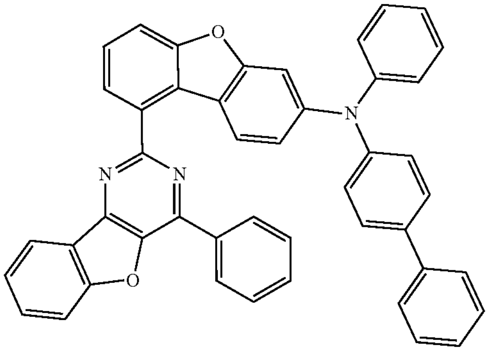
A149
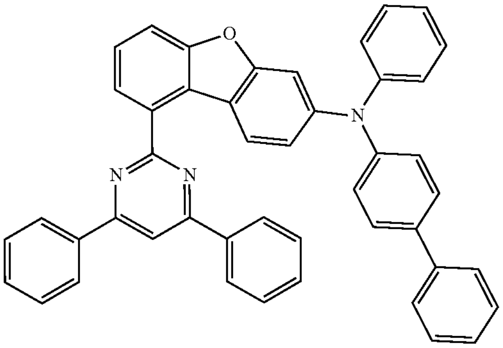
-continued
A150
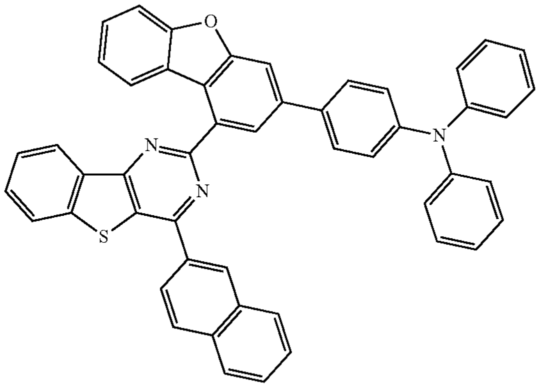
A151
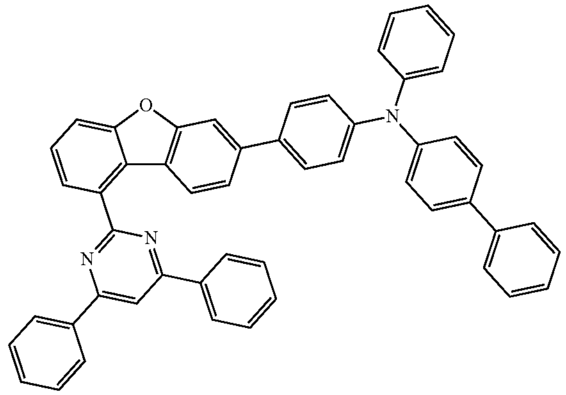
A152
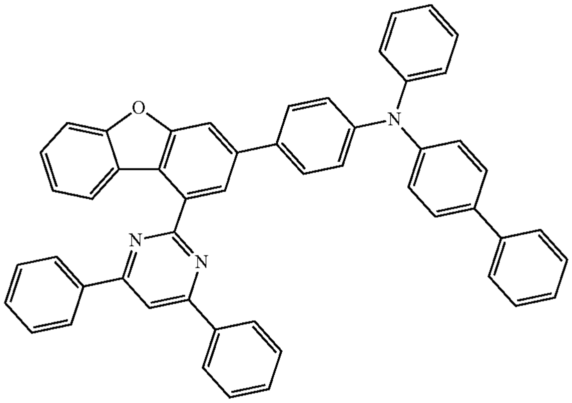
A153
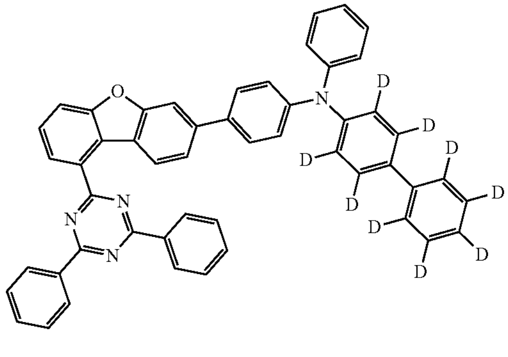

-continued
A154
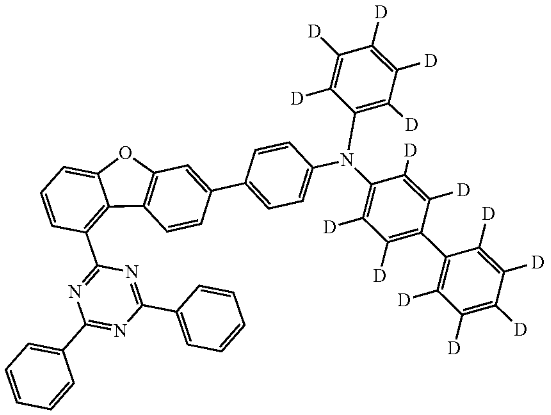
A155
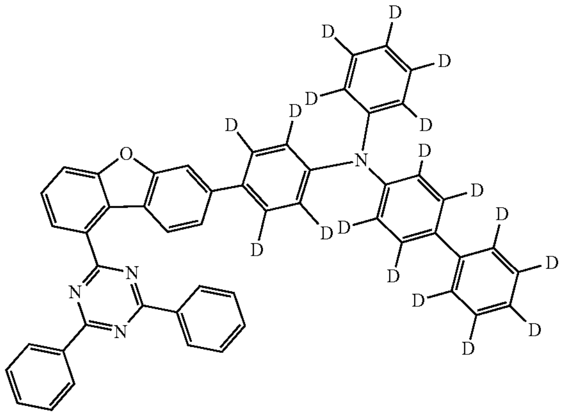
A156
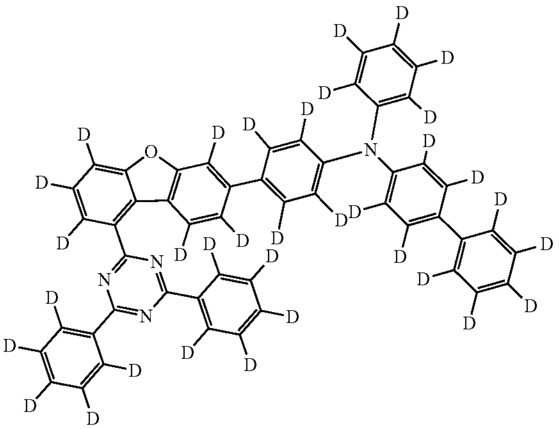
-continued
A157
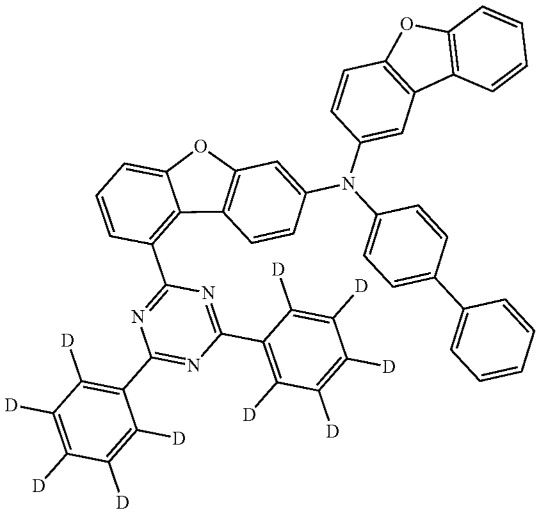
A158
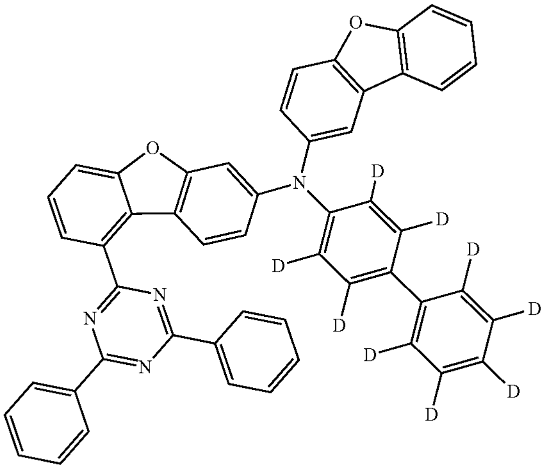
A159
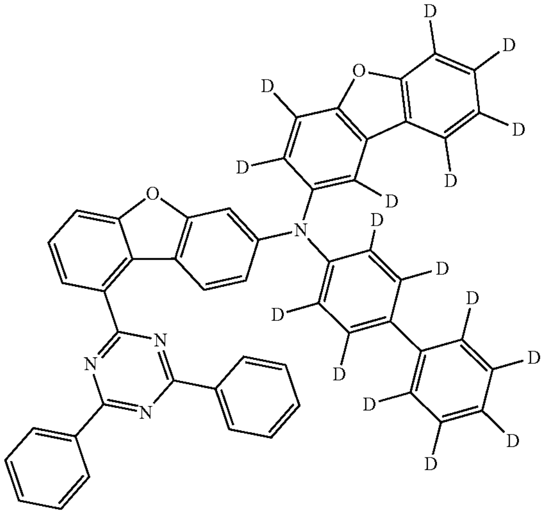

-continued
A160
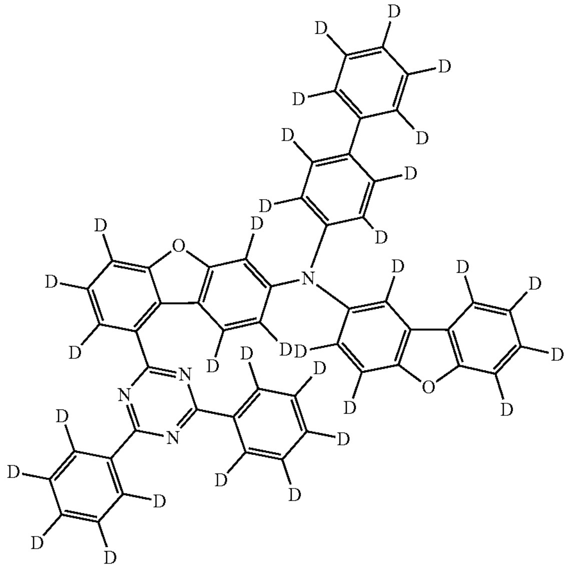
A161
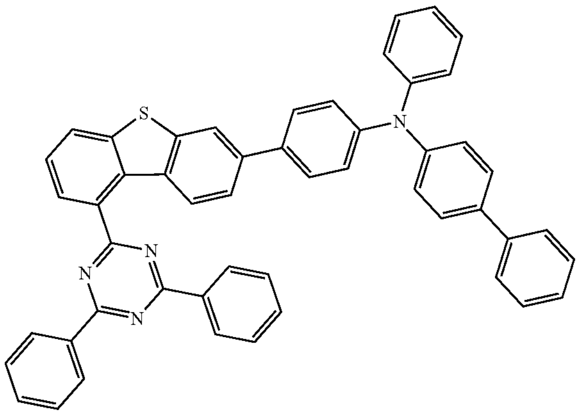
A162
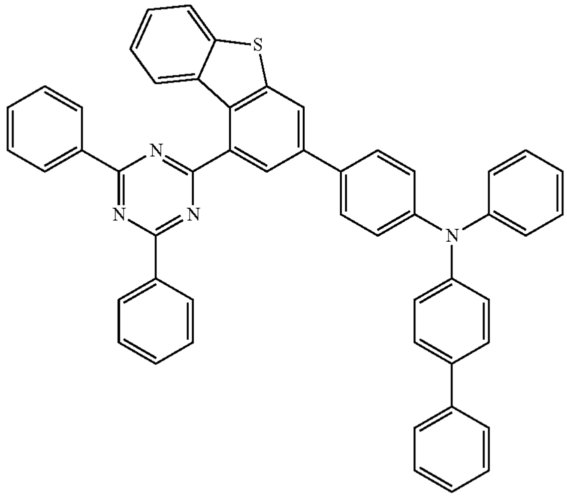
-continued
A163
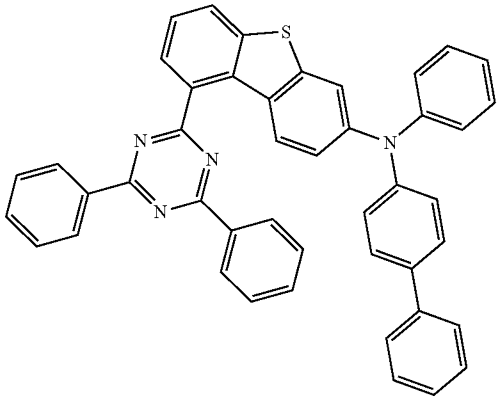
A164
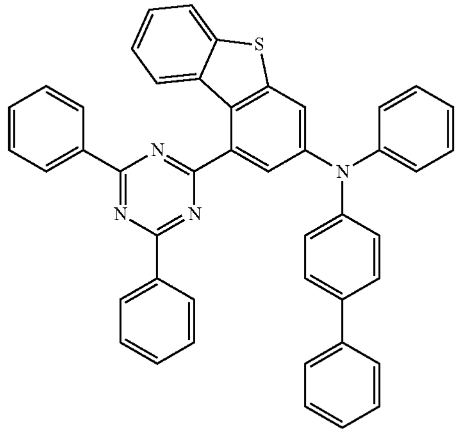
A165
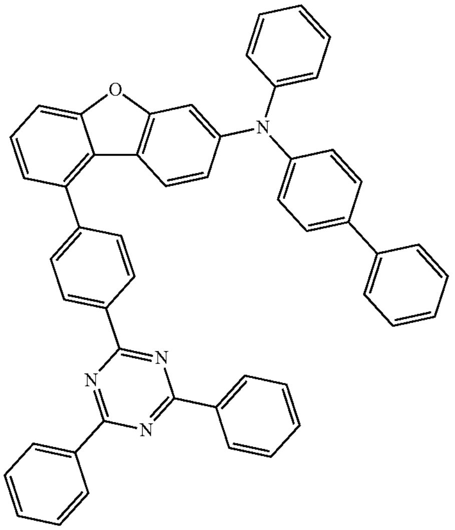

-continued
A166
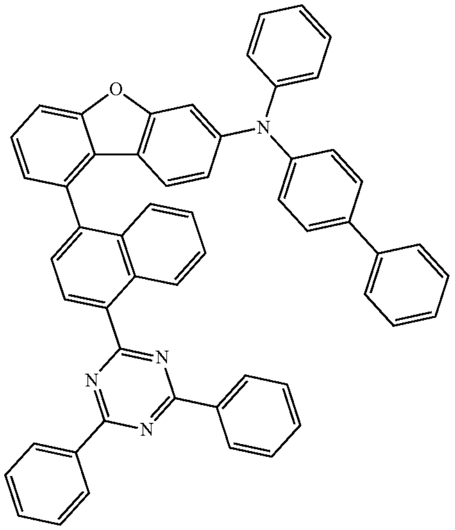
A167
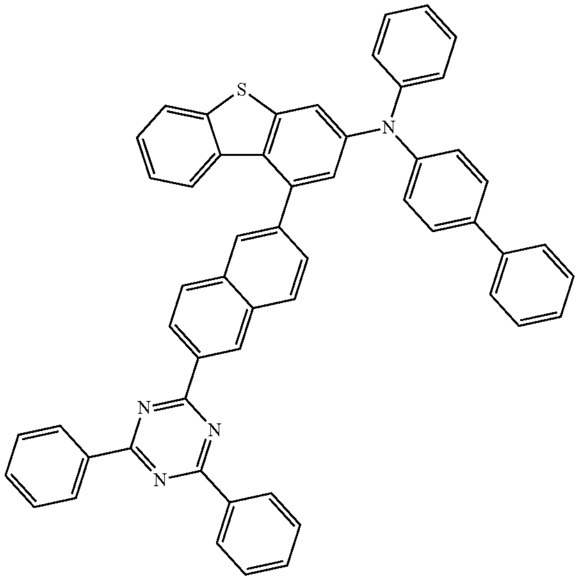
-continued
A168
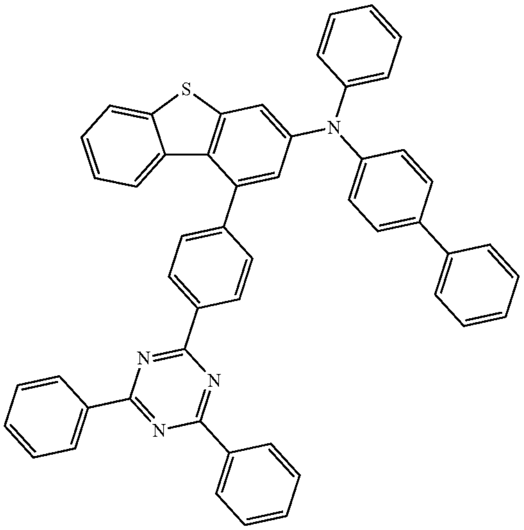
In an exemplary embodiment of the present invention, Chemical Formula B may include any one of the following compounds.
B1
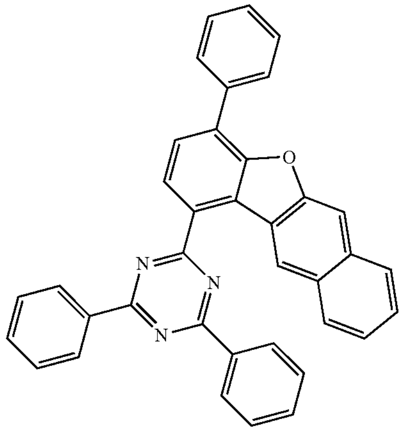

-continued
B2
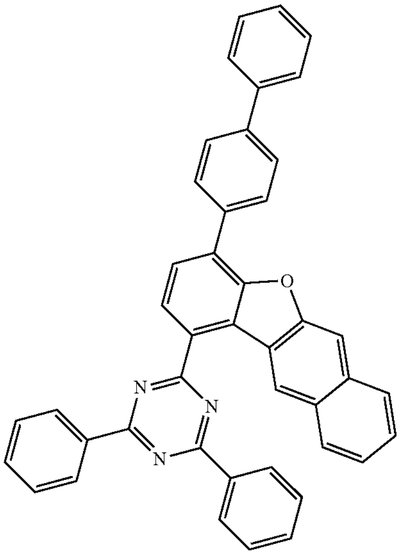
B3
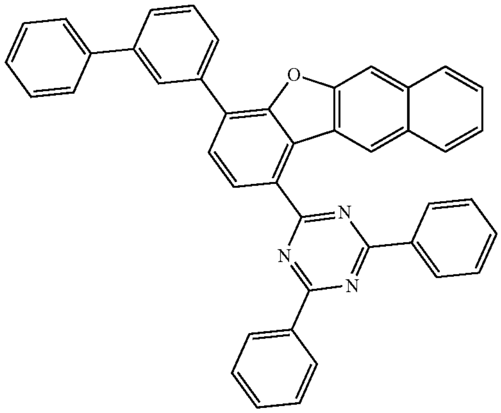
B4
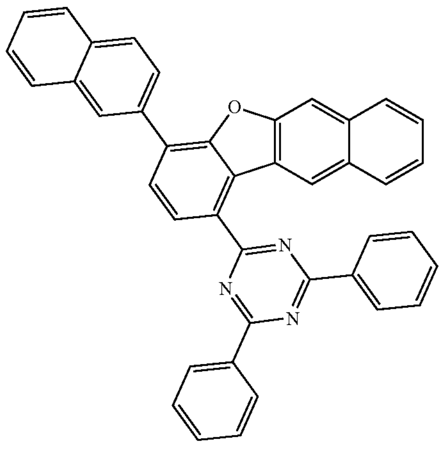
-continued
B5
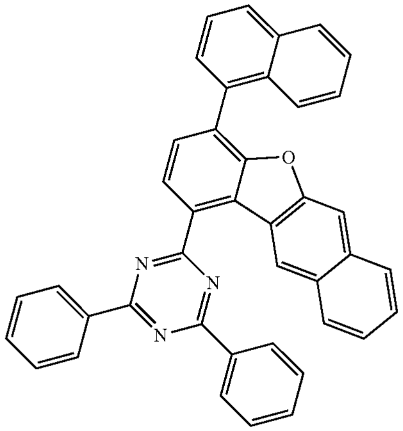
B6
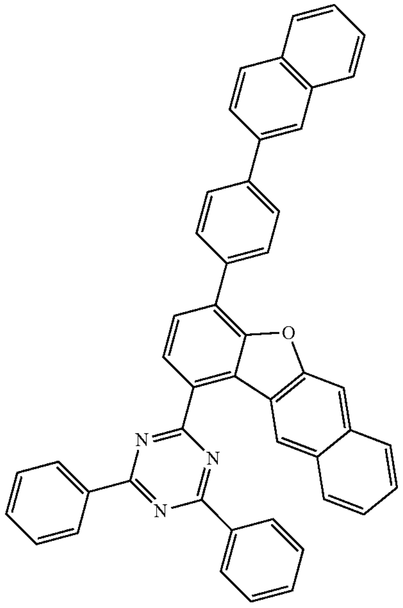
B7
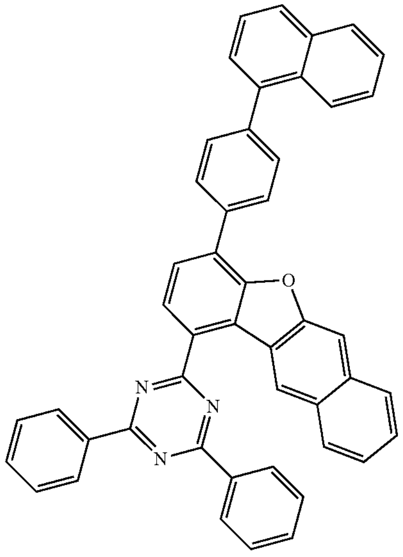

B8
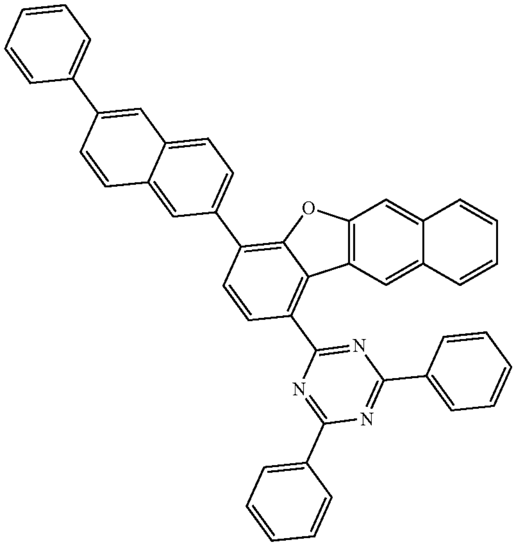
B9
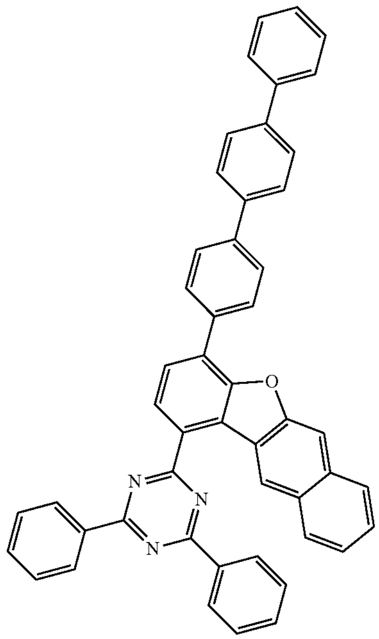
B10
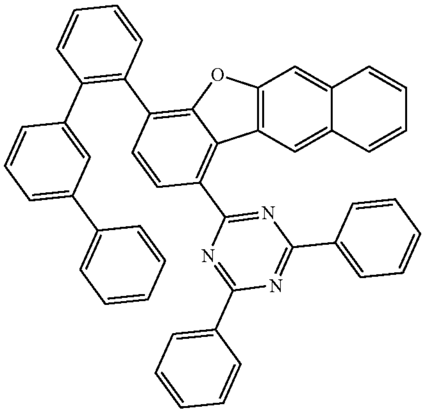
B11
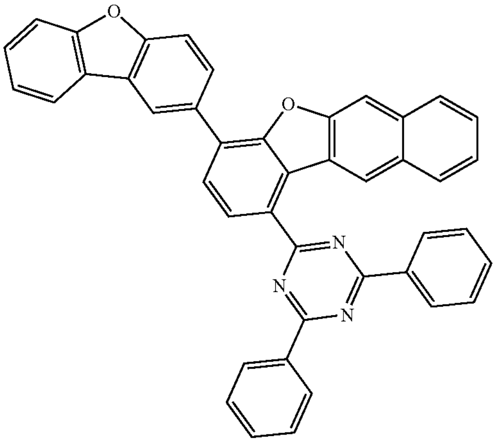
B12
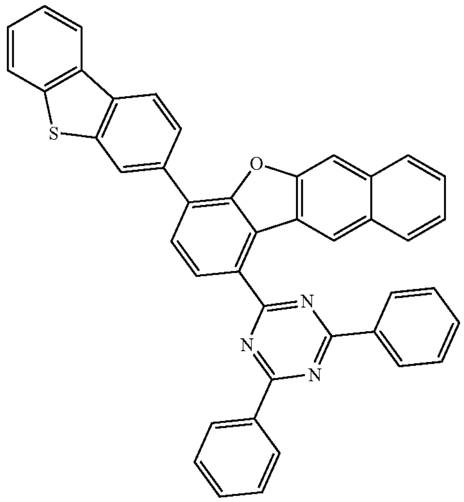
B13
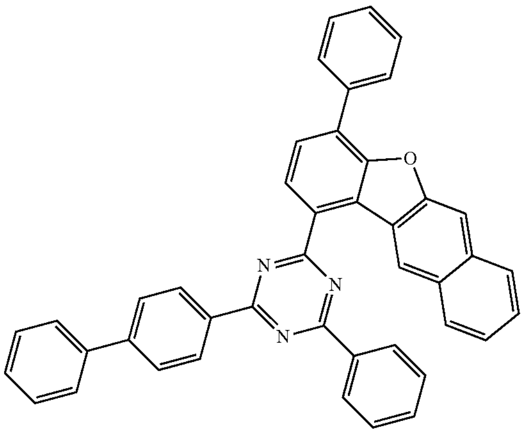

-continued
B14
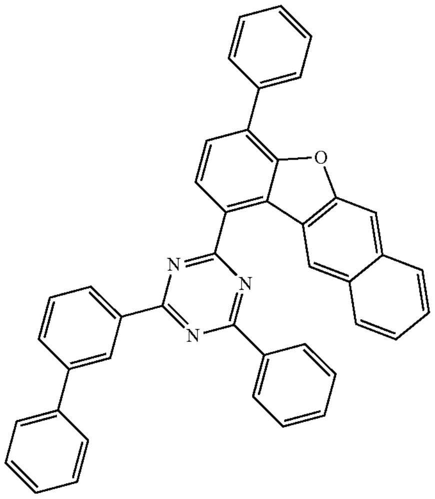
B15
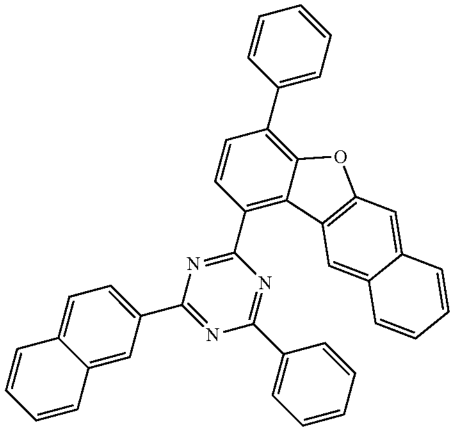
B16
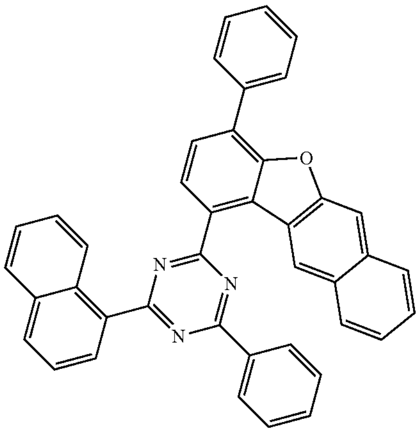
-continued
B17
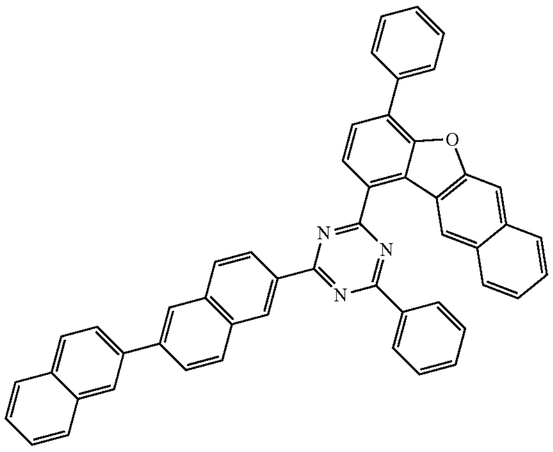
B18
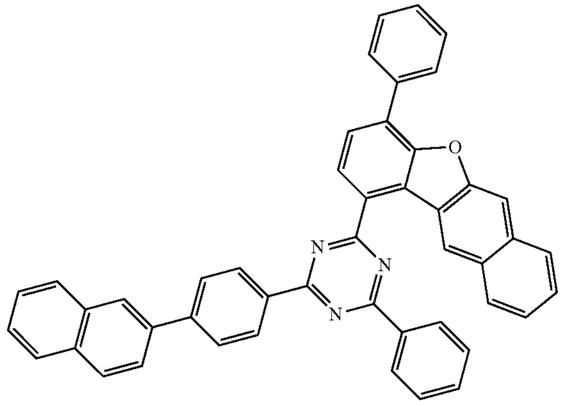
B19
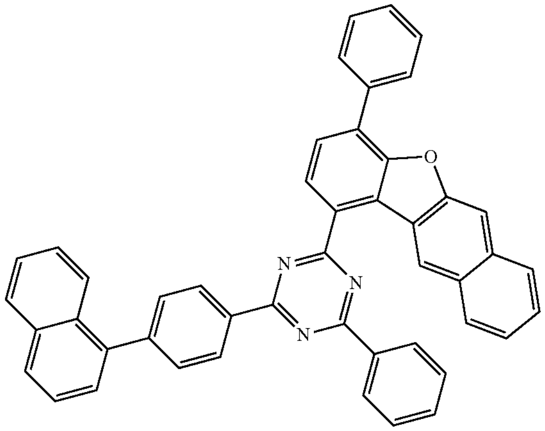

-continued
B20
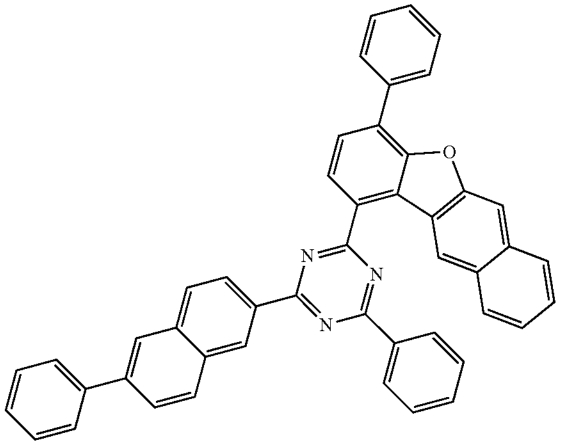
B21
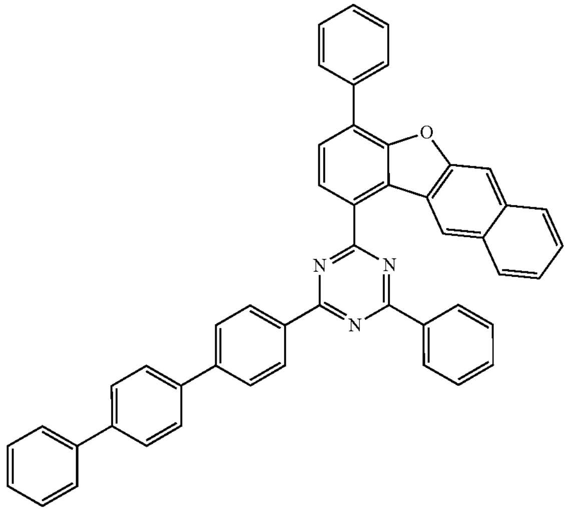
B22
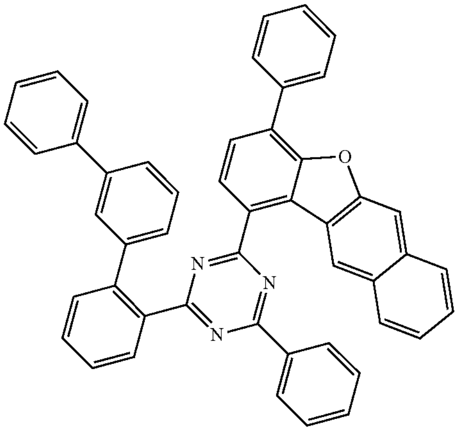
-continued
B23
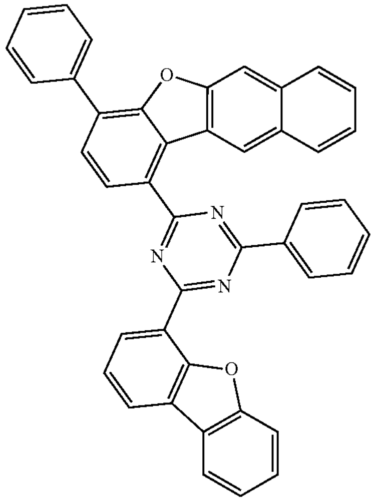
B24
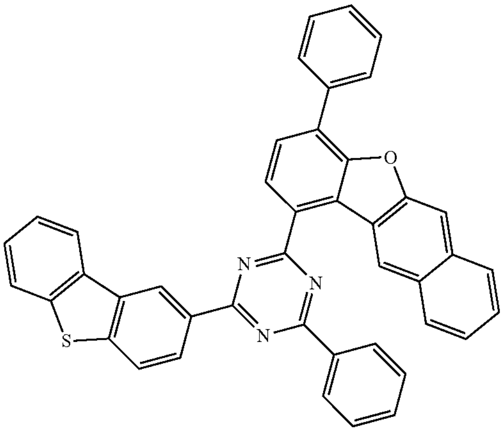
B25
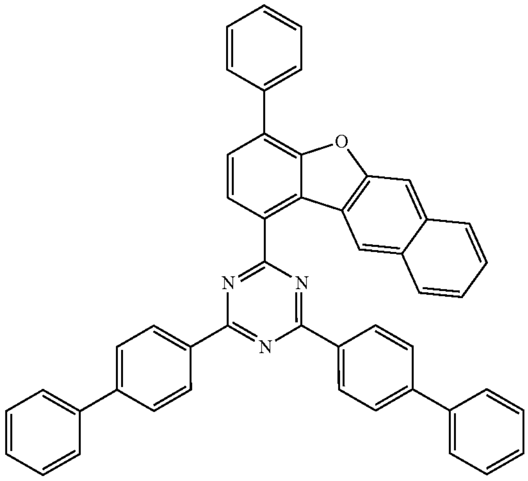

-continued
B26
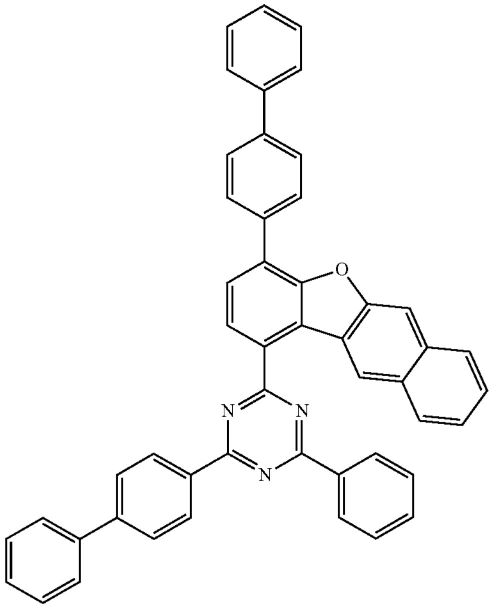
B27
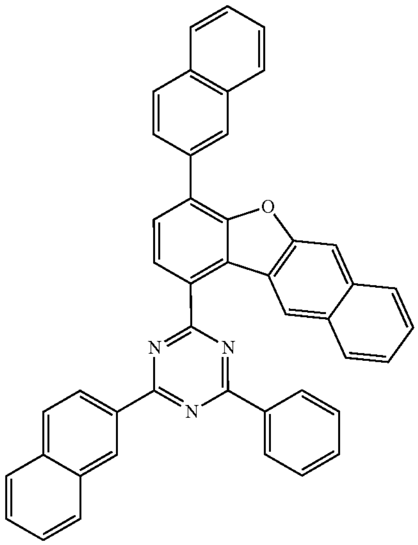
B28
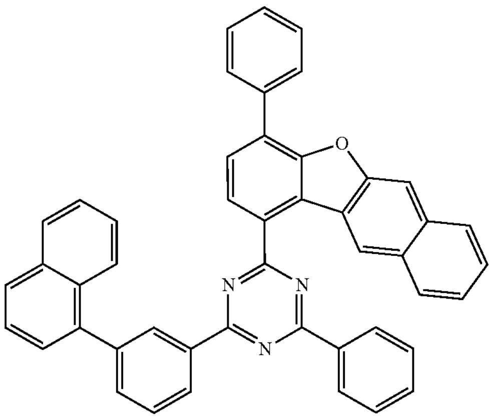
-continued
B29
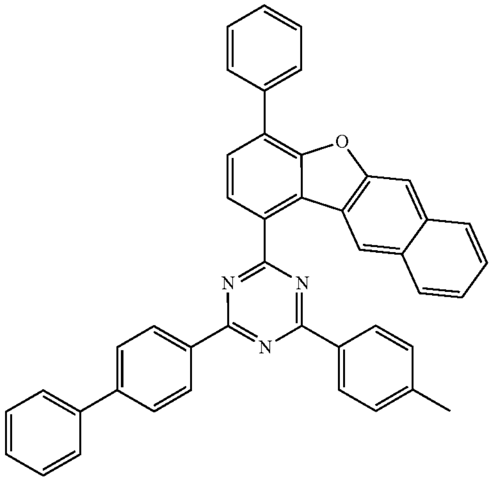
B30
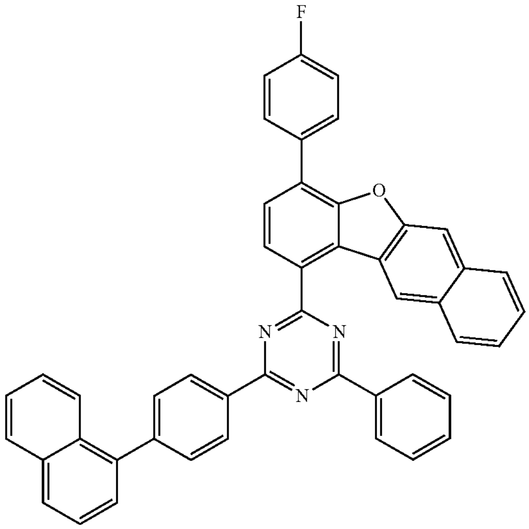
B31
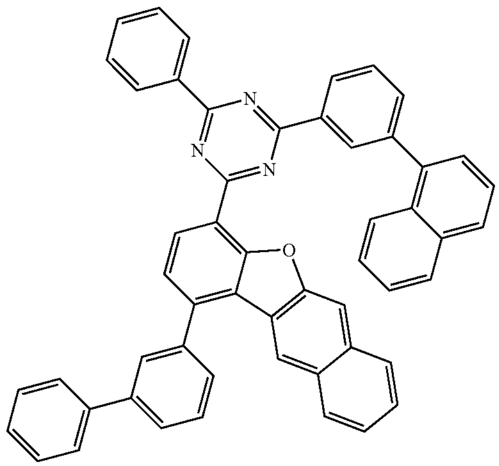

-continued
B32
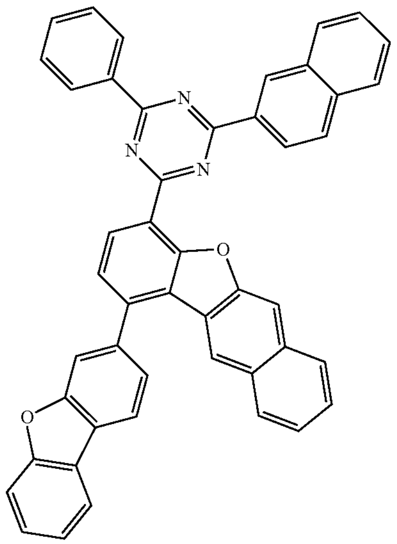
B33
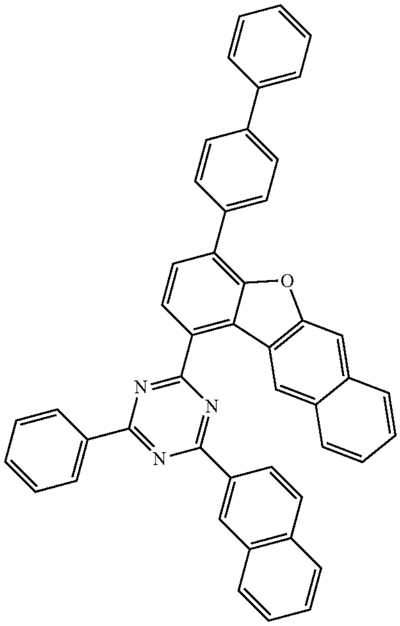
-continued
B34
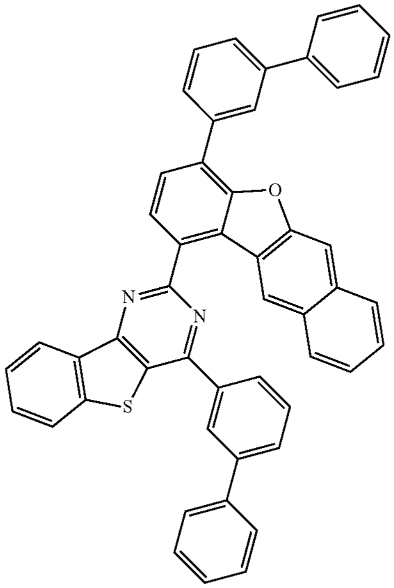
B35
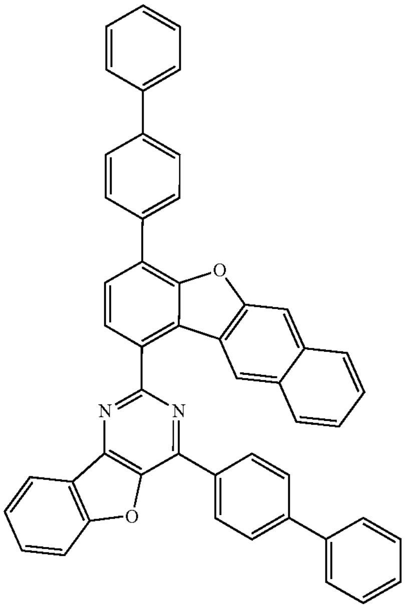

-continued
B36
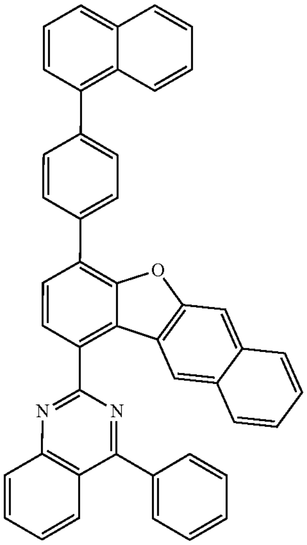
B37
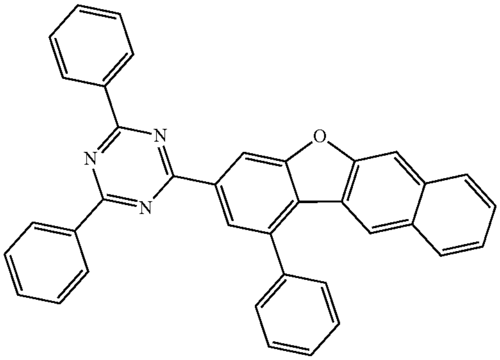
B38
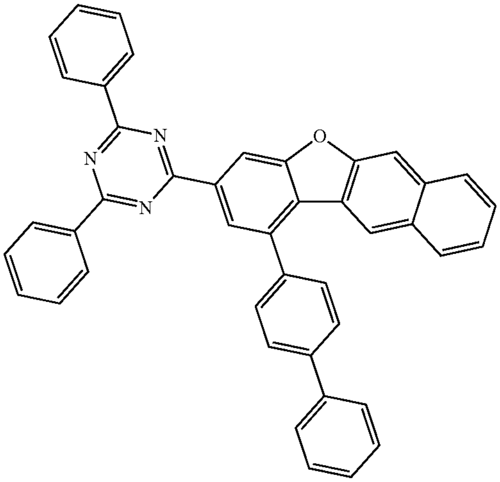
-continued
B39
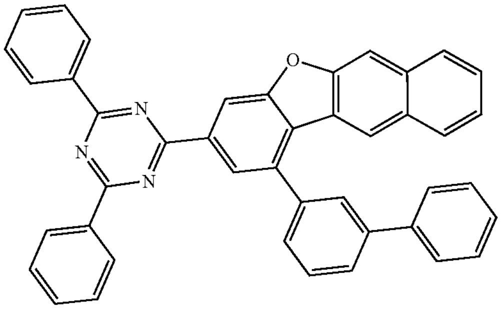
B40
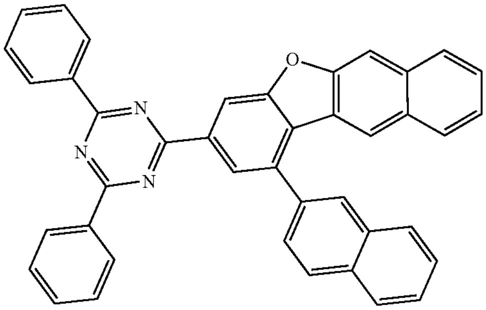
B41
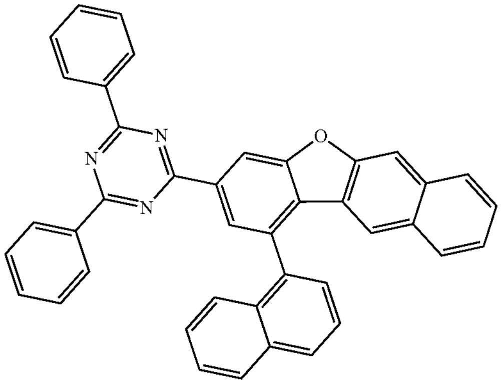
B42
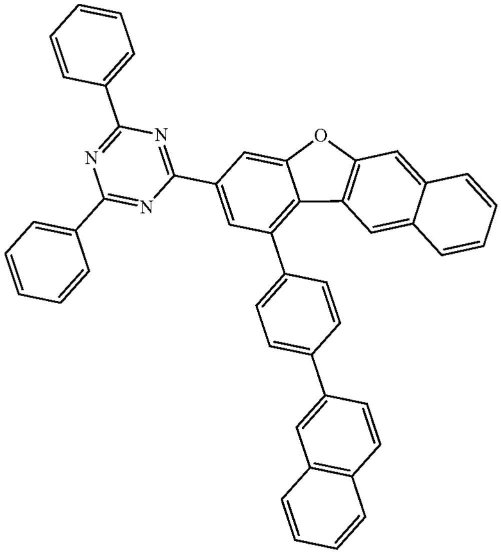

-continued
B43
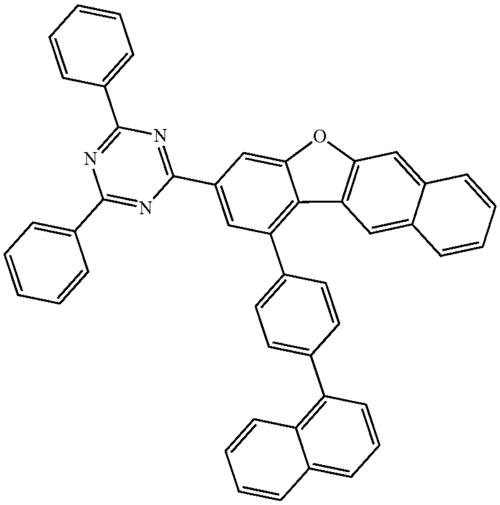
B44
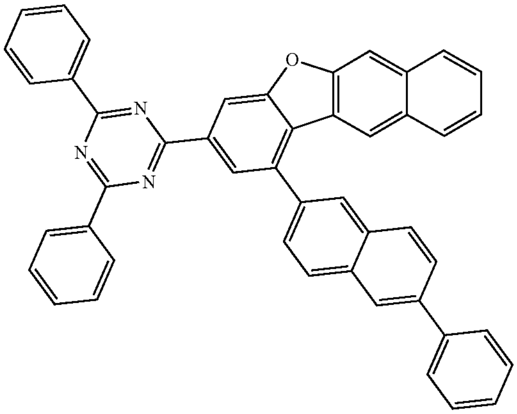
B45
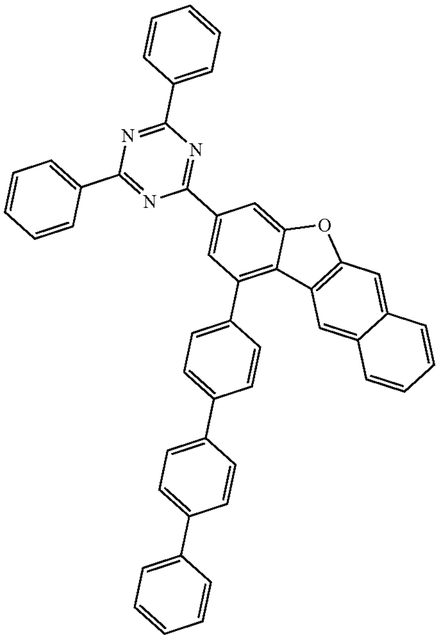
-continued
B46
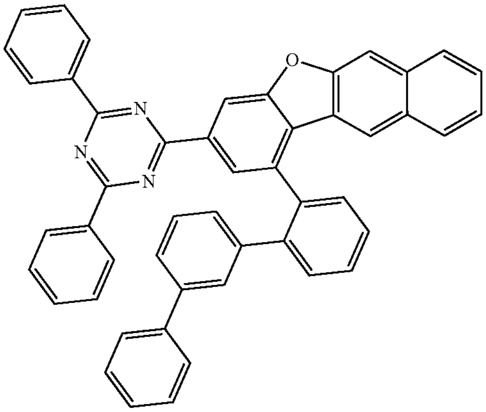
B47
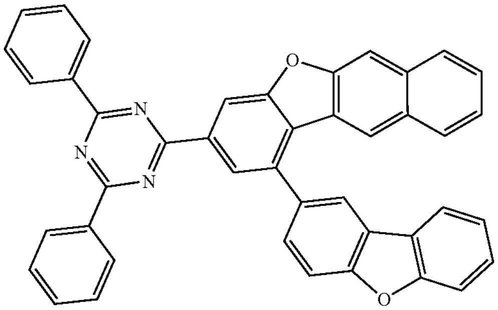
B48
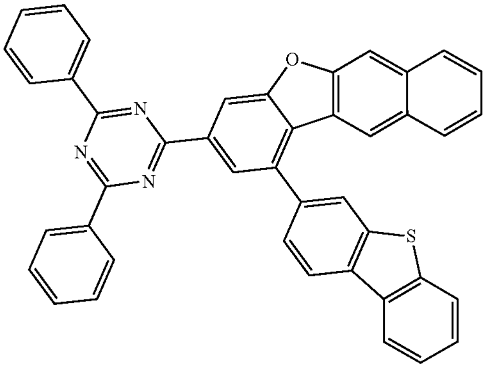
B49
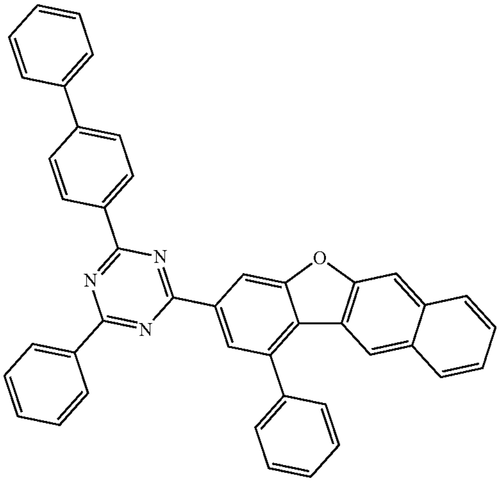

B50
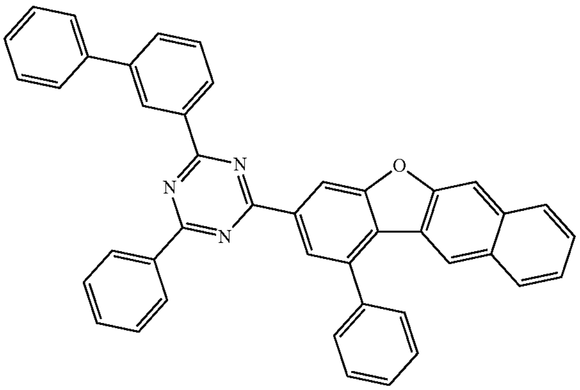
B51
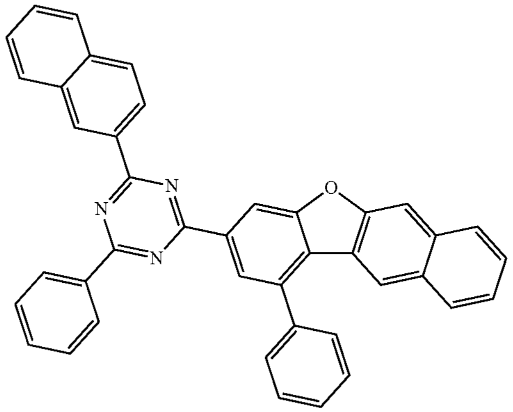
B52
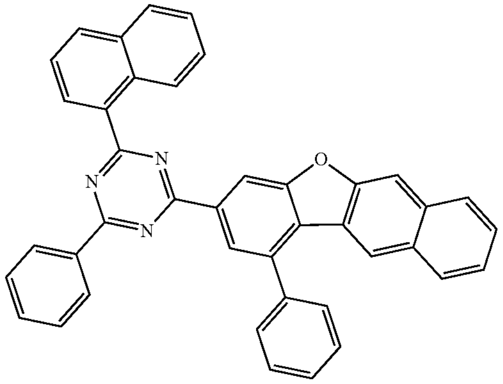
B53
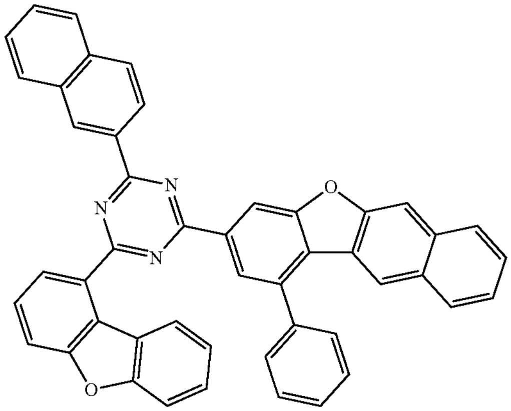
B54
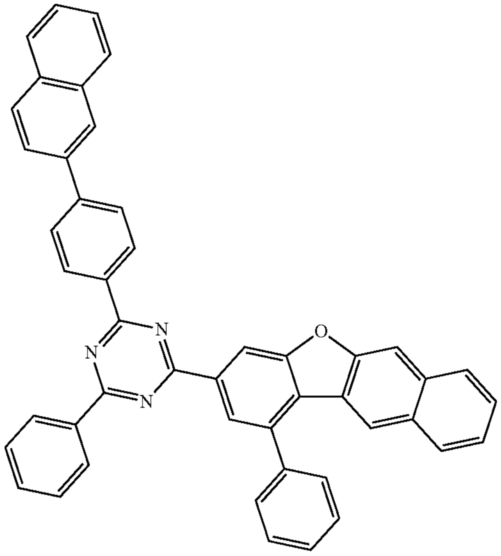
B55
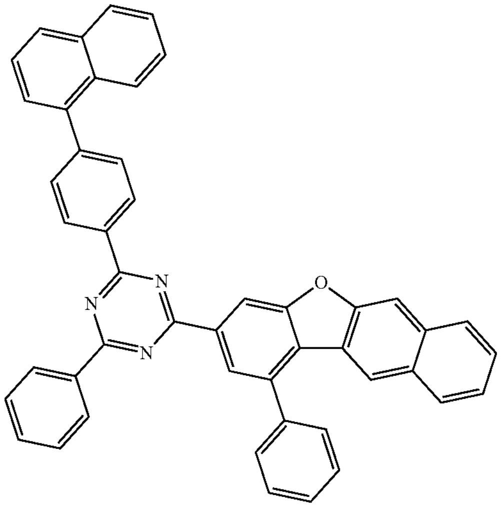

-continued
B56
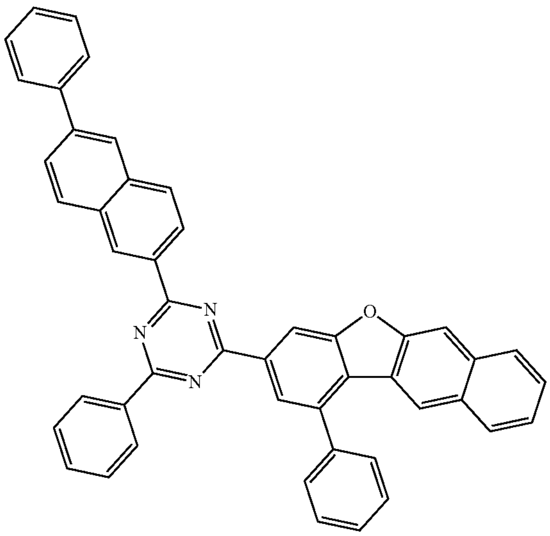
B57
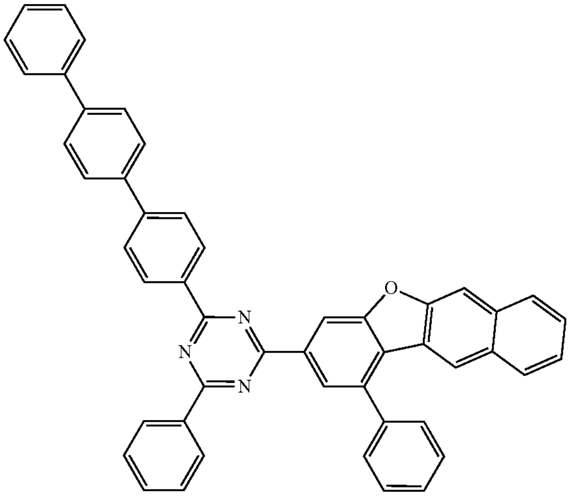
B58
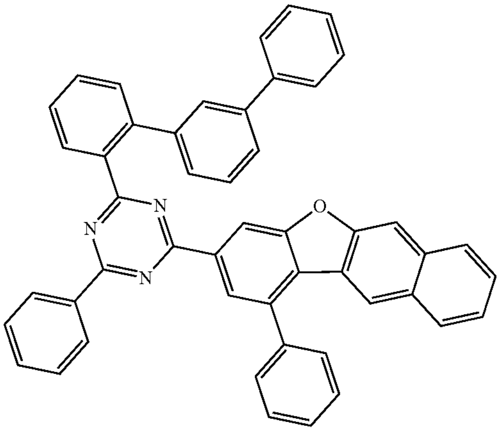
-continued
B59
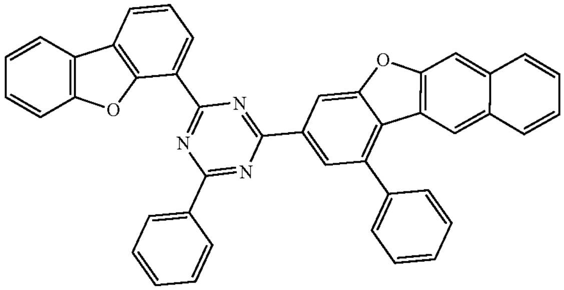
B60
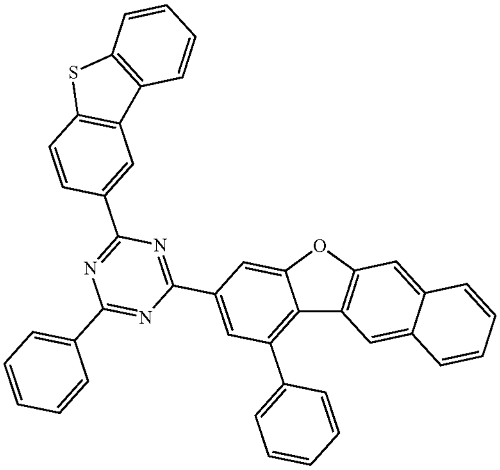
B61
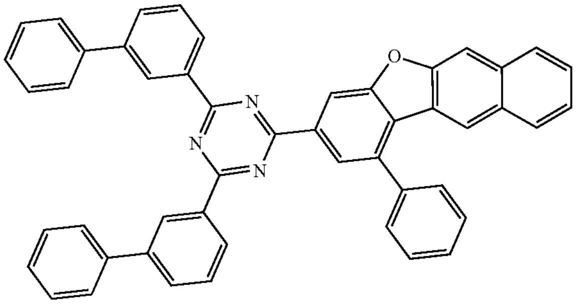

-continued
B62
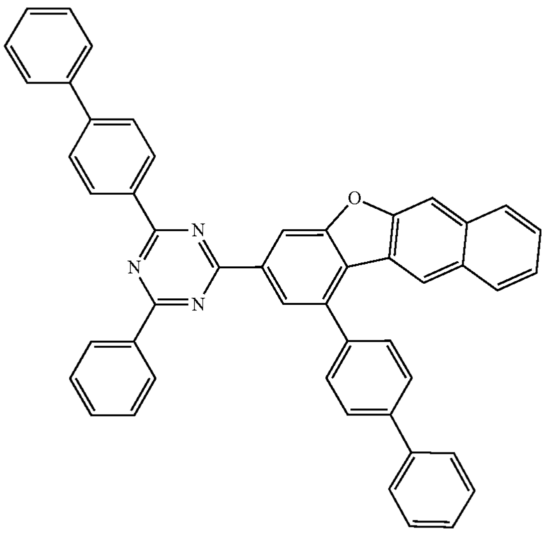
B63
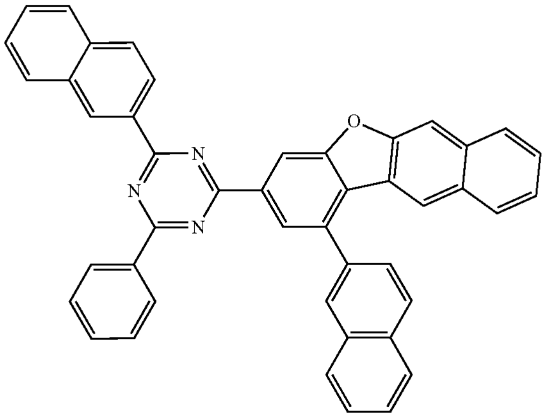
B64
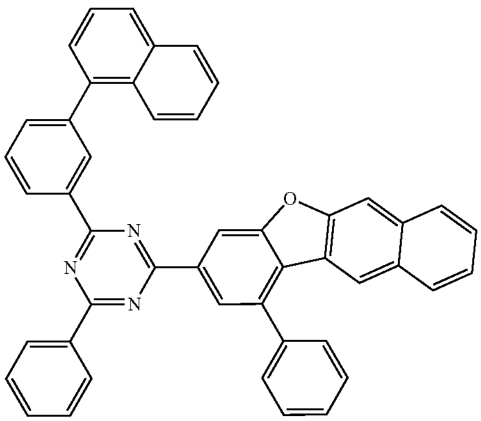
-continued
B65
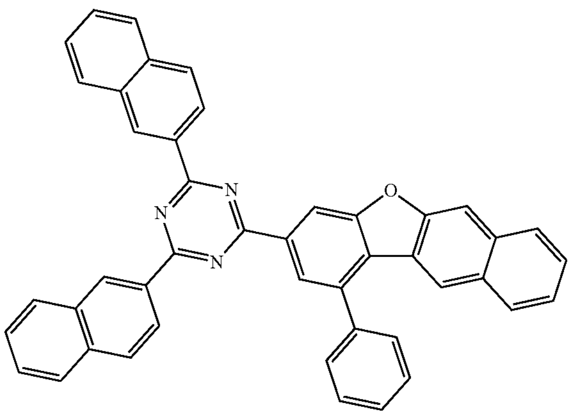
B66
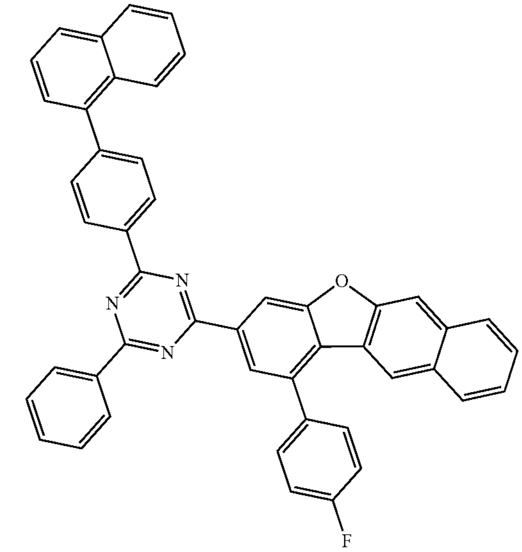
B67
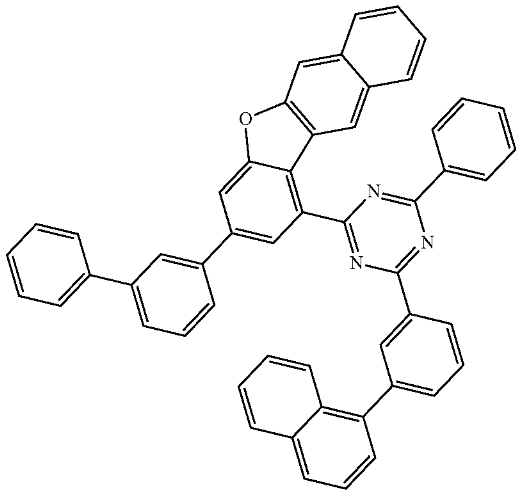

-continued
B68
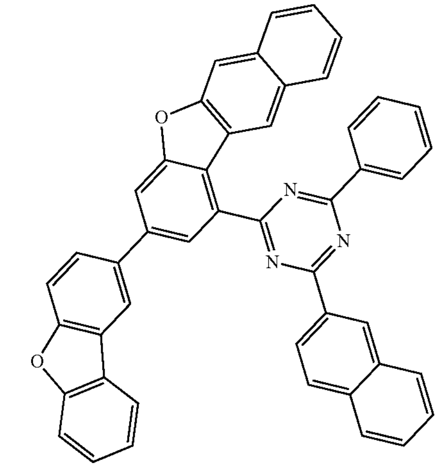
B69
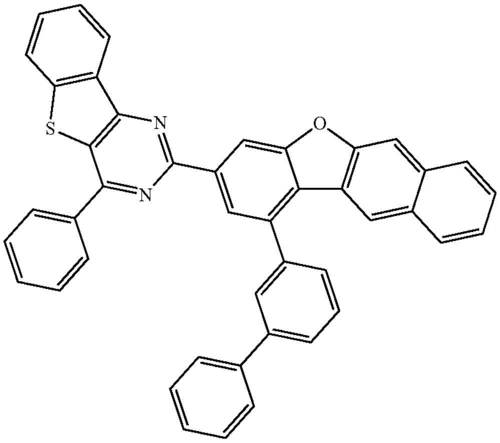
B70
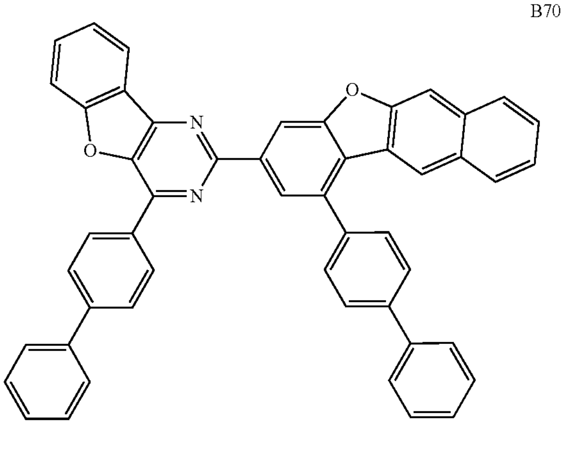
-continued
B71
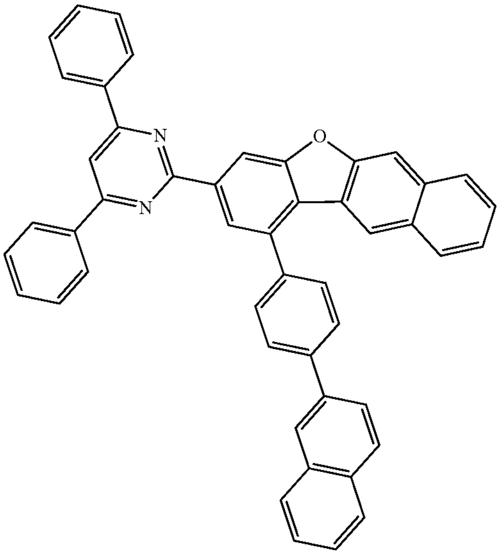
B72
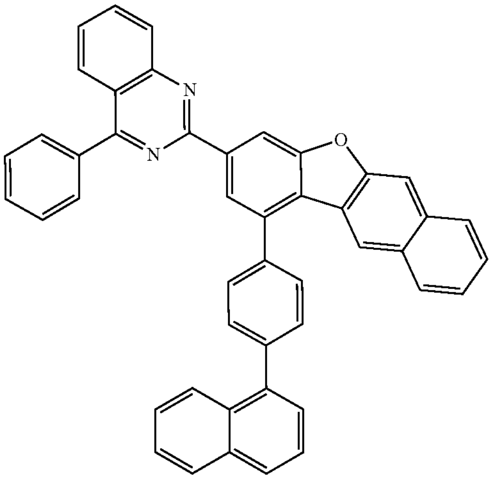
B73
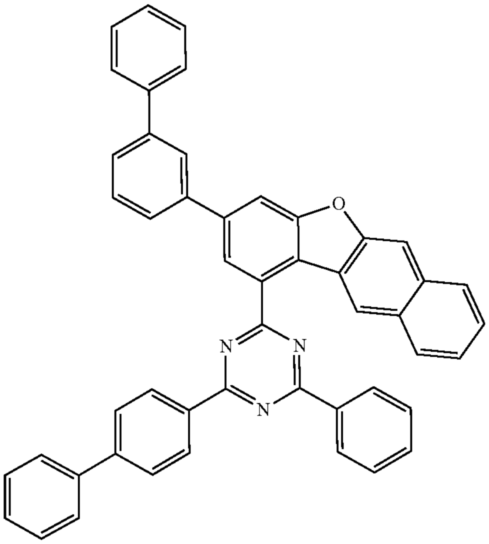

-continued
B74
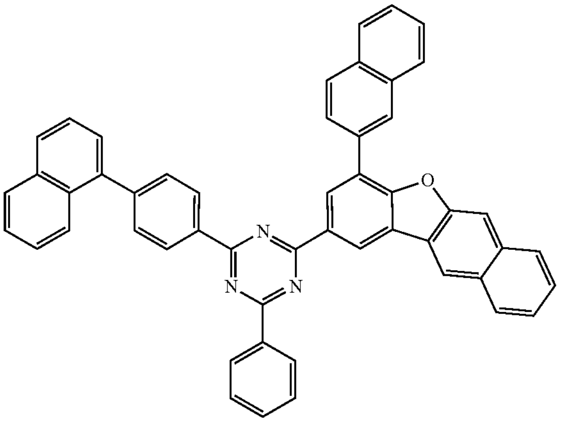
B75
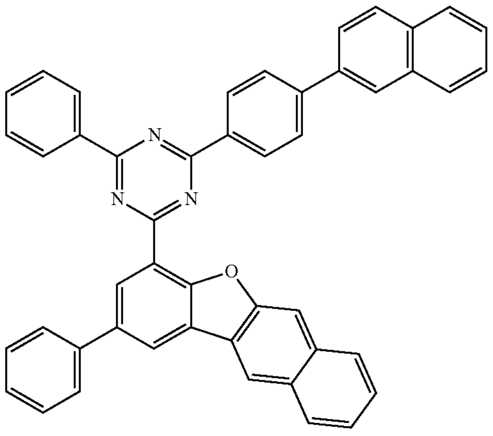
B76
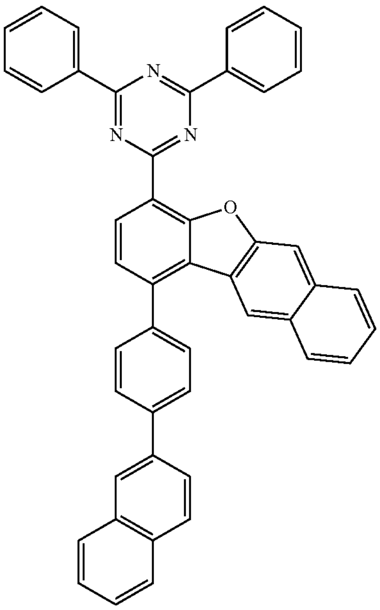
-continued
B77
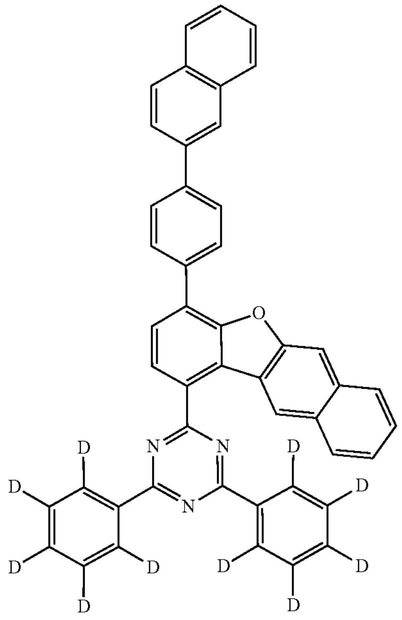
B78
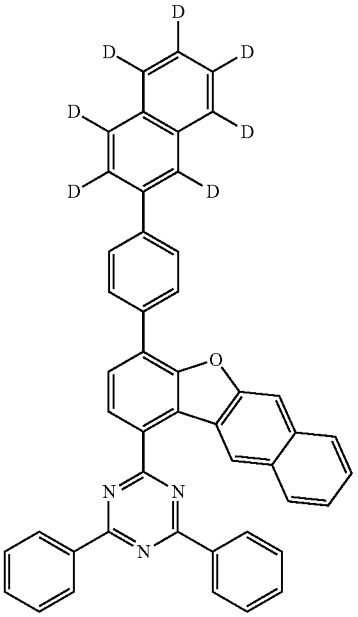

-continued
B79
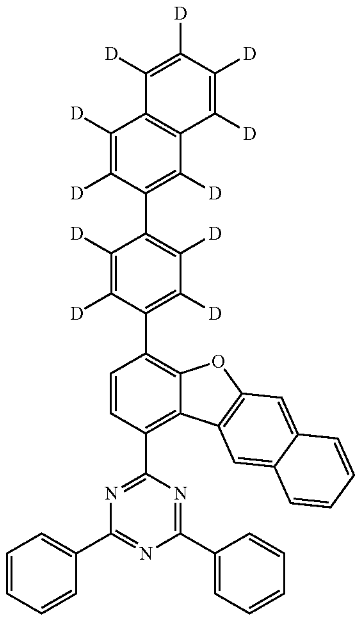
-continued
B81
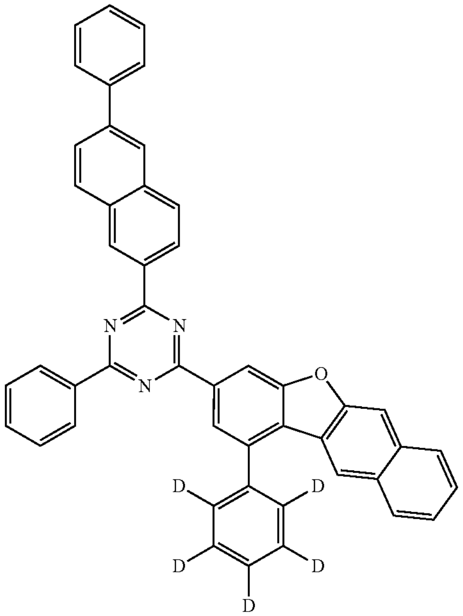
B80
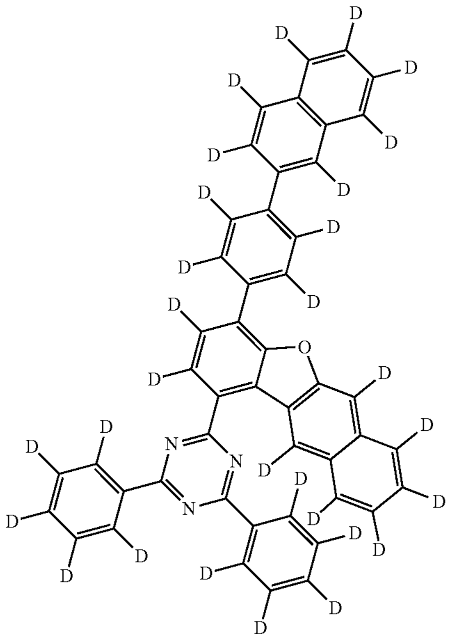
B82
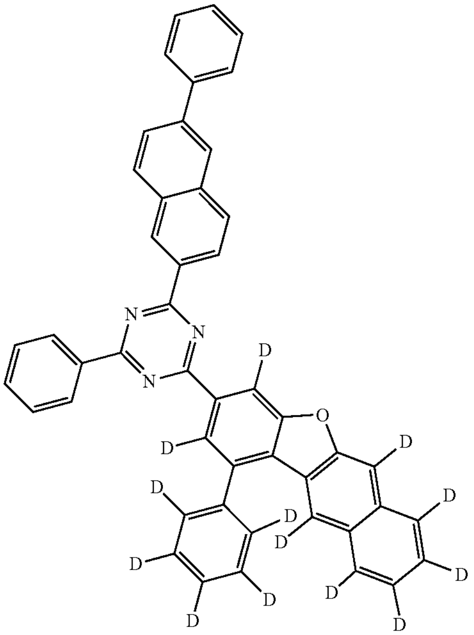

-continued
B83
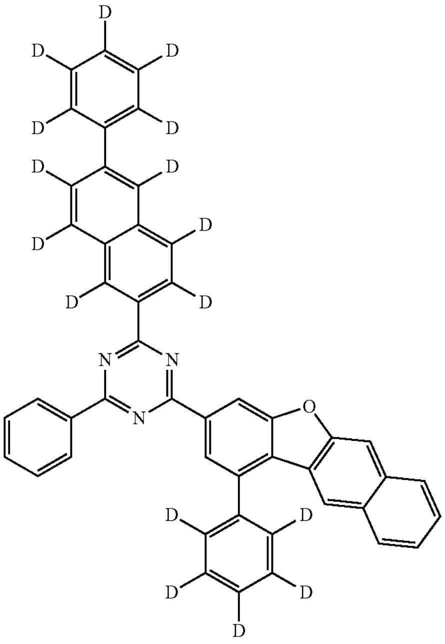
B84
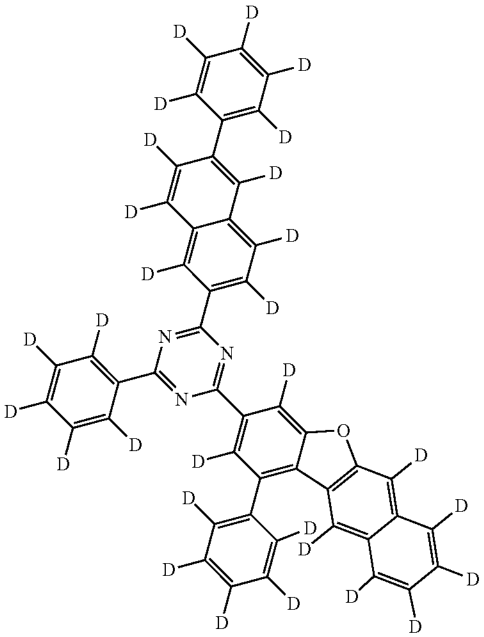
-continued
B85
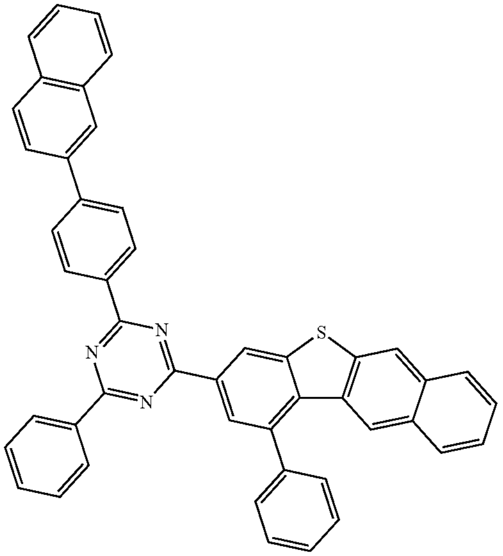
B86
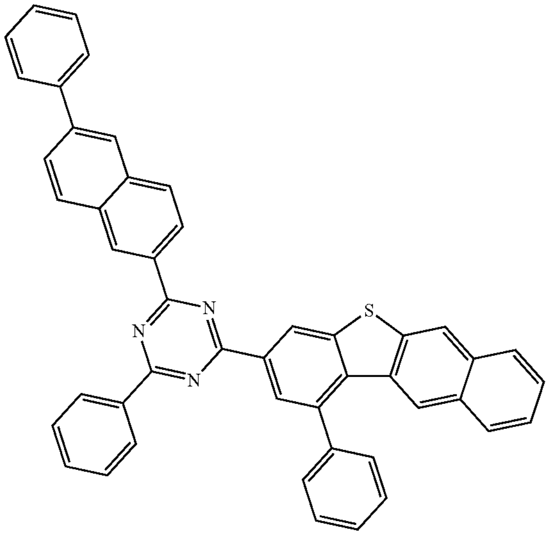
B87
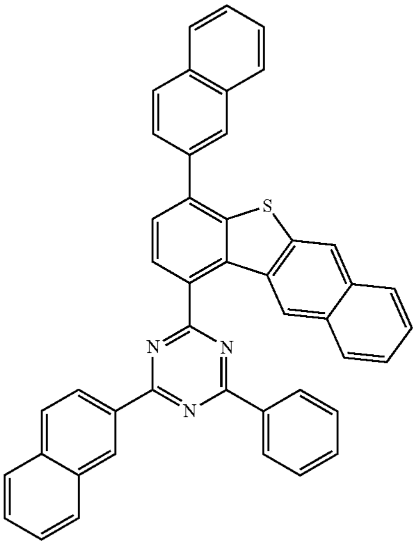

-continued
B88
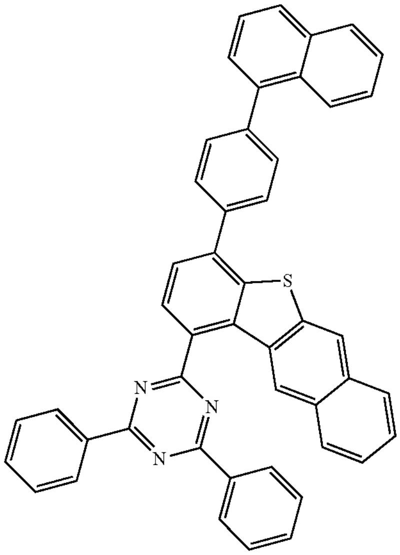
B89
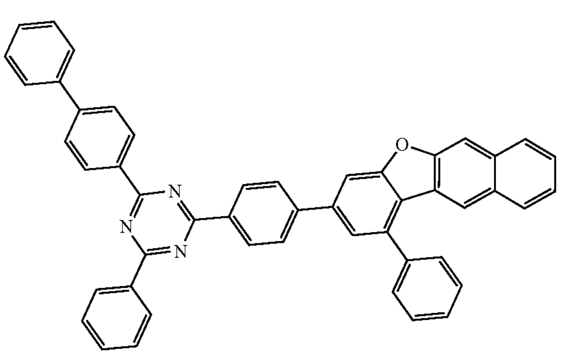
B90
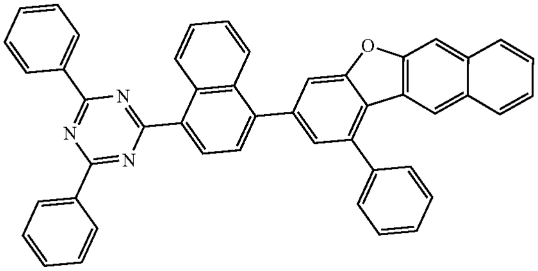
-continued
B91
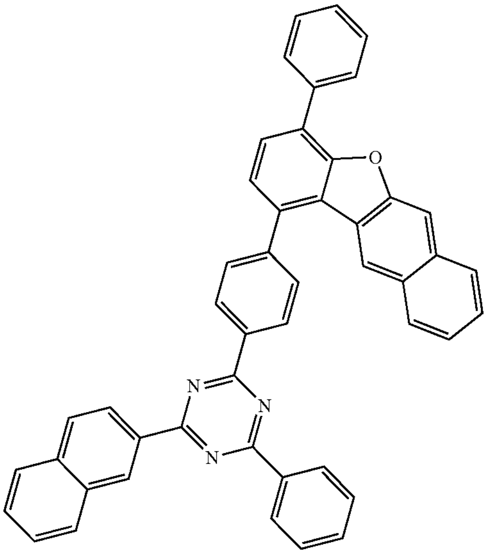
B92
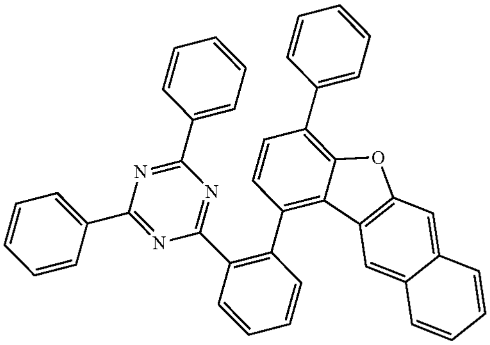
In an exemplary embodiment of the present invention, Chemical Formula C may include any one of the following compounds.
C1
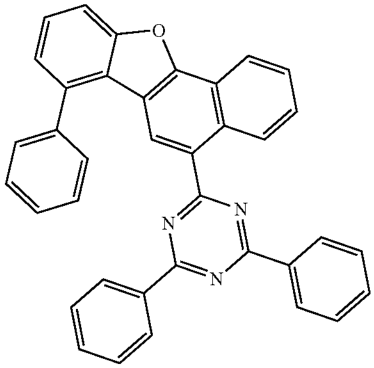

-continued
C2
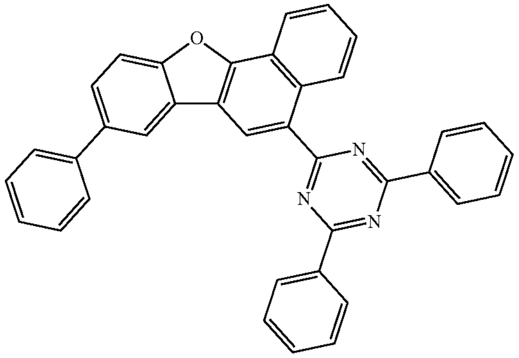
C3
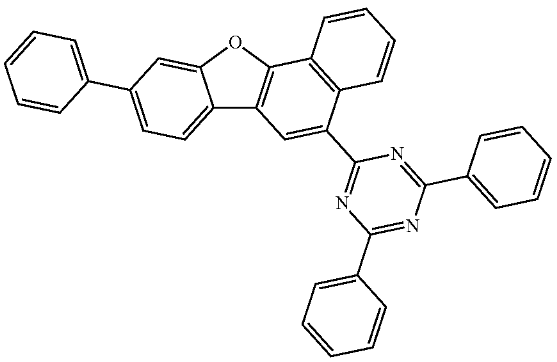
C4
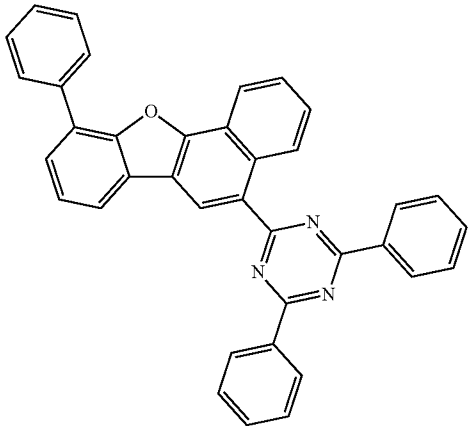
C5
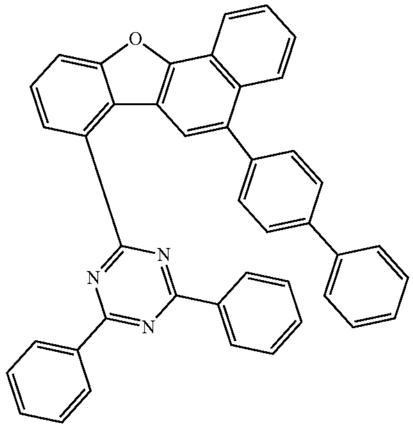
-continued
C6
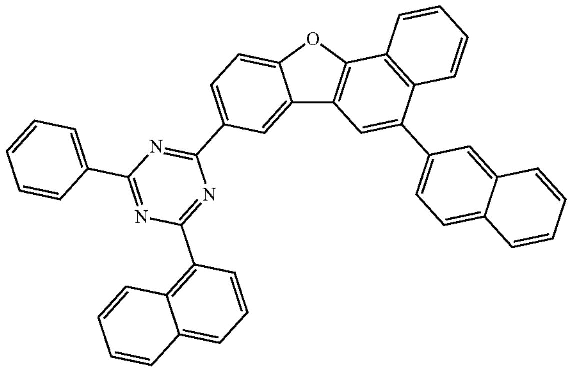
C7
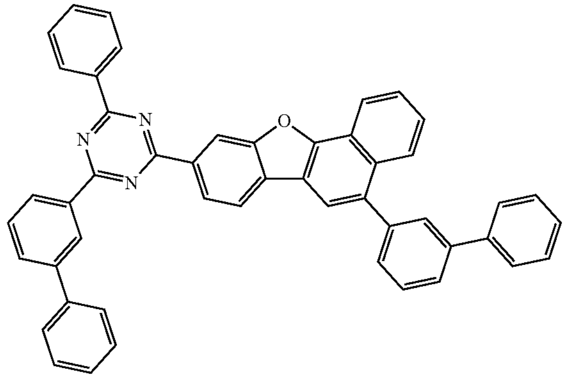
C8
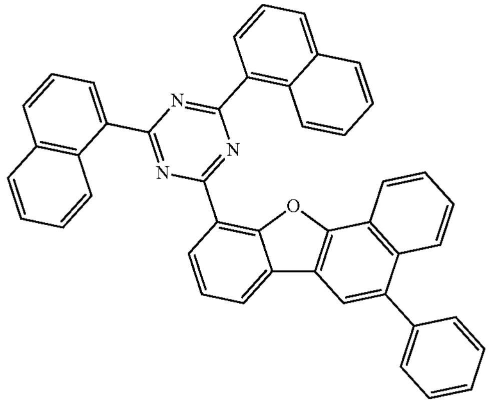

-continued
C9
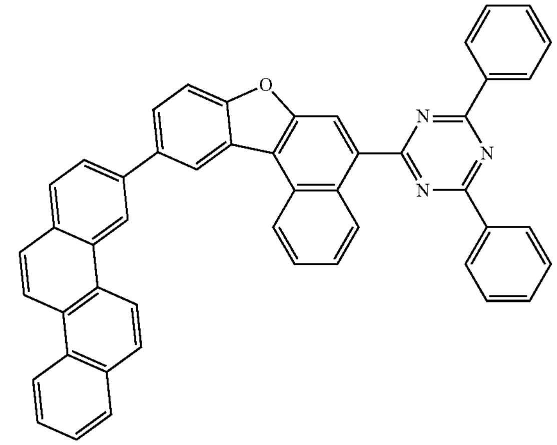
C10
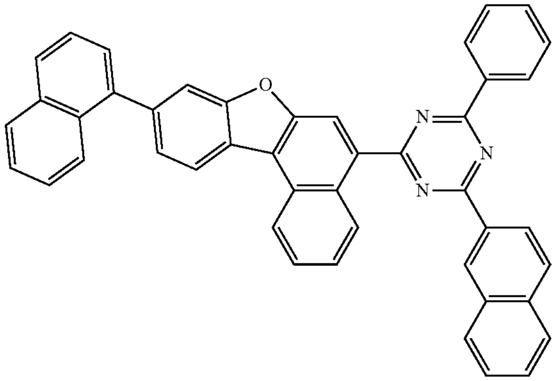
C11
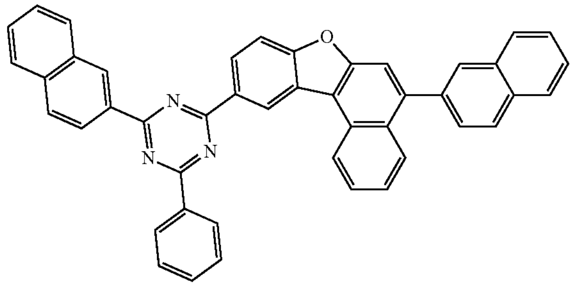
C12
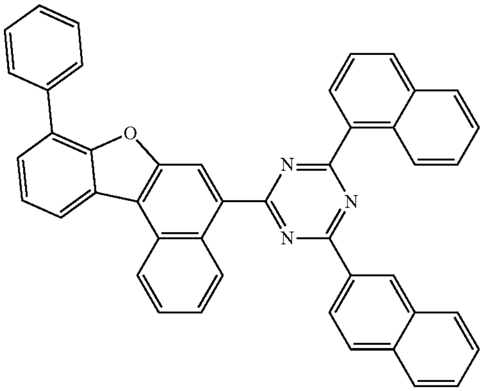
-continued
C13
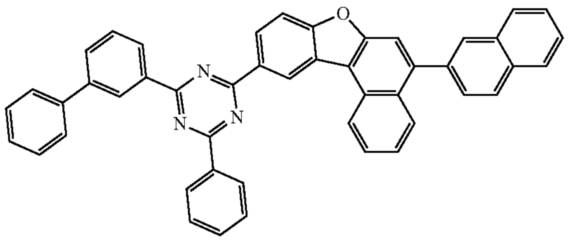
C14
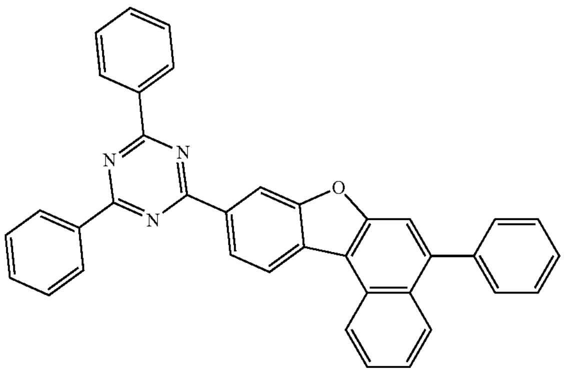
C15
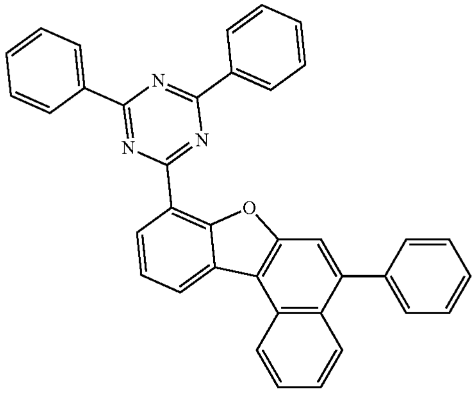
C16
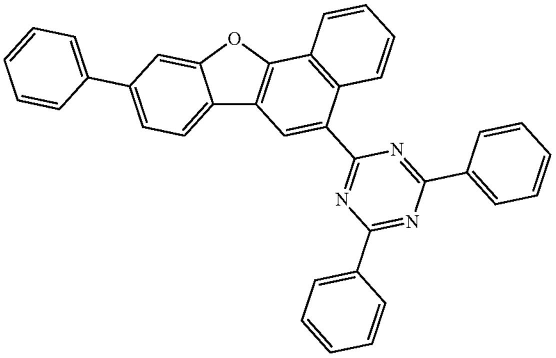

C17
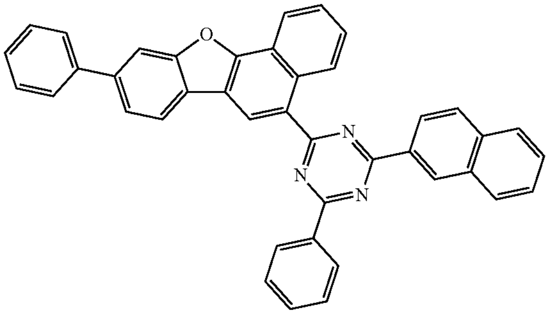
C18
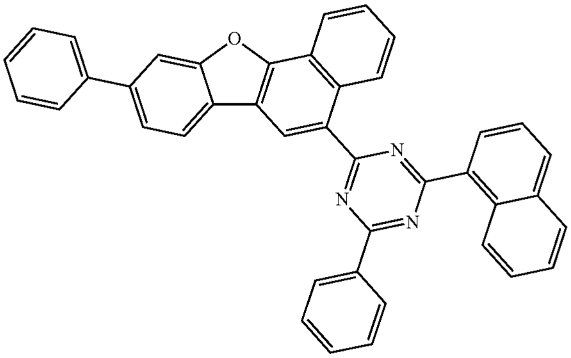
C19
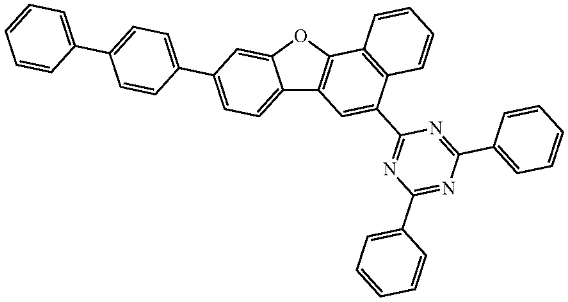
C20
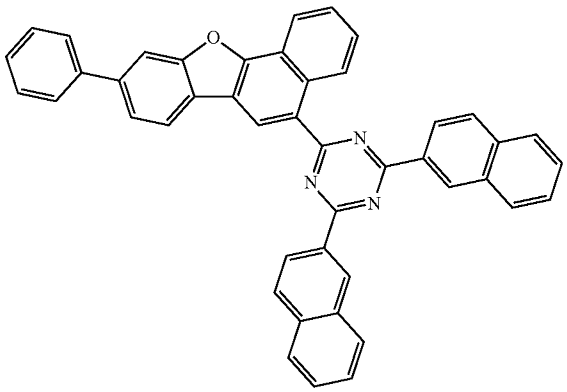
C21
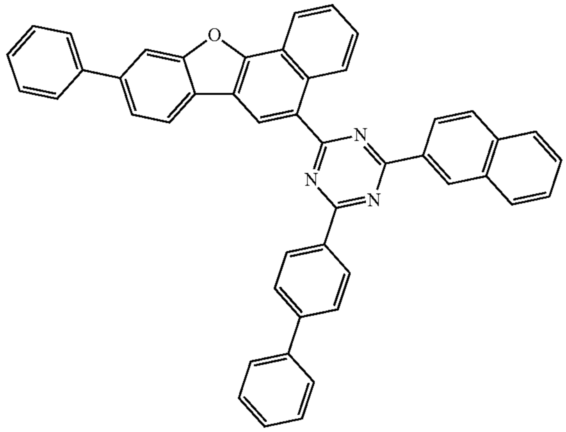
C22
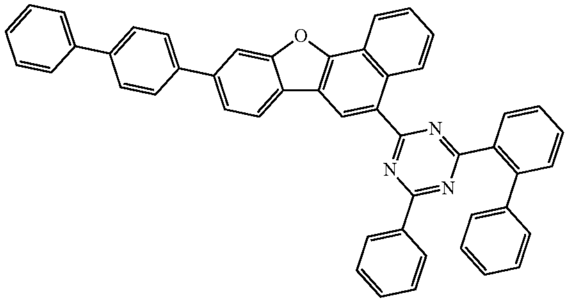
C23
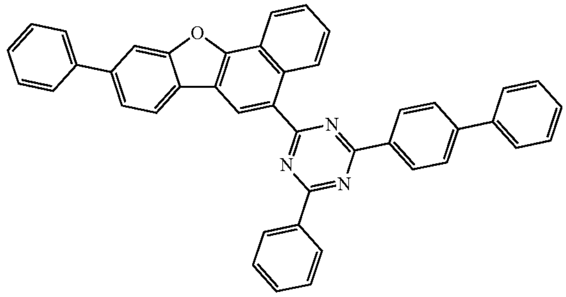
C24
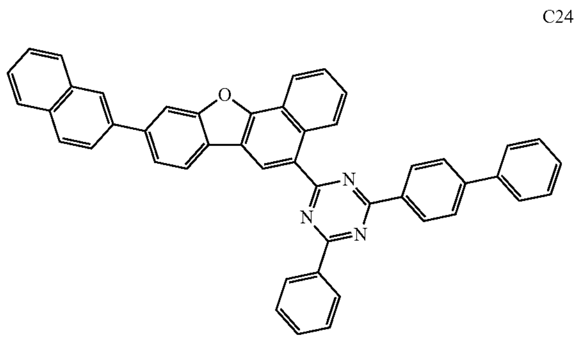

-continued
C25
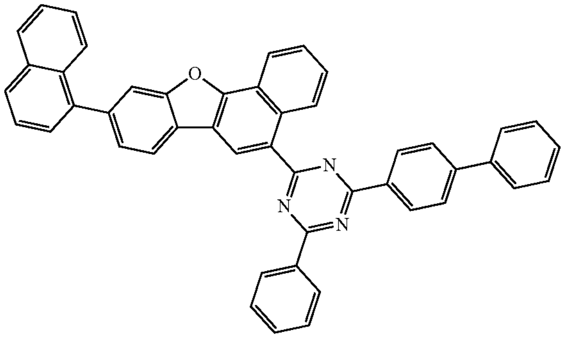
C26
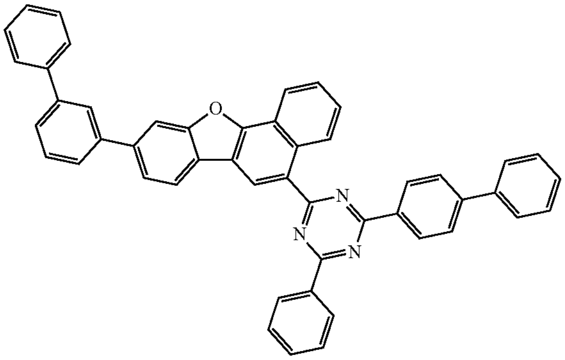
C27
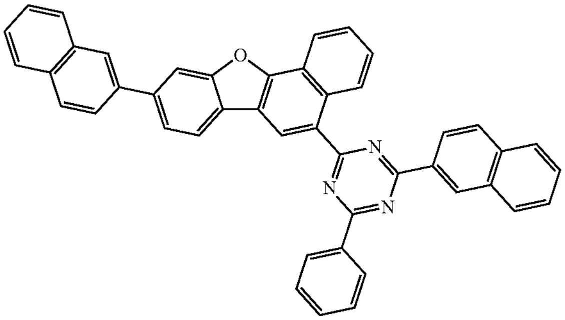
C28
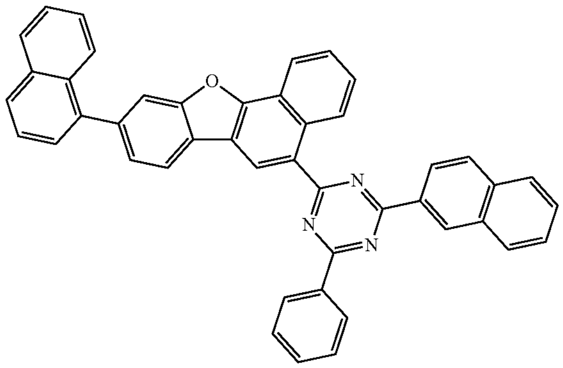
-continued
C29
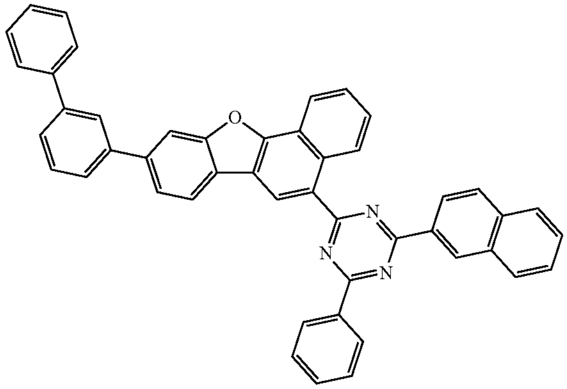
C30
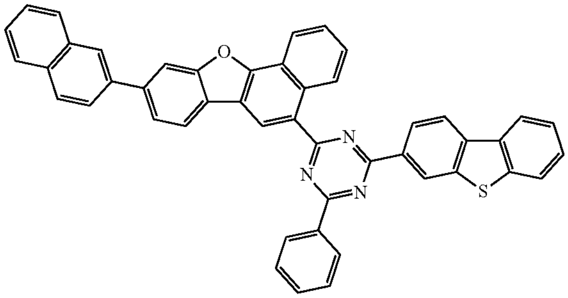
C31
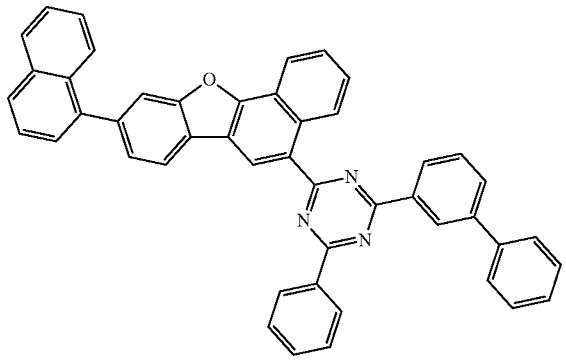
C32
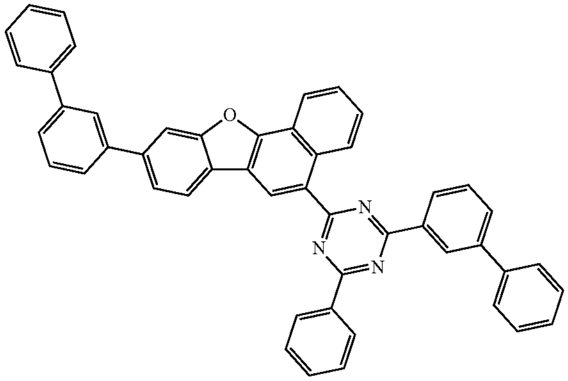

-continued
C33
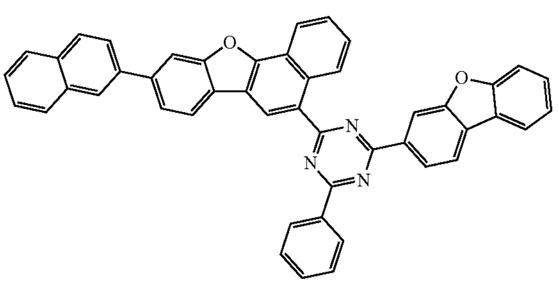
C34
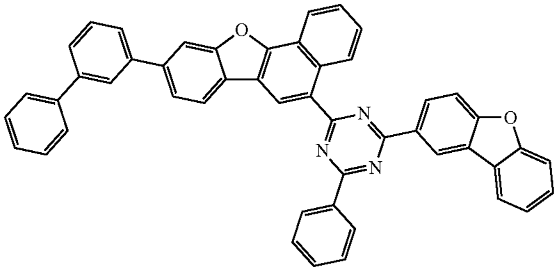
C35
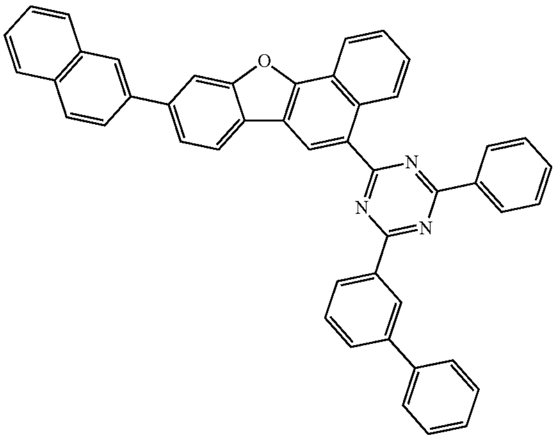
C36
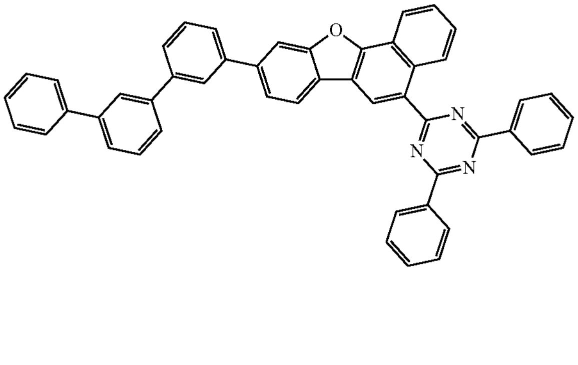
-continued
C37
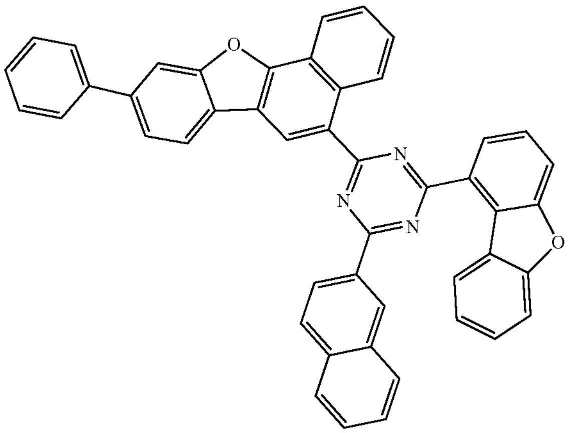
C38
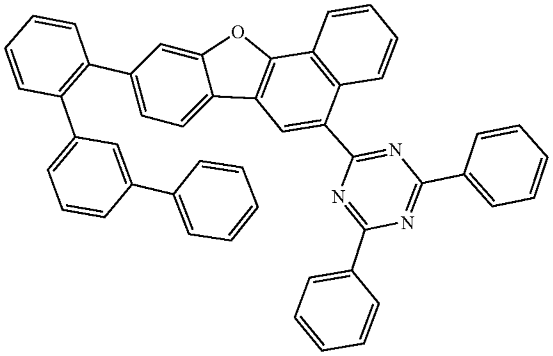
C39
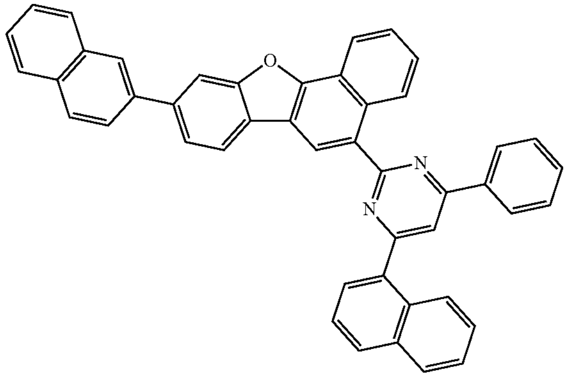
C40
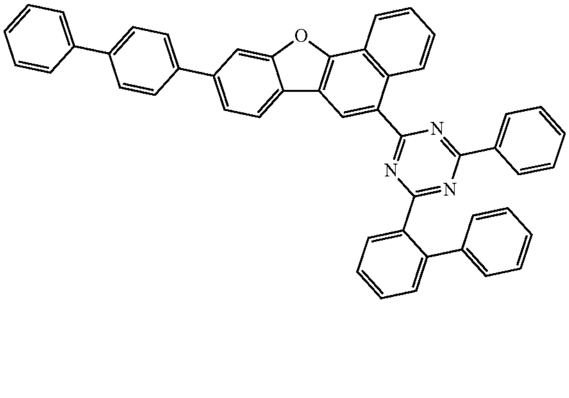

-continued
C41
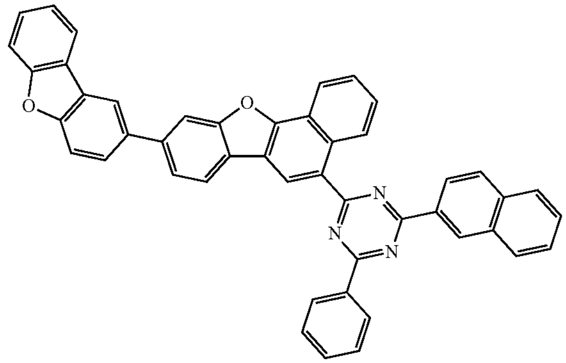
C42
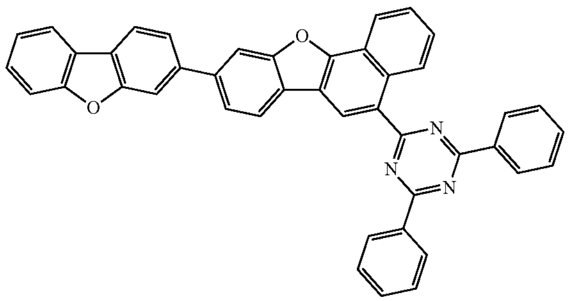
C43
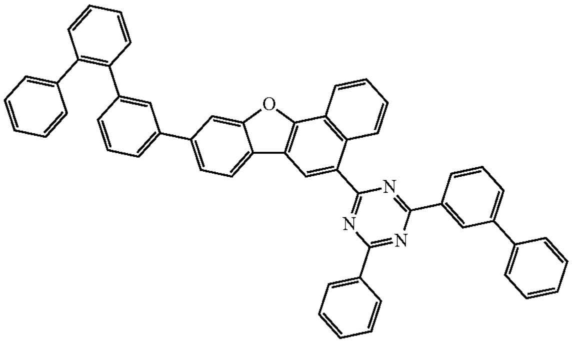
C44
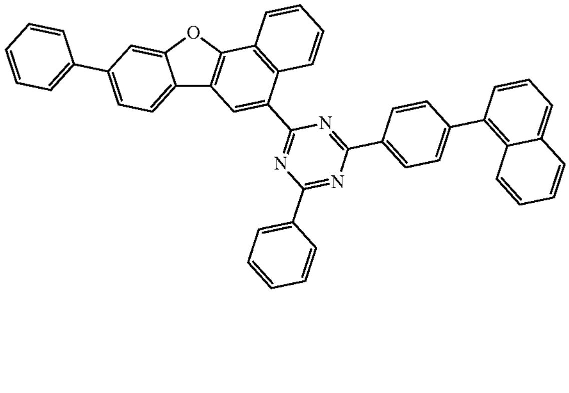
-continued
C45
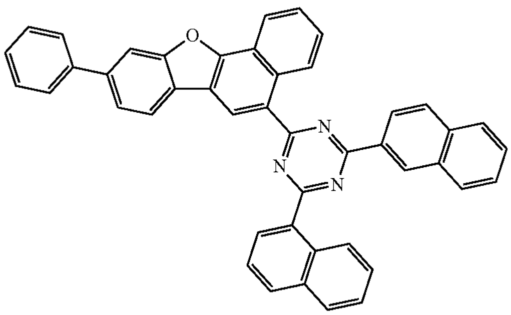
C46
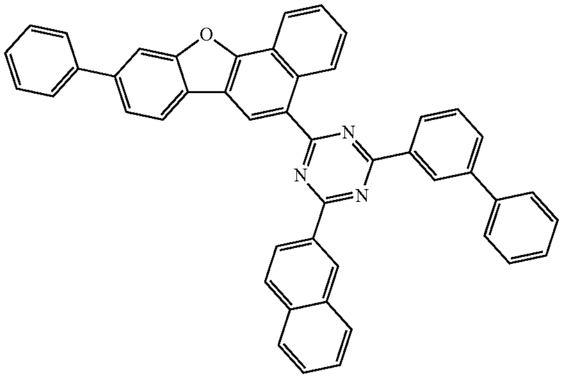
C47
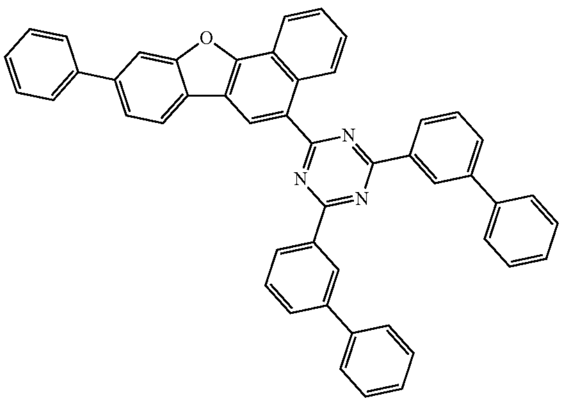
C48
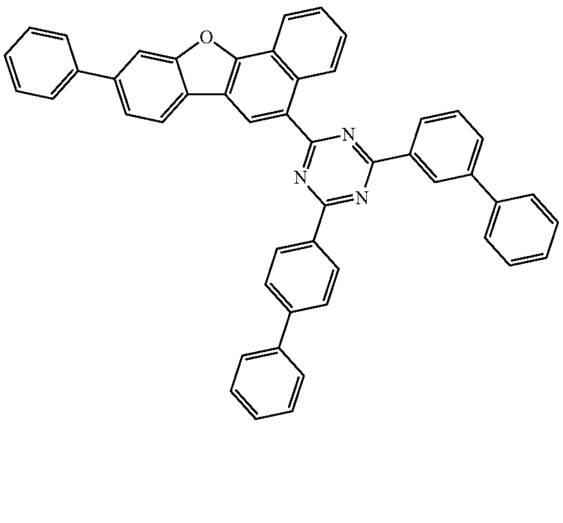

C49
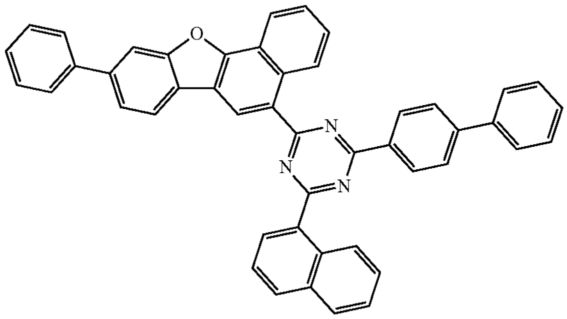
C50
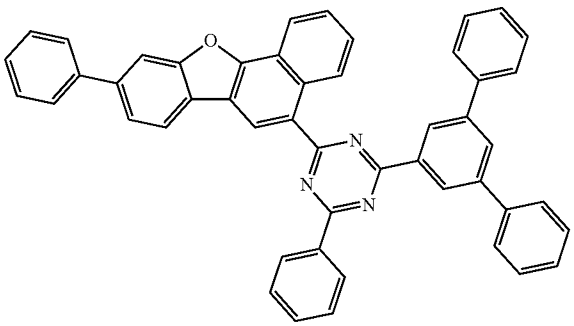
C51
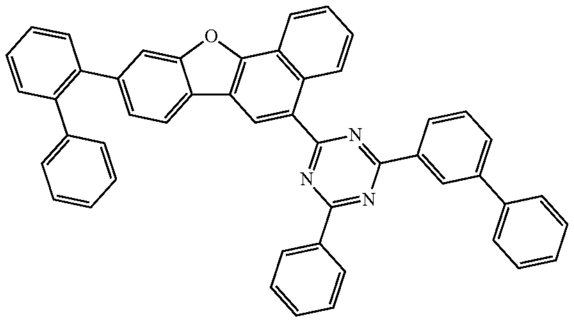
C52
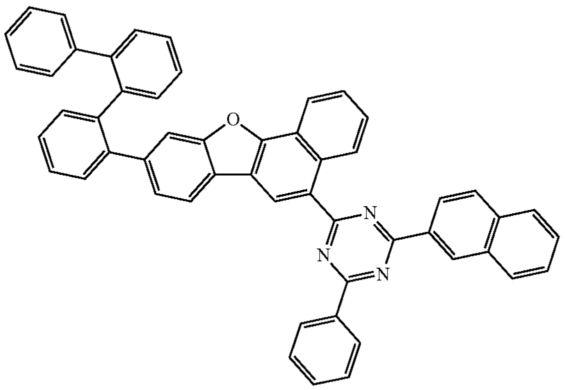
C53
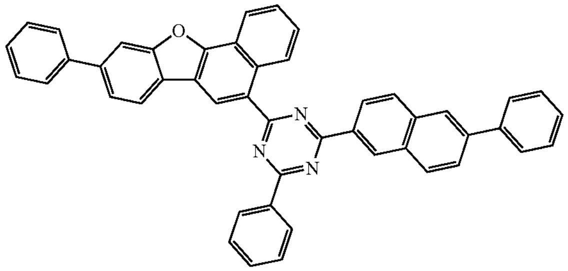
C54
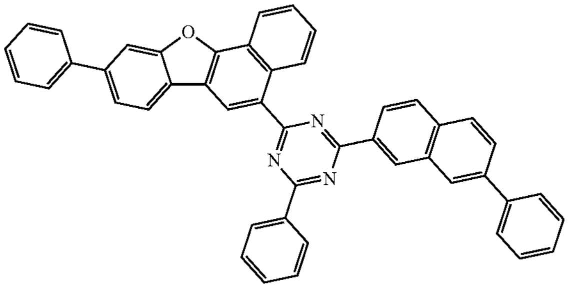
C55
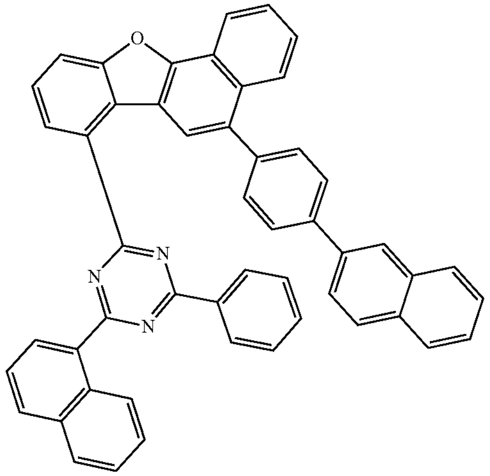
C56
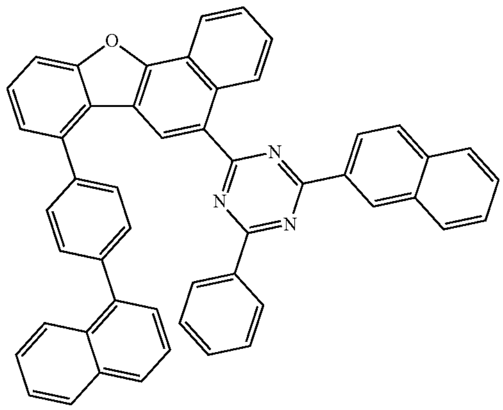

-continued
C57
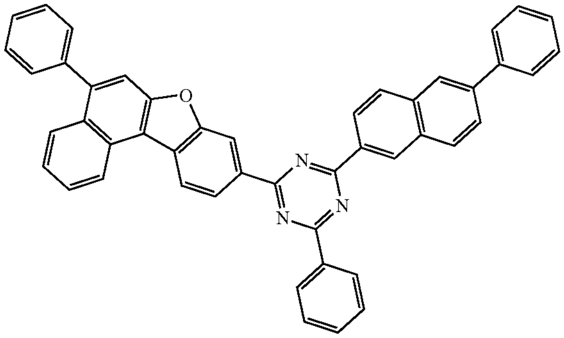
C58
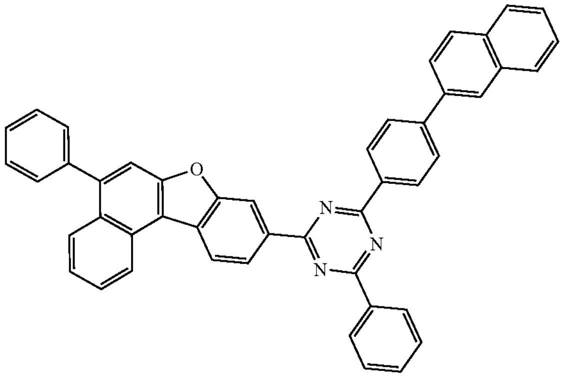
C59
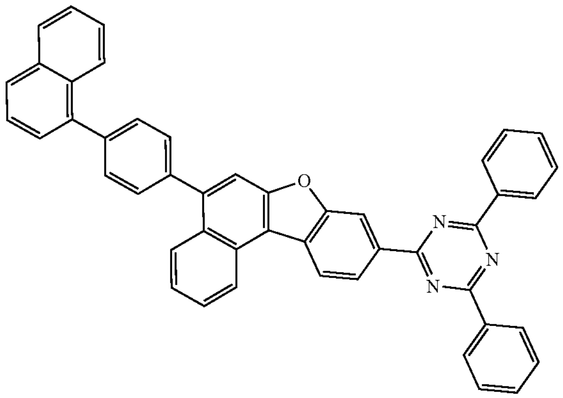
C60
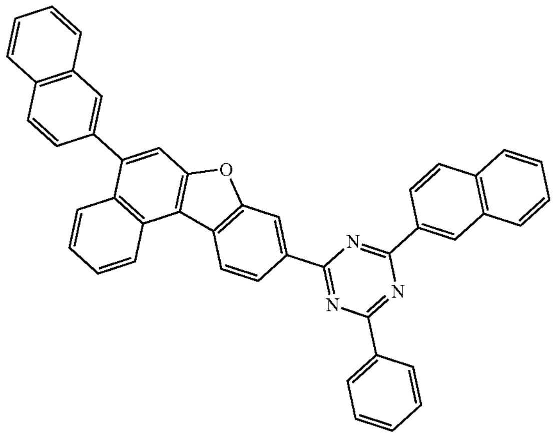
-continued
C61
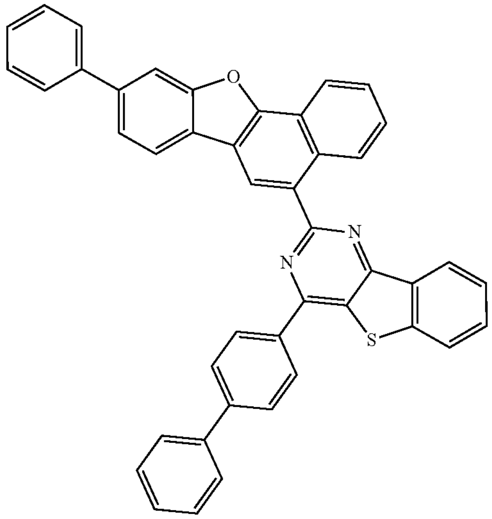
C62
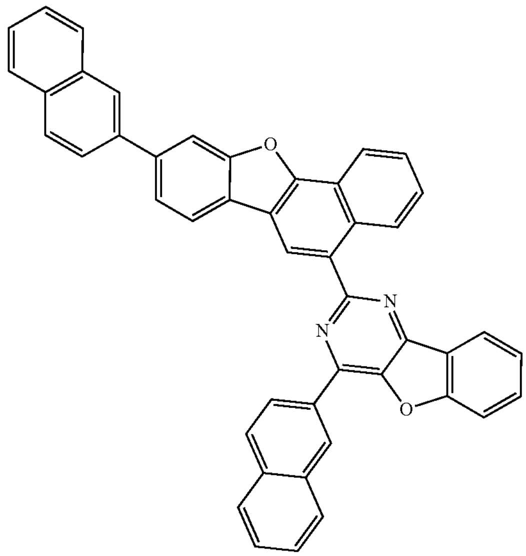
C63
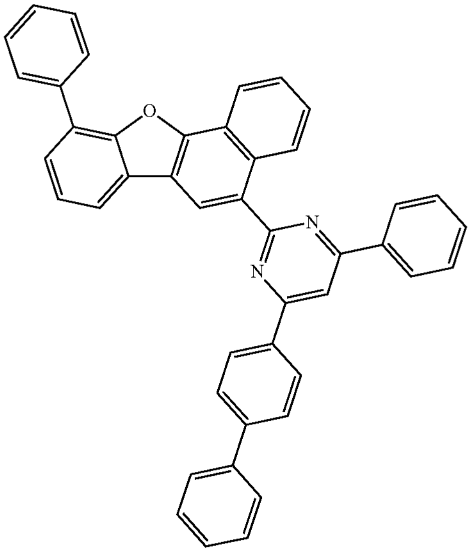

-continued
C64
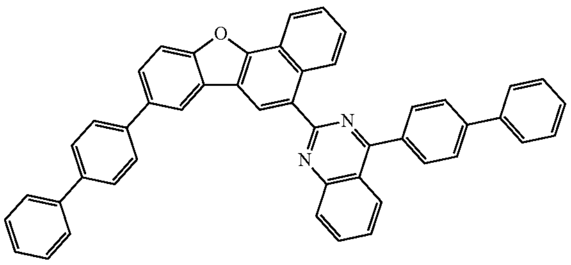
C65
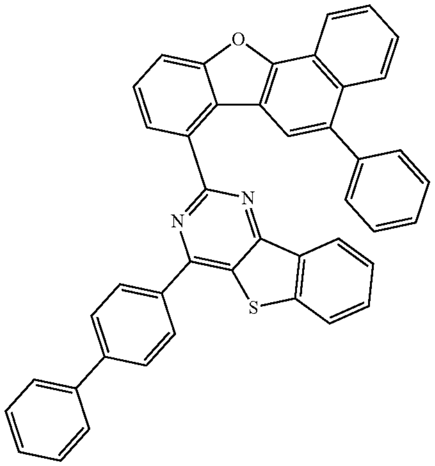
C66
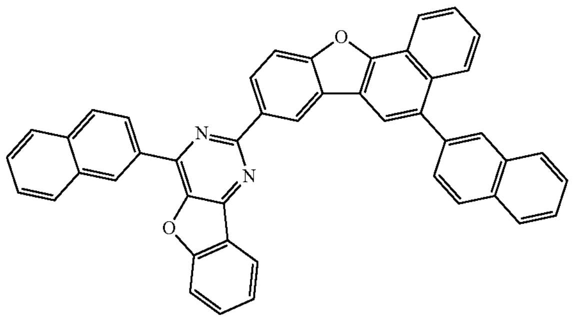
C67
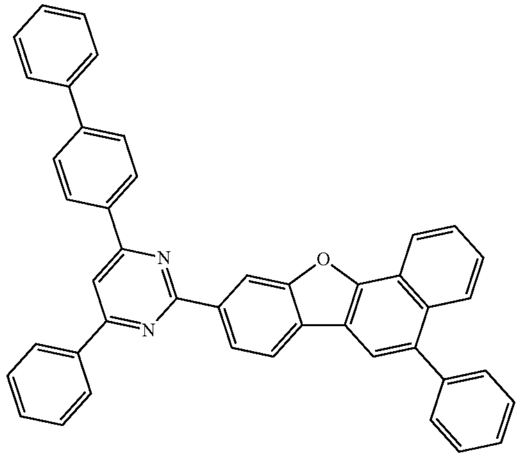
-continued
C68
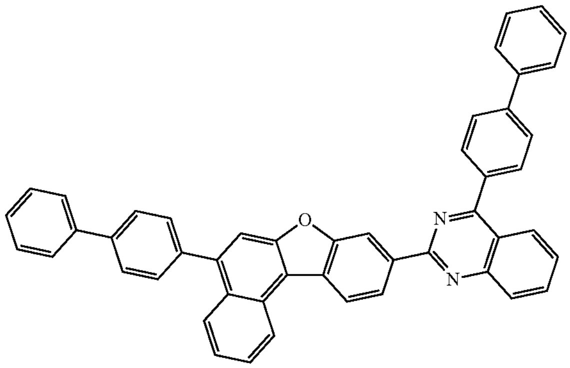
C69
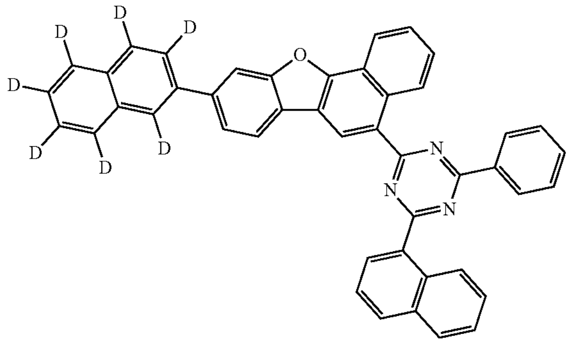
C70
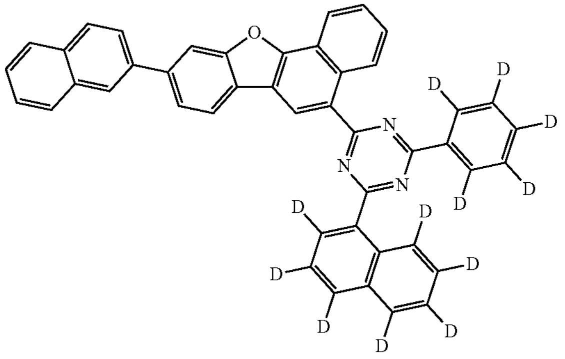
C71
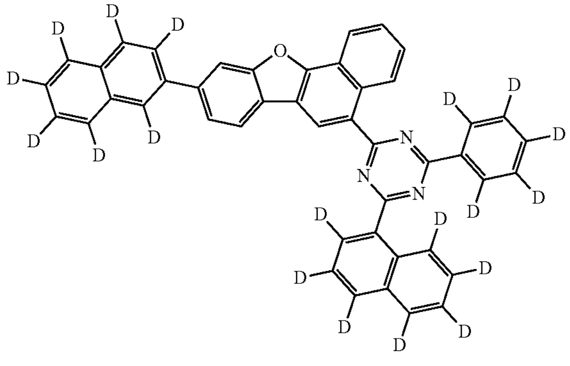

-continued
C72
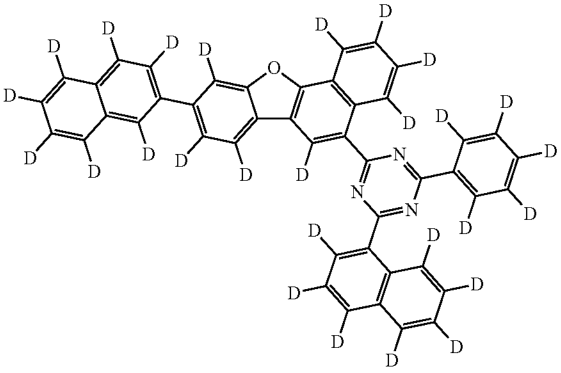
C73
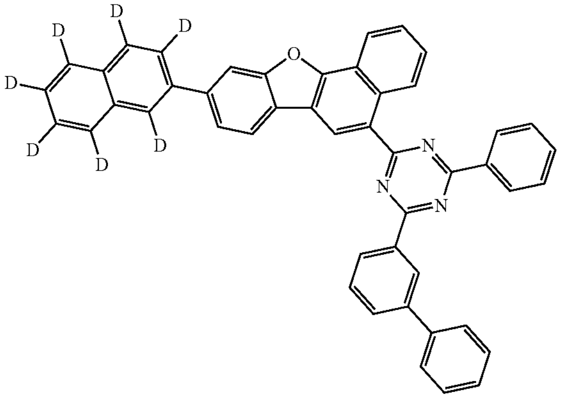
C74
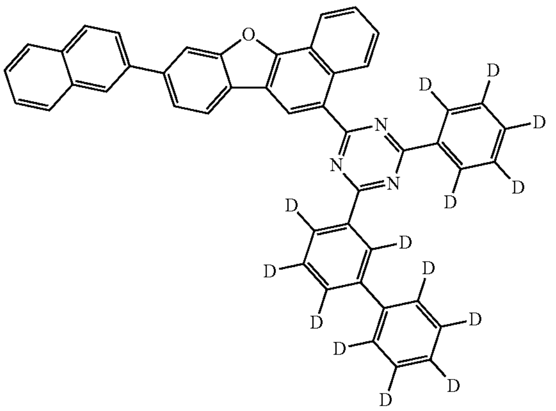
-continued
C75
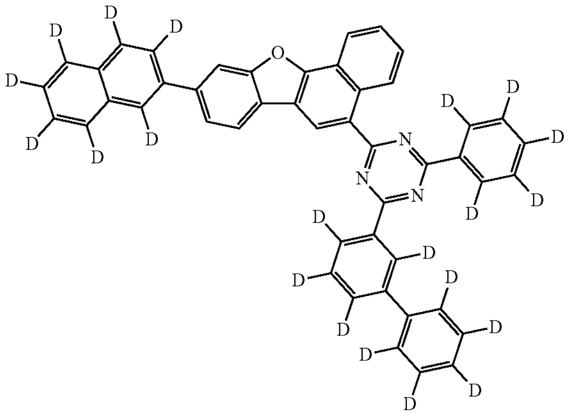
C76
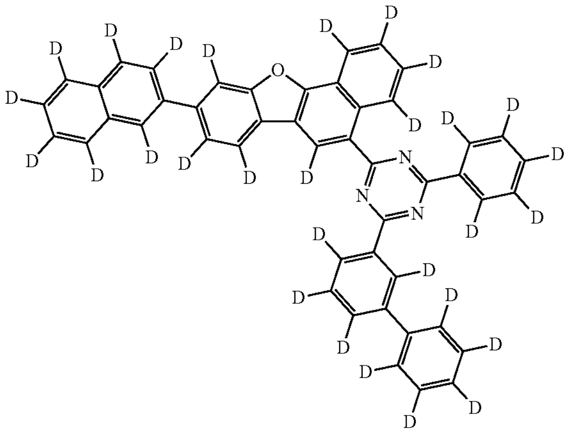
C77
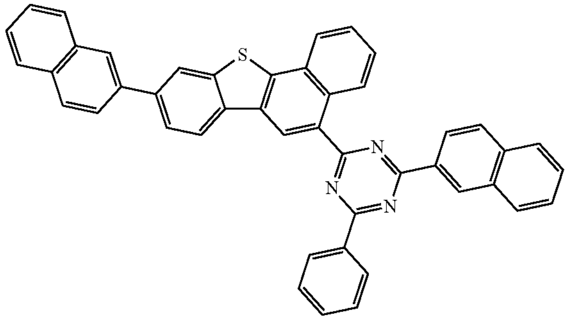
C78
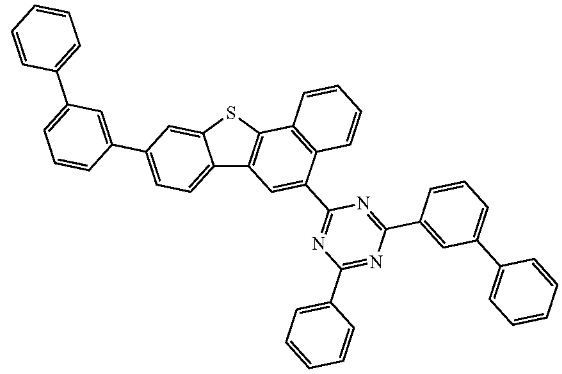

-continued

C79

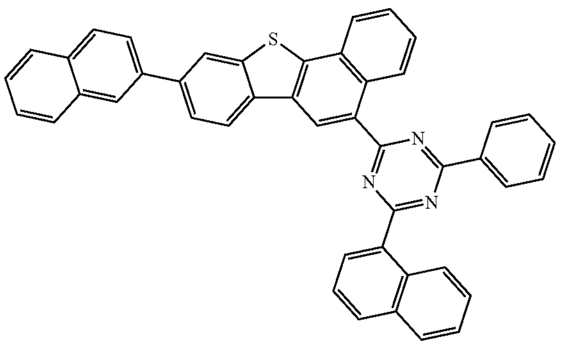

C80

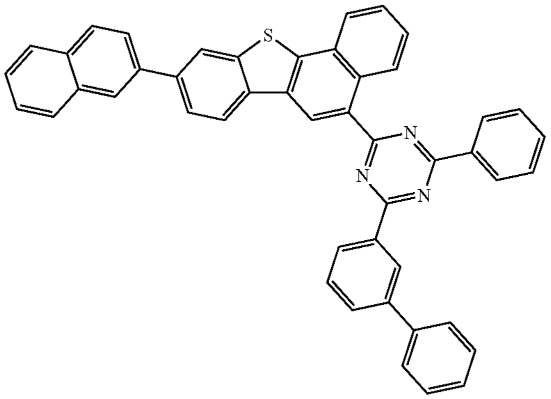

It is possible to synthesize a compound having inherent characteristics of a substituent introduced by introducing various substituents into the heterocyclic compounds represented by Chemical Formulae A, B, and C. For example, a substituent usually used for a hole injection material, a hole transport material, a light emitting material, an electron transport material and an electron injection material, particularly, a light emitting material, which are used when manufacturing an organic light emitting device, may be introduced into the core structure to synthesize a material which satisfies conditions required for each organic material layer.

In an exemplary embodiment of the present invention, the molar ratio of the heterocyclic compound represented by Chemical Formula A, the heterocyclic compound represented by Chemical Formula B, and the heterocyclic compound represented by Chemical Formula C may be 0.1 to 3:0.1 to 2.5:0.1 to 2.

In another exemplary embodiment of the present invention, the molar ratio of the heterocyclic compound represented by Chemical Formula A, the heterocyclic compound represented by Chemical Formula B, and the heterocyclic compound represented by Chemical Formula C may be about 0.1 to 2:0.1 to 2:0.1 to 2, or about 1 to 2:0.5 to 1.5:0.5 to 1.

In still another exemplary embodiment of the present invention, the molar ratio of the heterocyclic compound represented by Chemical Formula A, the heterocyclic compound represented by Chemical Formula B, and the heterocyclic compound represented by Chemical Formula C may be about 2:1:1, or about 1.5:1.5:1.

Furthermore, the heterocyclic compound of Chemical Formula A, the heterocyclic compound of Chemical Formula B, and the heterocyclic compound of Chemical Formula C have excellent thermal stability, and such thermal stability provides driving stability to the organic light emitting device and improves service life characteristics.

In yet another exemplary embodiment of the present application, provided is an organic light emitting device including a first electrode; a second electrode; and an organic material layer having one or more layers provided between the first electrode and the second electrode, in which one or more layers of the organic material layer include the composition for an organic light emitting device.

In an exemplary embodiment of the present application, provided is an organic light emitting device including: a first electrode; a second electrode provided to face the first electrode; and an organic material layer having one or more layers provided between the first electrode and the second electrode, in which one or more layers of the organic material layer include the composition for an organic light emitting device.

In an exemplary embodiment of the present application, the organic material layer further includes a light emitting layer (emission layer), and the light emitting layer may include the composition for an organic light emitting device.

In another exemplary embodiment of the present application, the light emitting layer may include the composition for an organic light emitting device as a host.

In an exemplary embodiment of the present application, the light emitting layer may include the composition for an organic light emitting device as a red host.

In an exemplary embodiment of the present application, the first electrode may be a positive electrode, and the second electrode may be a negative electrode.

In another exemplary embodiment, the first electrode may be a negative electrode, and the second electrode may be a positive electrode.

The organic light emitting device of the present invention may further include one or two or more layers selected from the group consisting of a light emitting layer, a hole injection layer, a hole transport layer, an electron blocking layer, a hole blocking layer, an electron transport layer and an electron injection layer.

FIGS. 1 to 3 exemplify the stacking sequence of the electrodes and the organic material layer of the organic light emitting device according to an exemplary embodiment of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented. The composition for an organic light emitting device may be included in the organic material layer 300, and the organic material layer 300 may be one or more layers.

FIG. 3 exemplifies a case where an organic material layer is a multilayer. An organic light emitting device according to FIG. 3 includes a hole injection layer 301, a hole transport layer 302, a light emitting layer 303, a hole blocking layer 304, an electron transport layer 305, and an electron injection layer 306. The composition for an organic light emitting device may be included in the light emitting layer 303.

However, the scope of the present application is not limited by the stacking structure as described above, and if necessary, the other layers except for the light emitting layer may be omitted, and another necessary functional layer may be further added.

The organic light emitting device according to an exemplary embodiment of the present application includes a first electrode; a first stack provided on the first electrode and including a first light emitting layer; a charge generation layer provided on the first stack; a second stack provided on the charge generation layer and including a second light emitting layer; and a second electrode provided on the second stack.

When the organic light emitting device according to an exemplary embodiment of the present application has a two-stack structure as described above, one or more layers of the first light emitting layer (first stack light emitting layer) and the second light emitting layer (second stack light emitting layer) may include the composition for an organic light emitting device.

Furthermore, the first stack and the second stack may each independently further include one or more of the above-described hole injection layer, hole transport layer, hole blocking layer, electron transport layer, electron injection layer, and the like.

The composition for an organic light emitting device may be used when an organic material layer of an organic light emitting device is formed, and particularly, may be preferably used as a material for the light emitting layer.

The composition is in the form of a premix of each of the heterocyclic compound of Chemical Formula A, the heterocyclic compound of Chemical Formula B, and the heterocyclic compound of Chemical Formula C, may be mixed with a material in a powder state before the organic material layer of the organic light emitting device is formed, and may be mixed with a compound in a liquid state at a suitable temperature or higher. The composition is in a solid state at a temperature which is equal to or less than the melting point of each material, and may be maintained as a liquid phase when the temperature is adjusted.

The composition may additionally include materials publicly known in the art such as solvents and additives.

In an exemplary embodiment of the present application, provided is a method for manufacturing an organic light emitting device, the method including: preparing a substrate; forming a first electrode on the substrate; forming an organic material layer having one or more layers on the first electrode; and forming a second electrode on the organic material layer, in which the forming of the organic material layer includes forming the organic material layer having one or more layers by using the composition for an organic light emitting device according to an exemplary embodiment of the present application.

In an exemplary embodiment of the present application, provided is a method for manufacturing an organic light emitting device, in which the forming of the organic material layer forms the heterocyclic compound represented by Chemical Formula A, the heterocyclic compound represented by Chemical Formula B, and the heterocyclic compound represented by Chemical Formula C using a thermal vacuum deposition method.

The organic light emitting device according to an exemplary embodiment of the present application may be manufactured by typical manufacturing methods and materials of the organic light emitting device, except that the above-described composition is used to form an organic material layer.

The organic light emitting device of the present invention may further include one or two or more layers selected from the group consisting of a light emitting layer, a hole injection layer, a hole transport layer, an electron blocking layer, an electron injection layer, an electron transport layer, a hole auxiliary layer, and a hole blocking layer.

In an exemplary embodiment of the present application, the organic light emitting device may be a blue organic light emitting device, and the composition for an organic light emitting device may be used as a material for the blue organic light emitting device.

In an exemplary embodiment of the present application, the organic light emitting device may be a green organic light emitting device, and the composition for an organic light emitting device may be used as a material for the green organic light emitting device.

In an exemplary embodiment of the present application, the organic light emitting device may be a red organic light emitting device, and the composition for an organic light emitting device may be used as a material for the red organic light emitting device.

The heterocyclic compound of Chemical Formula A, the heterocyclic compound of Chemical Formula B, and/or the heterocyclic compound of Chemical Formula C may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

The organic material layer of the organic light emitting device of the present invention may be composed of a single-layered structure, but may be composed of a multi-layered structure in which two or more organic material layers are stacked. For example, the organic light emitting device of the present invention may have a structure including a hole injection layer, a hole transport layer, a light emitting layer, an electron transport layer, an electron injection layer, and the like as organic material layers. However, the structure of the organic light emitting device is not limited thereto, and may include a fewer number of organic material layers.

In an exemplary embodiment of the present application, the organic material layer may include an iridium-based dopant.

In an exemplary embodiment of the present application, as the iridium-based dopant, $Ir(ppy)_3$, which is a green phosphorescent dopant, may be used, but is not limited thereto.

In an exemplary embodiment of the present application, as the iridium-based dopant, $(piq)_2(Ir)_{(acac)}$, which is a red phosphorescent dopant, may be used, but is not limited thereto.

The organic light emitting device of the present invention may be manufactured using typical manufacturing methods and materials of an organic light emitting device, except that the above-described composition for an organic light emitting device is used to form an organic material layer having one or more layers.

In the organic light emitting device of the present application, as a positive electrode material, materials having a relatively high work function may be used, and a transparent conductive oxide, a metal or a conductive polymer, and the like may be used. Specific examples of the positive electrode material include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene](PEDOT), polypyrrole, and polyaniline; and the like, but are not limited thereto.

In the organic light emitting device of the present application, as a negative electrode material, materials having a relatively low work function may be used, and a metal, a metal oxide, or a conductive polymer, and the like may be used. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

In the organic light emitting device of the present application, as a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tri[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid or polyaniline/poly(4-styrene-sulfonate), and the like.

In the organic light emitting device of the present application, as a hole transport material, a pyrazoline derivative, an arylamine-based derivative, a stilbene derivative, a triphenyldiamine derivative, and the like may be used, and a low-molecular weight or polymer material may also be used.

In the organic light emitting device of the present application, as an electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

In the organic light emitting device of the present application, as an electron injection material, for example, LiF is representatively used in the art, but the present application is not limited thereto.

In the organic light emitting device of the present application, as a light emitting material, a red, green, or blue light emitting material may be further used, and if necessary, two or more light emitting materials may be mixed and used. In this case, two or more light emitting materials are deposited and used as an individual supply source, or pre-mixed to be deposited and used as one supply source. Further, a fluorescent material may also be used as the light emitting material, but may also be used as a phosphorescent material. As the light emitting material, it is also possible to use alone a material which emits light by combining holes and electrons each injected from a positive electrode and a negative electrode, but materials in which a host material and a dopant material are involved in light emission together may also be used.

When hosts of the light emitting material are mixed and used, the same series of hosts may also be mixed and used, and different series of hosts may also be mixed and used. For example, two or more types of materials selected from n-type host materials or p-type host materials may be used as a host material for a light emitting layer.

The organic light emitting device according to an exemplary embodiment of the present application may be a top emission type, a bottom emission type, or a dual emission type according to the material to be used.

The heterocyclic compound according to an exemplary embodiment of the present application may act even in organic electronic devices including organic solar cells, organic photoconductors, organic transistors, and the like, based on the principle similar to those applied to organic light emitting devices.

Hereinafter, the present specification will be described in more detail through Examples, but these Examples are provided only for exemplifying the present application, and are not intended to limit the scope of the present application.

EXAMPLES

[Preparation Example 1] Preparation of Compound A3

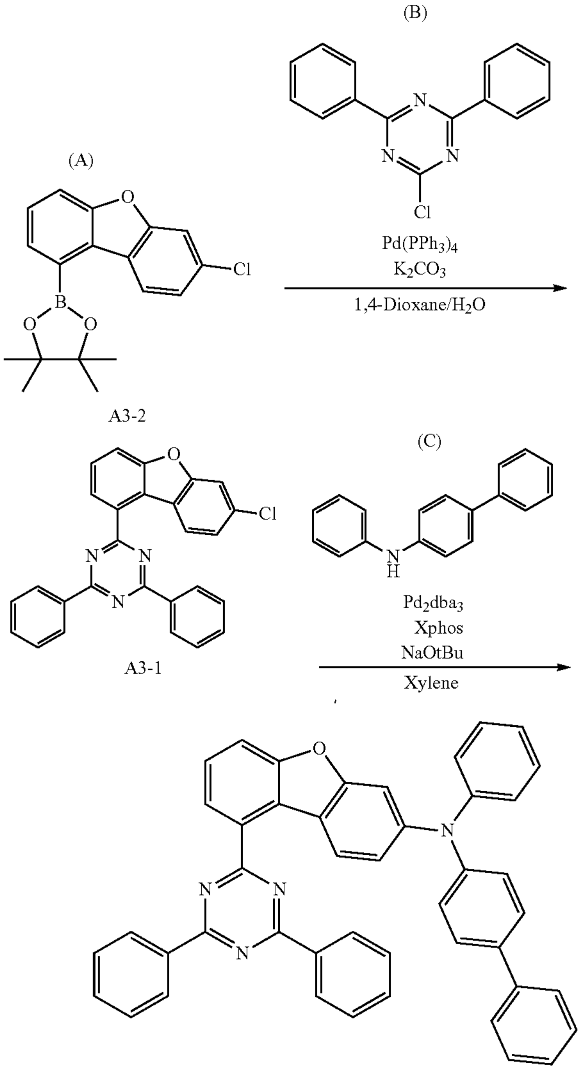

A3

1) Preparation of Intermediate A3-1

2-(7-chlorodibenzo[b,d]furan-1-yl)-4,4,5,5-tetramethyl-1,3,2-dioxaborolane (20.0 g, 60.9 mmol), 2-chloro-4,6-diphenyl-1,3,5-triazine (16.3 g, 60.9 mmol), $Pd(PPh_3)_4$ (3.52 g, 3.04 mmol), and $K_2CO_3$ (25.2 g, 183 mmol) were put into 1,4-dioxane/$H_2O$ (200 mL/60 mL), and the resulting mixture was stirred at 100° C. for 2 hours. After the mixture was cooled to room temperature, the resulting solid was filtered to obtain Intermediate A3-1 (22.7 g, 86%).

2) Preparation of Compound A3

After Intermediate A3-1 (10.0 g, 23.1 mmol), N-phenyl-[1,1'-biphenyl]-4-amine (5.69 g, 23.1 mmol), $pd_2dba_3$ (1.06 g, 1.15 mmol), Xphos (1.10 g, 2.31 mmol), and NaOtBu (6.64 g, 69.1 mmol) were put into xylene (100 mL), the resulting mixture was stirred at 150° C. for 2 hours. After the mixture was cooled to room temperature, the solid was filtered. The filtered solid was filtered with silica gel to obtain Compound A3 (11.7 g, 79%).

The following compounds were synthesized in the same manner as in the preparation of Compound A3, except that (A), (B), and (C) were used as intermediates in Preparation Example 1.

TABLE 1

| Compound | (A) | (B) | (C) | Yield |
|---|---|---|---|---|
| A12 | 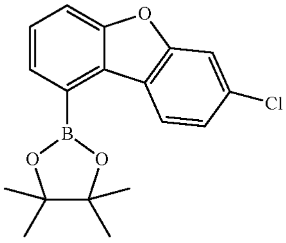 | 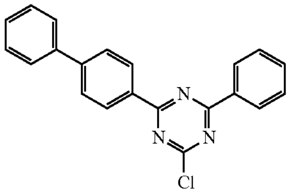 | 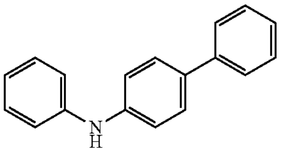 | 75% |
| A14 | 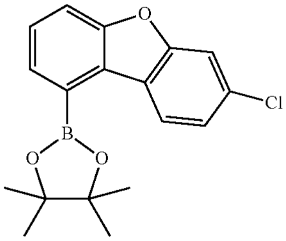 | 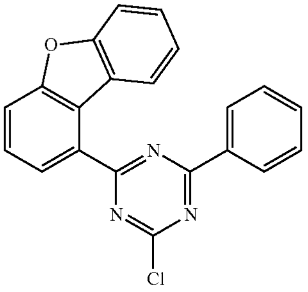 | 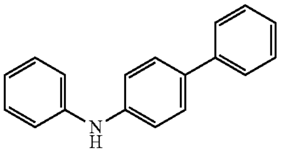 | 79% |
| A15 | 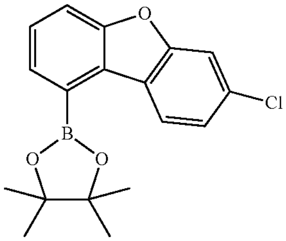 | 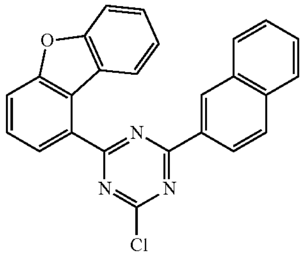 | 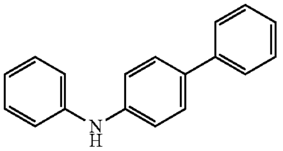 | 73% |
| A21 | 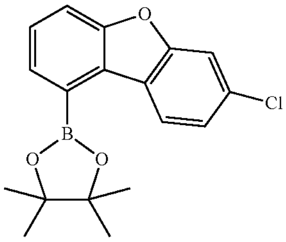 | 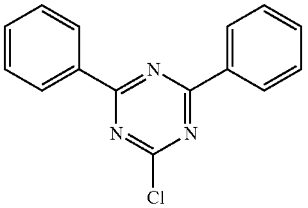 | 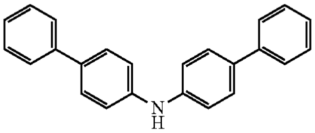 | 66% |

TABLE 1-continued
| Compound | (A) | (B) | (C) | Yield |
|---|---|---|---|---|
| A27 | 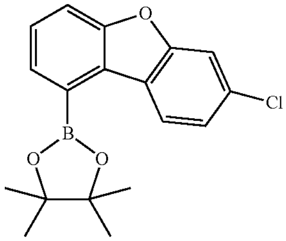 | 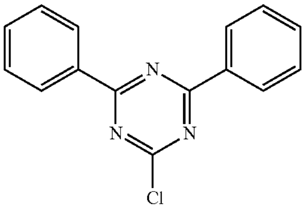 | 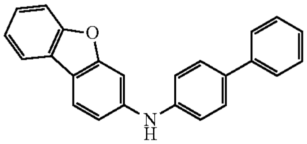 | 81% |
| A28 | 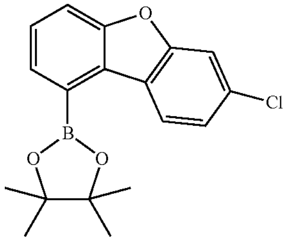 | 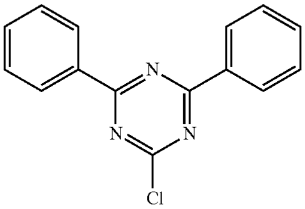 | 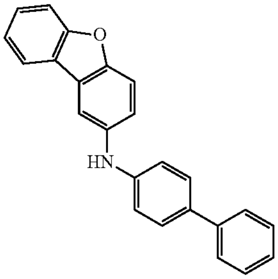 | 75% |
| A29 | 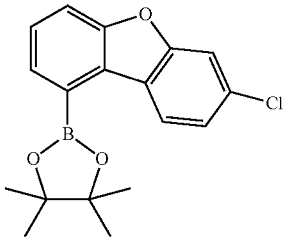 | 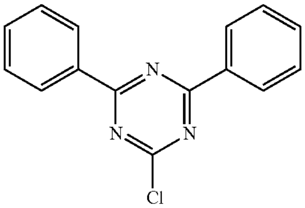 | 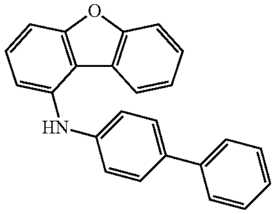 | 74% |
| A32 | 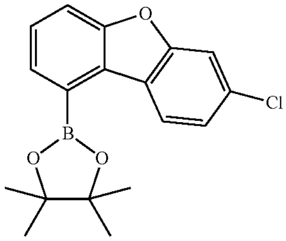 | 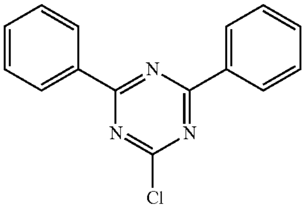 | 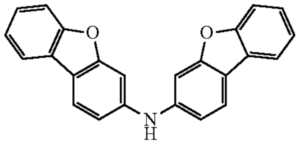 | 72% |
| A34 | 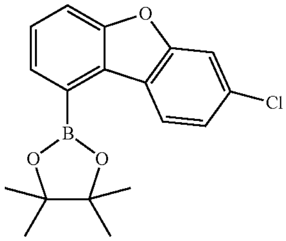 | 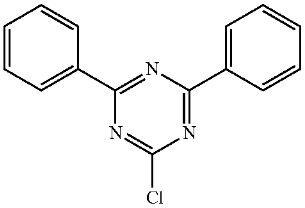 | 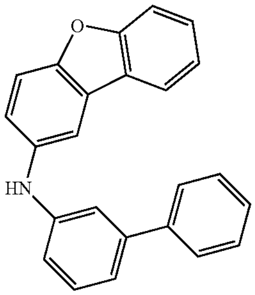 | 70% |

TABLE 1-continued
| Compound | (A) | (B) | (C) | Yield |
|---|---|---|---|---|
| A36 | 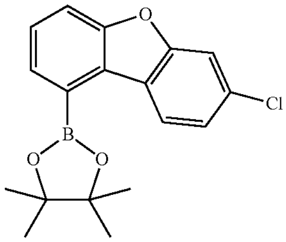 | 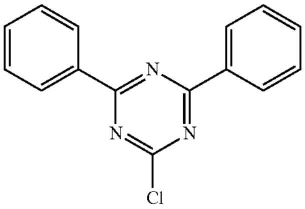 | 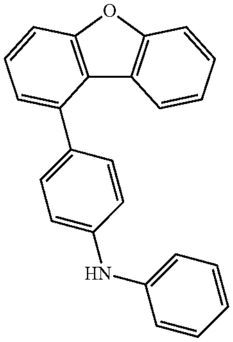 | 80% |
| A58 | 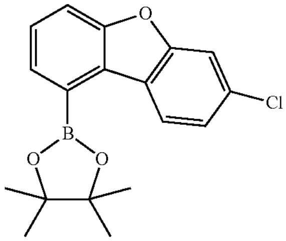 | 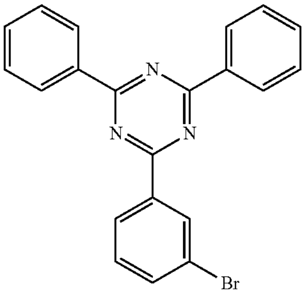 | 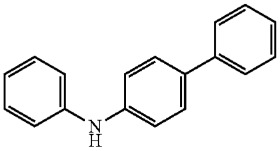 | 75% |
| A99 | 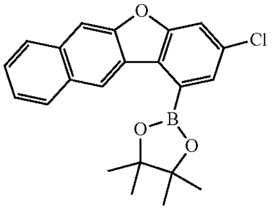 | 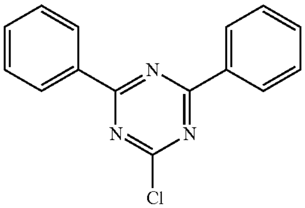 | 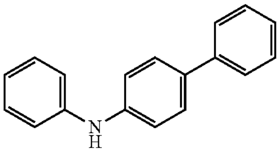 | 77% |
| A102 | 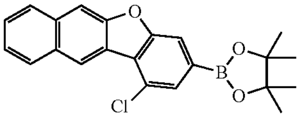 | 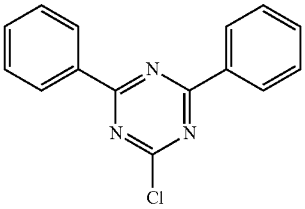 | 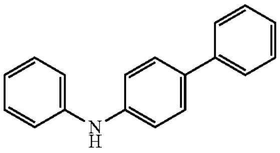 | 72% |
| A135 | 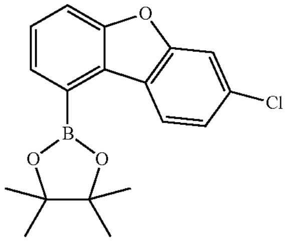 | 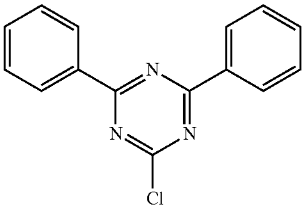 | 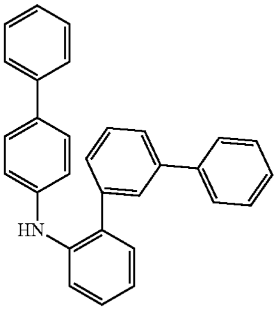 | 70% |

TABLE 1-continued
| Compound | (A) | (B) | (C) | Yield |
|---|---|---|---|---|
| A159 | 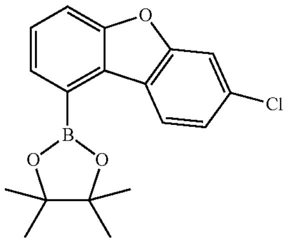 | 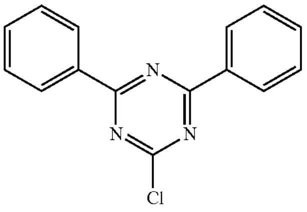 | 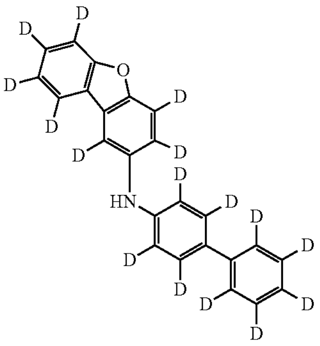 | 68% |
| A160 | 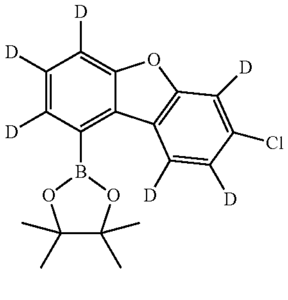 | 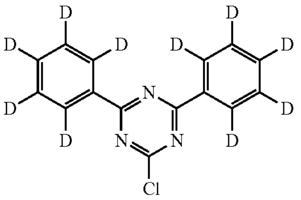 | 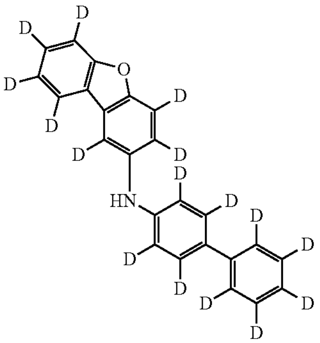 | 73% |
[Preparation Example 2] Preparation of Compound A46
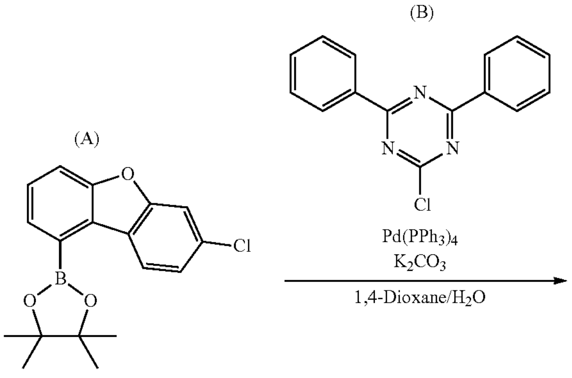
A46-2
-continued
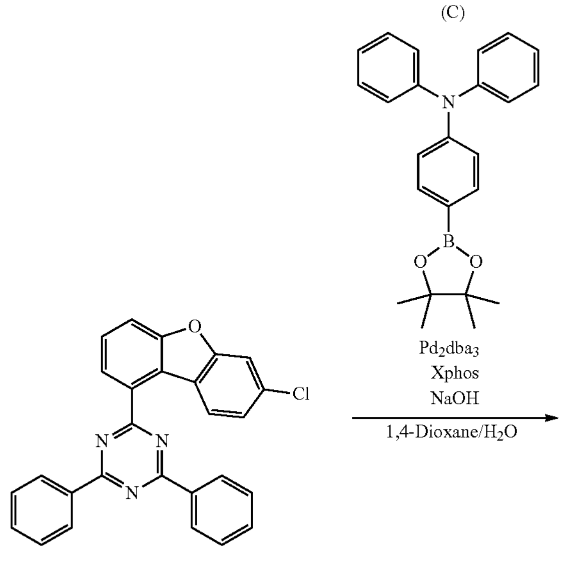
A46-1

-continued

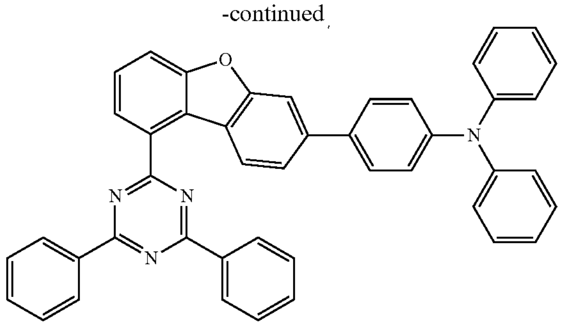

A46

1) Preparation of Intermediate A46-1

2-(7-chlorodibenzo[b,d]furan-1-yl)-4,4,5,5-tetramethyl-1,3,2-dioxaborolane (20.0 g, 60.9 mmol), 2-chloro-4,6-diphenyl-1,3,5-triazine (16.3 g, 60.9 mmol), $Pd(PPh_3)_4$ (3.52 g, 3.04 mmol), and $K_2CO_3$ (19.4 g, 183 mmol) were put into 1,4-dioxane/$H_2O$ (200 mL/60 mL), and the resulting mixture was stirred at 100° C. for 2 hours. After the mixture was cooled to room temperature, the resulting solid was filtered to obtain Intermediate A46-1 (21.4 g, 81%).

2) Preparation of Compound A46

After Intermediate A46-1 (10.0 g, 23.1 mmol), N,N-diphenyl-4-(4,4,5,5-tetramethyl-1,3,2-dioxaborolan-2-yl) aniline (8.56 g, 23.1 mmol), $pd_2dba_3$ (1.06 g, 1.15 mmol), Xphos (1.10 g, 2.30 mmol), and NaOH (2.77 g, 69.1 mmol) were put into 1,4-dioxane/$H_2O$ (100 mL/30 mL), the resulting mixture was stirred at 120° C. for 2 hours. After the mixture was cooled to room temperature, the resulting solid was filtered. The filtered solid was filtered with silica gel to obtain Compound A46 (11.9 g, 80%).

The following compounds were synthesized in the same manner as in the preparation of Compound A46, except that (A), (B), and (C) were used as intermediates in Preparation Example 2.

TABLE 2

| Compound | (A) | (B) | (C) | Yield |
|---|---|---|---|---|
| A62 | 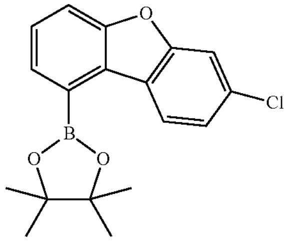 | 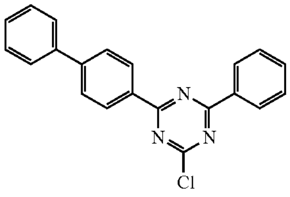 | 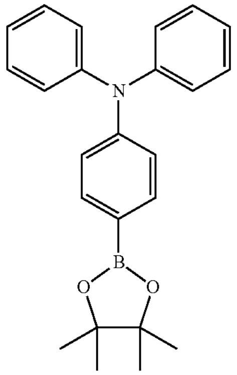 | 75% |
| A75 | 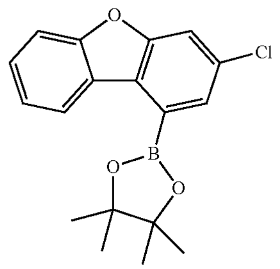 | 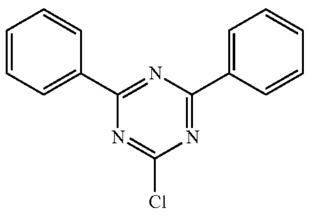 | 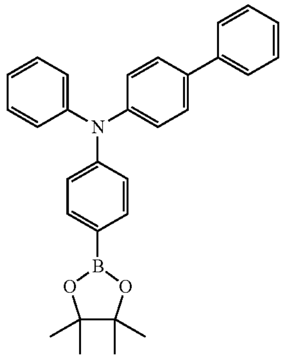 | 78% |

TABLE 2-continued
| Compound | (A) | (B) | (C) | Yield |
|---|---|---|---|---|
| A76 | 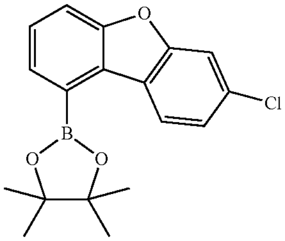 | 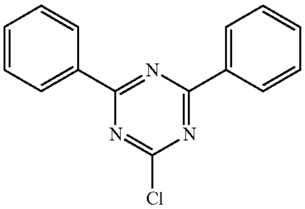 | 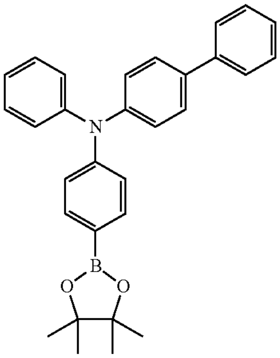 | 81% |
| A155 | 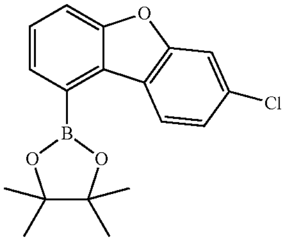 | 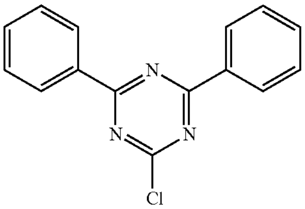 | 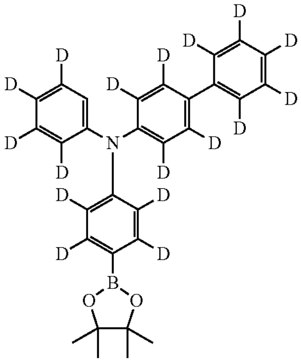 | 75% |
| A156 | 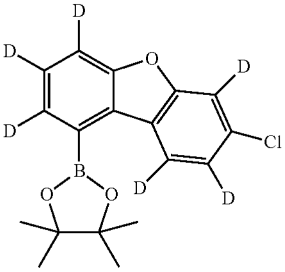 | 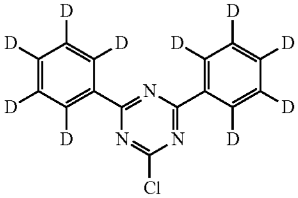 | 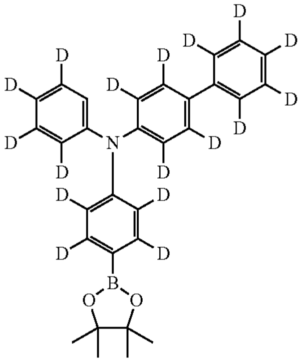 | 77% |
| B3 | 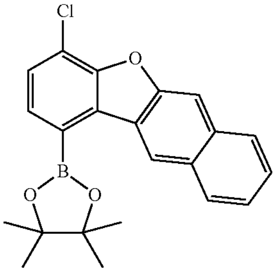 | 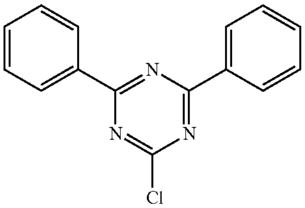 | 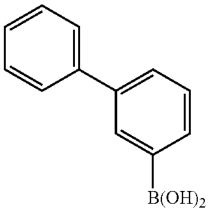 | 71% |

TABLE 2-continued
| Compound | (A) | (B) | (C) | Yield |
|---|---|---|---|---|
| B6 | 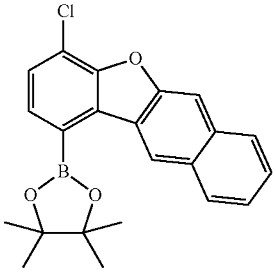 | 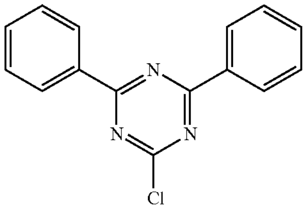 | 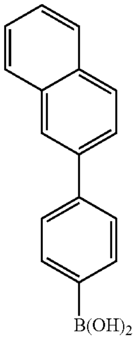 | 79% |
| B18 | 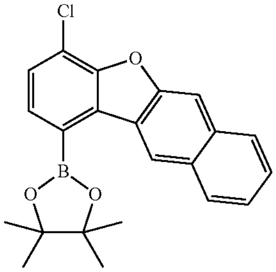 | 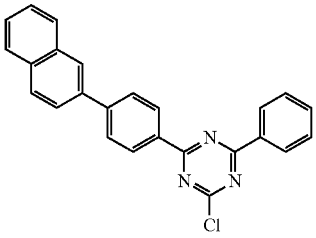 | 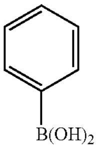 | 73% |
| B51 | 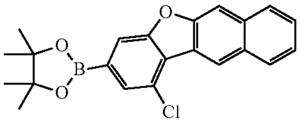 | 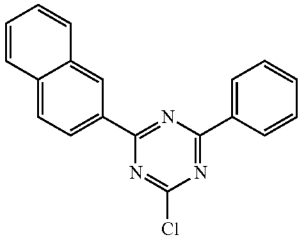 | 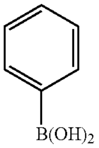 | 72% |
| B54 | 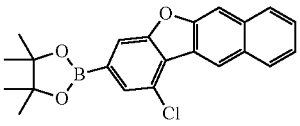 | 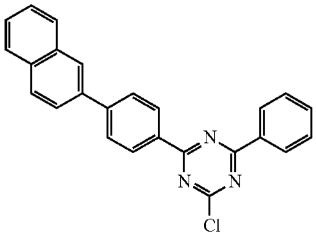 | 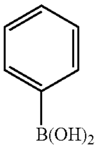 | 75% |
| B56 | 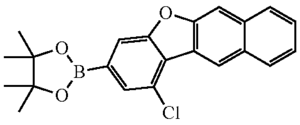 | 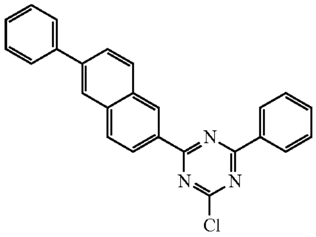 | 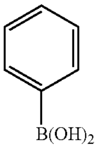 | 74% |

TABLE 2-continued
| Compound | (A) | (B) | (C) | Yield |
|---|---|---|---|---|
| B57 | 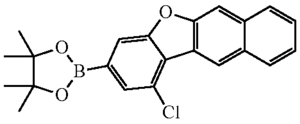 | 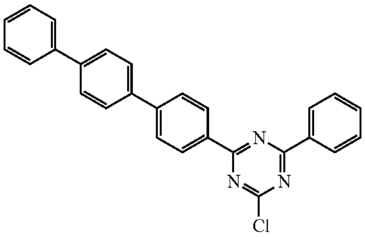 | 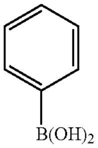 | 72% |
| B59 | 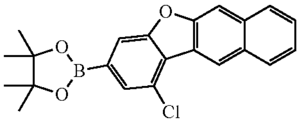 | 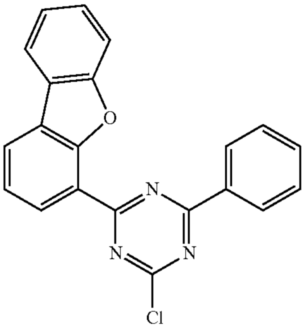 | 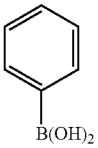 | 76% |
| B61 | 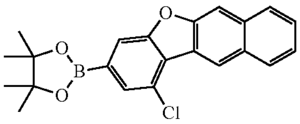 | 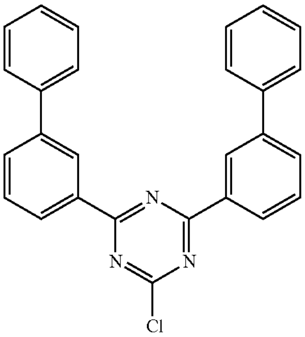 | 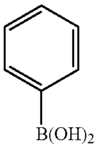 | 74% |
| B64 | 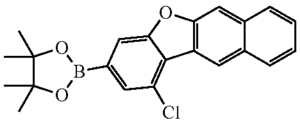 | 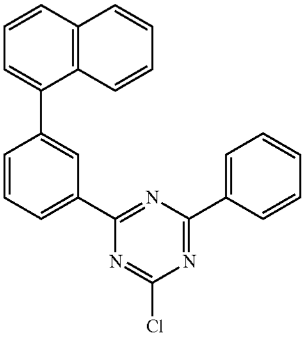 | 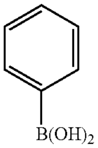 | 65% |
| B65 | 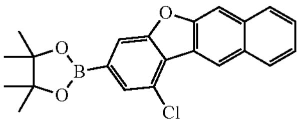 | 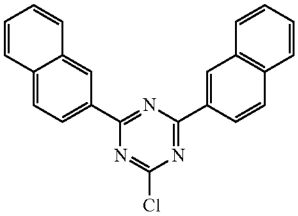 | 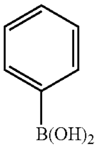 | 73% |

TABLE 2-continued
| Compound | (A) | (B) | (C) | Yield |
|---|---|---|---|---|
| B79 | 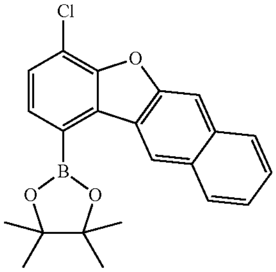 | 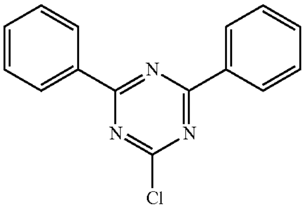 | 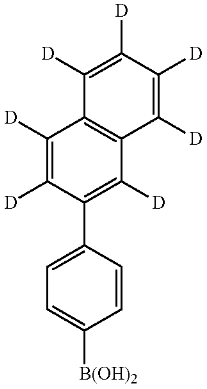 | 71% |
| B80 | 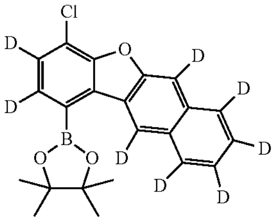 | 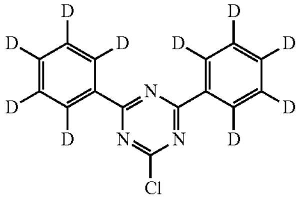 | 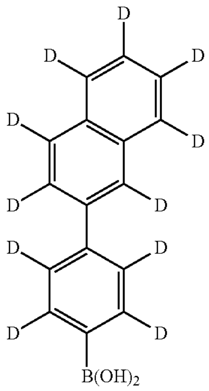 | 65% |
| B82 | 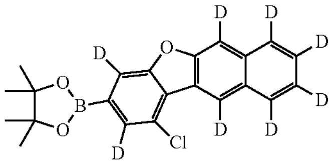 | 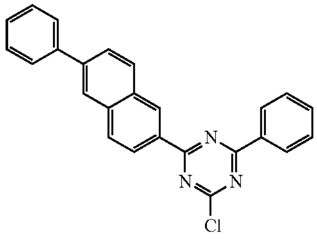 | 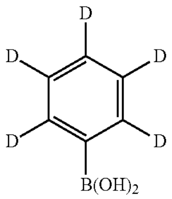 | 75% |
| B84 | 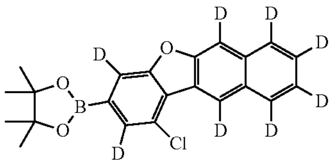 | 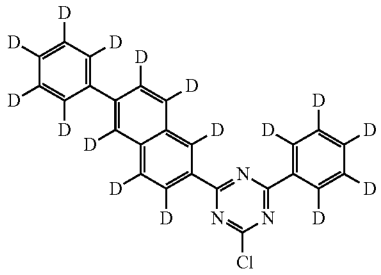 | 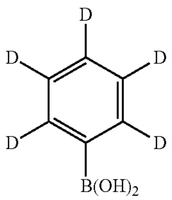 | 71% |

TABLE 2-continued
| Compound | (A) | (B) | (C) | Yield |
|---|---|---|---|---|
| C7 | 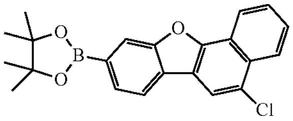 | 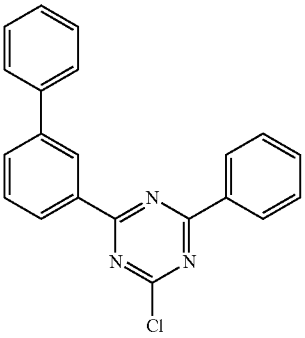 | 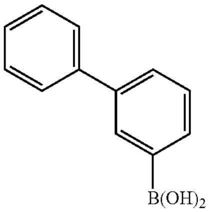 | 76% |
| C18 | 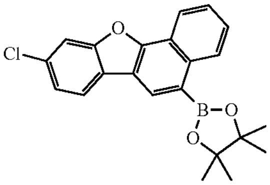 | 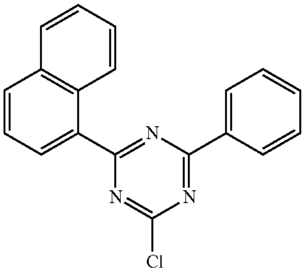 | 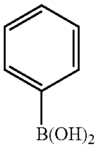 | 76% |
| C19 | 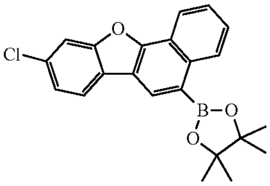 | 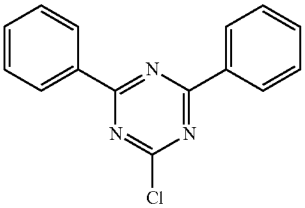 | 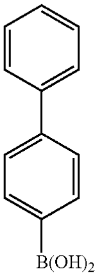 | 74% |
| C22 | 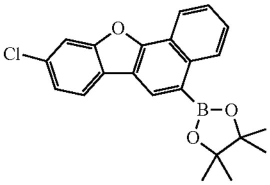 | 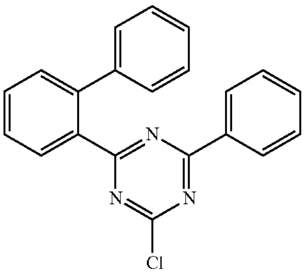 | 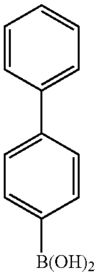 | 79% |
| C23 | 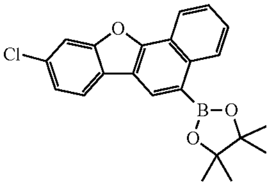 | 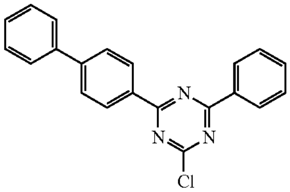 | 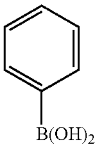 | 74% |

TABLE 2-continued
| Com-pound | (A) | (B) | (C) | Yield |
|---|---|---|---|---|
| C27 | 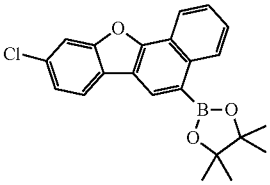 | 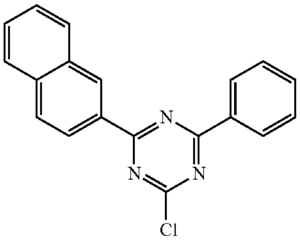 | 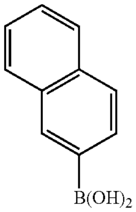 | 86% |
| C29 | 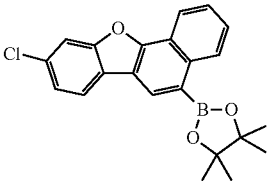 | 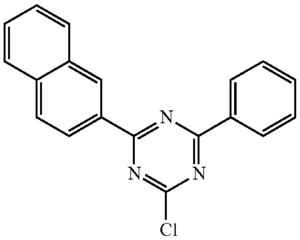 | 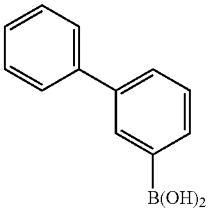 | 82% |
| C33 | 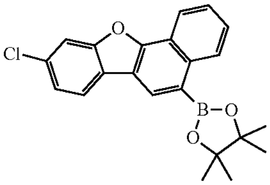 | 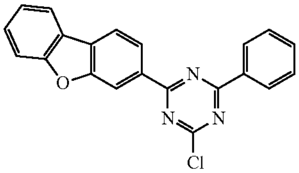 | 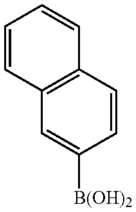 | 74% |
| C35 | 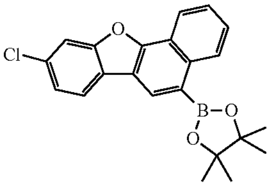 | 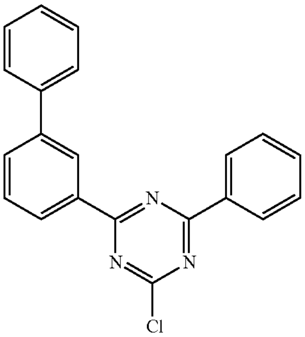 | 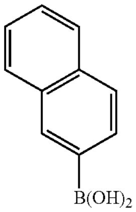 | 69% |
| C38 | 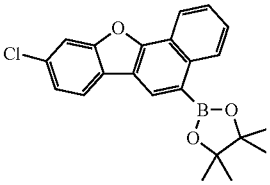 | 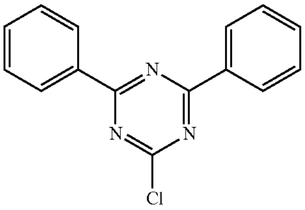 | 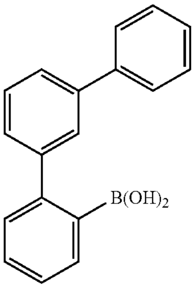 | 70% |

TABLE 2-continued
| Compound | (A) | (B) | (C) | Yield |
|---|---|---|---|---|
| C39 | 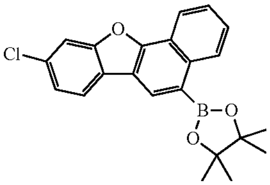 | 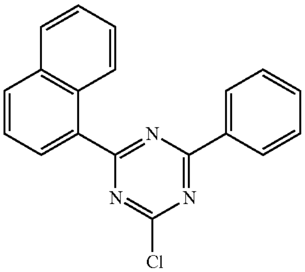 | 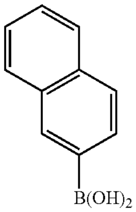 | 73% |
| C42 | 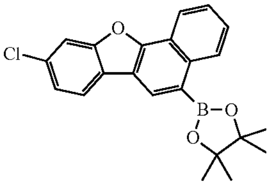 | 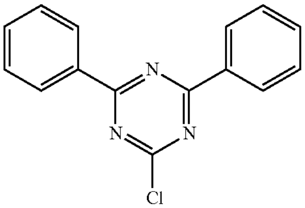 | 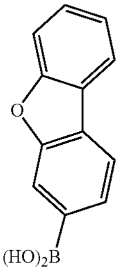 | 74% |
| C59 | 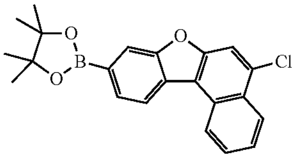 | 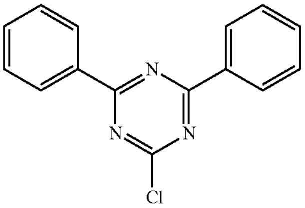 | 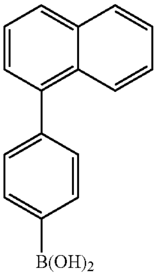 | 81% |
| C69 | 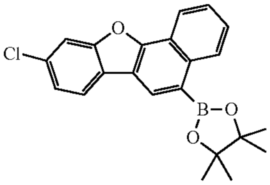 | 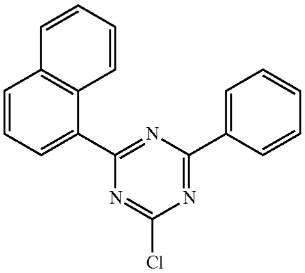 | 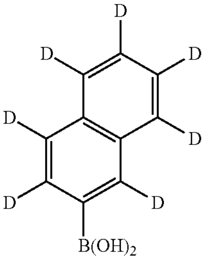 | 61% |
| C72 | 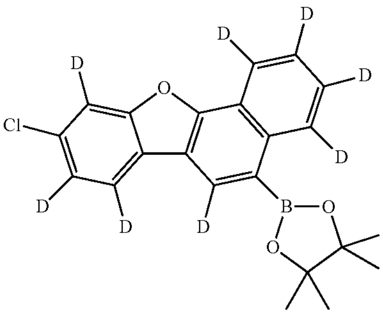 | 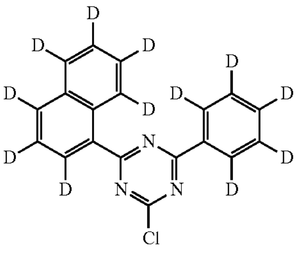 | 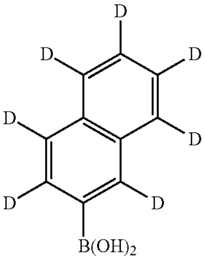 | 72% |

TABLE 2-continued

| Compound | (A) | (B) | (C) | Yield |
|---|---|---|---|---|
| C73 | 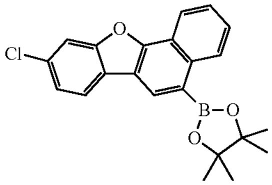 | 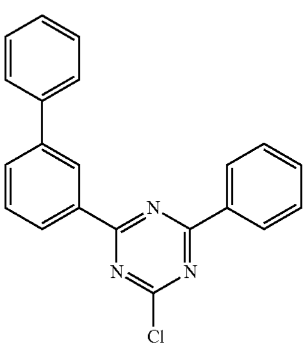 | 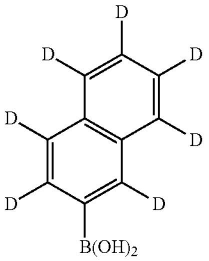 | 69% |
| C76 | 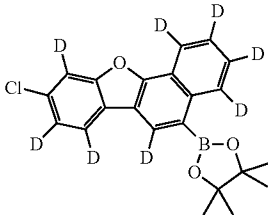 | 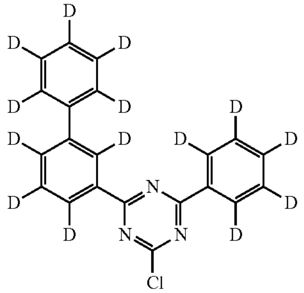 | 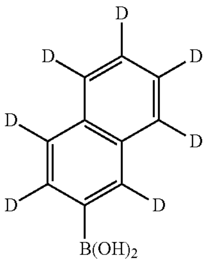 | 77% |

TABLE 3

| NO | $^1$H NMR ($CDCl_3$, 300 Mz) |
|---|---|
| A3 | 8.28 (4H, d), 7.75 (1H, d), 7.64 (1H, d), 7.62 (1H, d), 7.54 (2H, d), 7.52 (2H, d), 7.51 (6H, dd), 7.44 (1H, dd), 7.43 (1H, s), 7.41 (3H, t), 7.2 (2H, dd), 6.81 (1H, t), 6.69 (2H, d), 6.63 (3H, d) |
| A12 | 8.28 (2H, d), 7.85 (2H, d), 7.75 (1H, d), 7.64 (1H, d), 7.62 (1H, d), 7.54 (2H, d), 7.52 (4H, d), 7.51 (6H, dd), 7.44 (1H, dd), 7.43 (1H, s), 7.41 (3H, t), 7.25 (2H, d), 7.20 (2H, dd), 6.81 (1H, t), 6.69 (2H, d), 6.63 (3H, d) |
| A14 | 8.28 (2H, d), 7.89 (1H, d), 7.75 (2H, d), 7. 66 (1H, d), 7.64 (1H, d), 7.62 (2H, d), 7.54 ((2H, d), 7.52 (2H, d), 7.51 (4H, dd), 7.44 (2H, dd), 7.43 (1H, s), 7.41 (2H, t), 7.38 (1H, dd), 7.32 (1H, dd), 7.20 (2H, dd), 6.81 (1H, t), 6.69 (2H, d), 6.63 (2H, d), 6.33 (1H, d) |
| A15 | 9.09 (1H, s), 8.49 (1H, d), 8 (2H, d), 7.92 (1H, d), 7.89 (1H, d), 7.75 (2H, d), 7.66 (1H, d), 7.64 (1H, d), 7.62 (2H, d), 7.59 (2H, dd), 7.54 (2H, d), 7.52 (2H, d), 7.51 (2H, dd), 7.44 (2H, dd), 7.43 (1H, s), 7.41 (1H, t), 7.38 (1H, t), 7.32 (1H, dd), 7.2 (2H, dd), 6.81 (1H, t), 6.69 (2H, d), 6.63 (2H, d), 6.33 (1H, d) |
| A21 | 8.28 (4H, d), 7.75 (1H, d), 7.64 (1H, s), 7.62 (1H, d), 7.54 (4H, d), 7.52 (4H, d), 7.51 (8H, dd), 7.44 (1H, dd), 7.43 (1H, s), 7.41 (4H, t), 6.69 (4H, d), 6.33 (1H, d) |
| A27 | 8.28 (4H, d), 7.89 (1H, d), 7.75 (1H, d), 7.66 (1H, d), 7.64 (2H, d), 7.62 (1H, d), 7.54 (2H, d), 7.52 (2H, d), 7.51 (6H, dd), 7.44 (1H, dd), 7.43 (2H, d), 7.41 (3H, t), 7.38 (1H, dd), 7.32 (1H, dd), 6.69 (2H, d), 6.33 (2H, d) |
| A28 | 8.28 (4H, d), 7.89 (1H, d), 7.75 (1H, d), 7.66 (1H, d), 7.65 (1H, s), 7.64 (1H, d), 7.62 (1H, d), 7.54 (2H, d), 7.52 (2H, d), 7.51 (6H, dd), 7.44 (1H, dd), 7.43 (1H, s), 7.41 (4H, t), 7.38 (1H, dd), 7.32 (1H, dd), 6.69 (2H, d), 6.39 (1H, dd), 6.33 (1H, d) |

TABLE 3-continued

| NO | $^1$H NMR ($CDCl_3$, 300 Mz) |
|---|---|
| A29 | 8.28 (4H, d), 7.89 (1H, d), 7.75 (1H, d), 7.66 (1H, d), 7.64 (1H, d), 7.62 (1H, d), 7.54 (2H, d), 7.52 (2H, d), 7.51 (6H, dd), 7.44 (1H, dd), 7.43 (1H, s), 7.41 (3H, t), 7.38 (1H, dd), 7.32 (1H, dd), 7.13 (1H, dd), 7.02 (1H, d), 6.69 (2H, d), 6.33 (2H, d) |
| A32 | 8.28 (4H, d), 7.89 (2H, d), 7.75 (1H, d), 7.66 (2H, d), 7.64 (3H, d), 7.62 (1H, d), 7.51 (4H, dd), 7.44 (1H, dd), 7.43 (3H, s), 7.41 (2H, t), 7.38 (2H, dd), 7.32 (2H, dd), 6.33 (3H, d) |
| A34 | 8.28 (4H, d), 7.89 (1H, d), 7.75 (1H, d), 7.66 (1H, d), 7.65 (1H, s), 7.64 (1H, d), 7.62 (1H, d), 7.52 (2H, d), 7.51 (6H, dd), 7.44 (2H, dd), 7.43 (1H, s), 7.41 (4H, t), 7.38 (1H, dd), 7.32 (1H, dd), 6.89 (1H, d), 6.88 (1H, d), 6.59 (1H, d), 6.39 (1H, d), 6.33 (1H, d) |
| A36 | 8.28 (4H, d), 7.89 (1H, d), 7.75 (2H, d), 7.66 (1H, d), 7.64 (1H, d), 7.62 (2H, d), 7.54 (2H, d), 7.51 (4H, dd), 7.44 (2H, dd), 7.43 (1H, s), 7.41 (2H, t), 7.38 (1H, dd), 7.32 (1H, dd), 7.2 (2H, dd), 6.81 (1H, t), 6.69 (2H, d), 6.63 (3H, d) |
| A46 | 8.28 (4H, d), 7.95 (1H, d), 7.75 (2H, d), 7.64 (1H, s), 7.62 (1H, d), 7.54 (2H, d), 7.51 (4H, dd), 7.44 (1H, dd), 7.41 (2H, t), 7.2 (4H, dd), 6.81 (2H, dd), 6.69 (2H, d), 6.63 (4H, d) |
| A58 | 8.28 (4H, d), 8.24 (1H, d), 7.75 (1H, d), 7.7 (1H, s), 7.64 (1H, d), 7.62 (1H, d), 7.57 (1H, dd), 7.54 (2H, d), 7.52 (2H, d), 7.51 (6H, dd), 7.48 (1H, d), 7.44 (1H, dd), 7.43 (1H, s), 7.41 (3H, t), 7.2 (2H, dd), 6.81 (1H, t), 6.69 (2H, d), 6.63 (3H, d) |
| A62 | 8.28 (2H, d), 7.95 (1H, d), 7.85 (2H, d), 7.75 (2H, d), 7.64 (1H, s), 7.62 (1H, d), 7.54 (2H, d), 7.52 (2H, d), 7.51 (4H, dd), 7.44 (1H, dd), 7.41 (2H, t), 7.25 (2H, d), 7.2 (4H, dd), 6.81 (2H, t), 6.69 (2H, d), 6.63 (4H, d) |
| A75 | 8.28 (4H, d), 7.89 (1H, d), 7.66 (1H, d), 7.6 (1H, s), 7.57 (1H, s), 7.54 (4H, d), 7.52 (2H, d), 7.51 (6H, dd), 7.41 (3H, t), 7.38 (1H, dd), 7.32 (1H, dd), 7.2 (2H, dd), 6.81 (1H, t), 6.69 (4H, d), 6.63 (2H, d) |

TABLE 3-continued

| NO | $^1$H NMR ($CDCl_3$, 300 Mz) |
|---|---|
| A76 | 8.28 (4H, d), 7.95 (1H, d), 7.75 (2H, d), 7.64 (1H, s), 7.62 (1H, d), 7.54 (4H, d), 7.52 (2H, d), 7.51 (6H, dd), 7.44 (1H, dd), 7.41 (3H, t), 7.2 (2H, dd), 6.81 (1H, t), 6.69 (4H, d), 6.63 (2H, d) |
| A99 | 8.55 (1H, d), 8.28 (4H, d), 8.18 (1H, d), 7.71 (1H, s), 7.64 (1H, d), 7.55 (2H, dd), 7.54 (2H, d), 7.52 (2H, d), 7.51 (6H, dd), 7.43 (1H, s), 7.41 (3H, t), 7.2 (2H, dd), 6.81 (1H, t), 6.69 (2H, d), 6.63 (2H, d), 6.33 (1H, d) |
| A102 | 8.28 (4H, d), 8.16 (2H, d), 7.67 (2H, dd), 7.54 (2H, d), 7.52 (2H, d), 7.51 (7H, dd), 7.49 (1H, s), 7.42 (1H, s), 7.41 (3H, t), 7.2 (2H, dd), 7 (1H, s), 6.81 (1H, t), 6.69 (2H, d), 6.63 (2H, d) |
| A135 | 8.28 (4H, d), 7.75 (1H, d), 7.7 (1H, s), 7.64 (1H, d), 7.62 (1H, d), 7.57 (1H, dd), 7.54 (3H, d), 7.52 (4H, d), 7.51 (8H, dd), 7.48 (2H, d), 7.44 (1H, dd), 7.43 (1H, s), 7.41 (4H, t), 7.16 (1H, dd), 6.87 (1H, dd), 6.69 (3H, d), 6.33 (1H, d) |
| A155 | 8.28 (4H, d), 7.95 (1H, d), 7.75 (2H, d), 7.64 (1H, s), 7.62 (1H, d), 7.51 (4H, dd), 7.44 (1H, dd), 7.41 (2H, t) |
| A159 | 8.28 (4H, d), 7.75 (1H, d), 7.64 (1H, d), 7.62 (1H, d), 7.51 (4H, dd), 7.44 (1H, dd), 7.43 (1H, s), 7.41 (2H, t), 6.33 (1H, d) |
| B3 | 8.28 (4H, d), 8.16 (2H, d), 7.87 (1H, d), 7.81 (1H, d), 7.7 (1H, s), 7.67 (2H, dd), 7.57 (1H, dd), 7.52 (2H, d), 7.51 (6H, dd), 7.49 (1H, s), 7.48 (2H, d), 7.42 (1H, s), 7.41 (3H, t) |
| B6 | 8.28 (4H, d), 8.16 (2H, d), 8 (2H, d), 7.92 (1H, d), 7.87 (1H, d), 7.81 (1H, d), 7.73 (1H, d), 7.67 (2H, dd), 7.59 (2H, dd), 7.58 (1H, s), 7.51 (4H, dd), 7.49 (1H, s), 7.42 (1H, s), 7.41 (2H, t), 7.25 (4H, d) |
| B18 | 8.28 (2H, d), 8.16 (2H, d), 8 (2H, d), 7.92 (1H, d), 7.87 (1H, d), 7.85 (2H, d), 7.81 (1H, d), 7.73 (1H, d), 7.67 (2H, dd), 7.59 (2H, dd), 7.58 (1H, s), 7.52 (2H, d), 7.51 (4H, dd), 7.49 (1H, s), 7.42 (1H, s), 7.41 (2H, t), 7.25 (2H, d) |
| B51 | 9.09 (1H, s), 8.49 (1H, d), 8.28 (2H, d), 8.16 (2H, d), 8 (2H, d), 7.92 (1H, d), 7.79 (2H, d), 7.67 (2H, dd), 7.6 (1H, s), 7.59 (2H, dd), 7.57 (1H, s), 7.51 (4H, dd), 7.49 (1H, s), 7.42 (1H, s), 7.41 (2H, t) |
| B54 | 8.28 (2H, d), 8.16 (2H, d), 8 (2H, d), 7.92 (1H, d), 7.85 (2H, d), 7.79 (2H, d), 7.73 (1H, d), 7.67 (2H, dd), 7.6 (1H, s), 7.59 (2H, dd), 7.58 (1H, d), 7.57 (1H, s), 7.51 (4H, dd), 7.49 (1H, s), 7.42 (1H, s), 7.41 (2H, t), 7.25 (2H, d) |
| B56 | 9.09 (1H, s), 8.49 (1H, d), 8.28 (2H, d), 8.16 (2H, d), 7.92 (2H, d), 7.79 (2H, dd), 7.73 (1H, d), 7.67 (2H, dd), 7.6 (1H, s), 7.58 (1H, s), 7.57 (1H, s), 7.52 (2H, d), 7.51 (6H, dd), 7.49 (1H, s), 7.42 (1H, s), 7.41 (3H, t) |
| B57 | 8.28 (2H, d), 8.16 (2H, d), 7.85 (2H, d), 7.79 (2H, d), 7.67 (2H, dd), 7.6 (1H, s), 7.57 (1H, s), 7.52 (2H, d), 7.51 (6H, dd), 7.49 (1H, s), 7.42 (1H, s), 7.41 (3H, t), 7.25 (6H, d) |
| B59 | 8.28 (2H, d), 8.16 (2H, d), 7.89 (1H, d), 7.85 (1H, d), 7.81 (1H, d), 7.79 (2H, d), 7.67 (2H, dd), 7.66 (1H, d), 7.6 (1H, s), 7.57 (1H, s), 7.51 (4H, dd), 7.49 (1H, s), 7.42 (1H, s), 7.41 (2H, t), 7.38 (2H, dd), 7.32 (1H, dd), |
| B61 | 8.24 (2H, d), 8.16 (2H, d), 7.79 (2H, d), 7.7 (2H, s), 7.67 (2H, dd), 7.6 (1H, s), 7.57 (3H, s), 7.52 (4H, d), 7.51 (6H, dd), 7.49 (1H, s), 7.48 (2H, d), 7.42 (1H, s), 7.41 (3H, t) |
| B64 | 8.55 (1H, d), 8.42 (1H, d), 8.28 (2H, d), 8.24 (1H, d), 8.16 (2H, d), 8.08 (1H, d), 8.04 (1H, d), 7.79 (2H, d), 7.7 (1H, s), 7.67 (2H, dd), 7.61 (1H, dd), 7.6 (1H, s), 7.57 (2H, s), 7.55 (2H, dd), 7.51 (4H, dd), 7.49 (1H, s), 7.48 (1H, d), 7.42 (1H, s), 7.41 (2H, t) |
| B65 | 9.09 (2H, s), 8.49 (2H, d), 8.16 (2H, d), 8 (4H, d), 7.92 (2H, d), 7.79 (2H, d), 7.67 (2H, dd), 7.6 (1H, s), 7.59 (4H, dd), 7.57 (1H, s), 7.51 (2H, dd), 7.49 (1H, s), 7.42 (1H, s), 7.41 (1H, t) |
| B79 | 8.28 (4H, d), 8.16 (2H, d), 7.87 (1H, d), 7.81 (1H, d), 7.67 (2H, dd), 7.51 (4H, dd), 7.49 (1H, s), 7.42 (1H, s), 7.41 (2H, t) |

TABLE 3-continued

| NO | $^1$H NMR ($CDCl_3$, 300 Mz) |
|---|---|
| B82 | 9.09 (1H, s), 8.49 (1H, d), 8.35 (2H, d), 7.98 (1H, dd), 7.91 (1H, ddd), 7.75 (2H, ddd), 7.55-7.37 (8H, m) |
| C7 | 8.55 (1H, d), 8.28 (2H, d), 8.24 (1H, d), 8.18 (1H, d), 7.95 (1H, d), 7.75 (1H, d), 7.71 (1H, s), 7.7 (2H, s), 7.64 (1H, s), 7.57 (2H, dd), 7.55 (2H, dd), 7.52 (4H, d), 7.51 (6H, dd), 7.48 (3H, d), 7.41 (3H, t) |
| C18 | 8.55 (2H, d), 8.28 (2H, d), 8.18 (1H, d), 8.08 (1H, d), 8.04 (1H, d), 7.95 (2H, d), 7.75 (1H, d), 7.71 (1H, s), 7.64 (1H, s), 7.61 (1H, d), 7.55 (4H, dd), 7.52 (2H, d), 7.51 (4H, dd), 7.41 (2H, t) |
| C19 | 8.55 (1H, d), 8.28 (4H, d), 8.18 (1H, d), 7.95 (1H, d), 7.75 (1H, d), 7.71 (1H, s), 7.64 (1H, s), 7.55 (2H, dd), 7.52 (2H, d), 7.51 (6H, dd), 7.41 (3H, t), 7.25 (4H, d) |
| C22 | 8.55 (1H, d), 8.28 (2H, d), 8.18 (1H, d), 7.95 (1H, d), 7.85 (2H, d), 7.79 (2H, d), 7.75 (1H, d), 7.71 (1H, s), 7.64 (1H, s), 7.55 (2H, dd), 7.52 (2H, d), 7.51 (6H, dd), 7.47 (2H, dd), 7.41 (3H, t), 7.25 (4H, d) |
| C23 | 8.55 (1H, d), 8.28 (2H, d), 8.18 (1H, d), 7.95 (1H, d), 7.85 (2H, d), 7.75 (1H, d), 7.71 (1H, s), 7.64 (1H, s), 7.55 (2H, dd), 7.52 (4H, d), 7.51 (6H, dd), 7.41 (3H, t), 7.25 (2H, d) |
| C27 | 9.09 (1H, s), 8.55 (1H, d), 8.49 (1H, d), 8.28 (2H, d), 8.18 (1H, d), 8 (4H, d), 7.95 (1H, d), 7.92 (2H, d), 7.75 (1H, d), 7.73 (1H, d), 7.71 (1H, s), 7.64 (1H, s), 7.59 (4H, dd), 7.58 (1H, s), 7.55 (2H, dd), 7.51 (2H, dd), 7.41 (1H, t) |
| C29 | 9.09 (1H, d), 8.55 (1H, d), 8.49 (1H, d), 8.28 (2H, d), 8.18 (1H, d), 8 (2H, d), 7.95 (1H, d), 7.92 (1H, d), 7.75 (1H, d), 7.71 (1H, s), 7.7 (1H, s), 7.64 (1H, s), 7.59 (2H, dd), 7.57 (1H, dd), 7.55 (2H, dd), 7.52 (2H, d), 7.51 (4H, dd), 7.48 (2H, d), 7.41 (2H, t) |
| C33 | 8.55 (1H, d), 8.28 (2H, d), 8.18 (1H, d), 8 (2H, d), 7.95 (2H, d), 7.92 (1H, d), 7.89 (1H, d), 7.75 (2H, dd), 7.73 (1H, d), 7.71 (1H, s), 7.66 (1H, d), 7.64 (2H, s), 7.59 (2H, dd), 7.58 (1H, s), 7.55 (2H, dd), 7.51 (2H, dd), 7.41 (1H, t), 7.38 (1H, dd), 7.32 (1H, dd) |
| C35 | 8.55 (1H, d), 8.28 (2H, d), 8.24 (1H, d), 8.18 (1H, d), 8 (2H, d), 7.95 (1H, d), 7.92 (1H, d), 7.75 (1H, d), 7.73 (1H, d), 7.71 (1H, s), 7.7 (1H, s), 7.64 (1H, s), 7.59 (2H, dd), 7.58 (1H, s), 7.57 (1H, dd), 7.55 (2H, dd), 7.52 (2H, d), 7.51 (4H, dd), 7.48 (1H, d), 7.41 (2H, t) |
| C38 | 8.55 (1H, d), 8.28 (4H, d), 8.18 (1H, d), 7.95 (1H, d), 7.85 (2H, d), 7.75 (1H, s), 7.71 (1H, s), 7.7 (1H, d), 7.64 (1H, s), 7.57 (1H, dd), 7.55 (2H, dd), 7.52 (2H, d), 7.51 (6H, dd), 7.48 (2H, d), 7.47 (2H, dd), 7.41 (3H, t) |
| C39 | 8.55 (2H, d), 8.28 (2H, d), 8.18 (1H, d), 8.08 (1H, d), 8.04 (1H, d), 8 (2H, d), 7.95 (2H, d), 7.92 (1H, d), 7.75 (1H, d), 7.73 (1H, d), 7.71 (1H, s), 7.64 (1H, s), 7.61 (1H, dd), 7.59 (2H, dd), 7.58 (1H, s), 7.55 (4H, dd), 7.51 (2H, dd), 7.41 (1H, t) |
| C42 | 8.55 (1H, d), 8.28 (4H, d), 8.18 (1H, d), 7.95 (2H, d), 7.89 (1H, d), 7.75 (2H, d), 7.71 (1H, s), 7.66 (1H, d), 7.64 (2H, s), 7.55 (2H, dd), 7.51 (4H, dd), 7.41 (2H, t), 7.38 (1H, dd), 7.32 (1H, dd) |
| C59 | 8.55 (3H, d), 8.42 (1H, d), 8.28 (4H, d), 8.08 (1H, d), 8.04 (1H, d), 7.95 (1H, d), 7.75 (1H, d), 7.64 (2H, s), 7.61 (1H, dd), 7.55 (4H, dd), 7.51 (4H, dd), 7.41 (2H, t), 7.25 (4H, d) |
| C69 | 8.55 (2H, d), 8.28 (2H, d), 8.18 (1H, d), 8.08 (1H, d), 8.04 (1H, d), 7.95 (2H, d), 7.75 (1H, d), 7.71 (1H, s), 7.64 (1H, s), 7.61 (1H, dd), 7.55 (4H, dd), 7.51 (2H, dd), 7.41 (1H, t) |
| C73 | 8.55 (1H, d), 8.28 (2H, d), 8.24 (1H, d), 8.18 (1H, d), 7.95 (1H, d), 7.75 (1H, d), 7.71 (1H, s), 7.7 (1H, s), 7.64 (1H, s), 7.57 (1H, dd), 7.55 (2H, dd), 7.52 (2H, d), 7.51 (4H, dd), 7.48 (1H, d), 7.41 (2H, t) |

TABLE 4

| Compound | FD-MS | Compound | FD-MS |
|---|---|---|---|
| A3 | m/z = 642.24 (C45H30N4O, 642.75) | B57 | m/z = 677.25 (C49H31N3O, 677.79) |
| A12 | m/z = 718.27 (C51H34N4O, 718.84) | B56 | m/z = 651.23 (C47H29N3O, 651.75) |
| A14 | m/z = 732.25 (C51H32N4O2, 732.83) | B59 | m/z = 615.19 C43H25N3O2, 615.68) |
| A15 | m/z = 782.27 (C55H34N4O2, 782.88) | B61 | m/z = 677.25 (C49H31N3O, 677.79) |
| A21 | m/z = 718.27 (C51H34N4O, 718.84) | B64 | m/z = 651.23 (C47H29N3O, 651.75) |
| A27 | m/z = 732.25 (C51H32N4O2, 732.83) | B65 | m/z = 625.22 (C45H27N3O, 625.72) |
| A28 | m/z = 732.25 (C51H32N4O2, 732.83) | B79 | m/z = 662.30 (C47H18D11N3O, 662.82) |
| A29 | m/z = 732.25 (C51H32N4O2, 732.83) | B80 | m/z = 680.41 (C47D29N3O, 680.93) |
| A32 | m/z = 746.23 (C51H30N4O3, 746.81) | B82 | m/z = 664.31 (C47H16D13N3O, 664.85) |
| A34 | m/z = 732.25 (C51H32N4O2, 732.83) | B84 | m/z = 680.41 (C47D29N3O, 680.93) |
| A36 | m/z = 732.25 (C51H32N4O2, 732.83) | C7 | m/z = 677.25 (C49H31N3O, 677.79) |
| A46 | m/z = 642.24 (C45H30N4O, 642.75) | C18 | m/z = 575.20 (C41H25N3O, 575.66) |
| A58 | m/z = 718.27 (C51H34N4O, 718.84) | C19 | m/z = 601.22 (C43H27N3O, 601.69) |
| A62 | m/z = 718.27 (C51H34N4O, 718.84) | C22 | m/z = 677.25 (C49H31N3O, 677.79) |
| A75 | m/z = 718.27 (C51H34N4O, 718.84) | C23 | m/z = 601.22 (C43H27N3O, 601.69) |
| A76 | m/z = 718.27 (C51H34N4O, 718.84) | C27 | m/z = 625.22 (C45H27N3O, 625.72) |
| A99 | m/z = 692.26 (C49H32N4O, 692.80) | C29 | m/z = 651.23 (C47H29N3O, 651.75) |
| A102 | m/z = 692.26 (C49H32N4O, 692.80) | C33 | m/z = 665.21 (C47H27N3O2, 665.74) |
| A135 | m/z = 794.30 (C57H38N4O, 794.94) | C35 | m/z = 651.23 (C47H29N3O, 651.75) |
| A155 | m/z = 736.39 (C51H16D18N4O, 736.95) | C38 | m/z = 677.25 (C49H31N3O, 677.79) |
| A156 | m/z = 752.49 (C51D34N4O, 753.05) | C39 | m/z = 625.22 (C45H27N3O, 625.72) |
| A159 | m/z = 748.35 (C51H16D16N4O2, 748.92) | C42 | m/z = 615.19 (C43H25N3O2, 615.68) |
| A160 | m/z = 764.45 (C51D32N4O2, 765.02) | C59 | m/z = 651.23 (C47H29N3O, 651.75) |
| B3 | m/z = 601.22 (C43H27N3O, 601.69) | C69 | m/z = 632.26 (C45H20D7N3O, 632.76) |
| B6 | m/z = 651.23 (C47H29N3O, 651.75) | C72 | m/z = 652.38 (C45D27N3O, 652.88) |
| B18 | m/z = 651.23 (C47H29N3O, 651.75) | C73 | m/z = 658.27 (C47H22D7N3O, 658.80) |
| B51 | m/z = 575.20 (C41H25N3O, 575.66) | C76 | m/z = 680.41 (C47D29N3O, 680.93) |
| B54 | m/z = 651.23 (C47H29N3O, 651.75) | | |

EXPERIMENTAL EXAMPLES

[Experimental Example 1] Manufacture of Organic Light Emitting Device

1) Manufacture of Organic Light Emitting Device

A glass substrate, in which indium tin oxide (ITO) was thinly coated to have a thickness of 1,500 Å, was ultrasonically washed with distilled water. When the washing with distilled water was finished, the glass substrate was ultrasonically washed with a solvent such as acetone, methanol, and isopropyl alcohol, dried and then subjected to ultraviolet ozone (UVO) treatment for 5 minutes using UV in an ultraviolet (I) washing machine. Thereafter, the substrate was transferred to a plasma washing machine (PT), and then was subjected to plasma treatment in a vacuum state for an ITO work function and in order to remove a residual film, and was transferred to a thermal deposition apparatus for organic deposition.

The hole injection layer 4,4',4"-tris[2-naphthyl(phenyl) amino] triphenylamine (2-TNATA) and the hole transport layer N,N'-diphenyl-(1,1'-biphenyl)-4,4'-diamine (NPB), which are common layers, were formed on the ITO transparent electrode (positive electrode).

A light emitting layer was thermally vacuum deposited thereon as follows. Specifically, the compounds described in Examples A3 to C73 of the following Tables 1 and 2 were used as the red host of the light emitting layer, and a light emitting layer having a thickness of 500 Å was deposited by doping the red host with a red phosphorescent dopant $(piq)_2(Ir)$ (acac) in an amount of 3 wt %. Thereafter, bathocuproine (hereinafter, referred to as BCP) as a hole blocking layer was deposited to have a thickness of 60 Å, and $Alq_3$ as an electron transport layer was deposited to have a thickness of 200 Å thereon.

Finally, an organic light emitting device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

2) Driving Voltage and Light Emitting Efficiency of Organic Light Emitting Device For the organic light emitting devices of Examples A3 to C 73 in Tables 1 and 2 manufactured as above, electroluminescent (EL) characteristics were measured using M7000 manufactured by McScience Inc., and with the measurement results, T90 when the standard luminance was 6,000 cd/$m^2$ was measured using a service life measurement apparatus (M6000) manufactured by McScience Inc. $T_{90}$ means the service life (unit: hour) of the device measured at the time when the luminance reaches 90% relative to the initial luminance.

The measured characteristics of the organic light emitting device are shown in the following Table 5.

TABLE 5

| No. | Composition | Ratio (A:B:C) | Threshold voltage ($V_{on}$) | Driving voltage ($V_{op}$) | efficiency (cd/A) | Color coordinate (x, y) | Service life ($T_{90}$) |
|---|---|---|---|---|---|---|---|
| Comparative Example 1 | A75:B6 | 2:1 | 2.79 | 3.76 | 24.2 | (0.672, 0.327) | 45 |
| Comparative Example 2 | A75:B6 | 1.5:1.5 | 2.76 | 3.71 | 23.1 | (0.673, 0.326) | 49 |
| Comparative Example 3 | A76:C27 | 2:1 | 2.84 | 4.25 | 25.7 | (0.678, 0.322) | 39 |
| Comparative Example 4 | A76:C27 | 1.5; 1.5 | 2.80 | 4.19 | 24.2 | (0.677, 0.320) | 41 |
| Comparative Example 5 | B6:C27 | 2:1 | 2.81 | 3.92 | 15.5 | (0.682, 0.317) | 62 |
| Comparative Example 6 | B6:C27 | 1.5; 1.5 | 2.77 | 3.86 | 16.7 | (0.681, 0.317) | 48 |
| Comparative Example 7 | A75:B6:E | 2:1:1 | 3.79 | 4.37 | 18.2 | (0.682, 0.317) | 25 |
| Comparative Example 8 | A76:C27: D | 2:1:1 | 3.95 | 4.54 | 19.5 | (0.677, 0.323) | 20 |
| Comparative Example 9 | A75:B6: C23 | 2:1:3 | 3.28 | 4.35 | 32.7. | (0.681, 0.317) | 31 |

TABLE 5-continued

| No. | Composition | Ratio (A:B:C) | Threshold voltage ($V_{on}$) | Driving voltage ($V_{op}$) | efficiency (cd/A) | Color coordinate (x, y) | Service life ($T_{90}$) |
|---|---|---|---|---|---|---|---|
| Example 1 | A75:B6: C23 | 2:1:1 | 2.56 | 3.74 | 57.6 | (0.681, 0.319) | 103 |
| Example 2 | | 1.5:1.5:1 | 2.54 | 3.70 | 55.1 | (0.677, 0.321) | 124 |
| Example 3 | A76:B56: C39 | 2:1:1 | 2.38 | 3.39 | 76.7 | (0.678, 0.321) | 220 |
| Example 4 | | 1.5:1.5:1 | 2.35 | 3.34 | 72.9 | (0.678, 0.322) | 253 |
| Example 5 | A3:B3: C18 | 2:1:1 | 2.45 | 3.52 | 62.6. | (0.680, 0.319) | 167 |
| Example 6 | | 1.5:1.5:1 | 2.41 | 3.48 | 60.5 | (0.677, 0.321) | 179 |
| Example 7 | A3:B51: C18 | 2:1:1 | 2.46 | 3.56 | 60.9 | (0.679, 0.321) | 171 |
| Example 8 | | 1.5:1.5:1 | 2.43 | 3.51 | 57.2 | (0.681, 0.318) | 186 |
| Example 9 | A29:B64: C19 | 2:1:1 | 2.43 | 3.49 | 61.2 | (0.680, 0.319) | 159 |
| Example 10 | | 1.5:1.5:1 | 2.41 | 3.45 | 60.1 | (0.682, 0.317) | 173 |
| Example 11 | A34:B61: C22 | 2:1:1 | 2.45 | 3.52 | 65.2 | (0.681, 0.318) | 165 |
| Example 12 | | 1.5:1.5:1 | 2.42 | 3.48 | 63.5 | (0.676, 0.324) | 171 |
| Example 13 | A36:B61: C22 | 2:1:1 | 2.48 | 3.59 | 63.2 | (0.679, 0.321) | 181 |
| Example 14 | | 1.5:1.5:1 | 2.43 | 3.54 | 61.9 | (0.683, 0.317) | 196 |
| Example 15 | A21:B65: C29 | 2:1:1 | 2.35 | 3.42 | 62.5 | (0.686, 0.313) | 186 |
| Example 16 | | 1.5:1.5:1 | 2.33 | 3.39 | 61.8 | (0.682, 0.317) | 194 |
| Example 17 | A159:B65: C29 | 2:1:1 | 2.39 | 3.45 | 68.2 | (0.687, 0.313) | 203 |
| Example 18 | | 1.5:1.5:1 | 2.36 | 3.41 | 67.5 | (0.681, 0.316) | 216 |
| Example 19 | A14:B59: C42 | 2:1:1 | 2.45 | 3.47 | 65.6 | (0.681, 0.318) | 174 |
| Example 20 | | 1.5:1.5:1 | 2.41 | 3.42 | 63.5 | (0.680, 0.317) | 182 |
| Example 21 | A12:B18: C35 | 2:1:1 | 2.49 | 3.56 | 61.3 | (0.682, 0.318) | 169 |
| Example 22 | | 1.5:1.5:1 | 2.43 | 3.47 | 60.8 | (0.685, 0.314) | 179 |
| Example 23 | A15:B56: C27 | 2:1:1 | 2.45 | 3.52 | 64.2 | (0.683, 0.316) | 165 |
| Example 24 | | 1.5:1.5:1 | 2.42 | 3.48 | 63.6 | (0.681, 0.319) | 184 |
| Example 25 | A27:B54: C7 | 2:1:1 | 2.45 | 3.58 | 63.4 | (0.683, 0.316) | 154 |
| Example 26 | | 1.5:1.5:1 | 2.40 | 3.51 | 61.2 | (0.682, 0.317) | 171 |
| Example 27 | A28:B6: C7 | 2:1:1 | 2.34 | 3.39 | 72.2 | (0.680, 0.318) | 203 |
| Example 28 | | 1.5:1.5:1 | 2.31 | 3.35 | 70.6 | (0.681, 0.319) | 221 |
| Example 29 | A32:B57: C33 | 2:1:1 | 2.39 | 3.45 | 65.3 | (0.680, 0.320) | 185 |
| Example 30 | | 1.5:1.5:1 | 2.34 | 3.40 | 64.6 | (0.677, 0.322) | 199 |
| Example 31 | A58:B64: C38 | 2:1:1 | 2.48 | 3.52 | 53.7 | (0.679, 0.321) | 114 |
| Example 32 | | 1.5:1.5:1 | 2.43 | 3.48 | 51.8 | (0.686, 0.313) | 131 |
| Example 33 | A62:B61: C59 | 2:1:1 | 2.35 | 3.40 | 58.5 | (0.684, 0.314) | 182 |
| Example 34 | | 1.5:1.5:1 | 2.31 | 3.37 | 57.0 | (0.682, 0.317) | 196 |
| Example 35 | A99:B51: C18 | 2:1:1 | 2.63 | 3.86 | 42.1 | (0.688, 0.312) | 75 |
| Example 36 | | 1.5:1.5:1 | 2.60 | 3.82 | 40.1 | (0.679, 0.321) | 81 |

TABLE 5-continued

| No. | Composition | Ratio (A:B:C) | Threshold voltage ($V_{on}$) | Driving voltage ($V_{op}$) | efficiency (cd/A) | Color coordinate (x, y) | Service life ($T_{90}$) |
|---|---|---|---|---|---|---|---|
| Example 37 | A102:B3: C23 | 2:1:1 | 2.55 | 3.78 | 45.3 | (0.678, 0.322) | 82 |
| Example 38 | | 1.5:1.5:1 | 2.51 | 3.72 | 44.1 | (0.680, 0.318) | 89 |
| Example 39 | A135:B57: C33 | 2:1:1 | 2.47 | 3.45 | 67.9 | (0.681, 0.319) | 215 |
| Example 40 | | 1.5:1.5:1 | 2.42 | 3.41 | 65.3 | (0.680, 0.318) | 229 |
| Example 41 | A155:B82: C69 | 2:1:1 | 2.46 | 3.44 | 78.7 | (0.679, 0.320) | 245 |
| Example 42 | | 1.5:1.5:1 | 2.44 | 3.40 | 77.6 | (0.683, 0.317) | 263 |
| Example 43 | A156:B84: C72 | 2:1:1 | 2.43 | 3.45 | 79.6 | (0.682, 0.317) | 274 |
| Example 44 | | 1.5:1.5:1 | 2.42 | 3.42 | 78.6 | (0.679, 0.321) | 291 |
| Example 45 | A159:B79: C73 | 2:1:1 | 2.45 | 3.59 | 53.4 | (0.683, 0.317) | 111 |
| Example 46 | | 1.5:1.5:1 | 2.41 | 3.55 | 52.9 | (0.685, 0.314) | 119 |
| Example 47 | A160:B80: C76 | 2:1:1 | 2.44 | 3.57 | 56.9 | (0.684, 0.316) | 131 |
| Example 48 | | 1.5:1.5:1 | 2.40 | 3.53 | 57.1 | (0.679, 0.321) | 146 |
| Example 49 | A161:B85: C77 | 2:1:1 | 2.65 | 3.91 | 39.1 | (0.685, 0.314) | 77 |
| Example 50 | A161:B85: C77 | 1.5:1.5:1 | 2.61 | 3.87 | 40.1 | (0.683, 0.317) | 85 |

Compounds D and E used in Table 5 above are as follows.

D

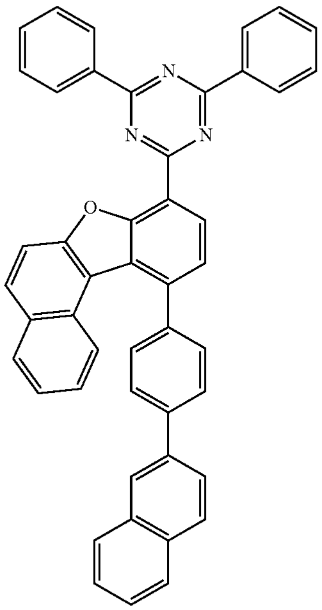

-continued

E

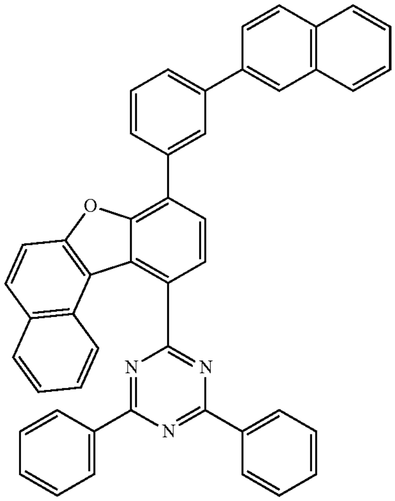

As can be seen from the results in Table 5 above, it could be confirmed that when the organic material layer of an organic light emitting device was deposited by mixing each of the three types of heterocyclic compounds according to the present application, the organic light emitting device can appropriately adjust a threshold voltage and driving voltage, and the efficiency or service life effect was improved.

Specifically, the heterocyclic compound represented by Chemical Formula A is characterized by low voltage, high efficiency, and long service life. Accordingly, it could be confirmed that when the heterocyclic compound represented by Chemical Formula B, which is characterized by a relatively longer service life, and the heterocyclic compound represented by Chemical Formula C, which is characterized by a relatively higher efficiency, are mixed at an appropriate ratio, the voltage, efficiency, and service life effects were additionally improved.

Since the heterocyclic compound represented by Chemical Formula A is a bipolar p-host including an amine substituent, the heterocyclic compound exhibits fast hole mobility. Since the heterocyclic compounds represented by Chemical Formulae B and C are unipolar n-hosts with fast electron mobility, it is assumed that the compounds serves to adjust the charge balance within the device when the compounds are combined, thereby improving efficiency and service life.

However, since the heterocyclic compound represented by Chemical Formula B is composed of this sterically planar naphthobenzofuran, whereas the heterocyclic compound represented by Chemical Formula C is composed of a non-planar naphthobenzofuran, conjugation scalability deteriorates, so that EOD tendency and structural stability may be weakened. Therefore, it is desirable to use the heterocyclic compound represented by Chemical Formula C by limiting the proportion of the heterocyclic compound to 25% or less.

Furthermore, it is assumed that when an azine and an aryl group are substituted on one side, as in Compounds D and E, steric hindrance occurs and allows structural stability to be decreased, thereby reducing efficiency or service life.

EXPLANATION OF REFERENCE NUMERALS AND SYMBOLS

100: Substrate
200: Positive electrode
300: Organic material layer
301: Hole injection layer
302: Hole transport layer
303: Light emitting layer
304: Hole blocking layer
305: Electron transport layer
306: Electron injection layer
400: Negative electrode

The invention claimed is:

1. A composition for an organic light emitting device, comprising a heterocyclic compound represented by the following Chemical Formula A, a heterocyclic compound represented by the following Chemical Formula B, and a heterocyclic compound represented by the following Chemical Formula C:

[Chemical Formual A]

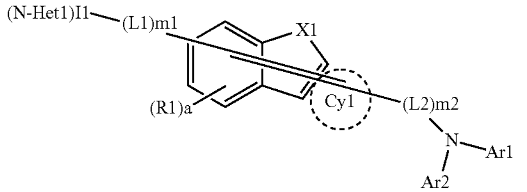

[Chemical Formula B]

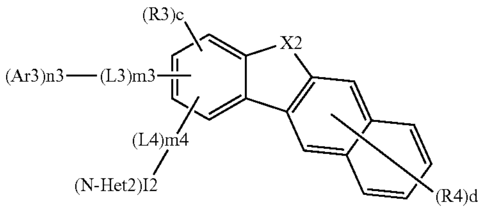

[Chemical Formula C]

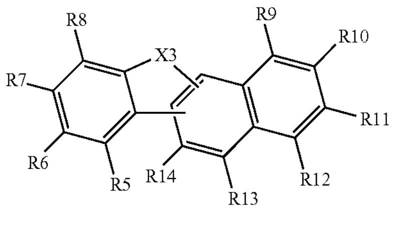

wherein, in Chemical Formulae A, B and C,

X1 to X3 are the same as or different from each other, and are each independently O; or S, Cy1 is a substituted or unsubstituted benzene ring; or a substituted or unsubstituted naphthalene ring, R1, R3, and R4 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(=O)RR', any one of R5 to R14 is -(L5)m5-(Ar4)n4, the other one is -(L6)m6-(N-Het3)l3, and the others are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(=O)RR', R, R', and R" are the same as or different from each other, and are each independently hydrogen; deuterium; —CN; a substituted or unsubstituted C1 to C60 alkyl group; a substituted or unsubstituted C2 to C60 cycloalkyl group; a substituted or unsubstituted C6 to C60 aryl group; or a substituted or unsubstituted C2 to C60 heteroaryl group, L1 to L6 are the same as or different from each other, and are each independently a direct bond; a substituted or unsubstituted C6 to C60 arylene group; or a substituted or unsubstituted C2 to C60 heteroarylene group, Ar1 to Ar4 are the same as or different from each other, and are each independently a substituted or unsubstituted C6 to C60 aryl group; a substituted or unsubstituted C2 to C60 heteroaryl group; or a combination thereof, N-Het1, N-Het2, and N-Het3 are the same as or different from each other, and are each independently represented by the following Structural Formula D,

[Structural Formula D]

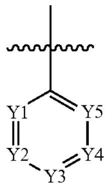

in Structural Formula D,

means a moiety linked to another structure,

Y1 to Y5 are the same as or different from each other, and are each independently CRa or N, and at least one is N, Ra is a substituted or unsubstituted C6 to C60 aryl group; or a substituted or unsubstituted C2 to C60 heteroaryl group, or two or more adjacent Ra groups are bonded to each other to form a ring, a is an integer from 0 to 4, c is an integer from 0 to 2, d is an integer from 0 to 6, l1 to l3, m1 to m6, n3, and n4 are the same as or different from each other, and are each independently an integer from 0 to 4, and when each of a, c, d, l1 to l3, m1 to m6, n3, and n4 is 2 or higher, substituents in the parenthesis are the same as or different from each other.

2. The composition of claim 1, wherein Chemical Formula A is represented by any one of the following Chemical Formulae A-1 to A-4:

[Chemical Formula A-1]

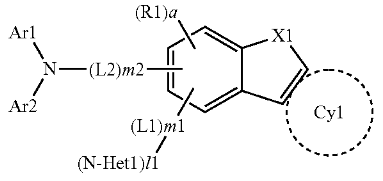

[Chemical Formula A-2]

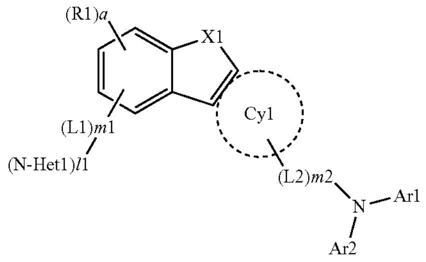

[Chemical Formula A-3]

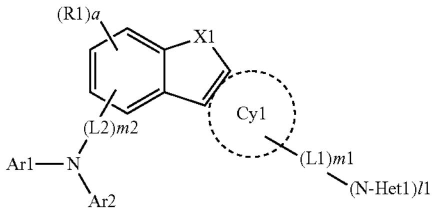

[Chemical Formula A-4]

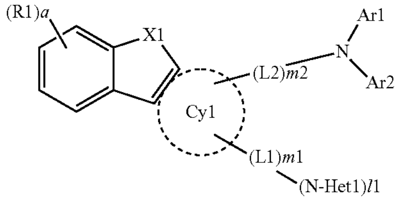

in Chemical Formulae A-1 to A-4, the definitions of X1, Cy1, R1, L1, L2, N-Het1, Ar1, Ar2, a, 11, m1, and m2 are the same as those described in Chemical Formula A.

3. The composition of claim 1, wherein Chemical Formula A is represented by any one of the following Chemical Formulae Aa to Ad:

[Chemical Formula Aa]

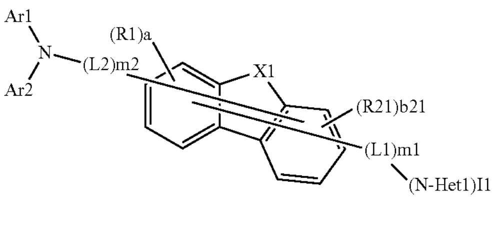

-continued

[Chemical Formula Ab]

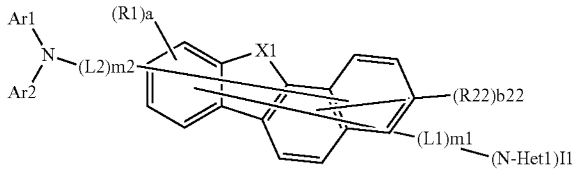

[Chemical Formula Ac]

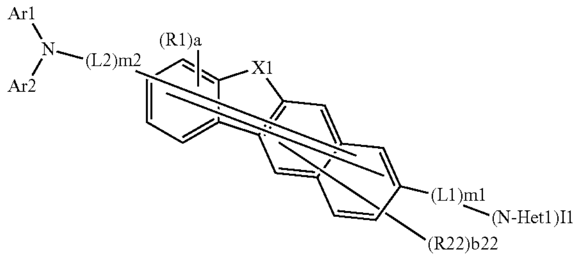

[Chemical Formula Ad]

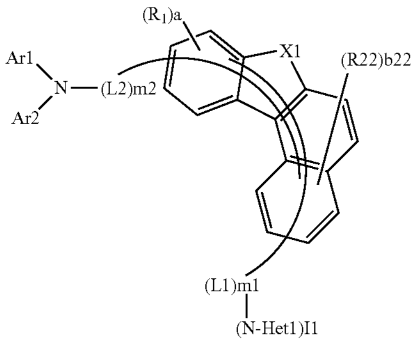

in Chemical Formulae Aa, Ab, Ac, and Ad, the definitions of X1, R1, L1, L2, N-Het1, Ar1, Ar2, a, 11, m1, and m2 are the same as those described in Chemical Formula A, R21 and R22 are the same as or different from each other, and are each independently selected from the group consisting of hydrogen; deuterium; a halogen; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; and —P(═O)RR', b21 is an integer from 0 to 4, b22 is an integer from 0 to 6, and when each of b21 and b22 is 2 or higher, substituents in the parenthesis are the same as or different from each other.

4. The composition of claim 1, wherein Chemical Formula B is represented by any one of the following Chemical Formulae B-1 to B-6:

[Chemical Formula B-1]

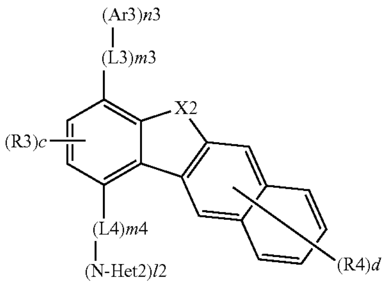

[Chemical Formula B-2]

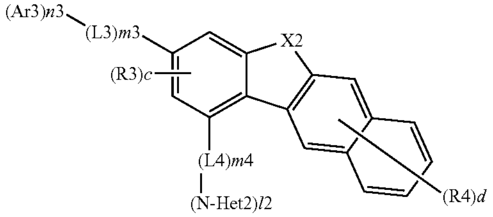

[Chemical Formula B-3]

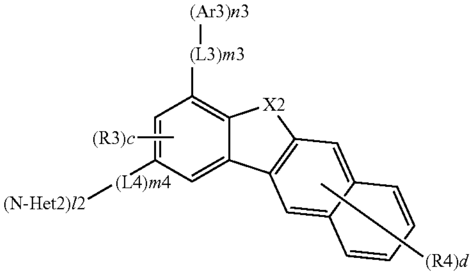

[Chemical Formula B-4]

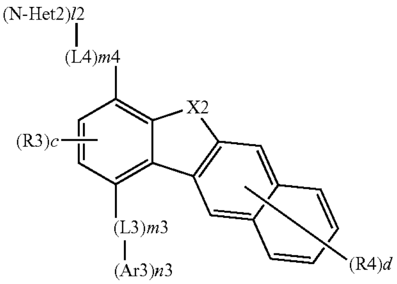

[Chemical Formula B-5]

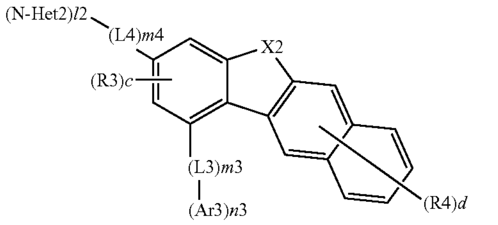

-continued

[Chemical Formula B-6]

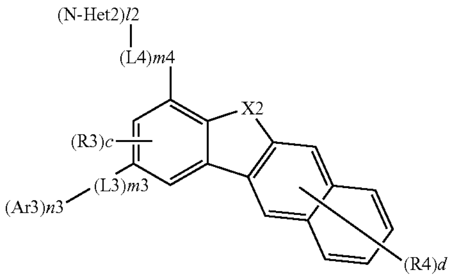

in Chemical Formulae B-1 to B-6, the definitions of X2, R3, R4, L3, L4, N-Het2, Ar3, c, d, l2, m3, m4, and n3 are the same as those described in Chemical Formula B.

5. The composition of claim 1, wherein Chemical Formula C is represented by the following Chemical Formula Ca or Cb:

[Chemical Formula Ca]

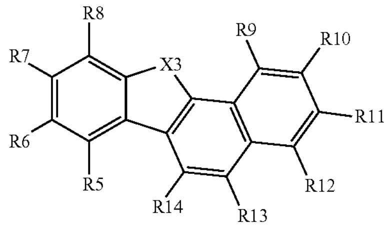

[Chemical Formula Cb]

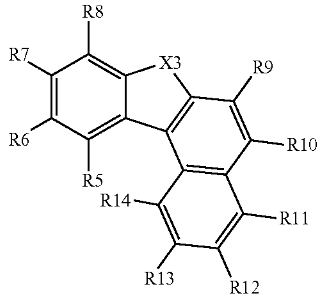

in Chemical Formulae Ca and Cb, the definitions of X3 and R5 to R14 are the same as those described in Chemical Formula C.

6. The composition of claim 1, wherein any one of R5 to R14 is -(L5)m5-(Ar4)n4, the other one is -(L6)m6-(N-Het3)l3, and the others are the same as or different from each other, and are each independently hydrogen; or deuterium.

7. The composition of claim 1, wherein any one of R5 to R8 is -(L5)m5-(Ar4)n4, any one of R9 to R14 is -(L6)m6-(N-Het3)l3, and the others are the same as or different from each other, and are each independently hydrogen; or deuterium; or any one of R9 to R14 is -(L5)m5-(Ar4)n4, any one of R5 to R8 is -(L6)m6-(N-Het3)l3, and the others are the same as or different from each other, and are each independently hydrogen, or deuterium.

8. The composition of claim 1, wherein Chemical Formula A comprises any one of the following compounds:
A1
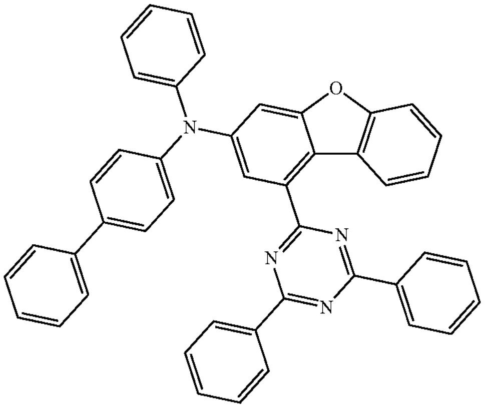
A2
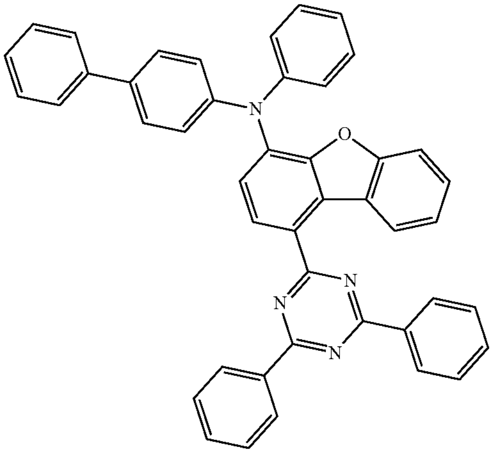
A3
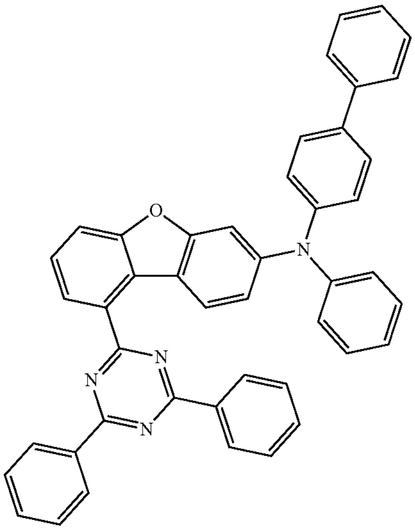
-continued
A4
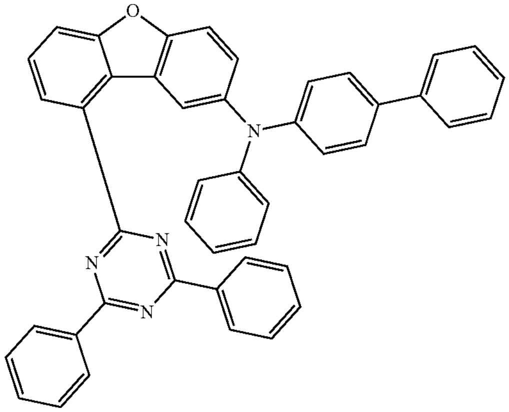
A5
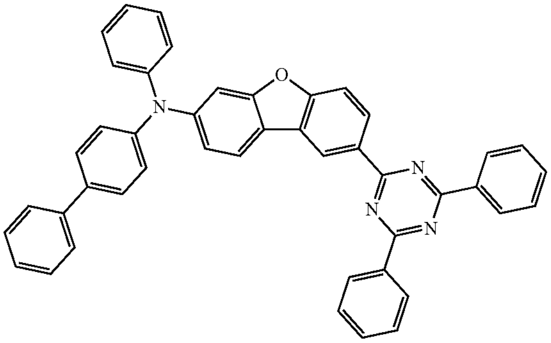
A6
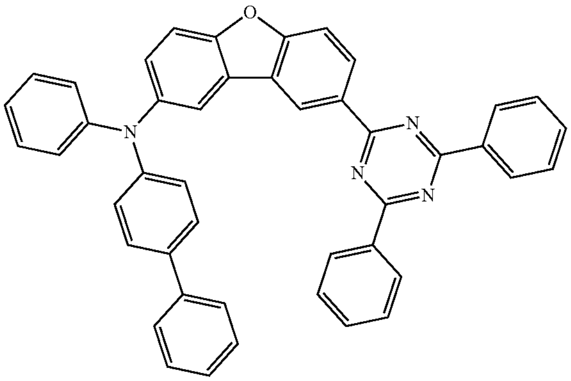

-continued
A7
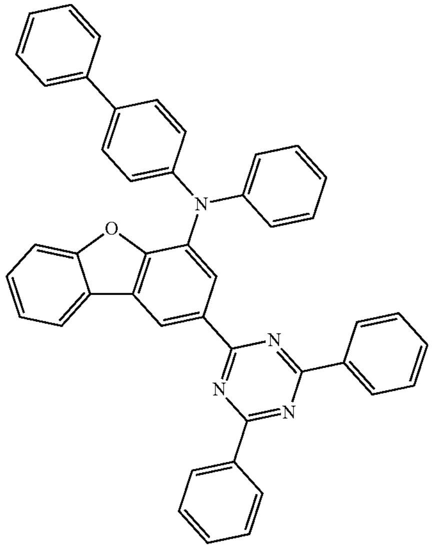
A8
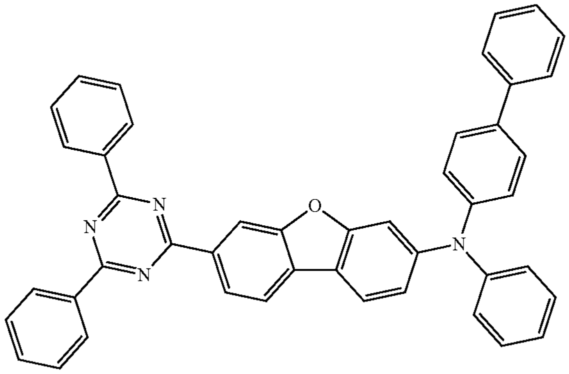
A9
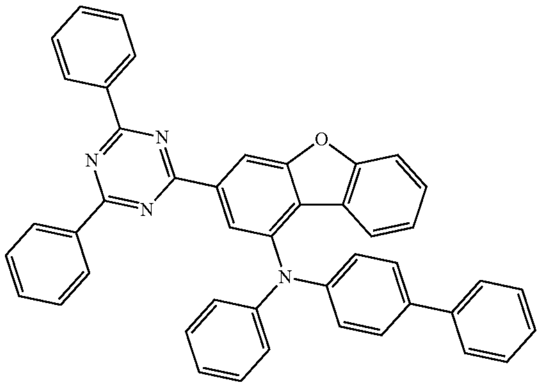
-continued
A10
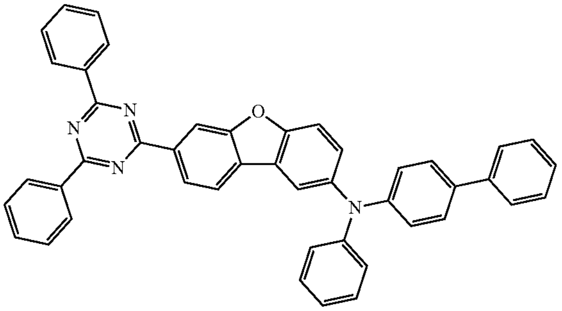
A11
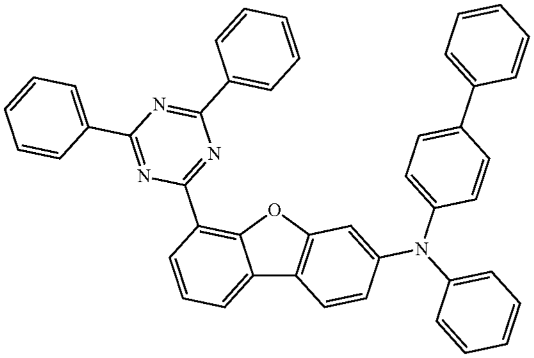
A12
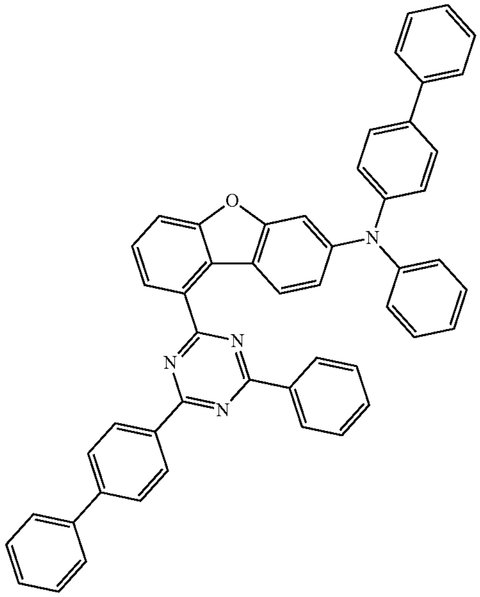

-continued
A13
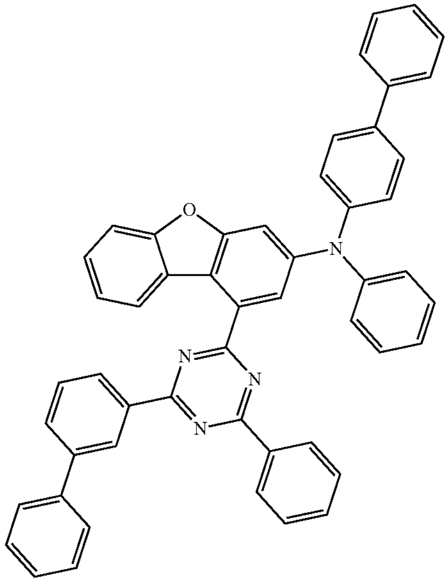
A14
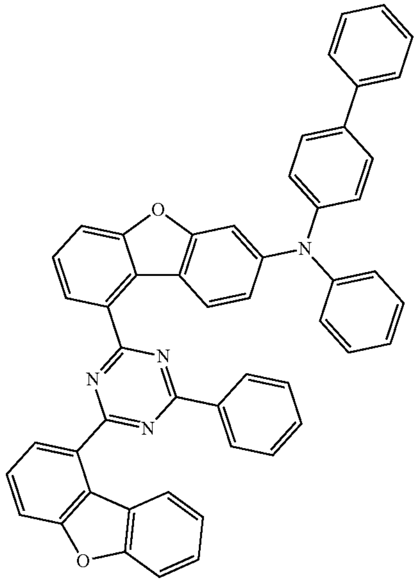
-continued
A15
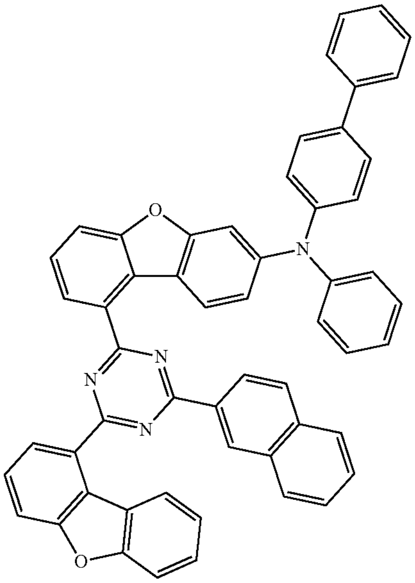
A16
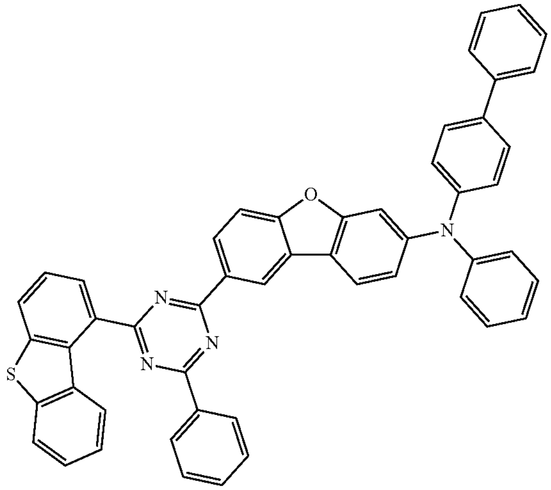

-continued
A17
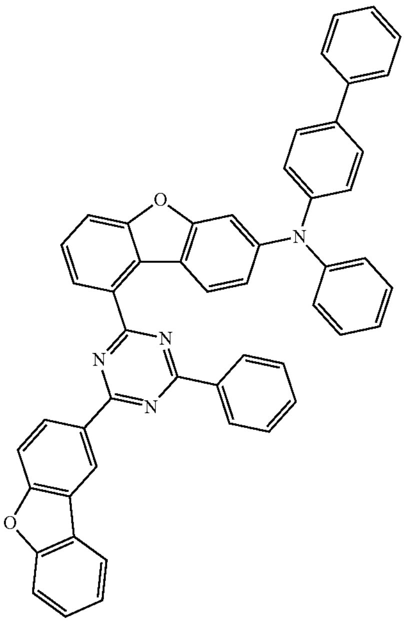
A18
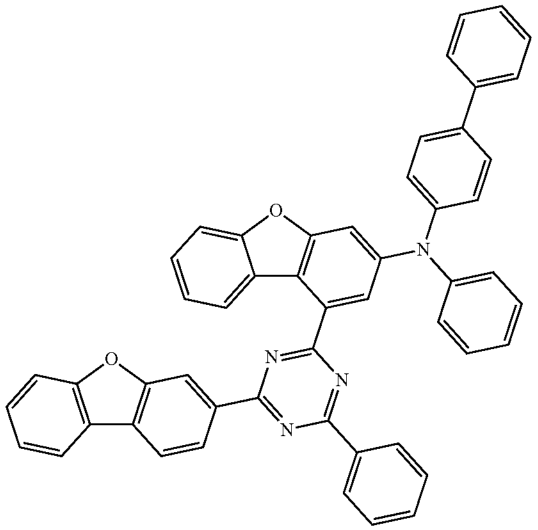
A19
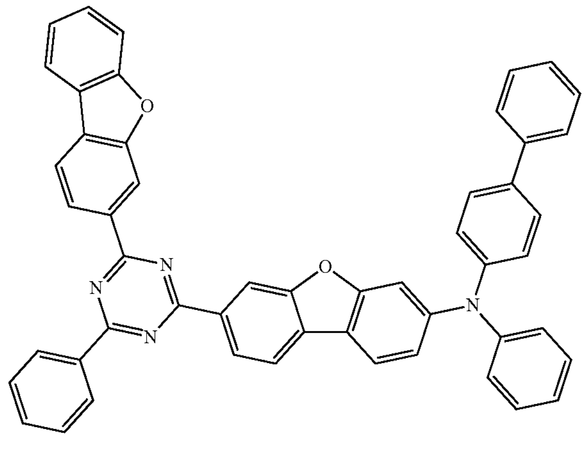
-continued
A20
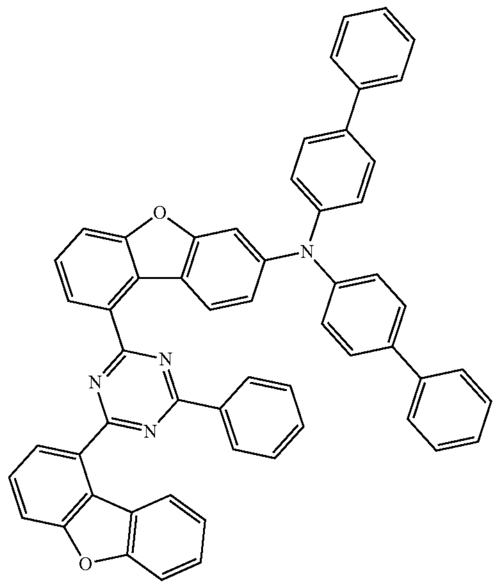
A21
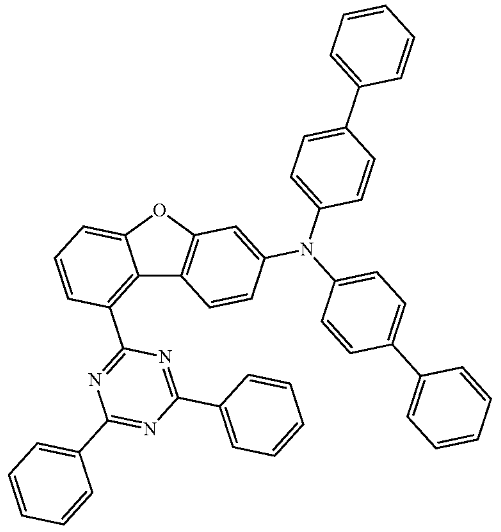
A22
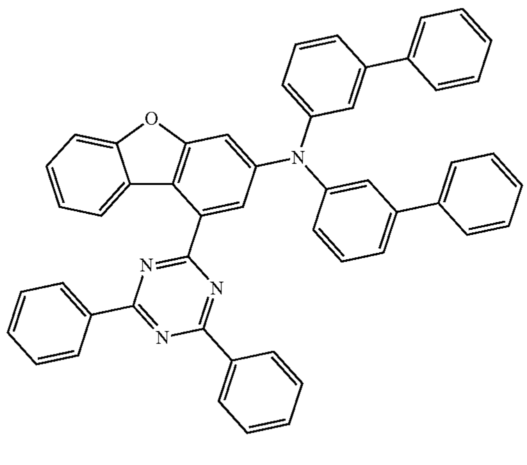

-continued
A23
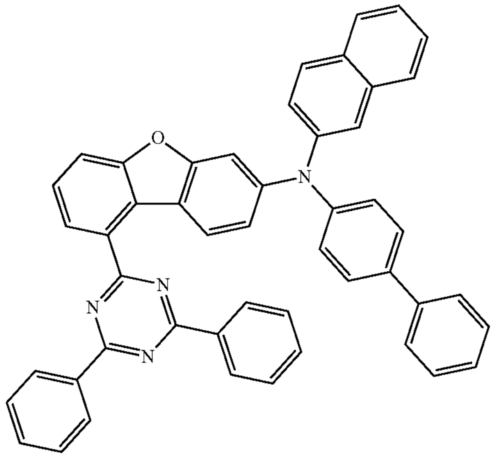
A24
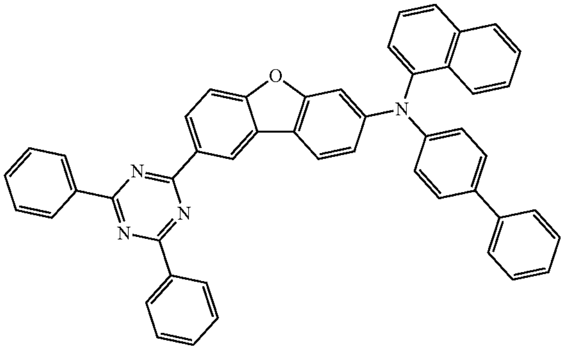
A25
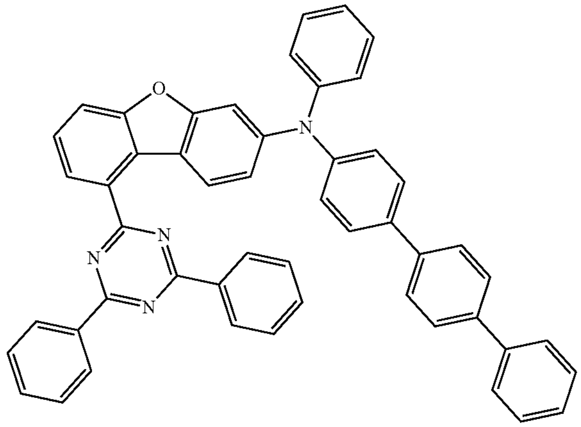
-continued
A26
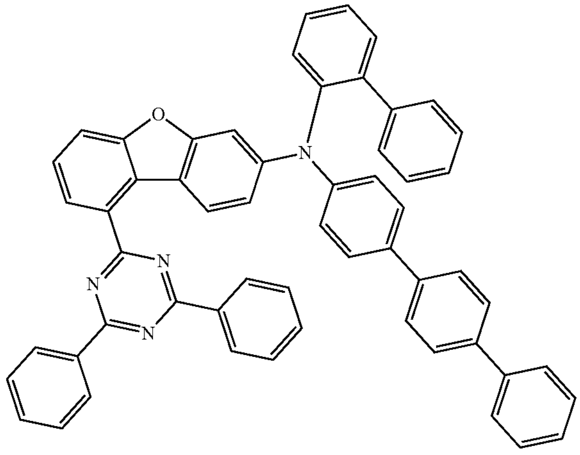
A27
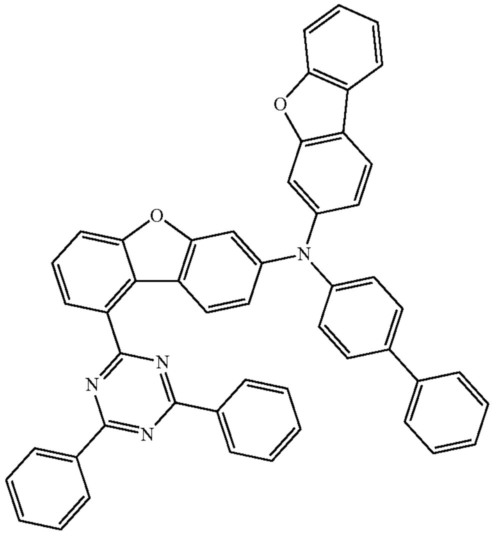
A28
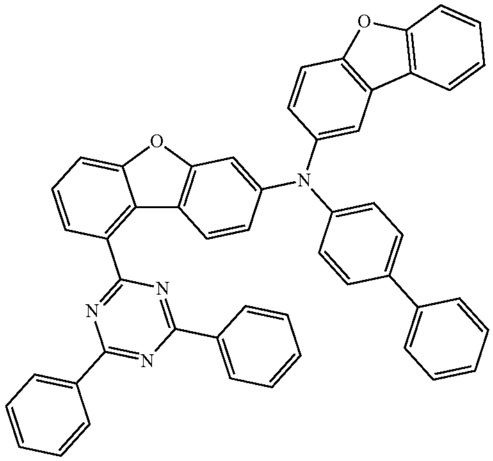

-continued
A29
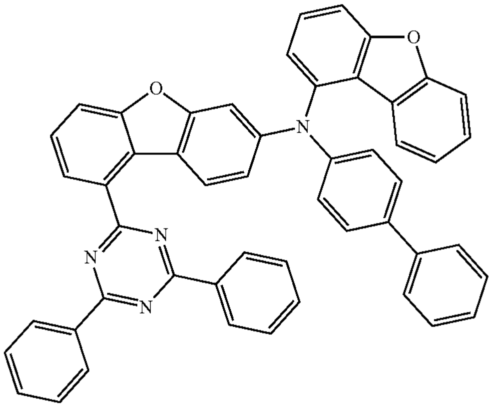
A30
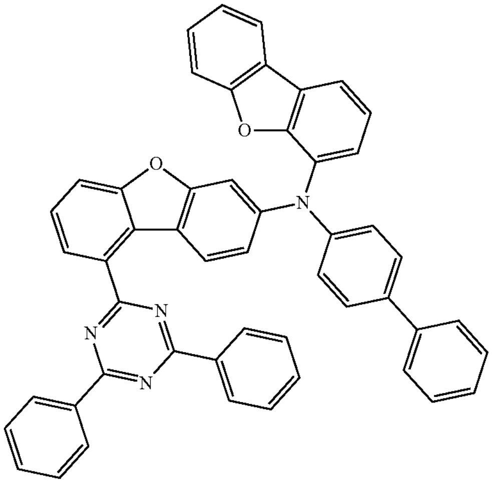
A31
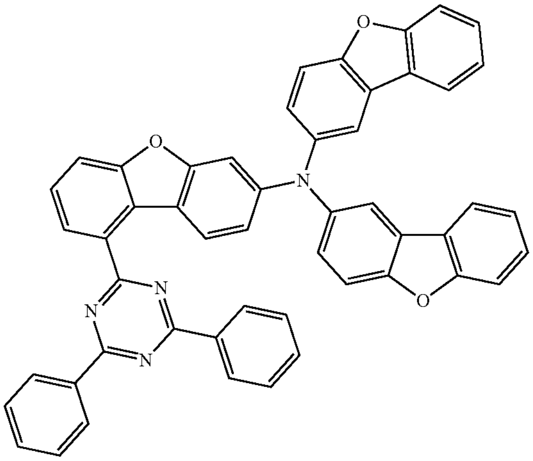
-continued
A32
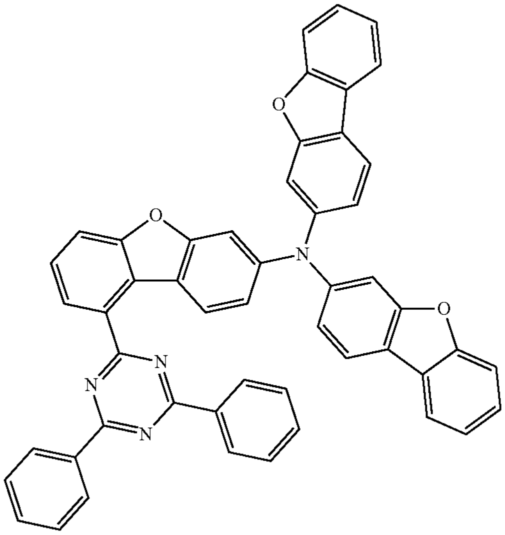
A33
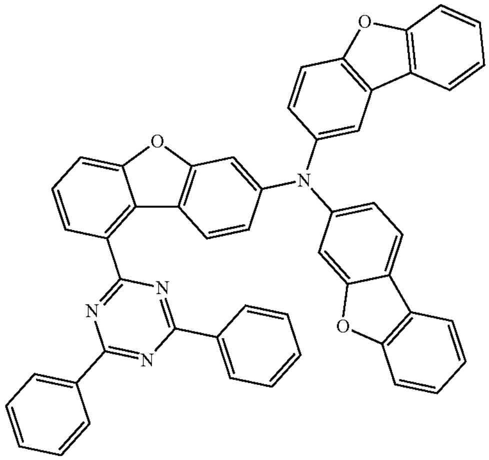
A34
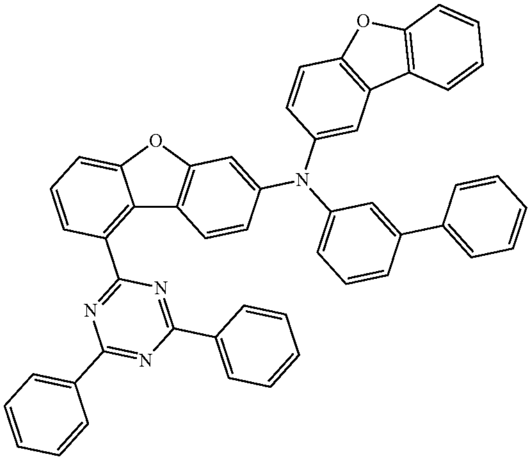

-continued
A35
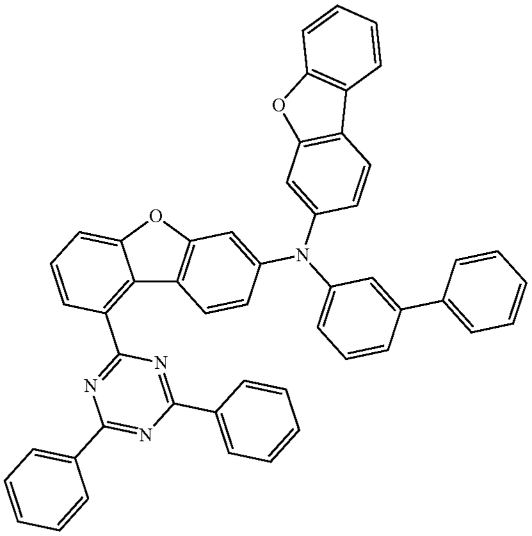
A36
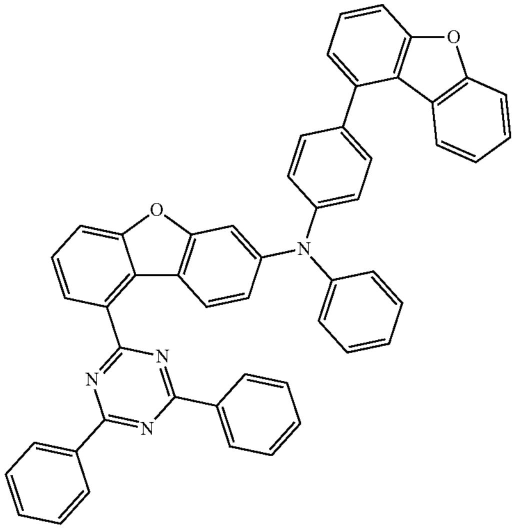
A37
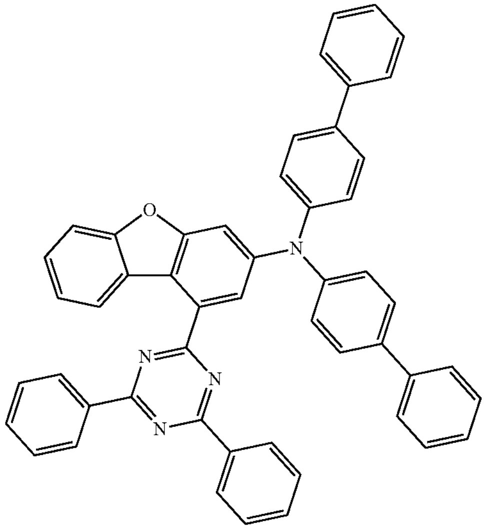
-continued
A38
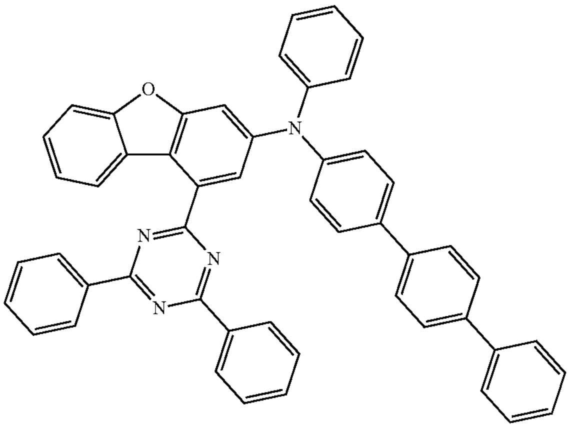
A39
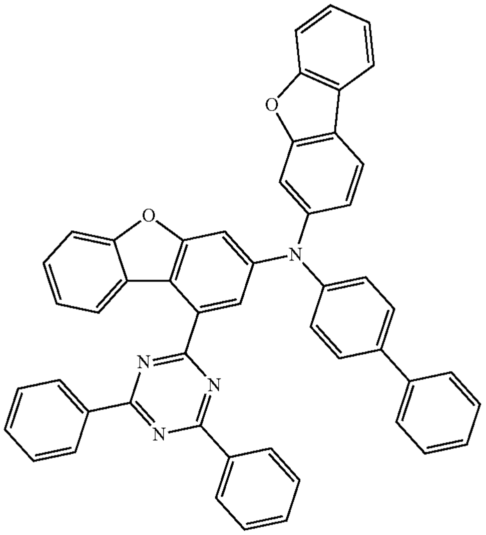
A40
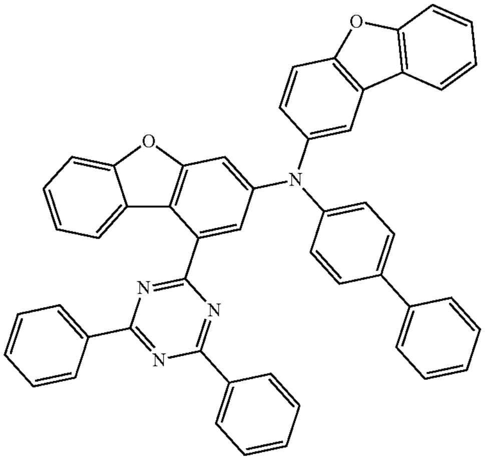

-continued
A41
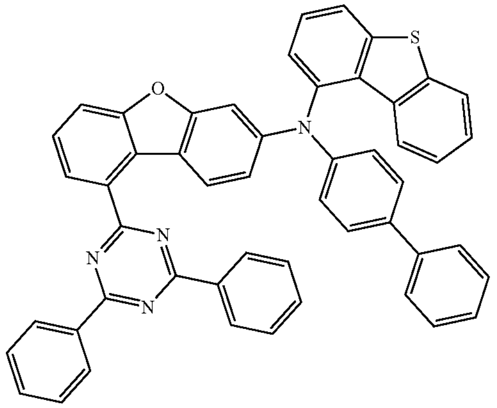
A42
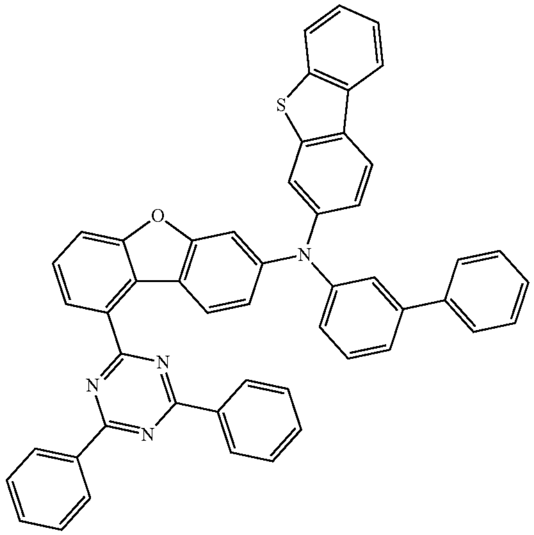
A43
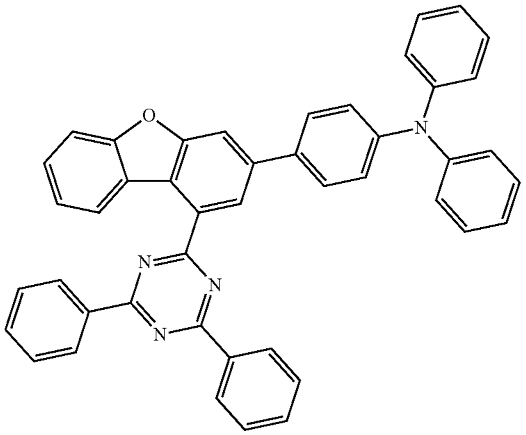
-continued
A44
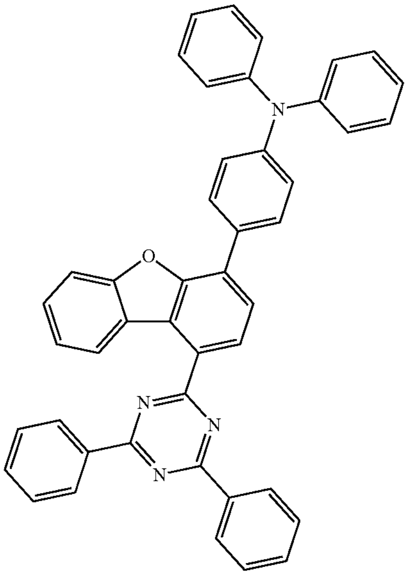
A45
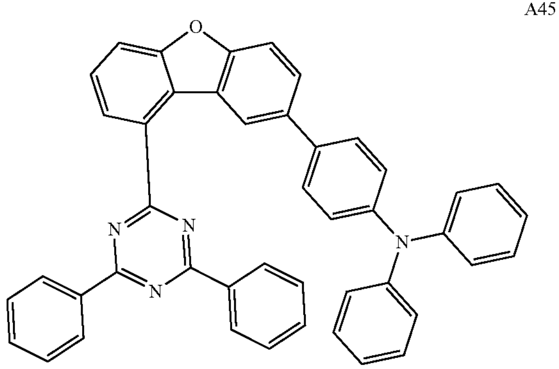
A46
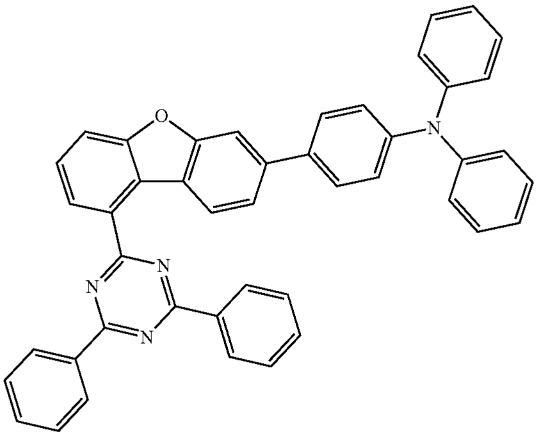

-continued
A47
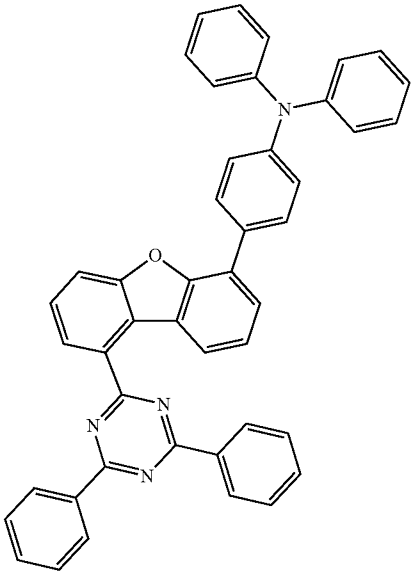
A48
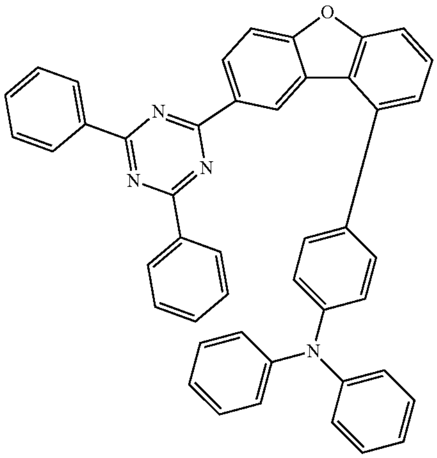
A49
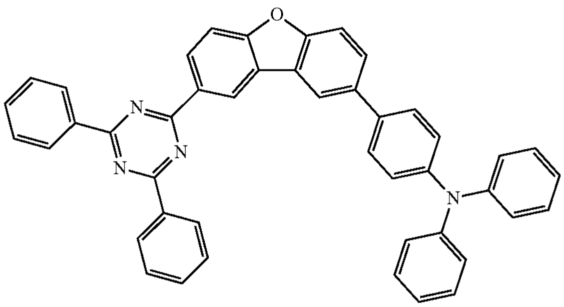
-continued
A50
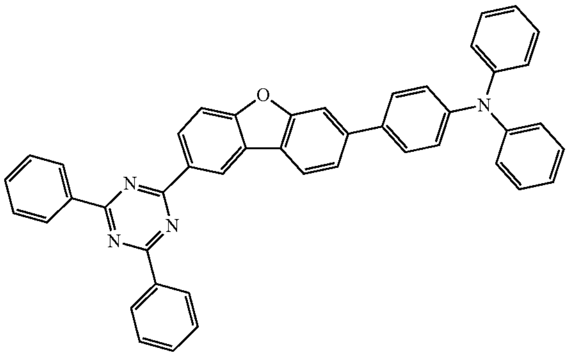
A51
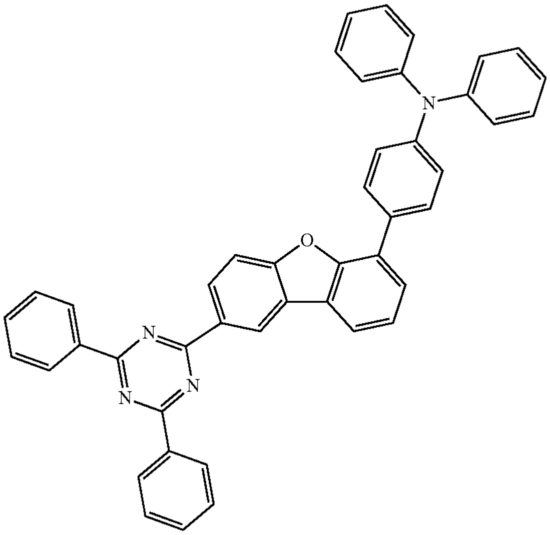
A52
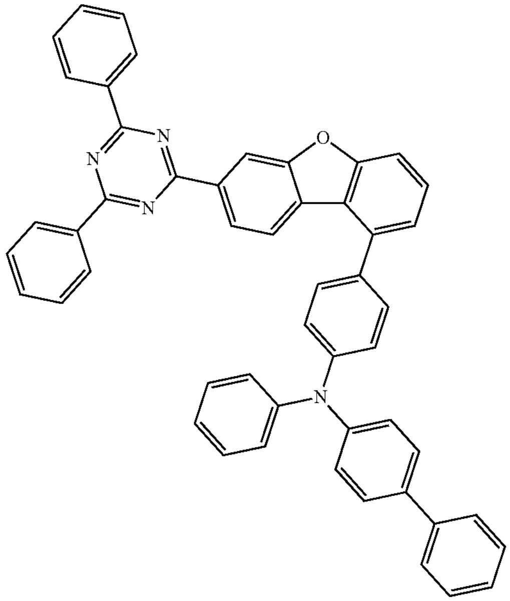

-continued
A53
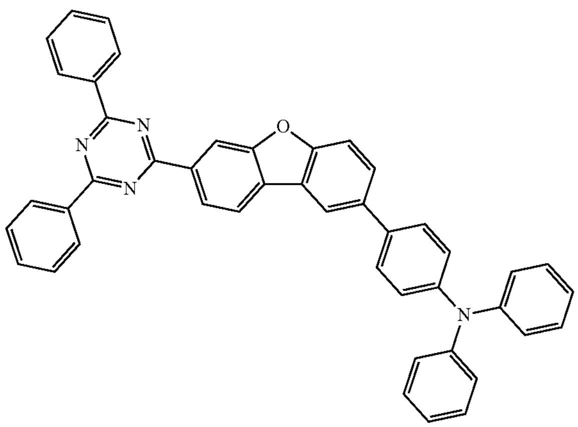
A54
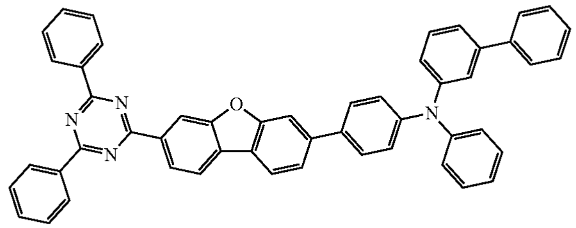
A55
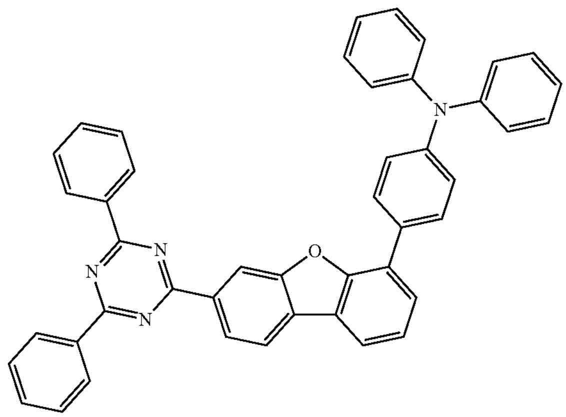
-continued
A56
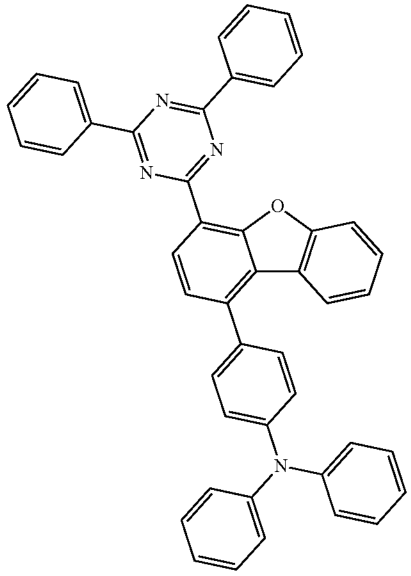
A57
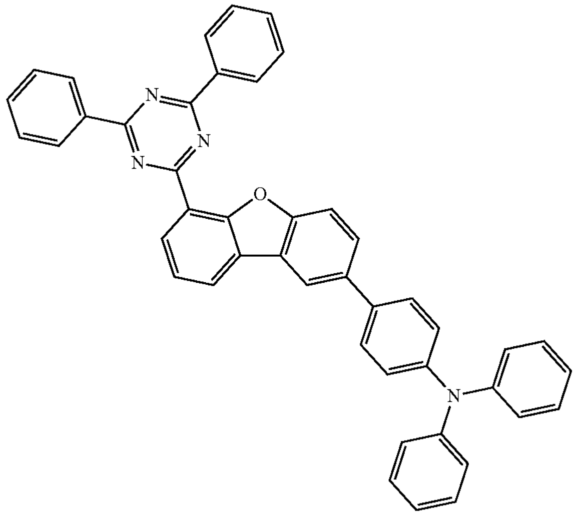
A58
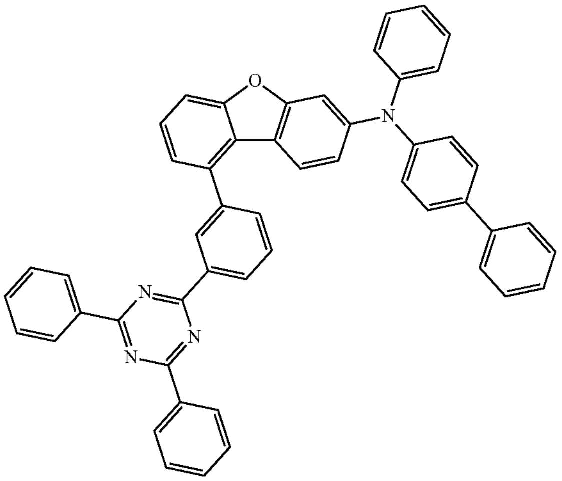

-continued
A59
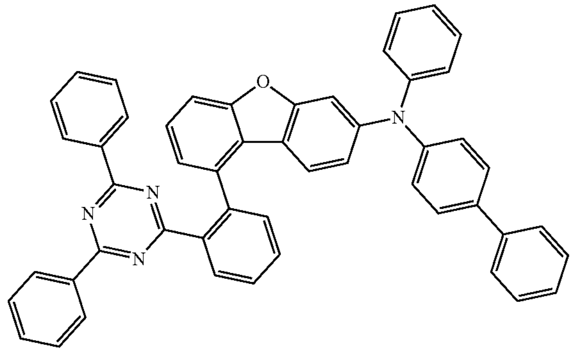
A60
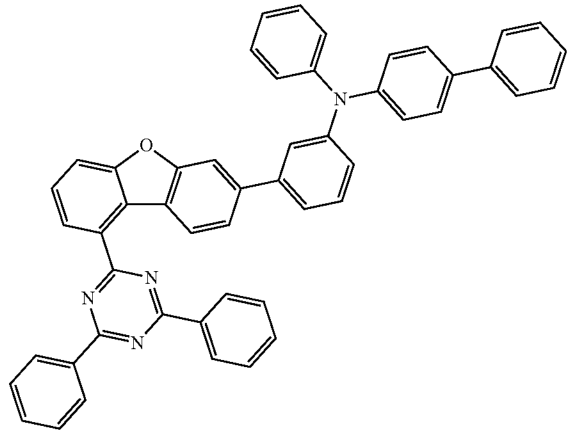
A61
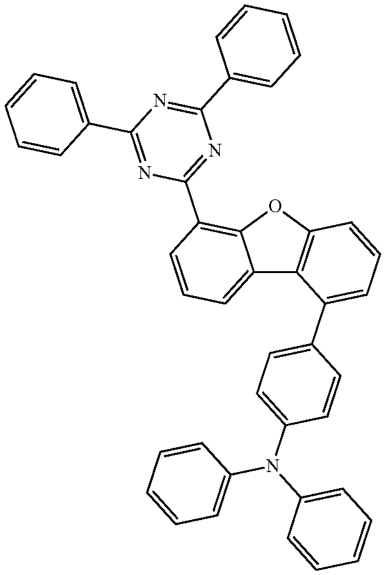
-continued
A62
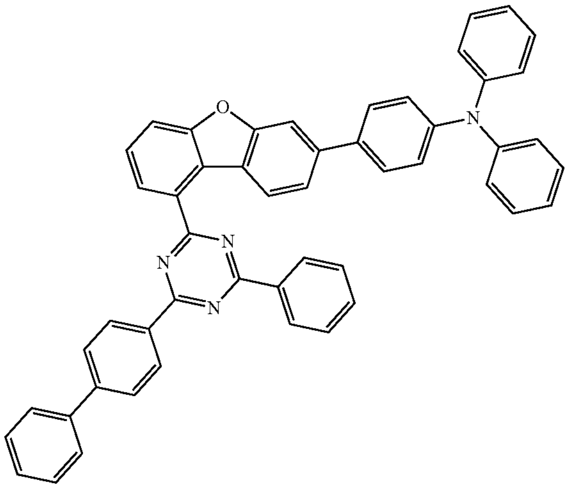
A63
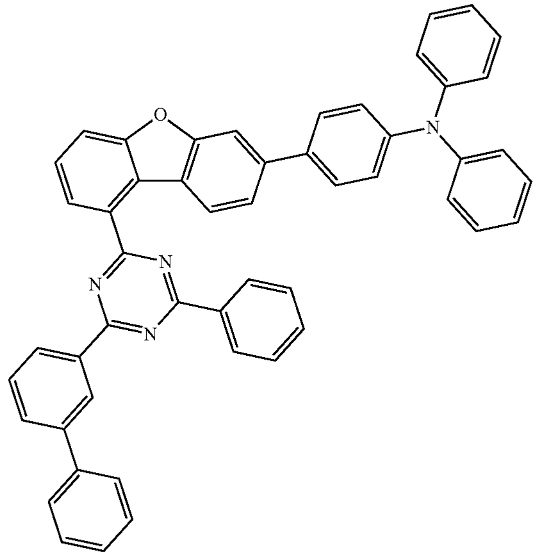
A64
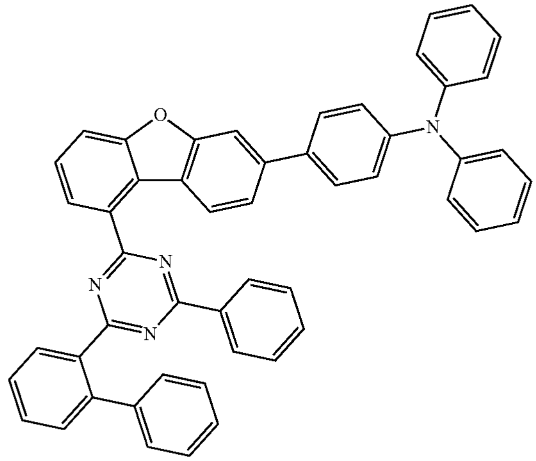

-continued
A65
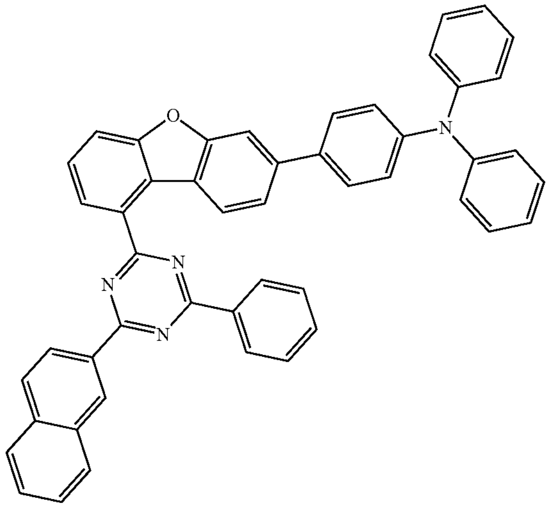
A66
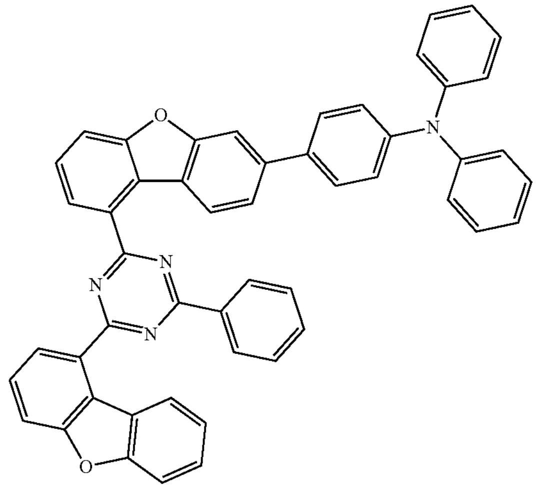
A67
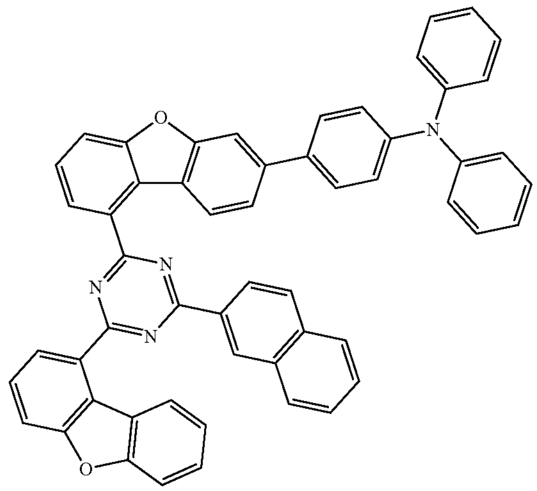
-continued
A68
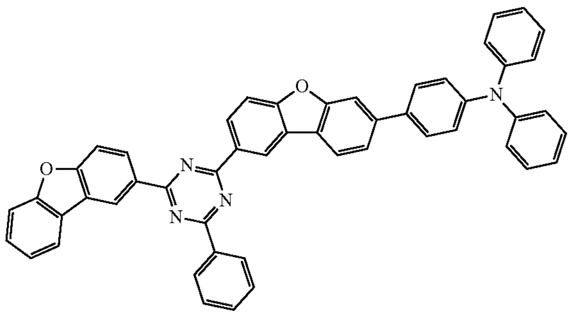
A69
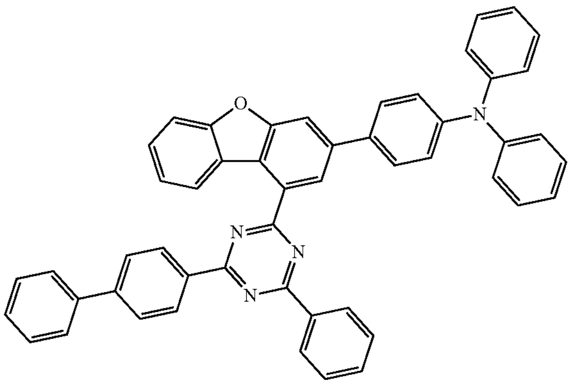
A70
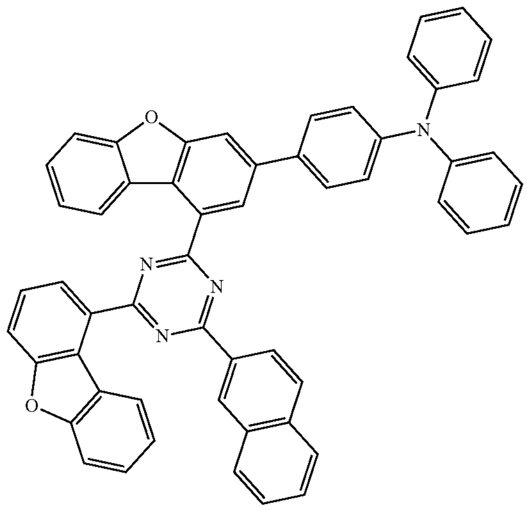

-continued
A71
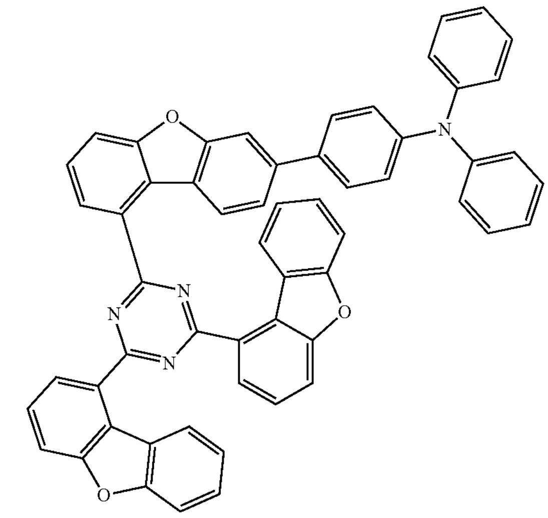
A72
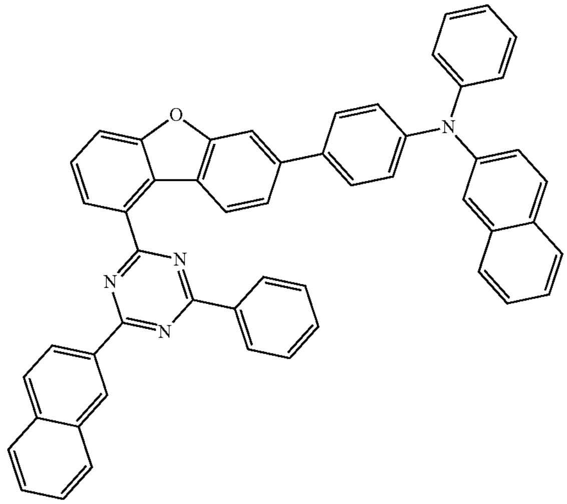
A73
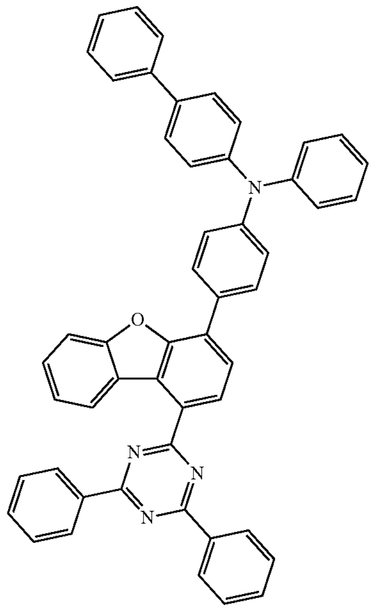
-continued
A74
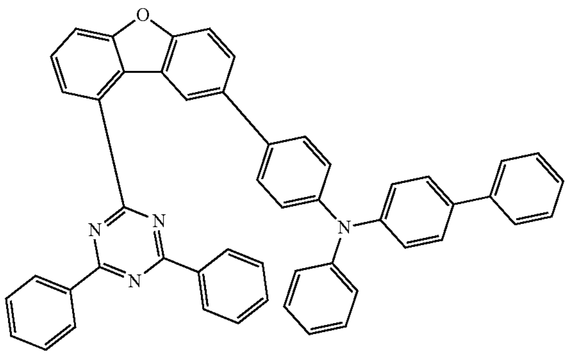
A75
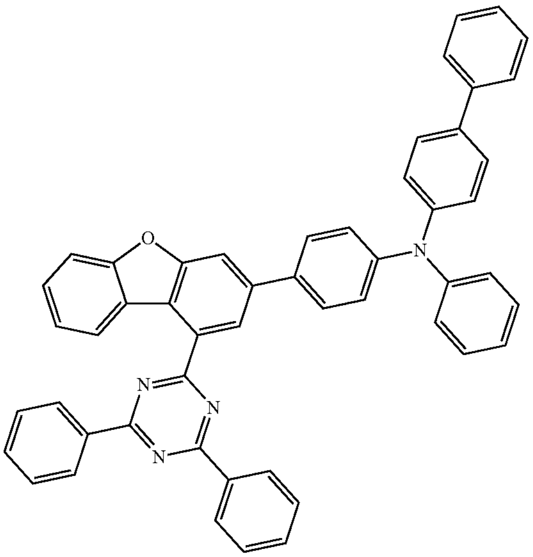
A76
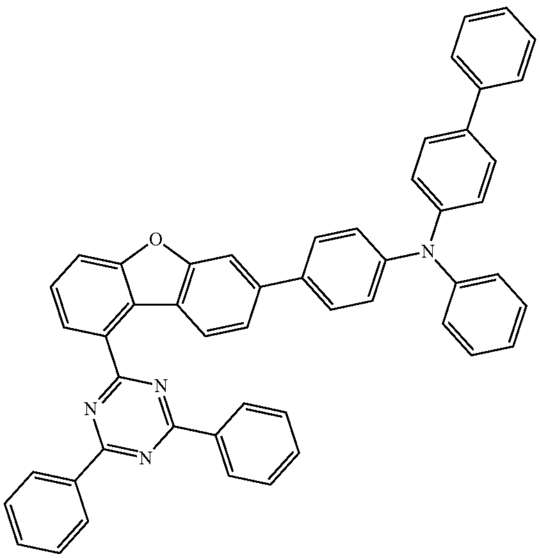

-continued
A77
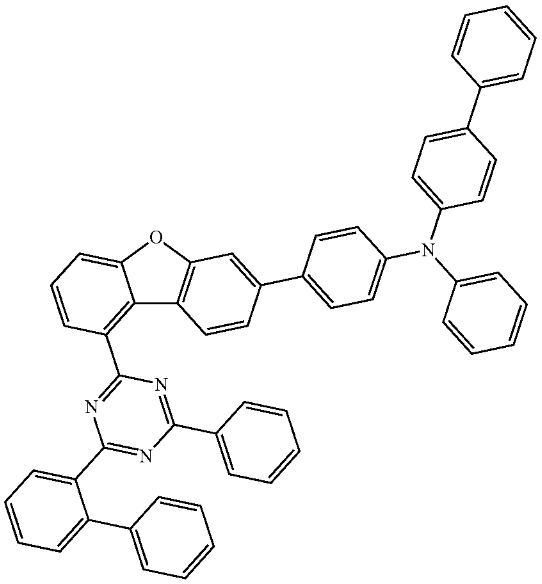
A78
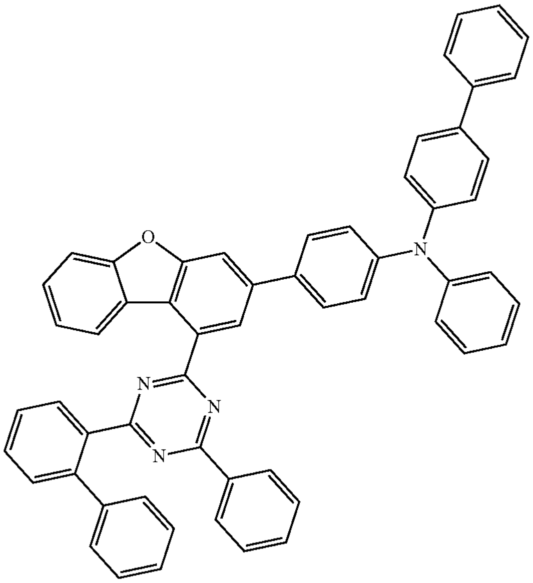
A79
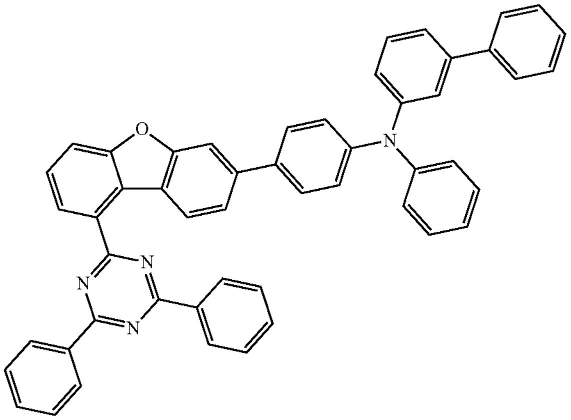
-continued
A80
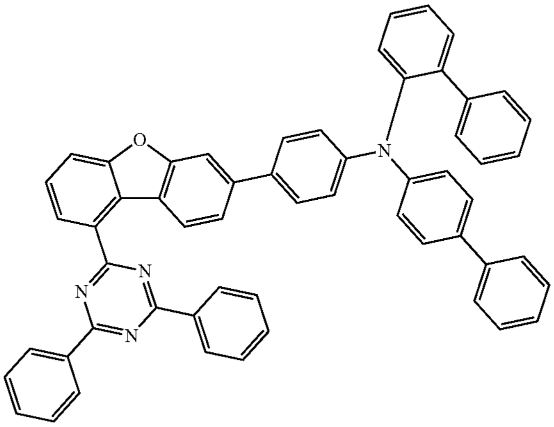
A81
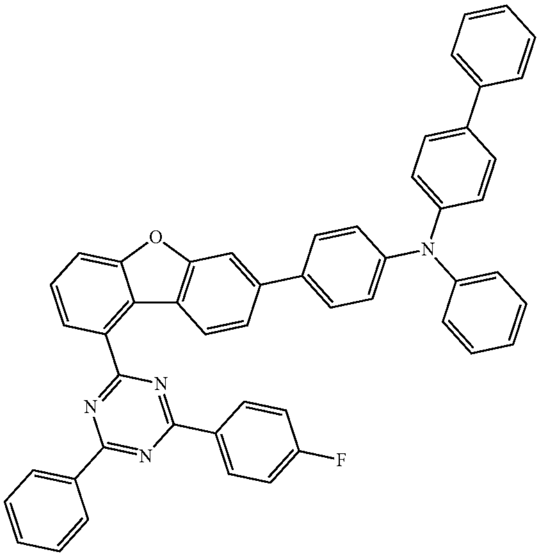
A82
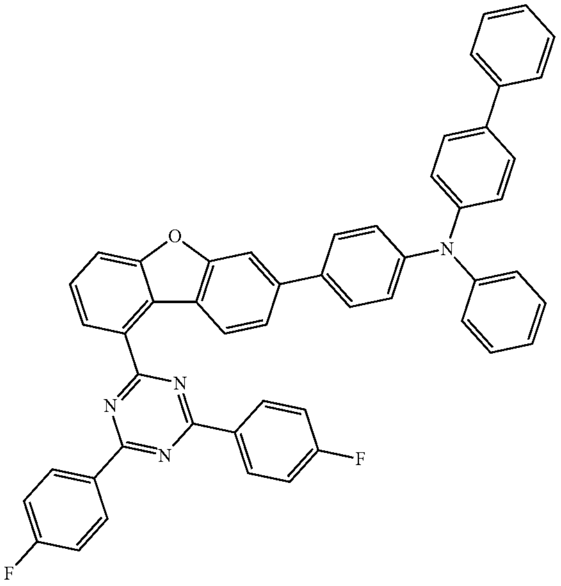

-continued
A83
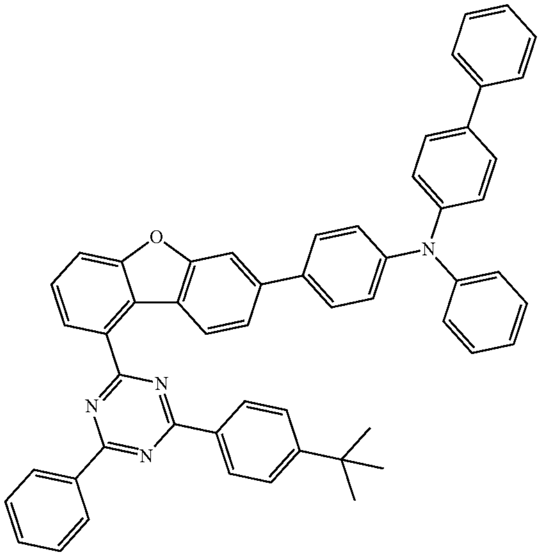
A84
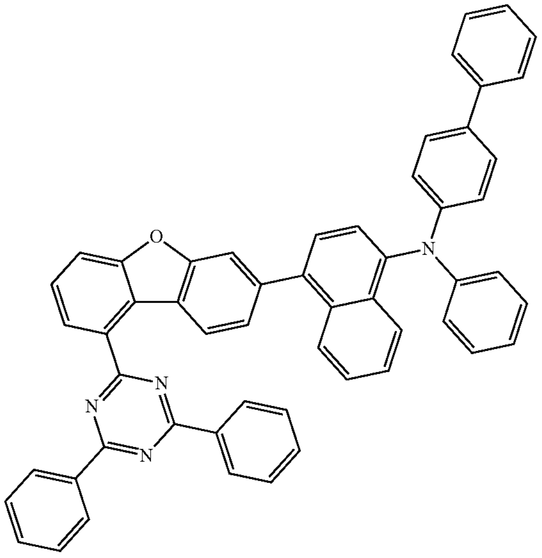
-continued
A85
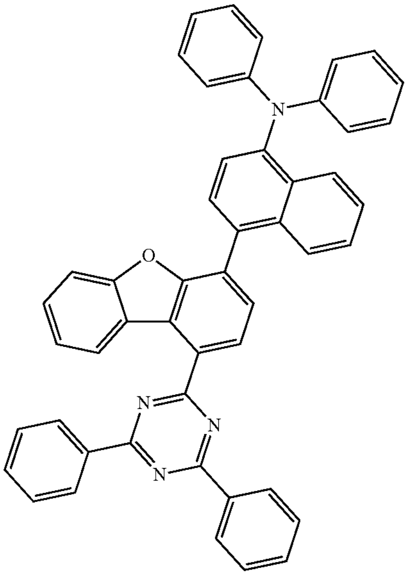
A86
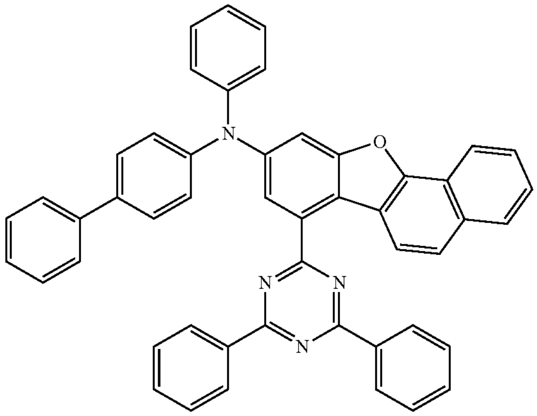
A87
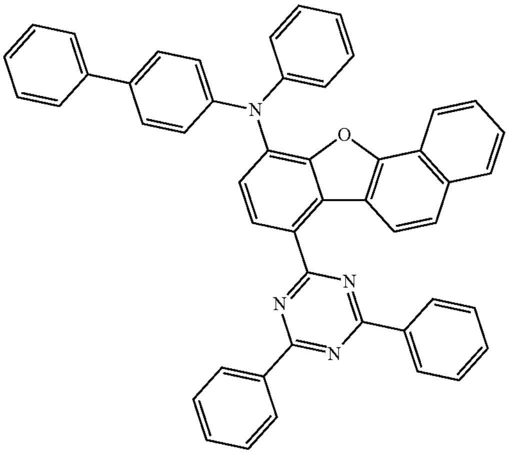

-continued
A88
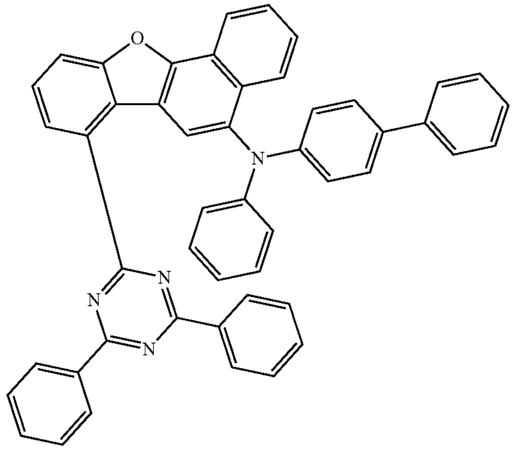
A89
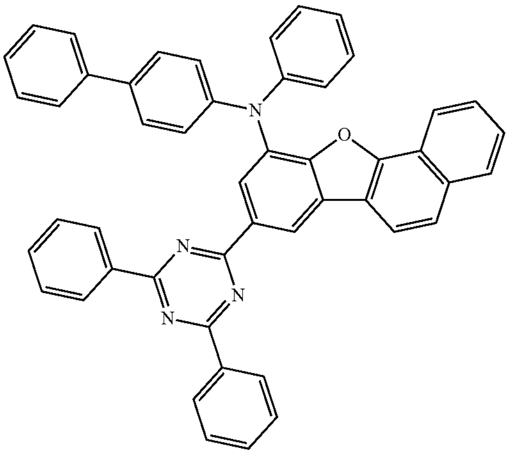
A90
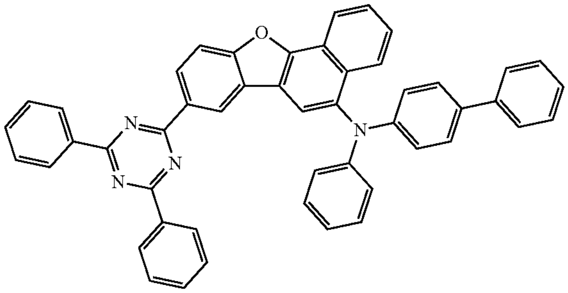
-continued
A91
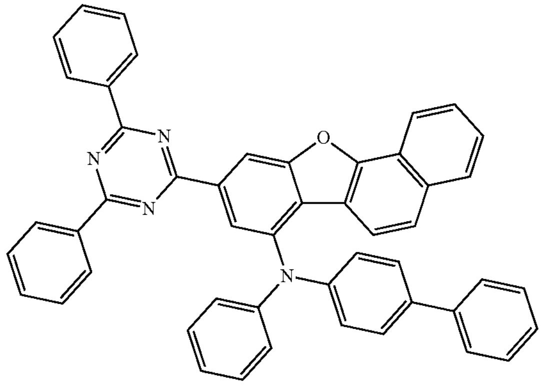
A92
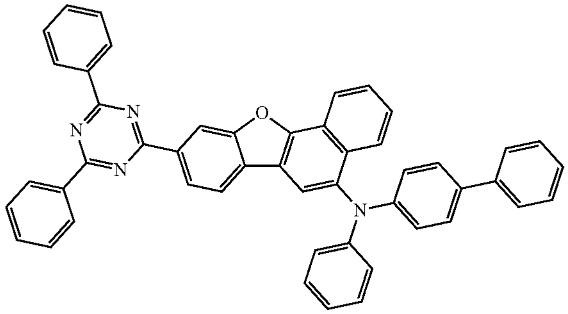
A93
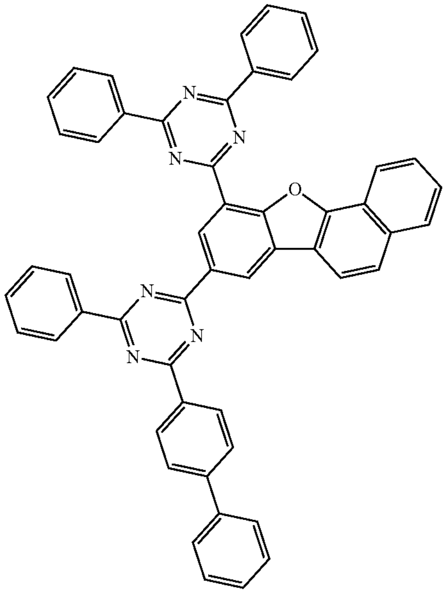

-continued
A94
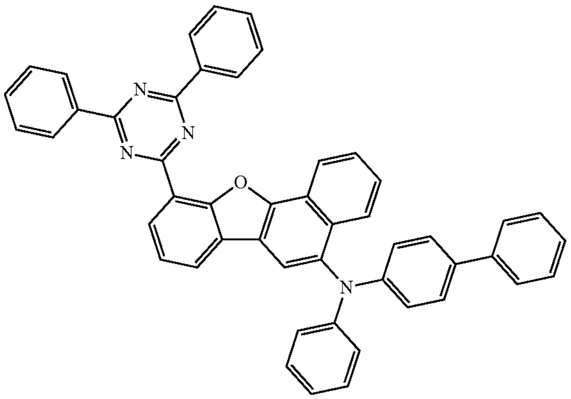
A95
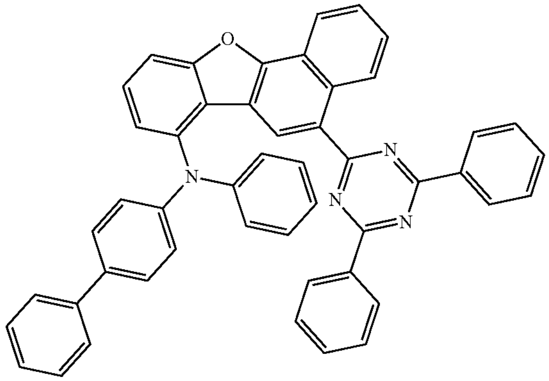
A96
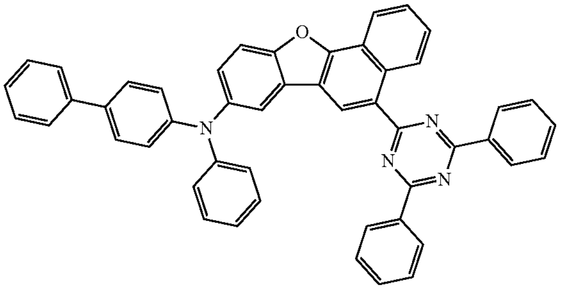
-continued
A97
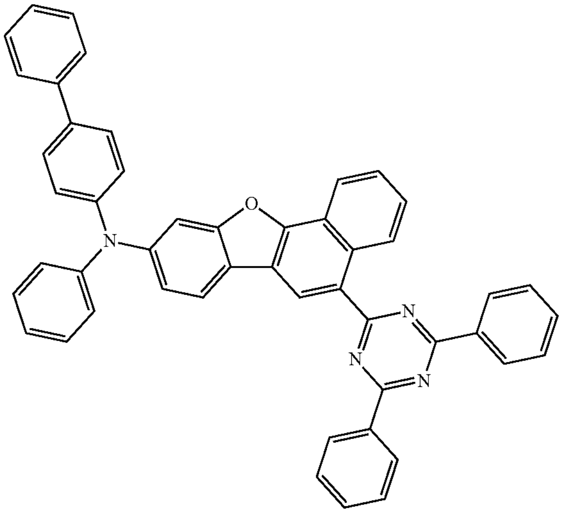
A98
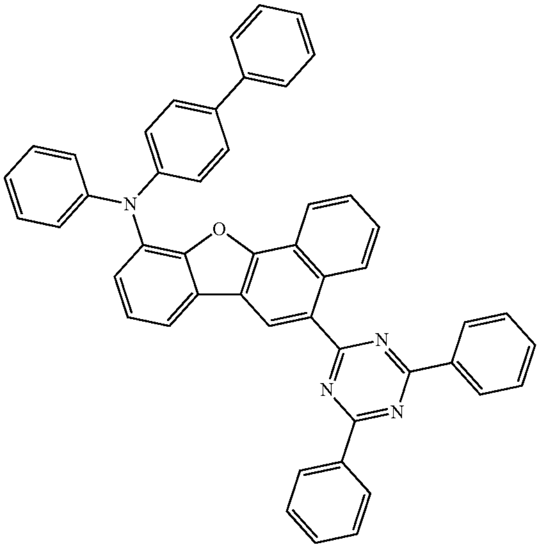
A99
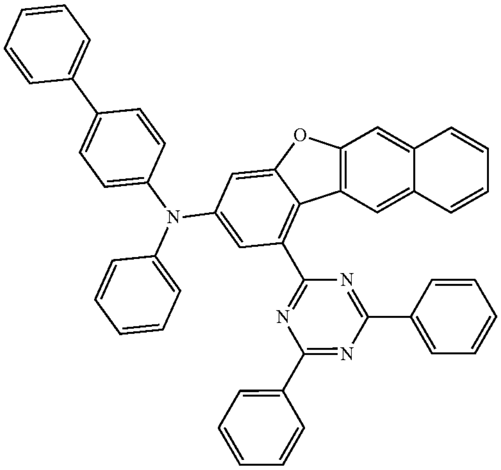

-continued
A100
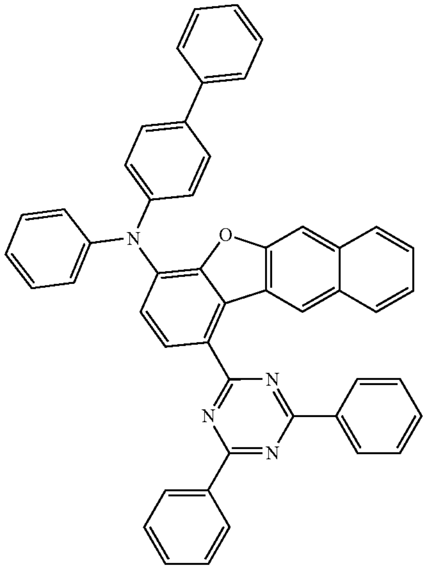
A101
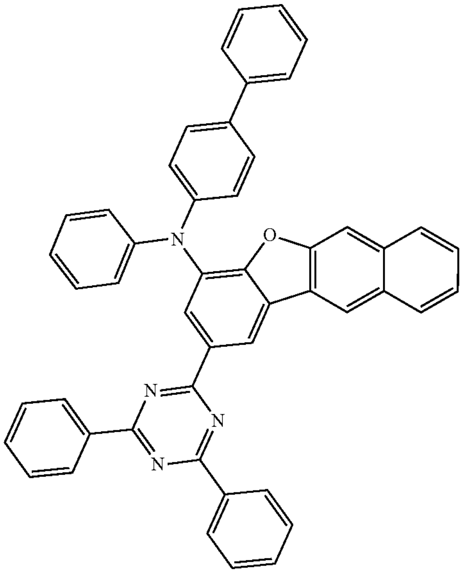
A102
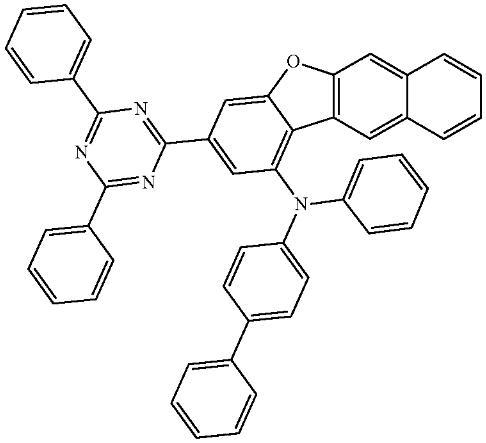
-continued
A103
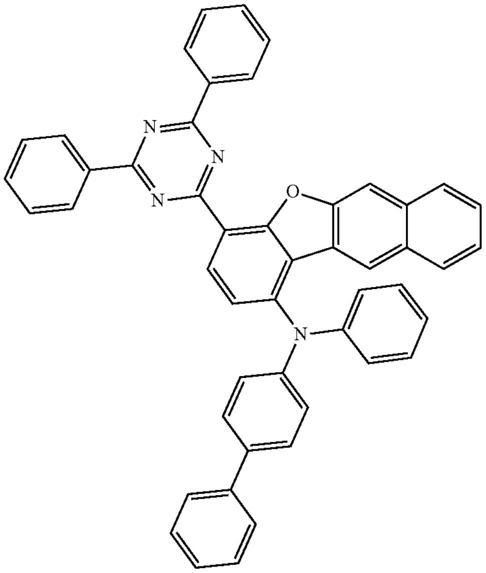
A104
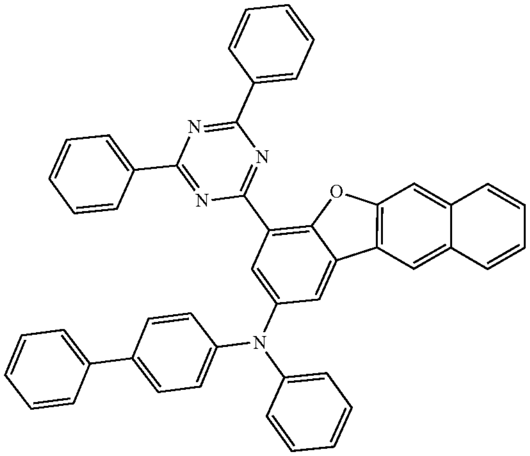
A105
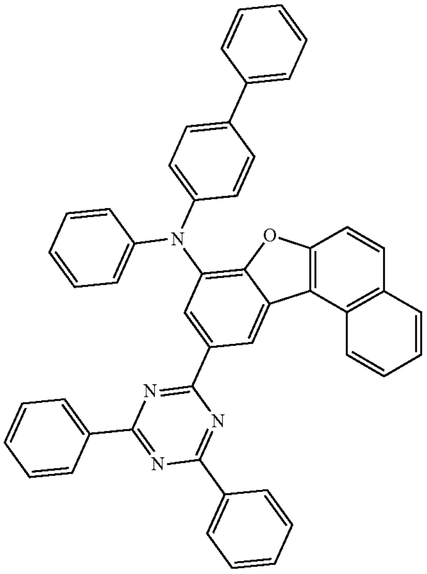

-continued
A106
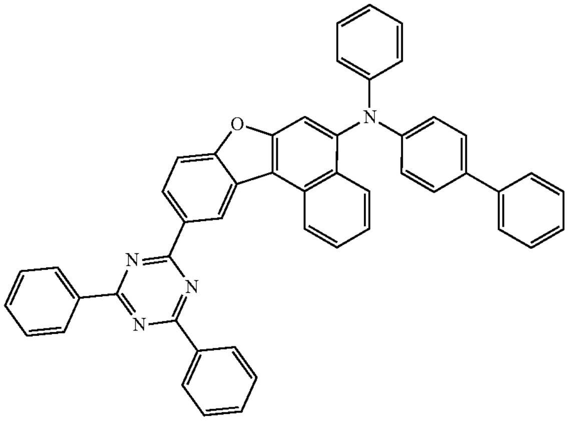
A107
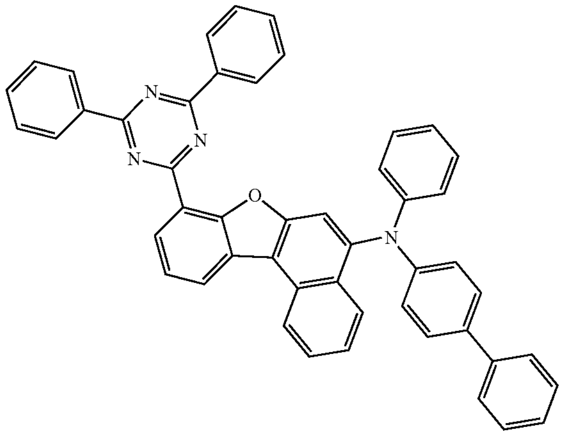
A108
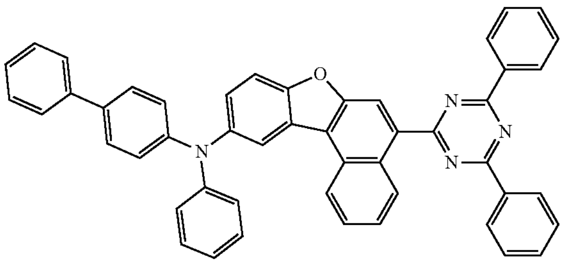
-continued
A109
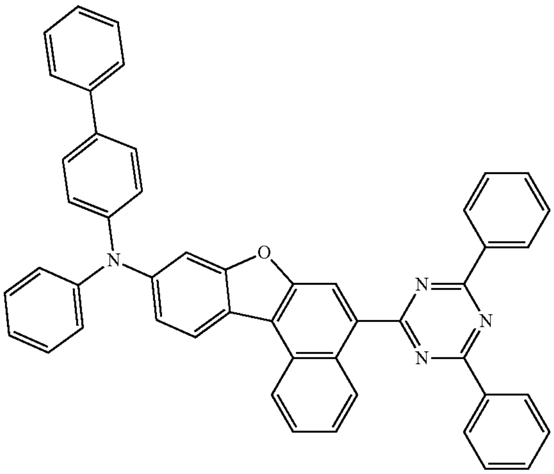
A110
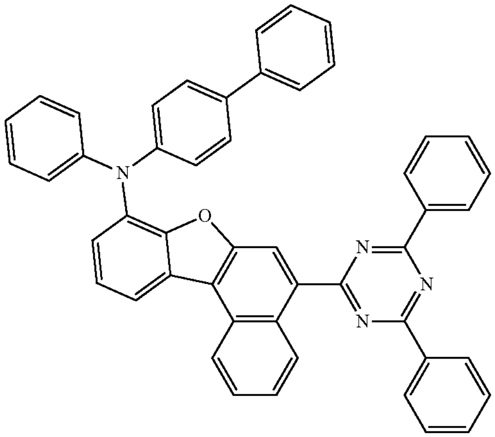
A111
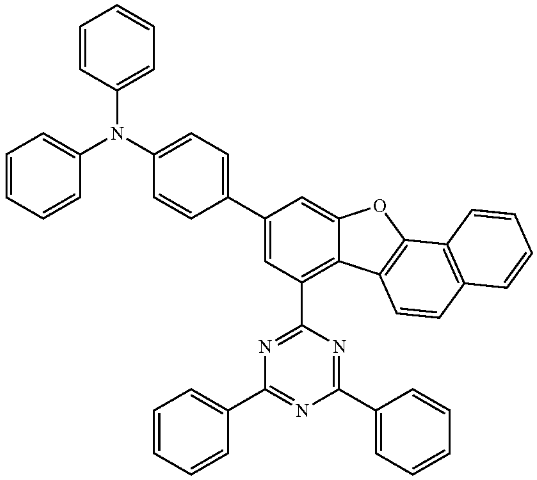

-continued
A112
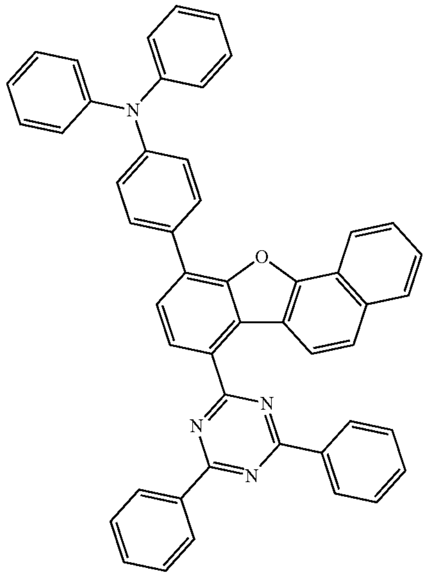
A113
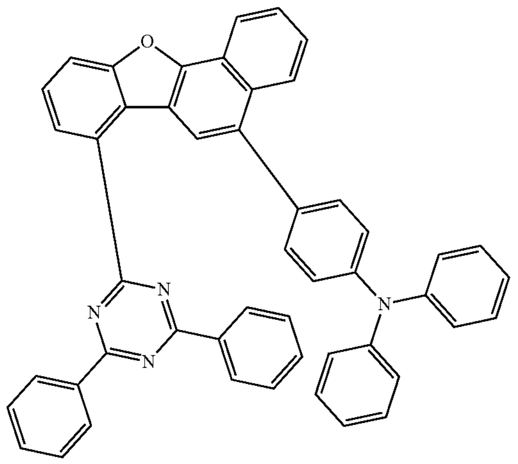
A114
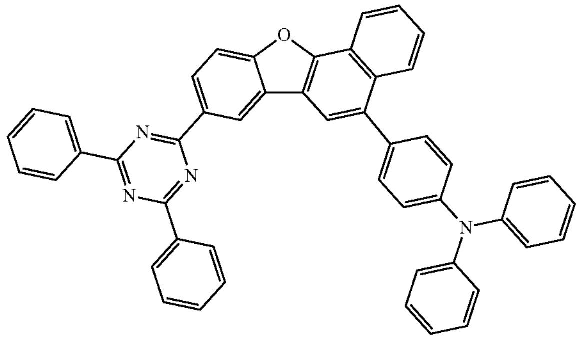
-continued
A115
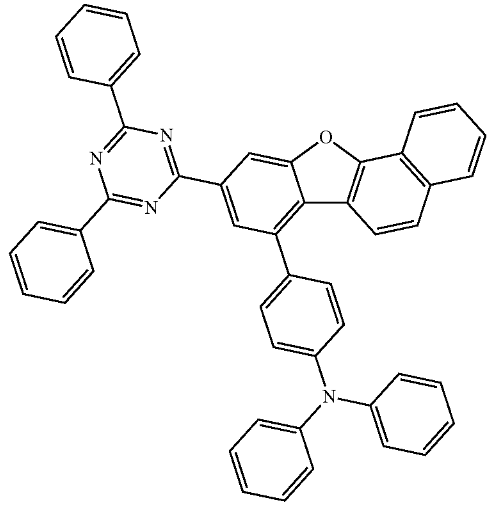
A116
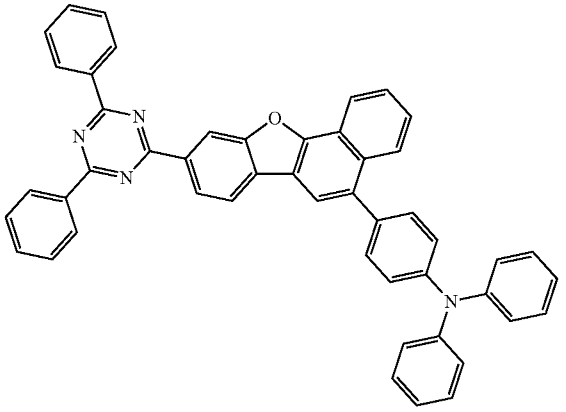
A117
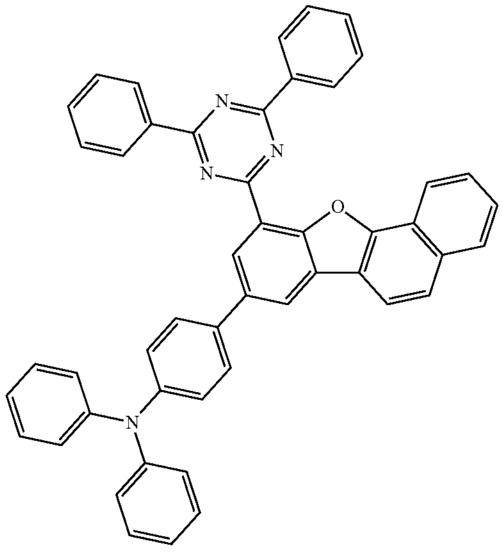

-continued
A118
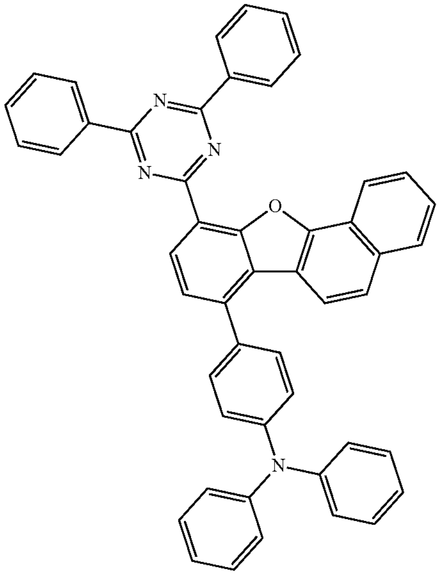
A119
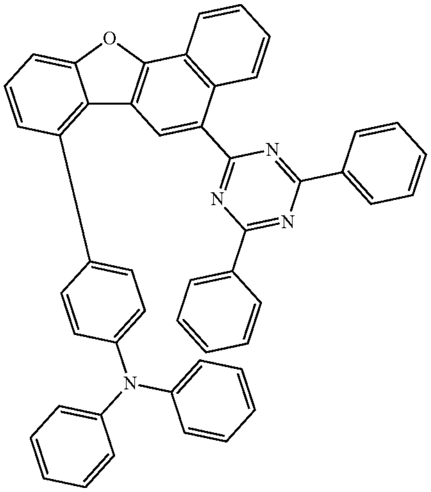
A120
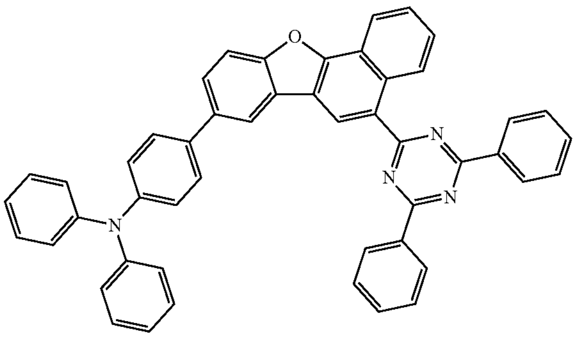
-continued
A121
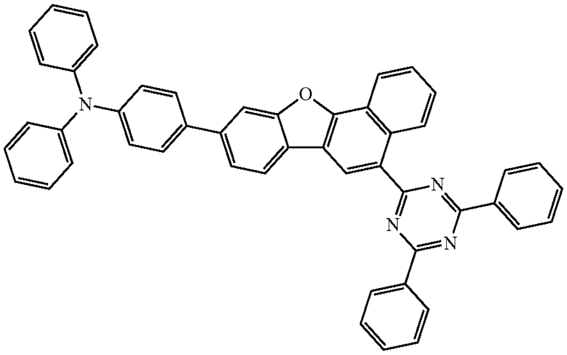
A122
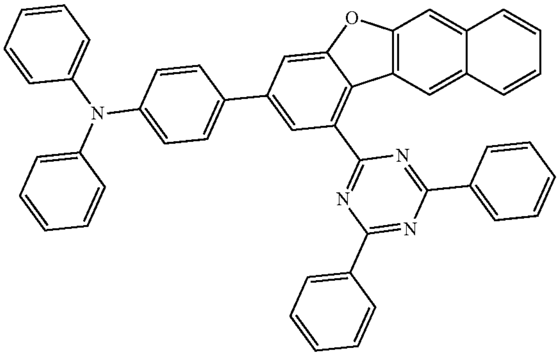
A123
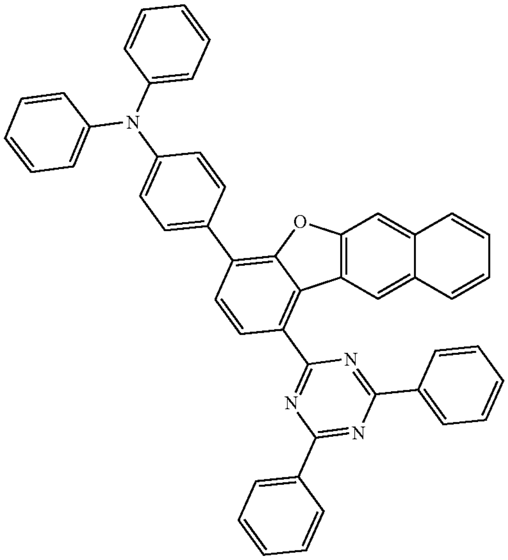

-continued
A124
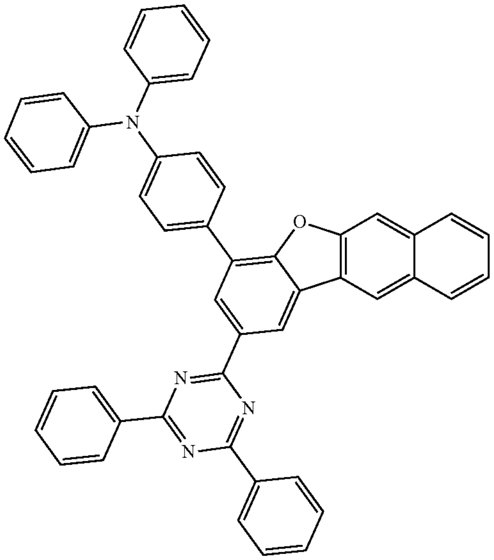
A125
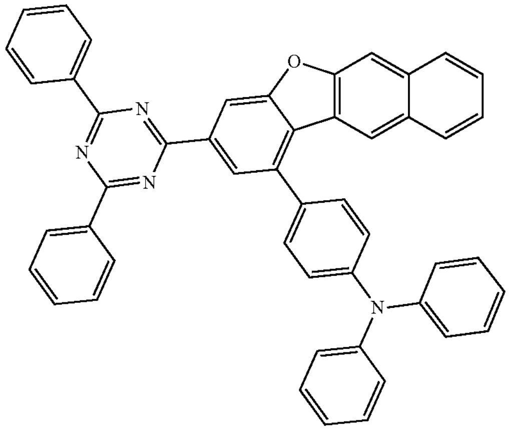
A126
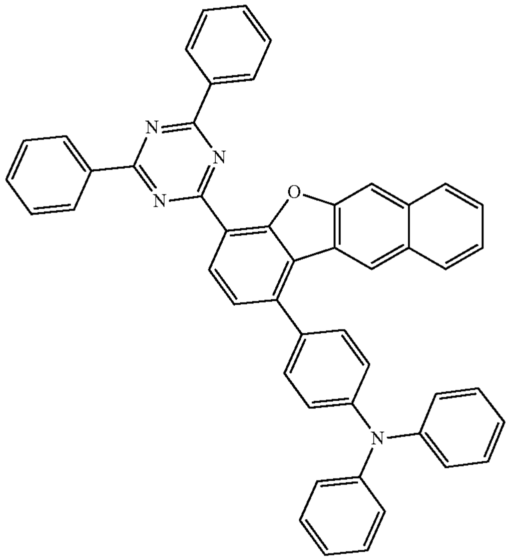
-continued
A127
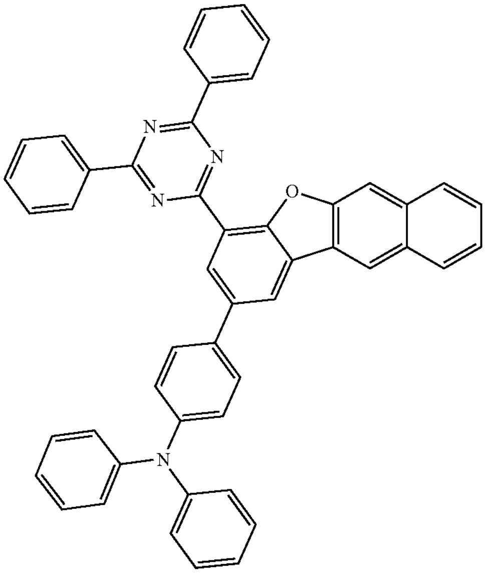
A128
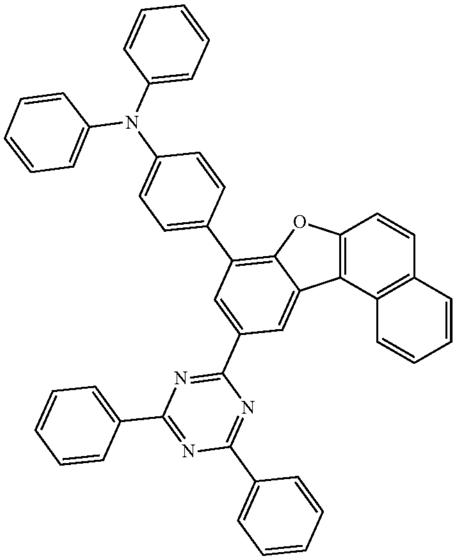
A129
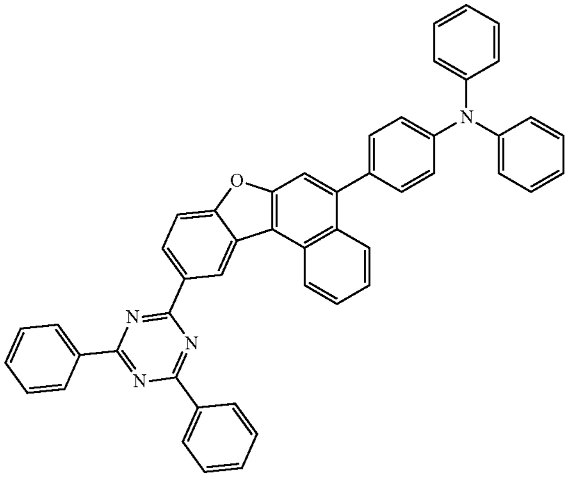

-continued
A130
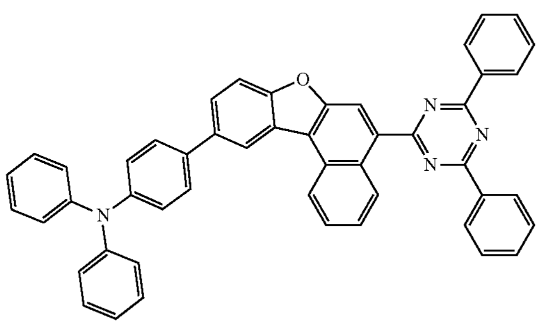
A131
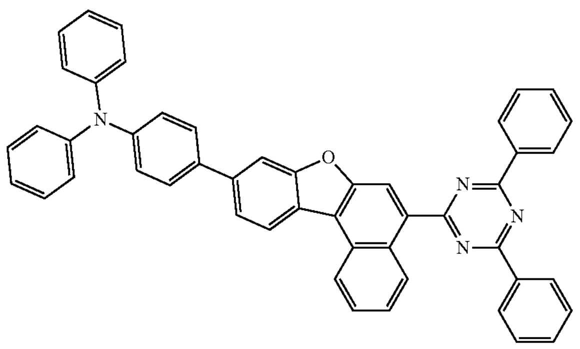
A132
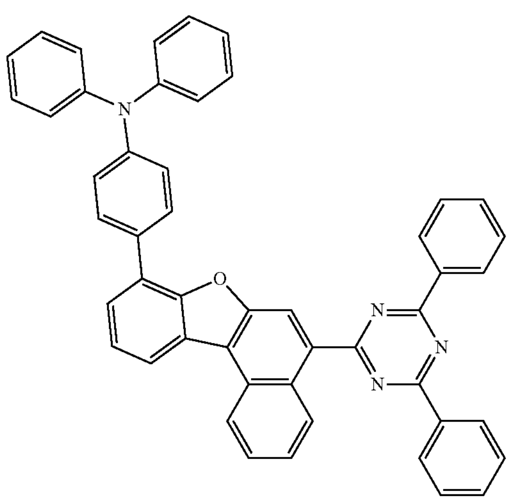
-continued
A133
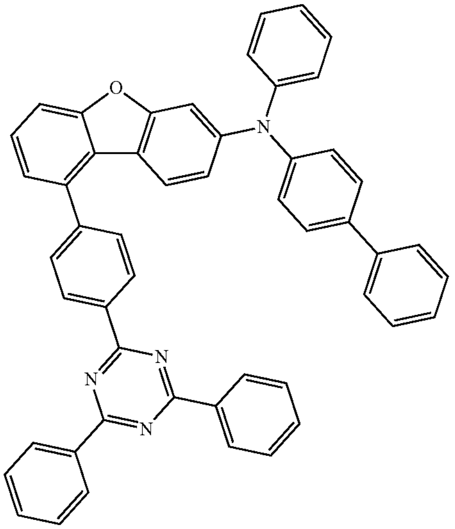
A134
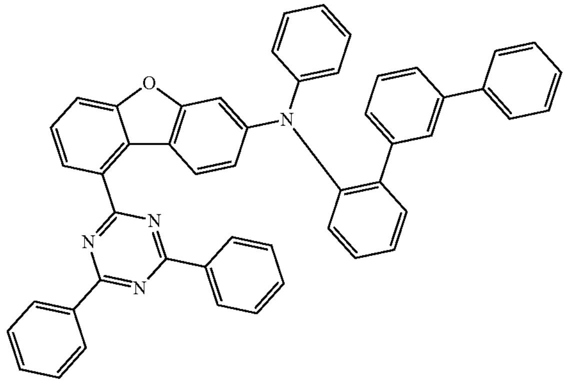
A135
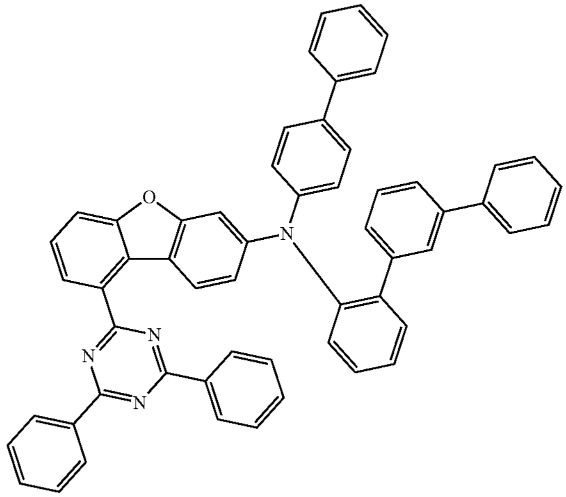

-continued
A136
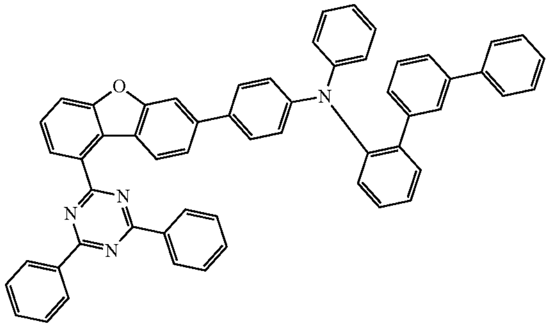
A137
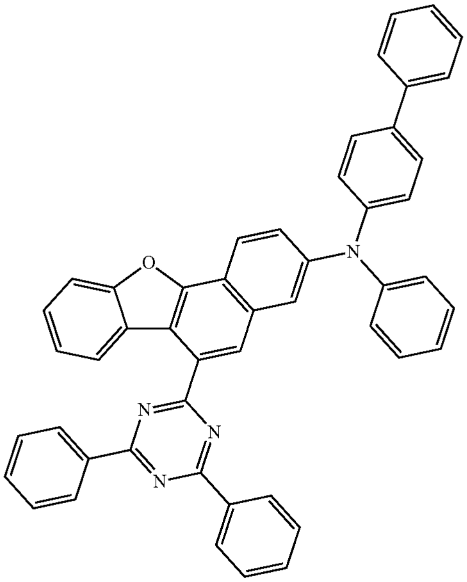
A138
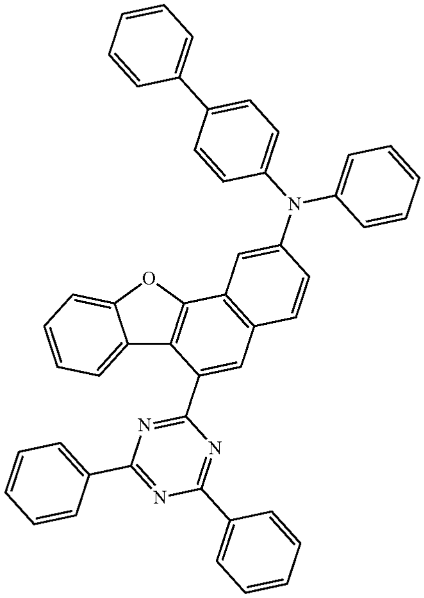
-continued
A139
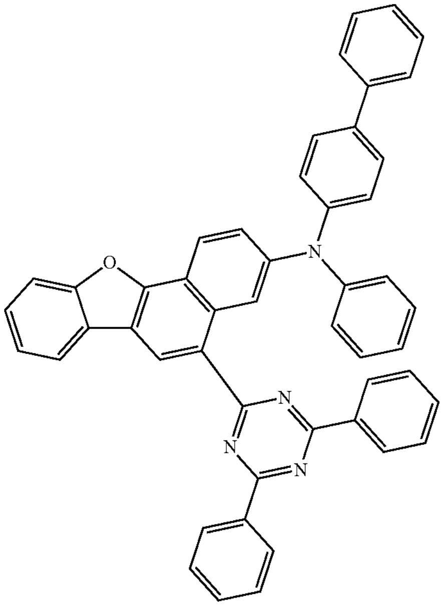
A140
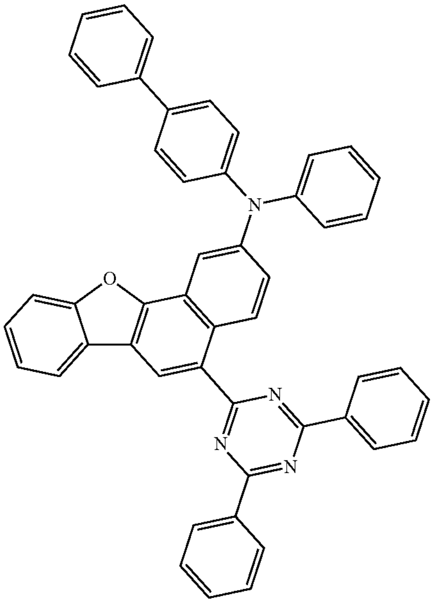
A141
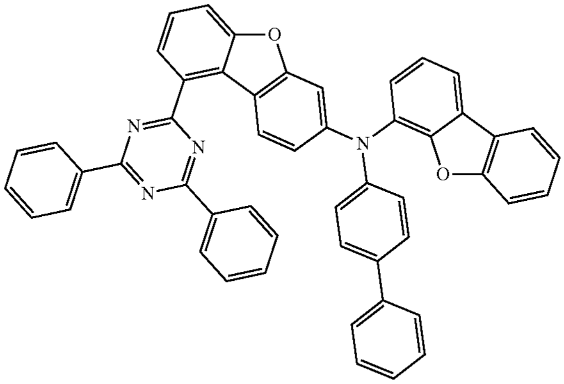

-continued
A142
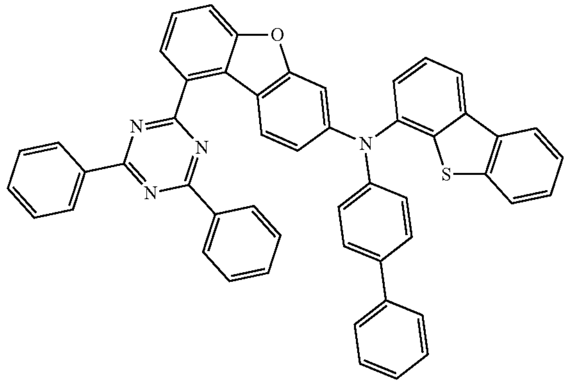
A143
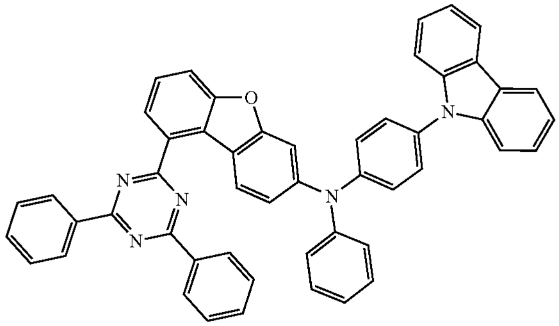
A144
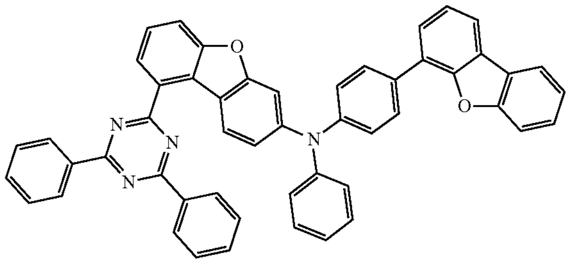
A145
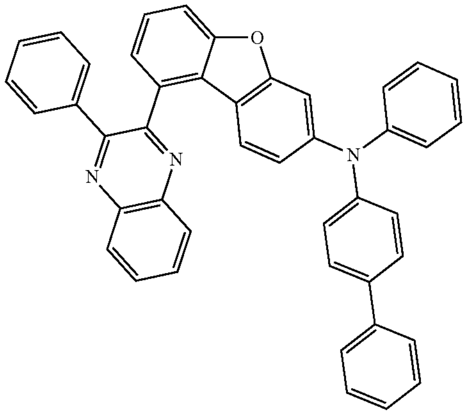
-continued
A146
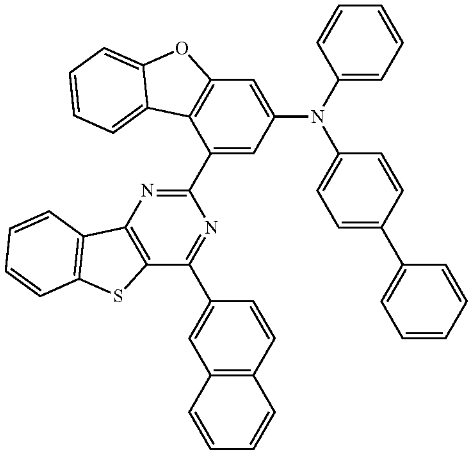
A147
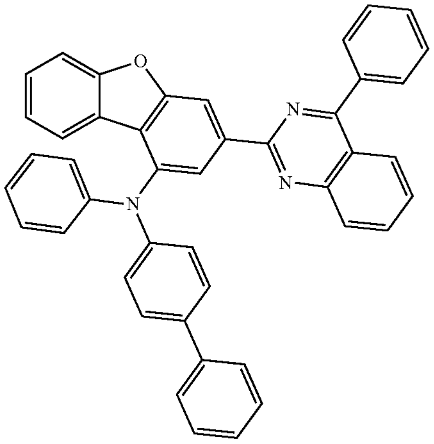
A148
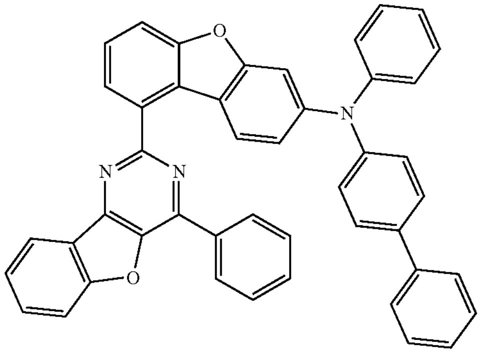
A149
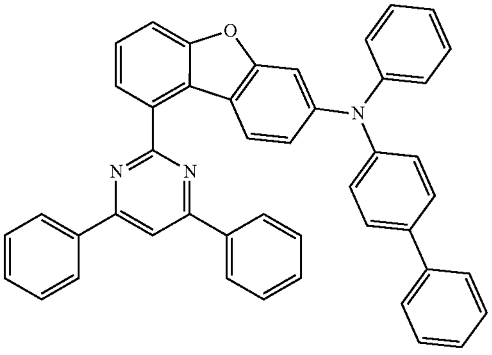

-continued
A150
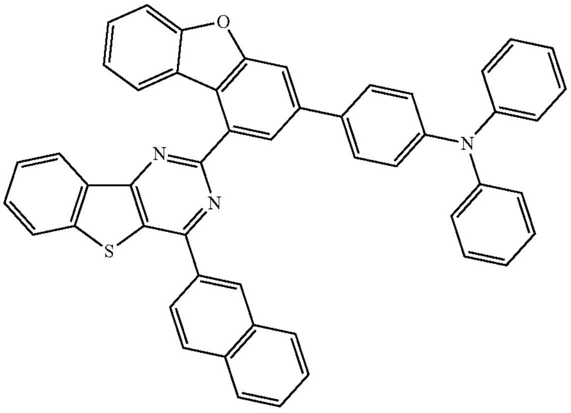
A151
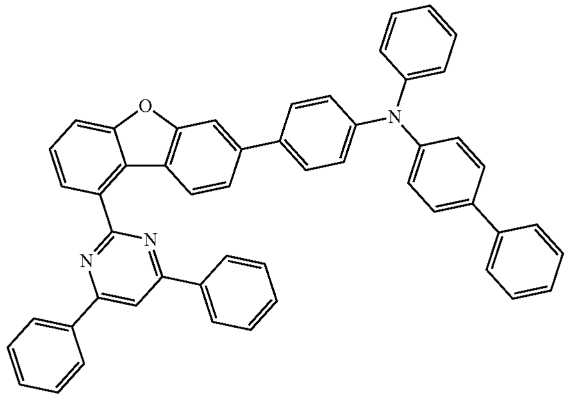
A152
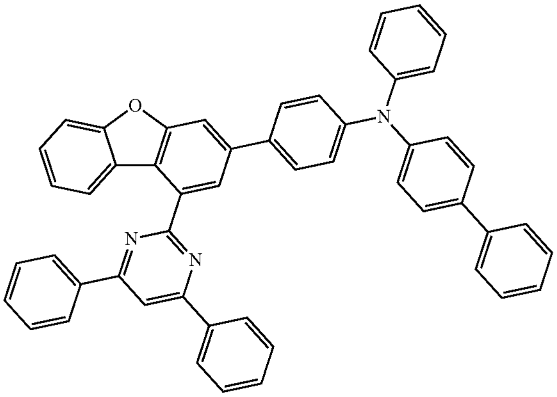
-continued
A153
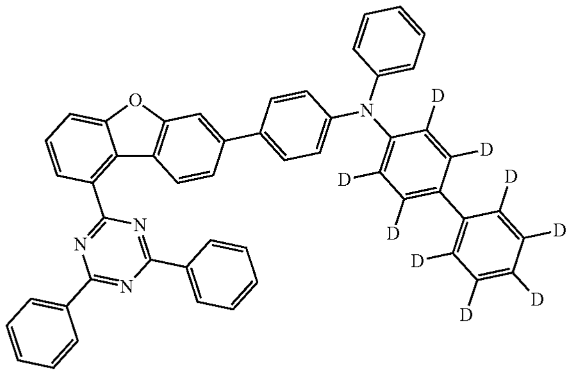
A154
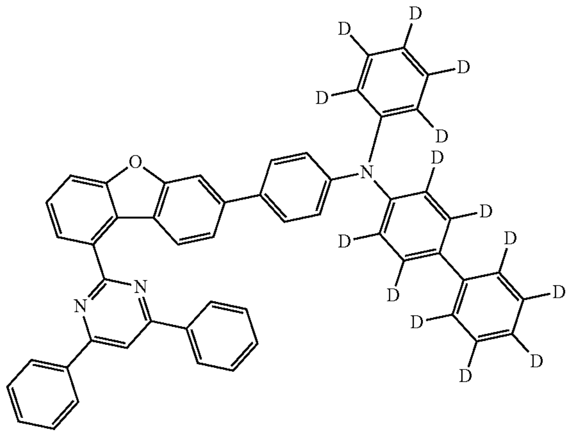
A155
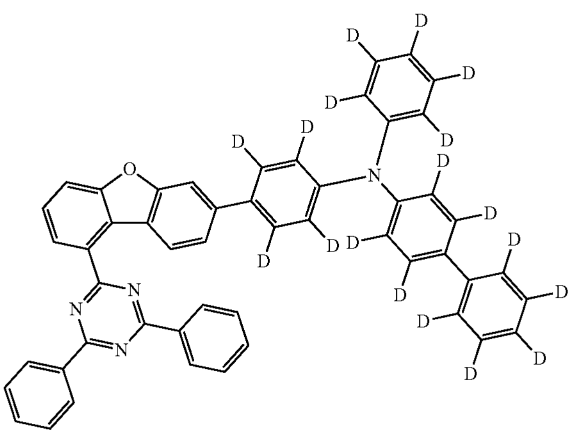

-continued
A156
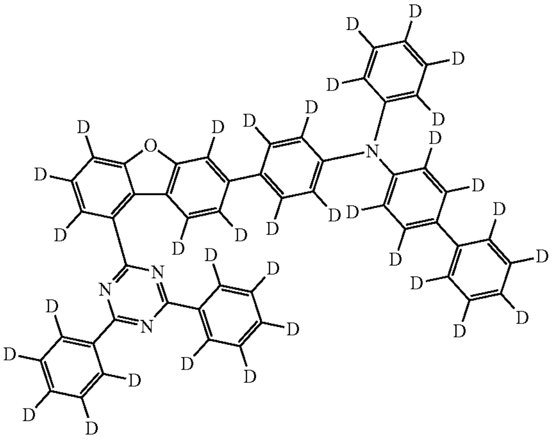
A157
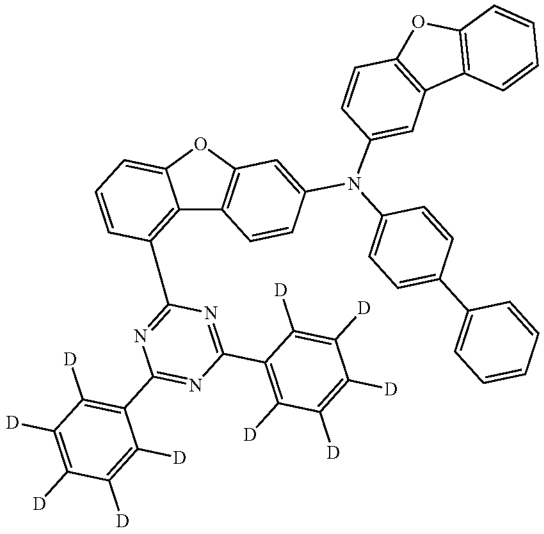
A158
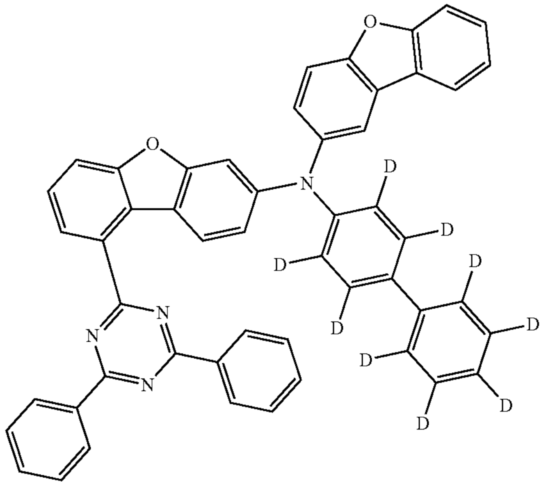
-continued
A159
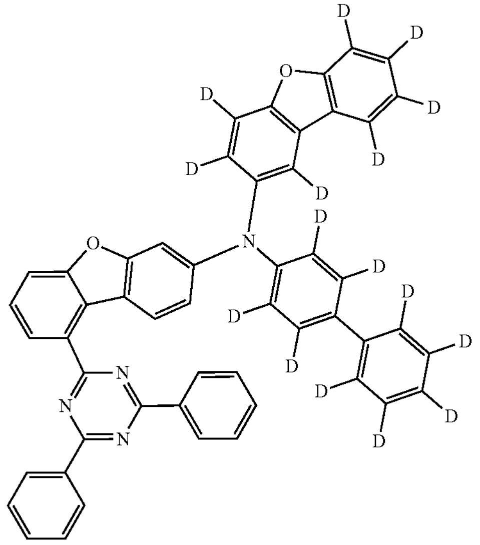
A160
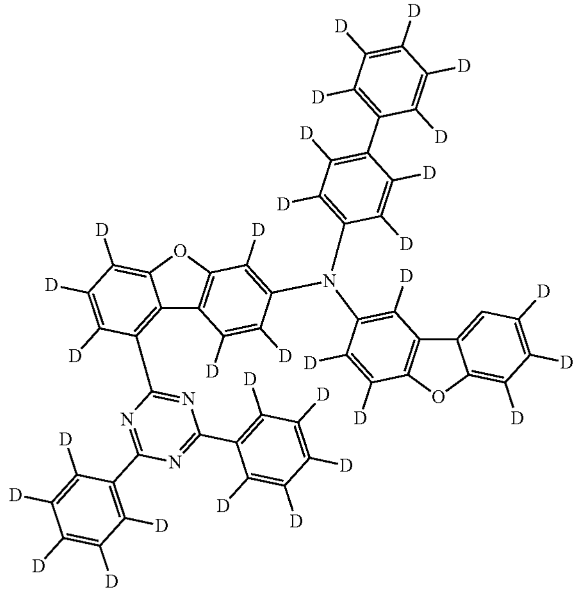
A161
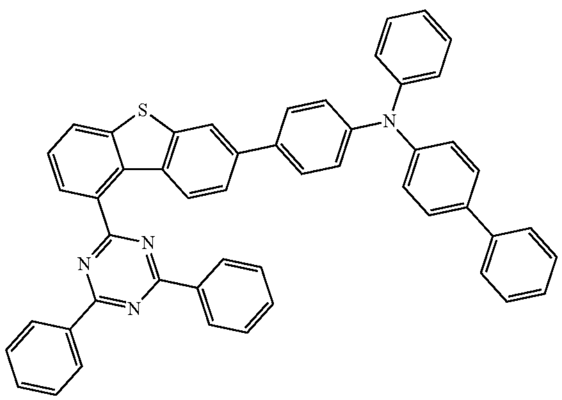

-continued
A162
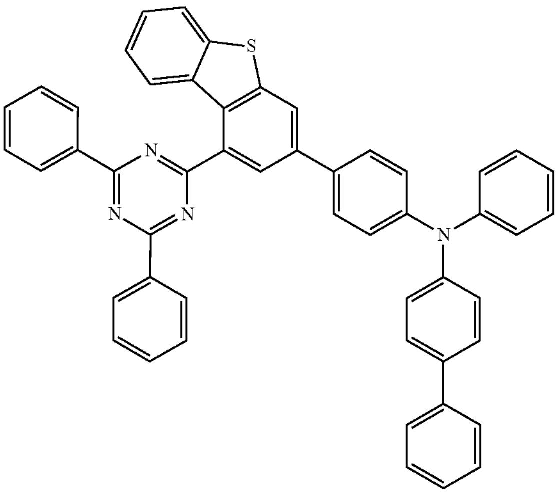
A163
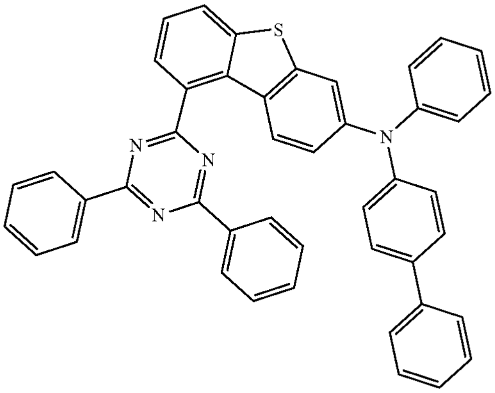
A164
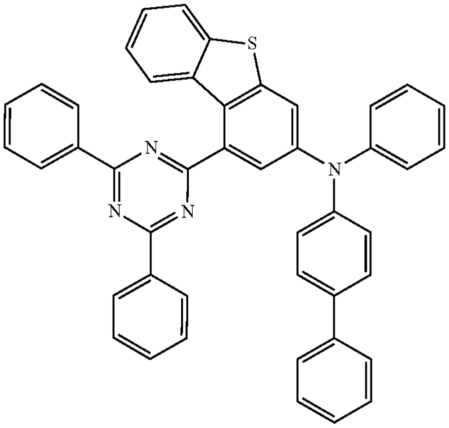
-continued
A165
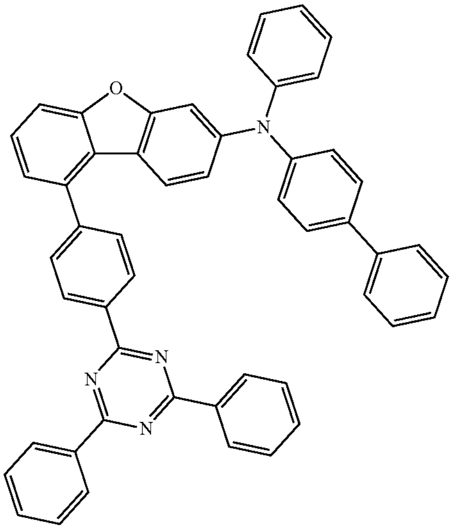
A166
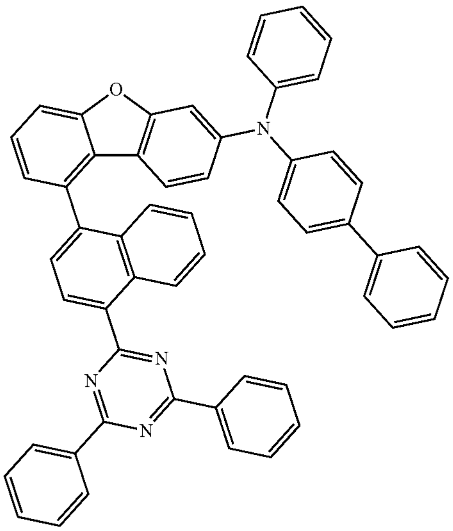
A167
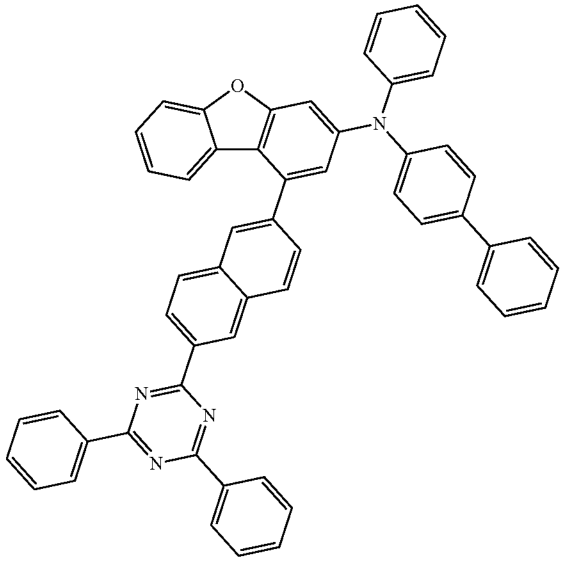

-continued
A168
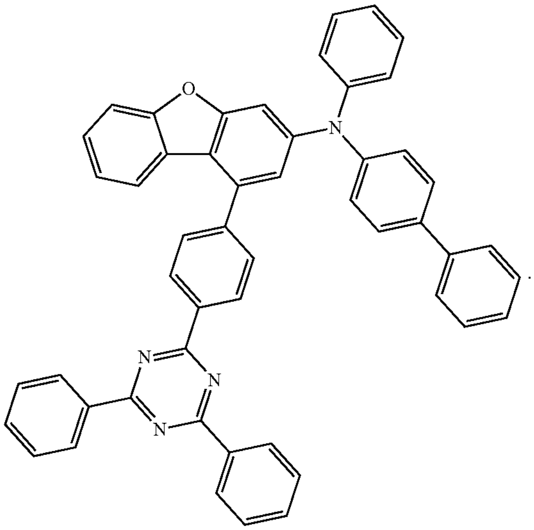
9. The composition of claim 1, wherein Chemical Formula B comprises any one of the following compounds:
B1
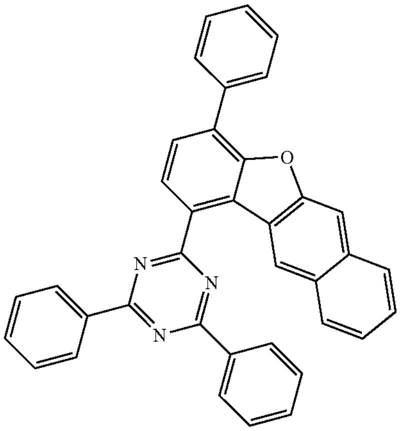
-continued
B2
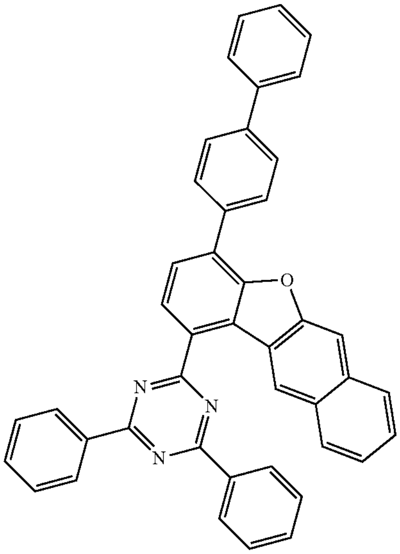
B3
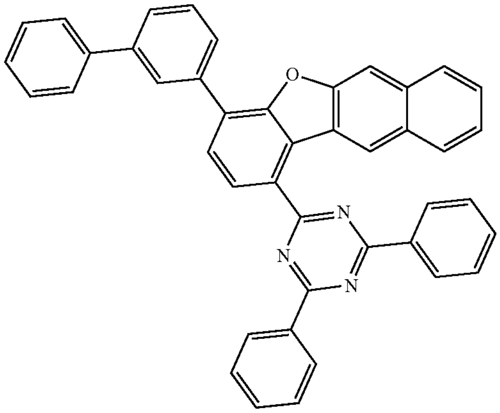
B4
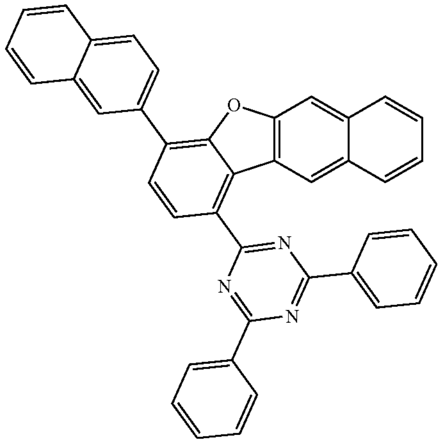

-continued
B5
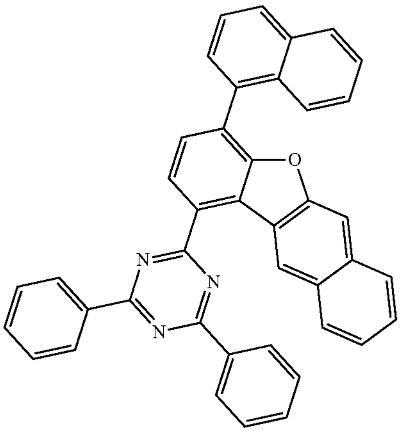
B6
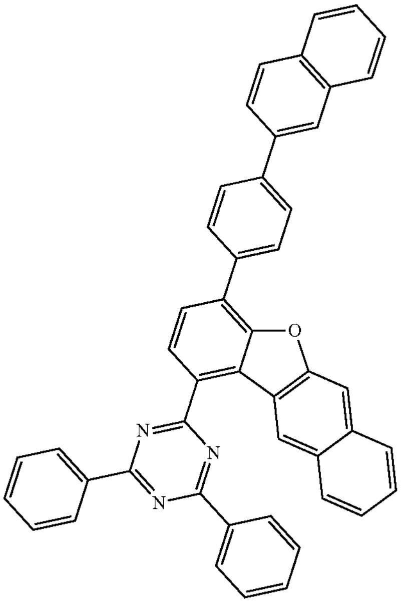
B7
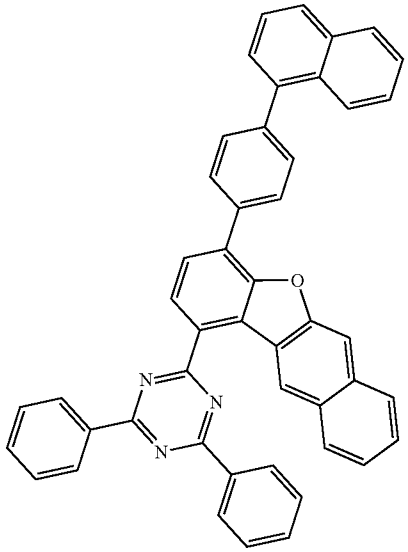
-continued
B8
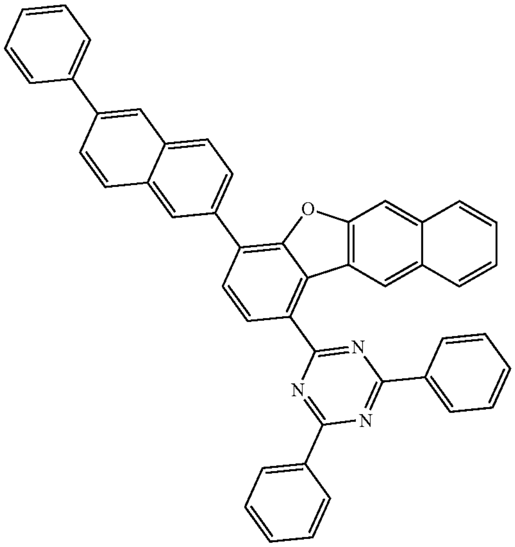
B9
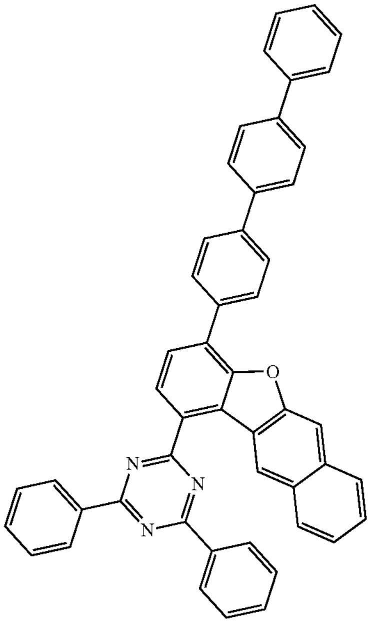
B10
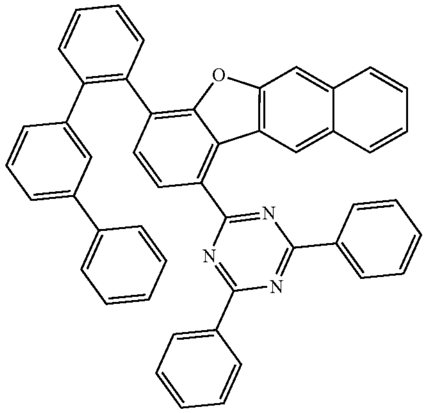

-continued
B11
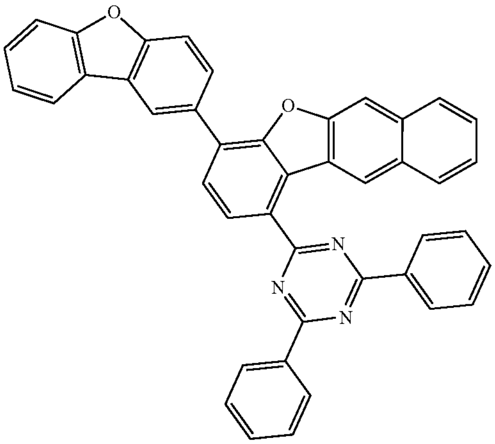
B12
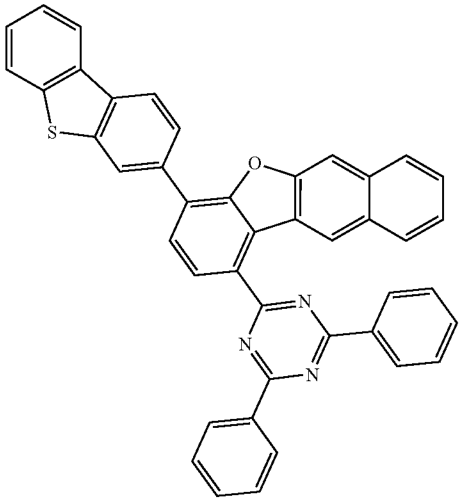
B13
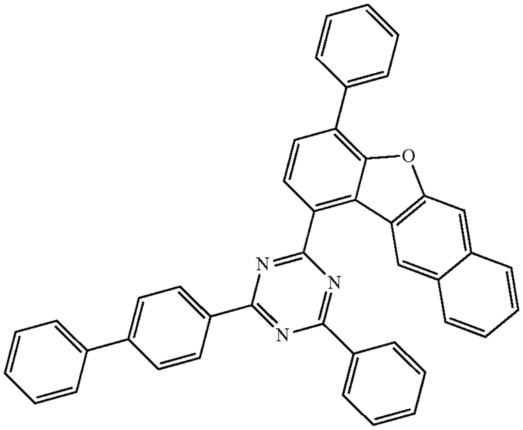
-continued
B14
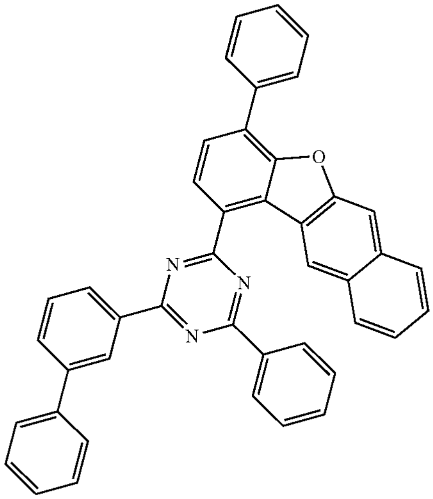
B15
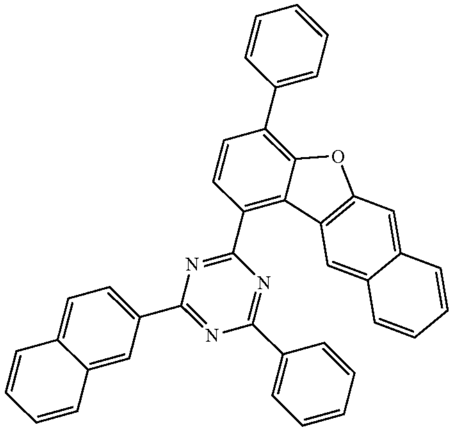
B16
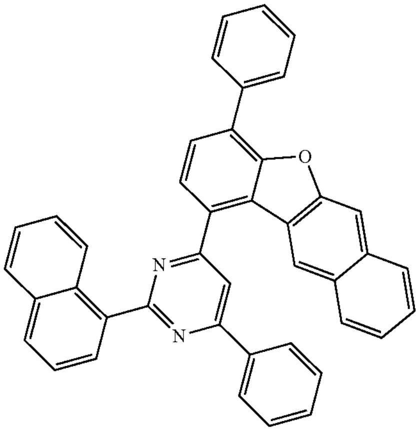

-continued
B17
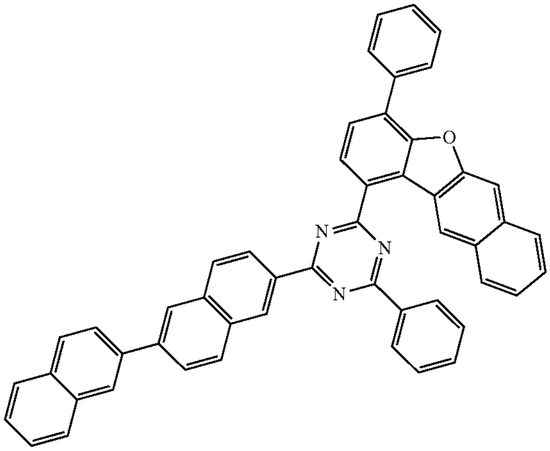
B18
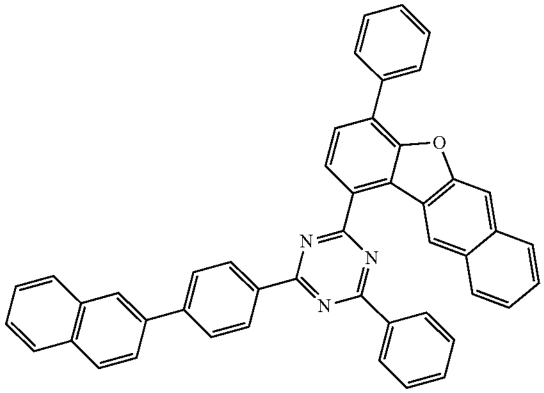
B19
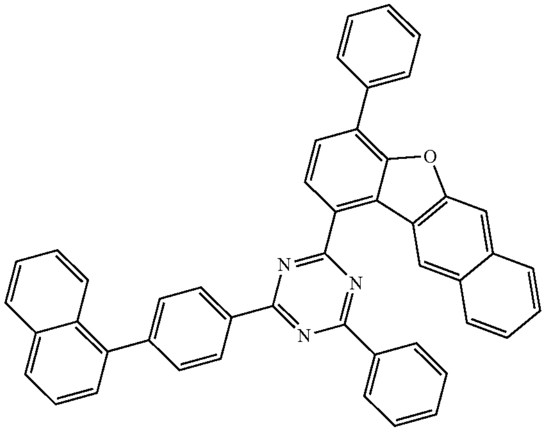
-continued
B20
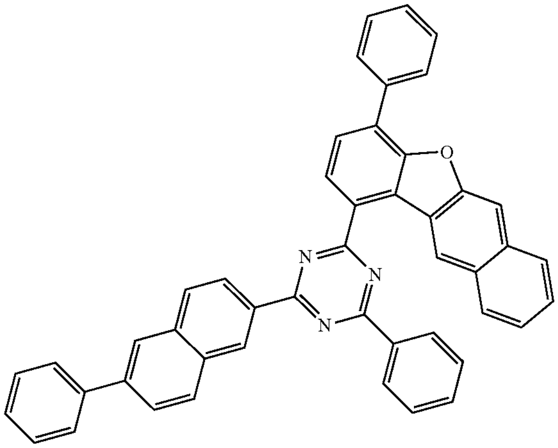
B21
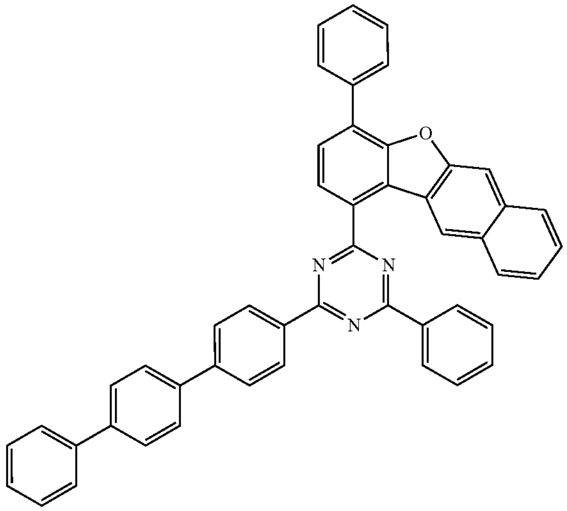
B22
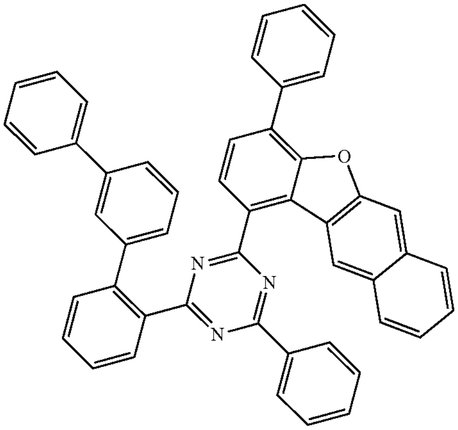

-continued
B23
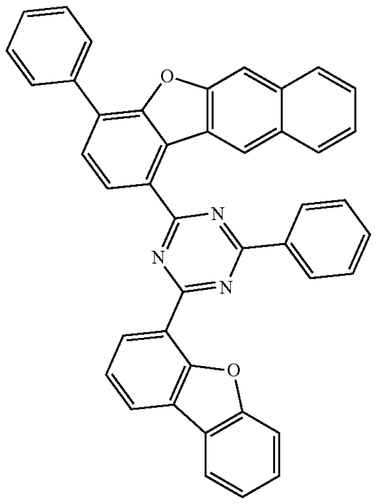
B24
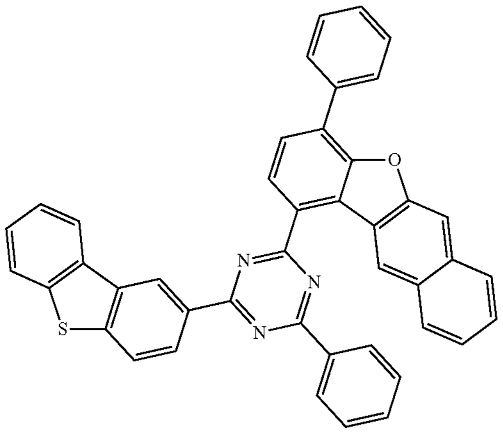
B25
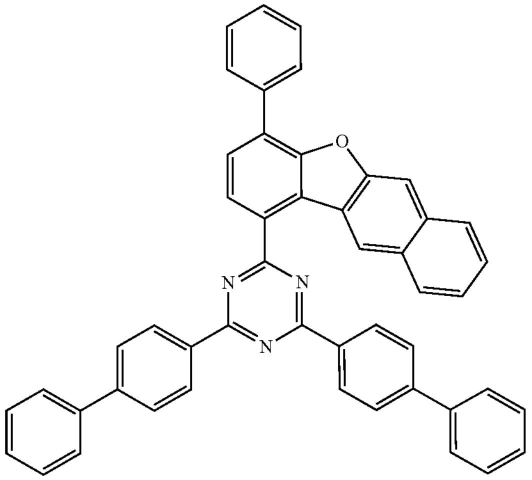
-continued
B26
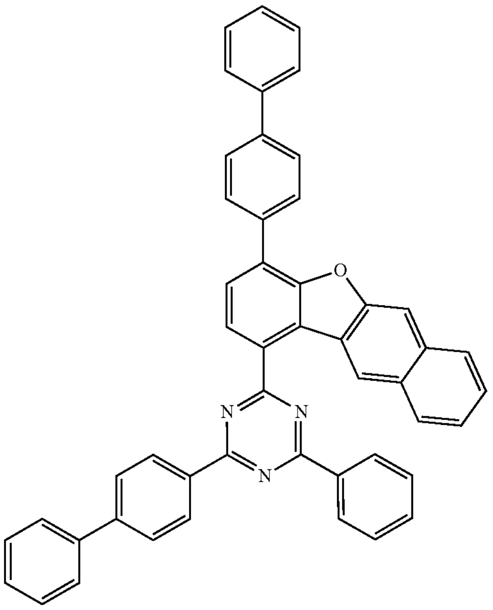
B27
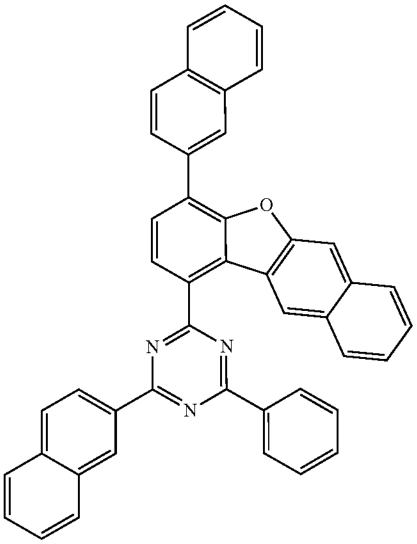
B28
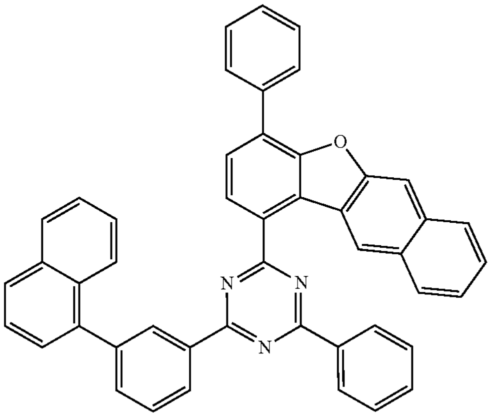

-continued
B29
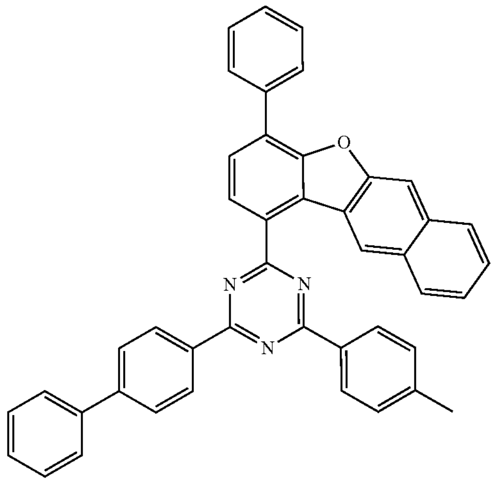
B30
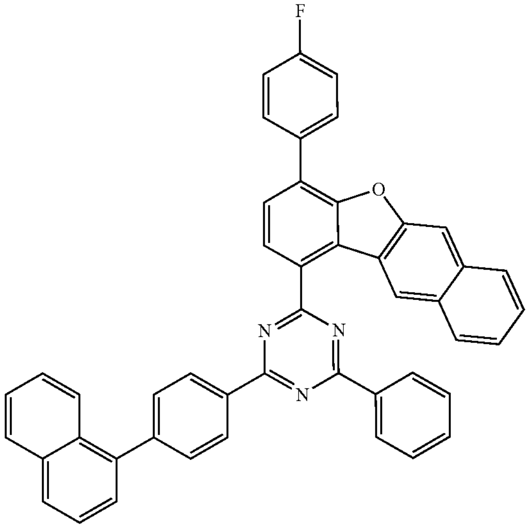
B31
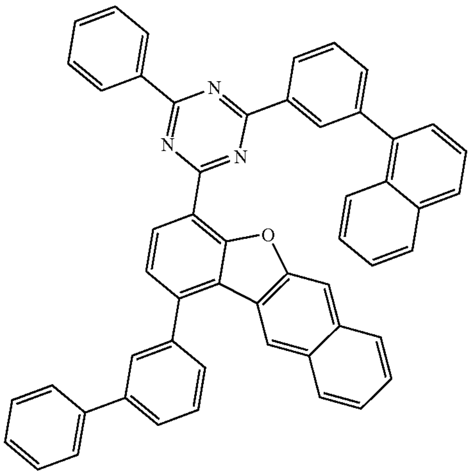
-continued
B32
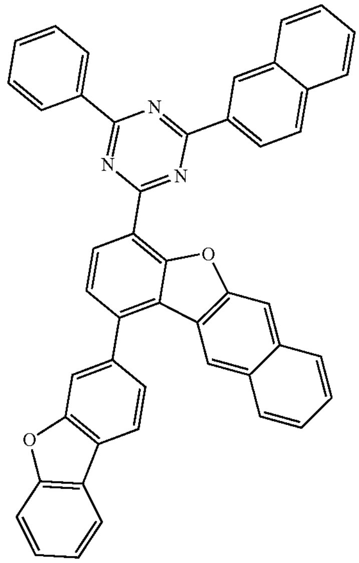
B33
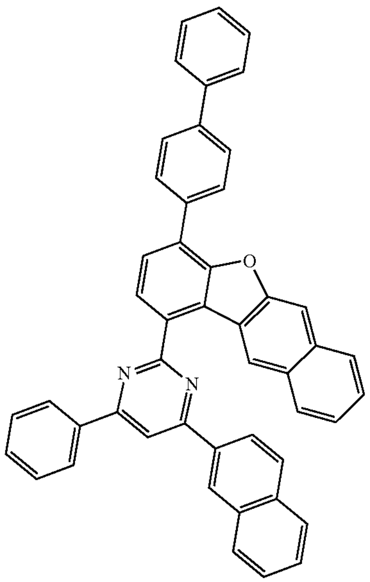

-continued
B34
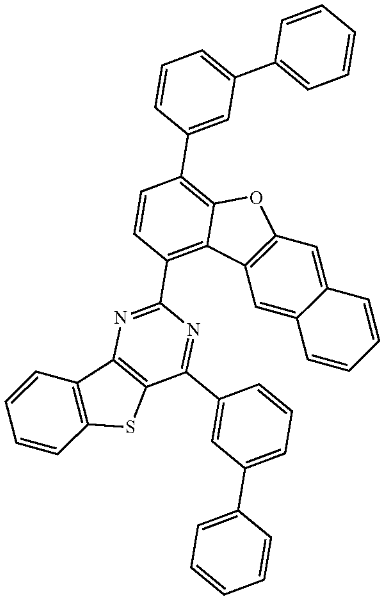
B35
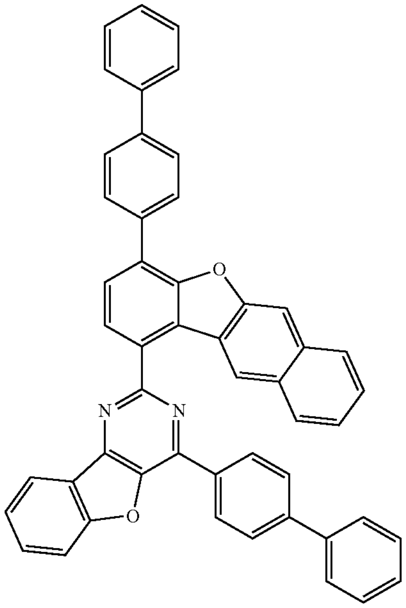
-continued
B36
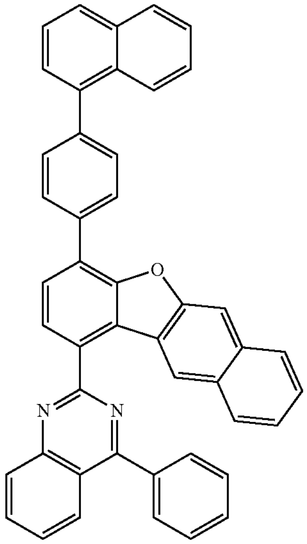
B37
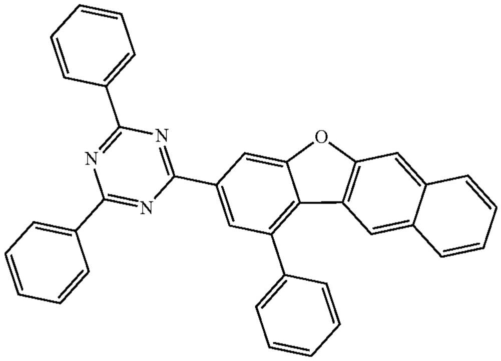
B38
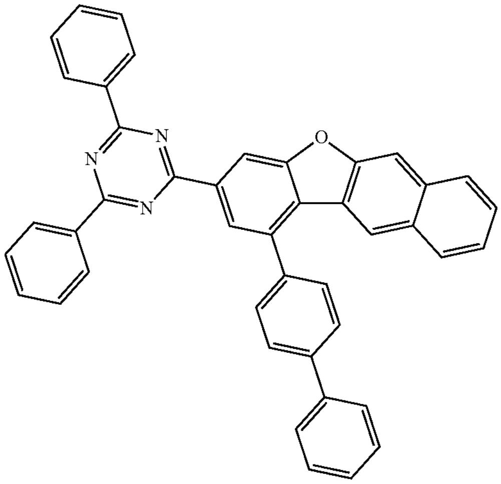

-continued
B39
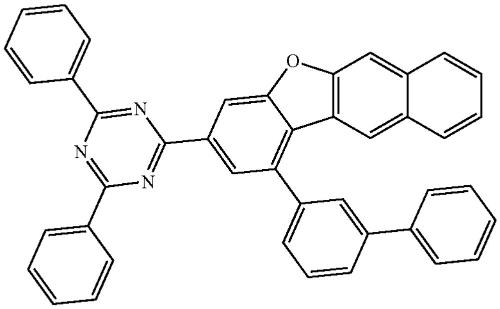
B40
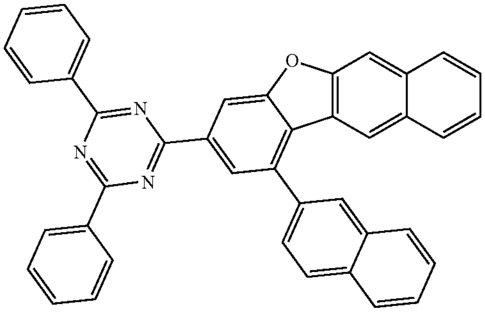
B41
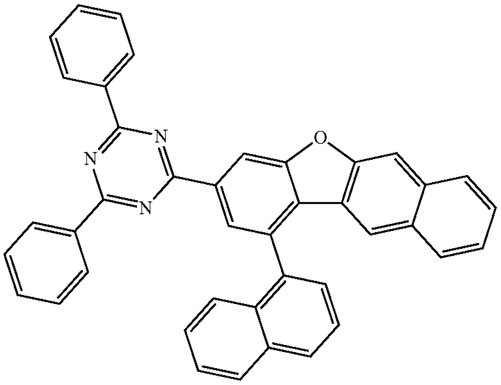
B42
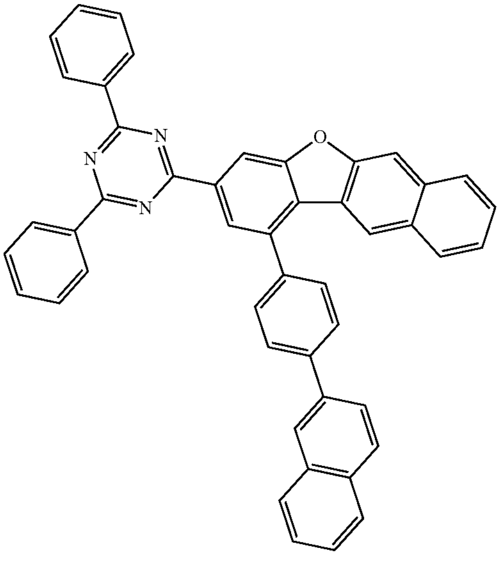
-continued
B43
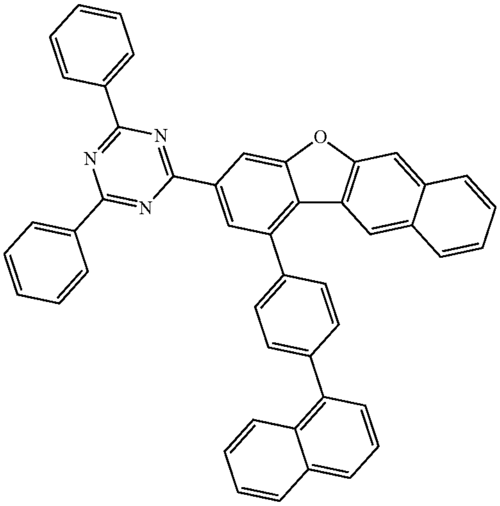
B44
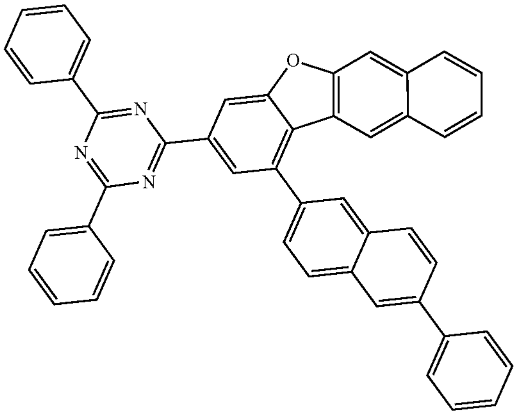
B45
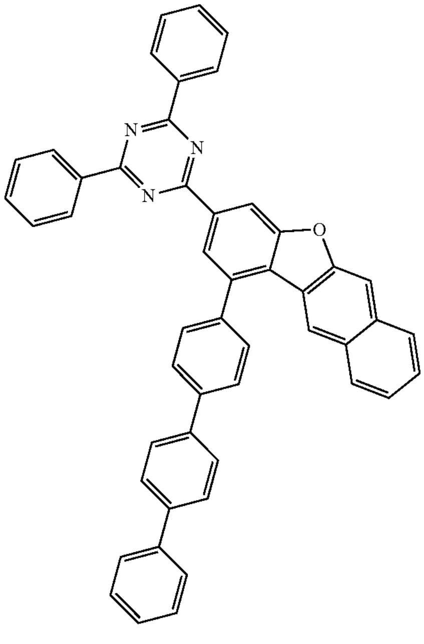

-continued
B46
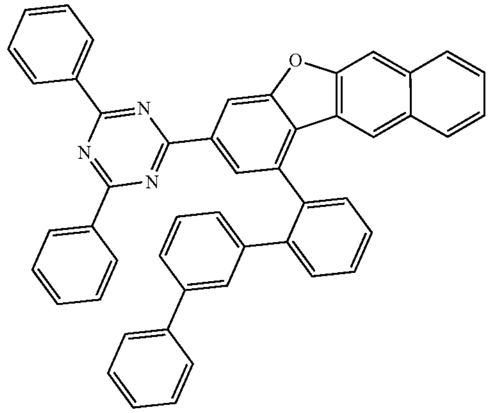
B47
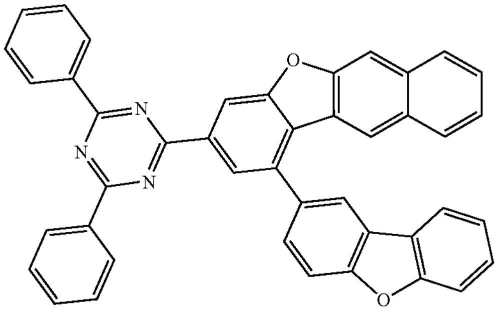
B48
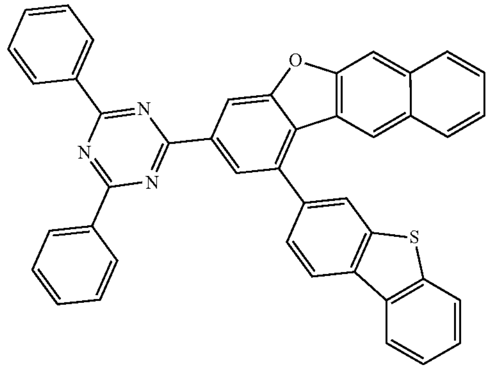
B49
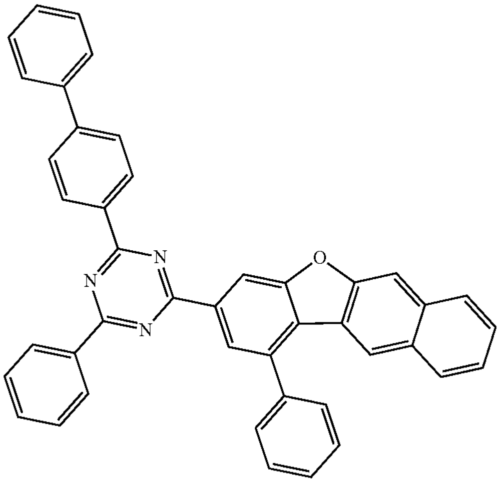
-continued
B50
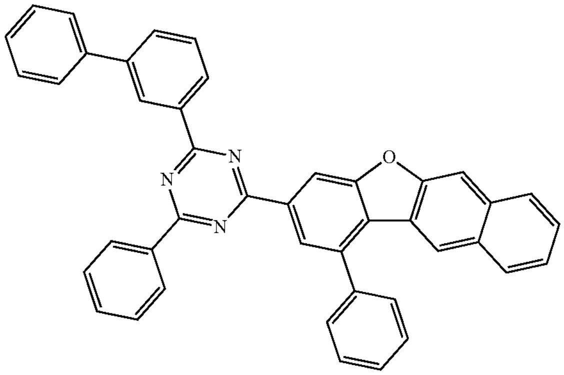
B51
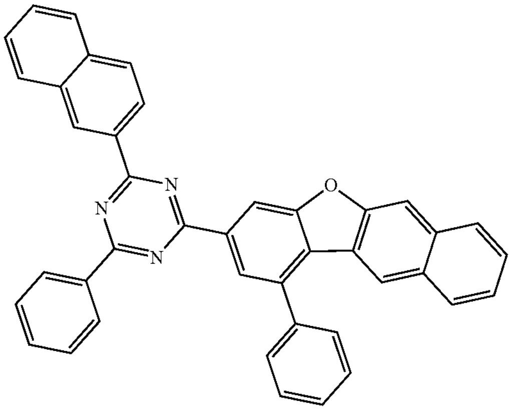
B52
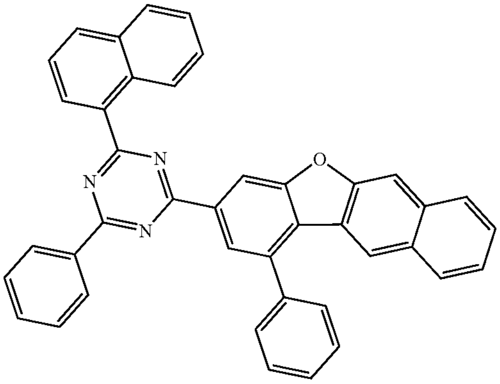
B53
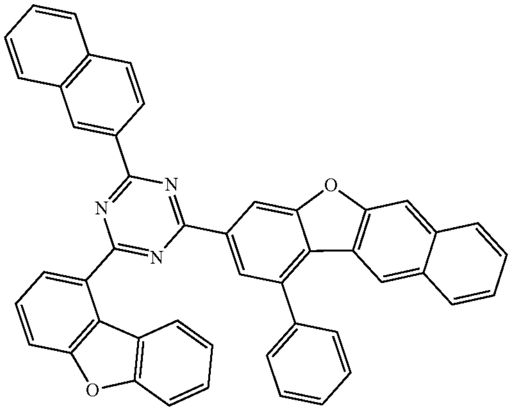

-continued
B54
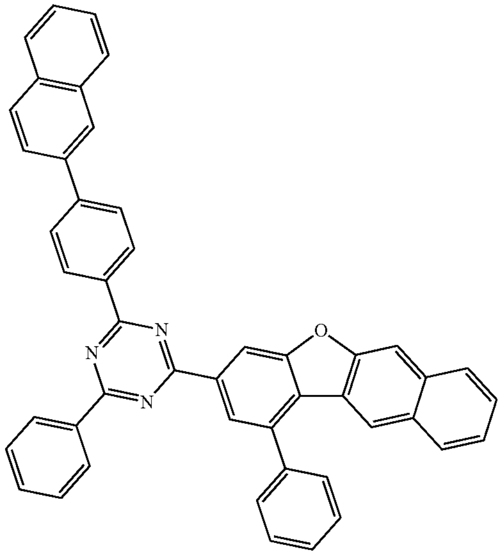
B55
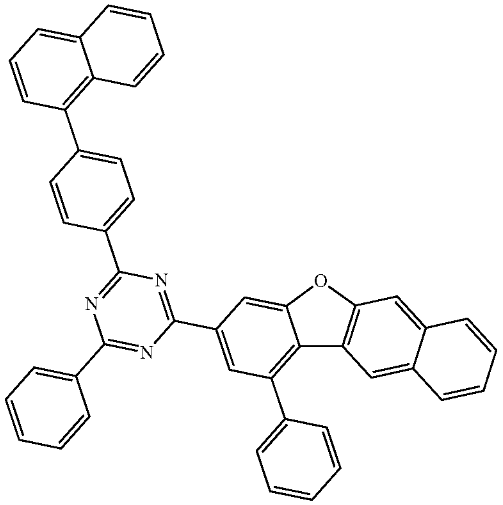
B56
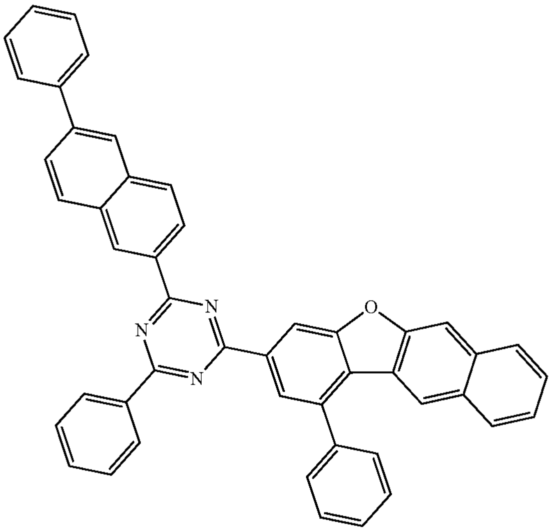
-continued
B57
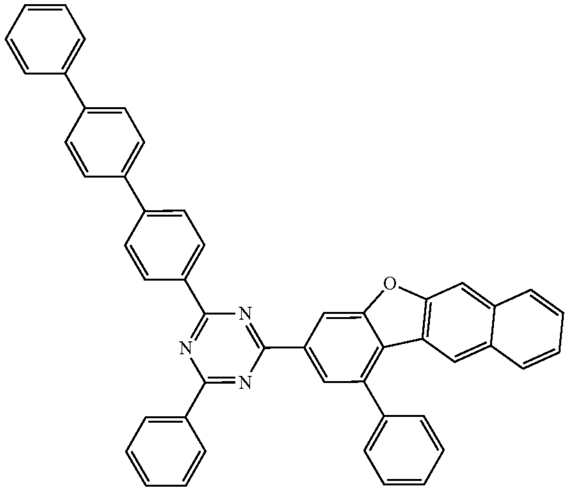
B58
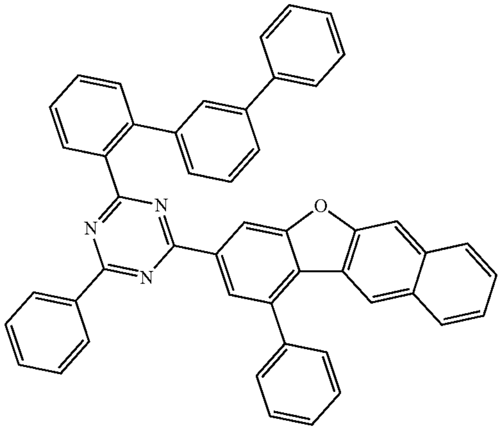
B59
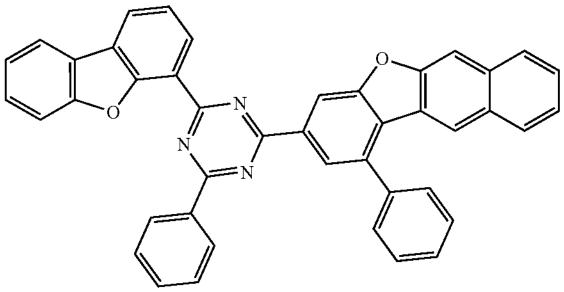

-continued
B60
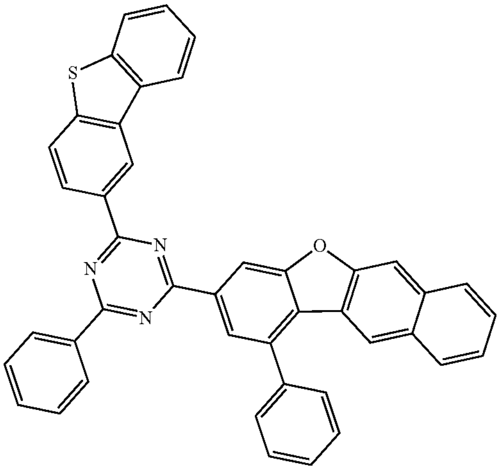
B61
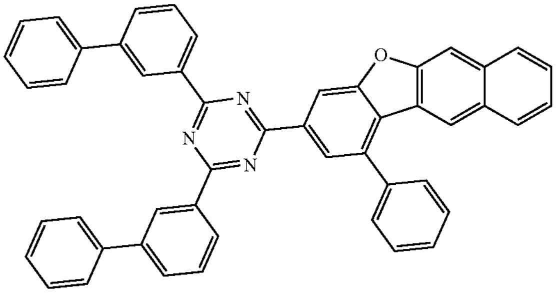
B62
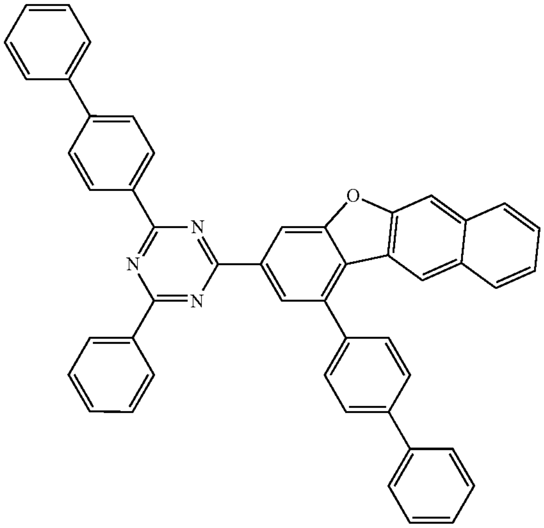
-continued
B63
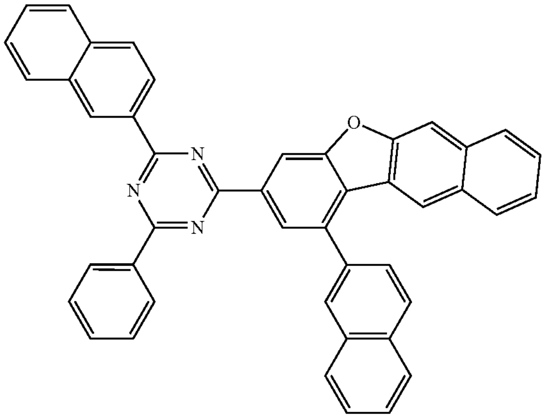
B64
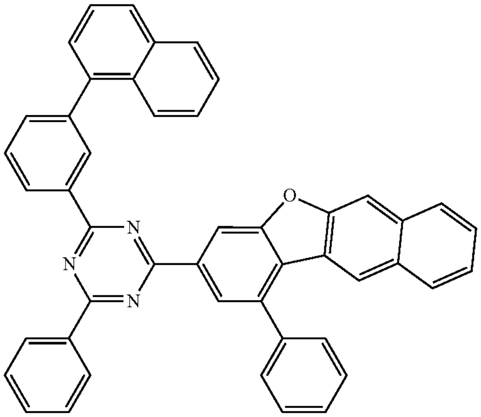
B65
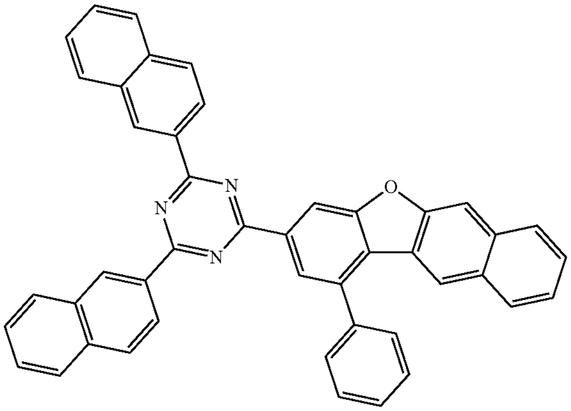

-continued
B66
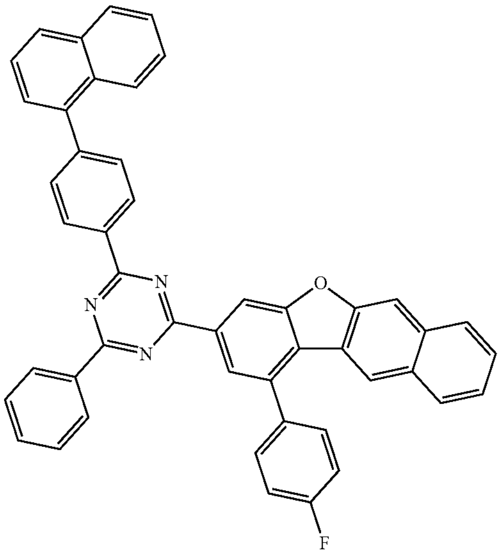
B67
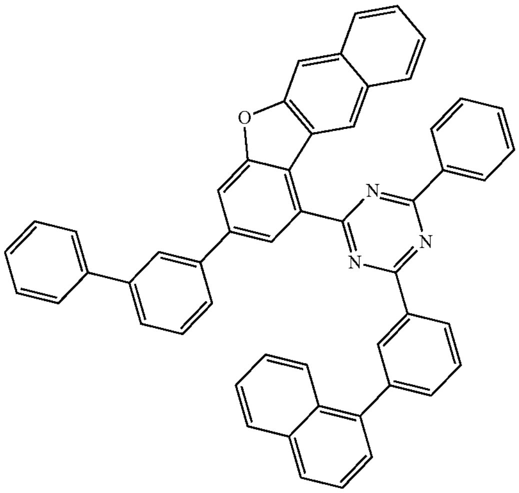
B68
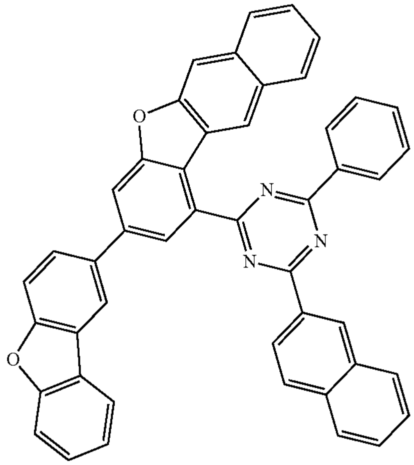
-continued
B69
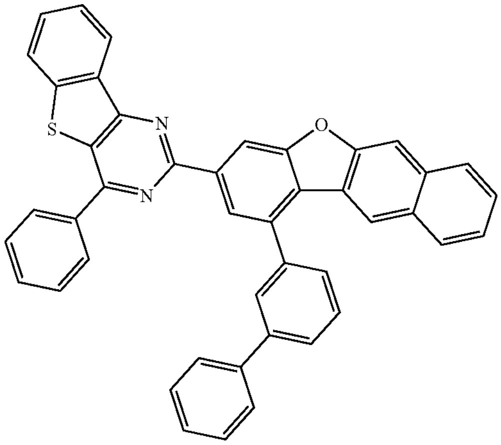
B70
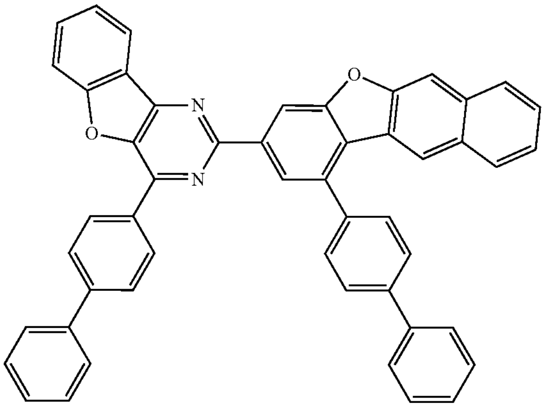
B71
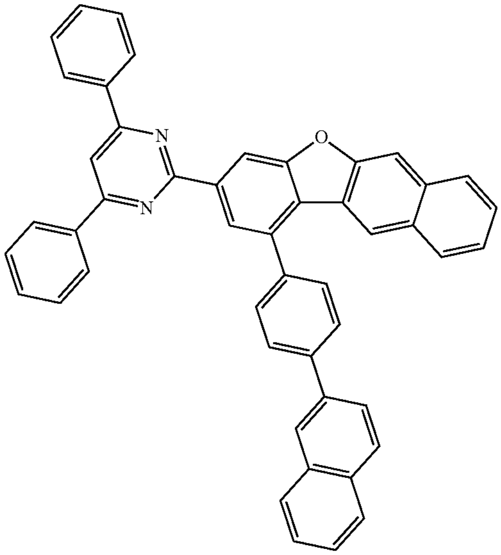

B72
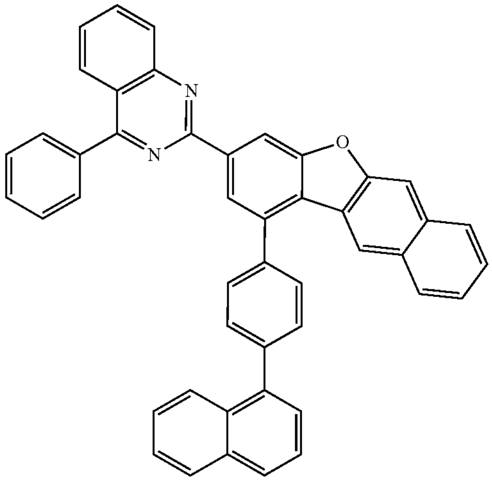
B73
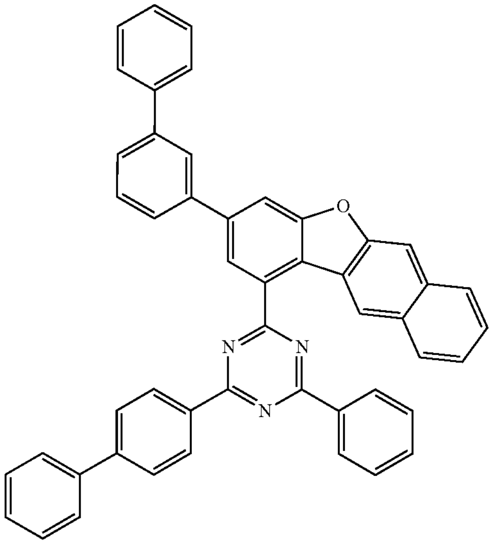
B74
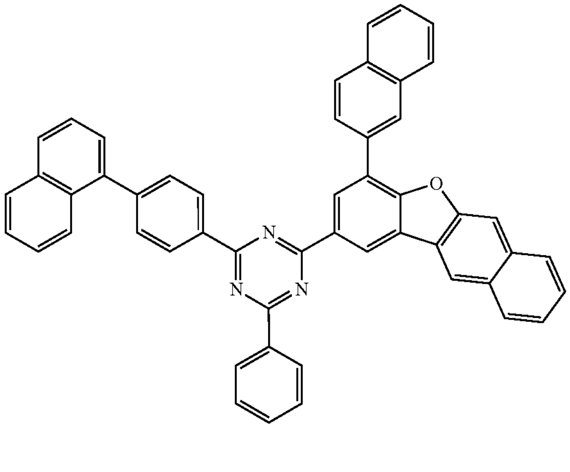
B75
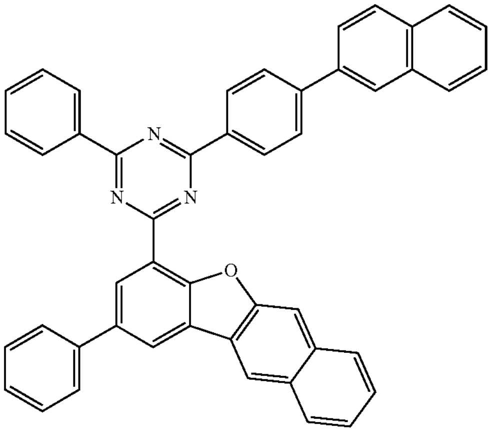
B76
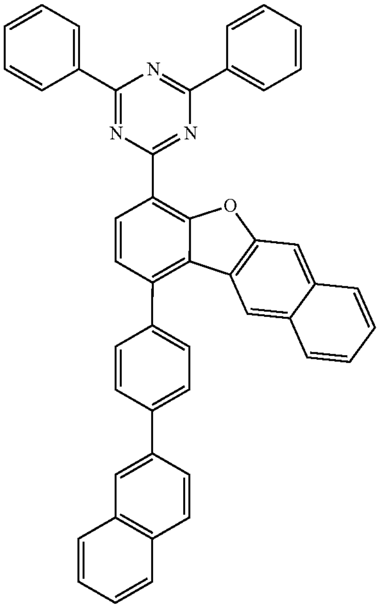
B77
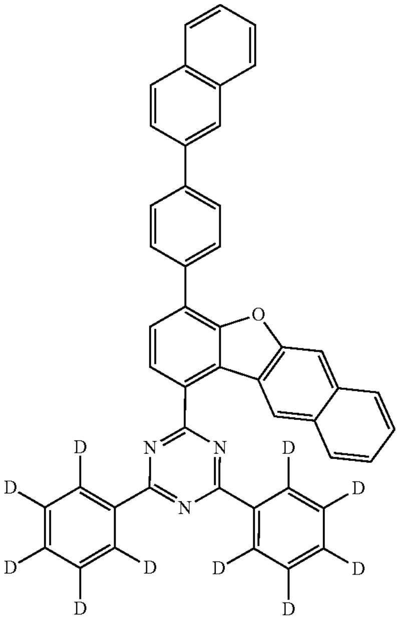

-continued
B78
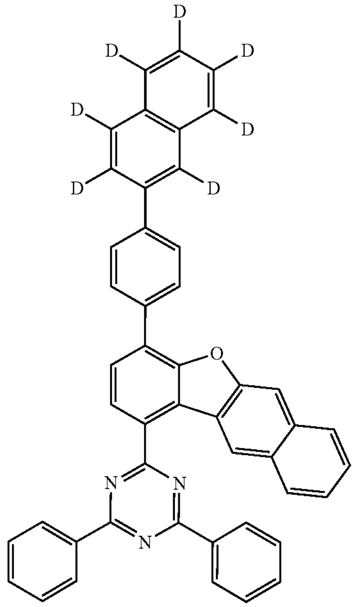
B79
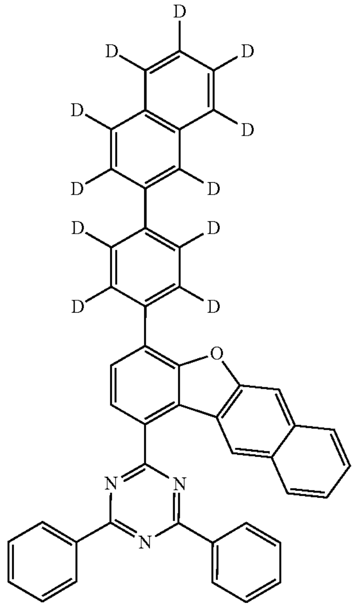
-continued
B80
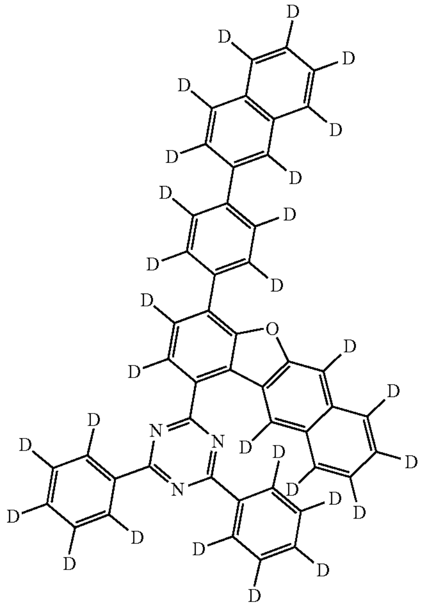
B81
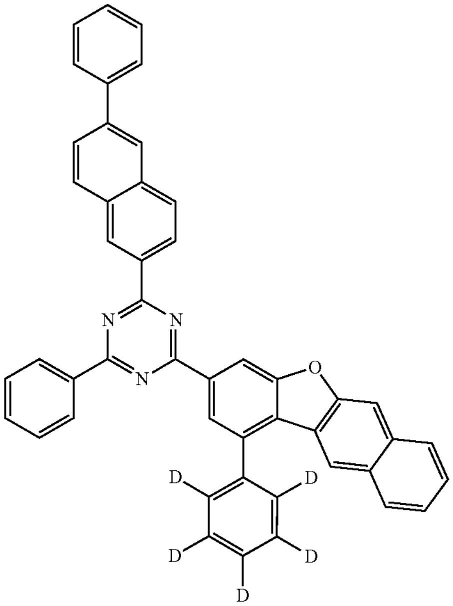

-continued
D82
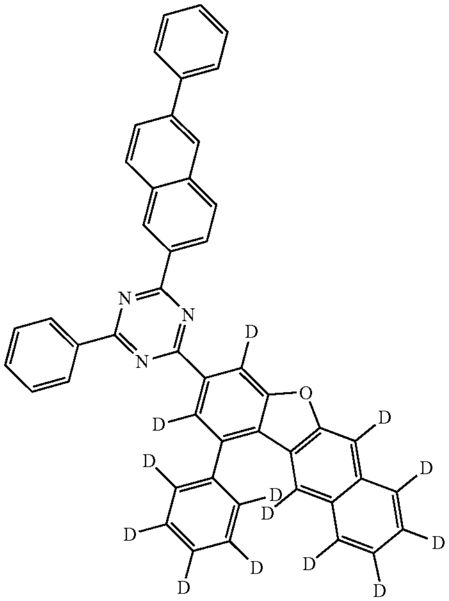
B83
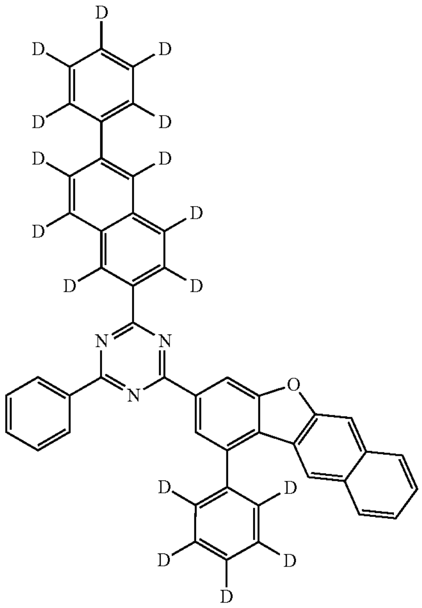
-continued
B84
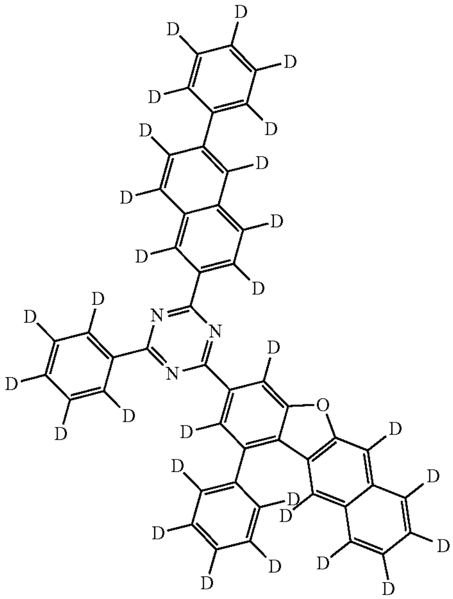
B85
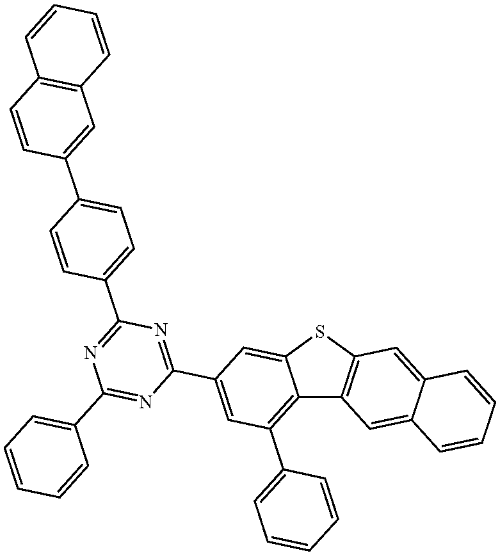

-continued
B86
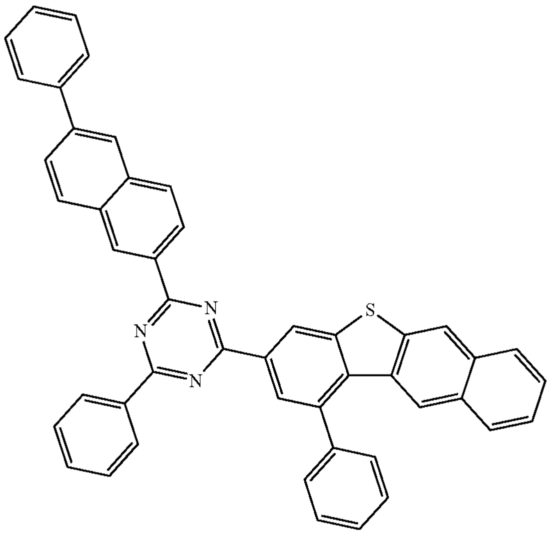
B87
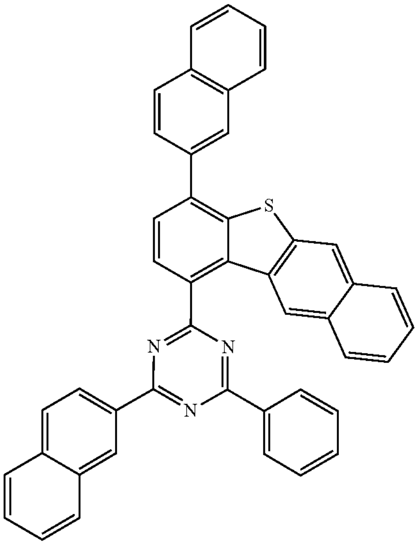
B88
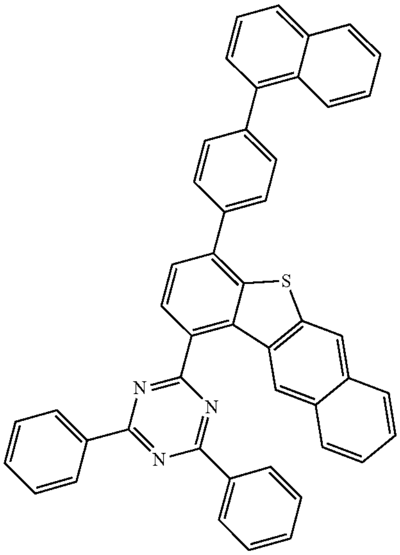
-continued
B89
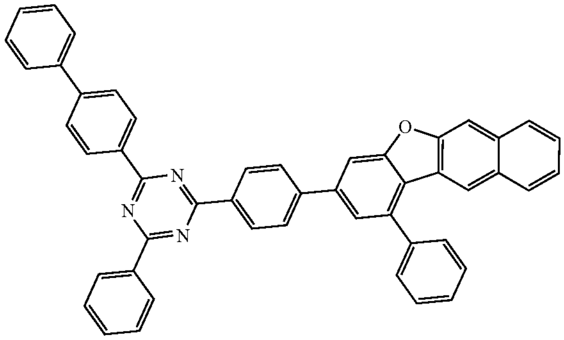
B90
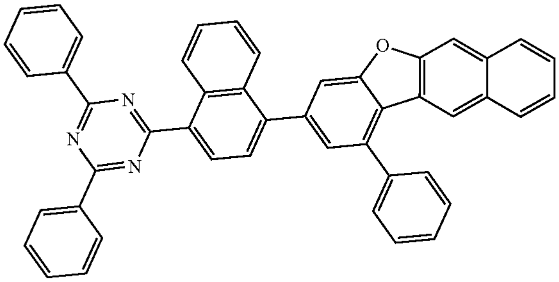
B91
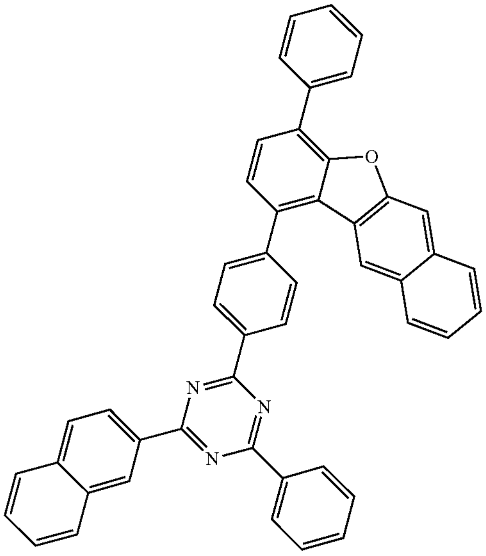
B92
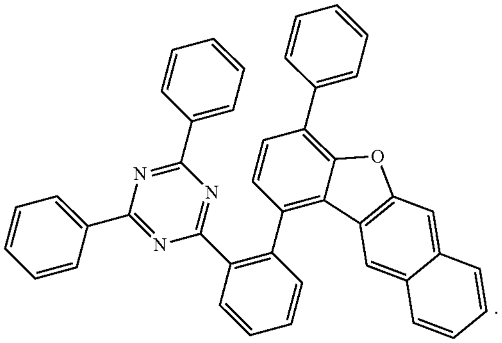

10. The composition of claim 1, wherein Chemical Formula C comprises any one of the following compounds:
C1
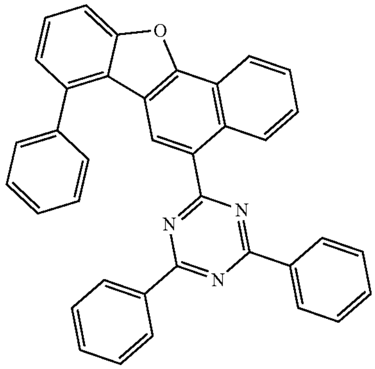
C2
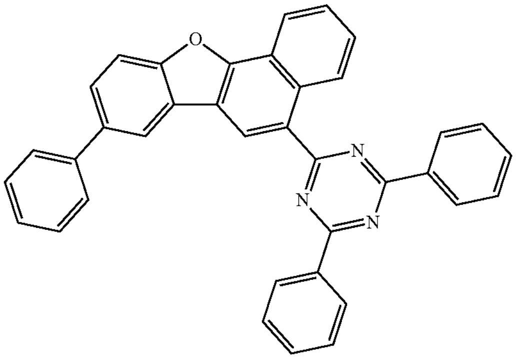
C3
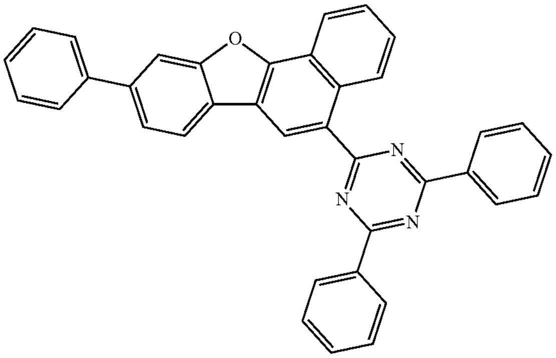
C4
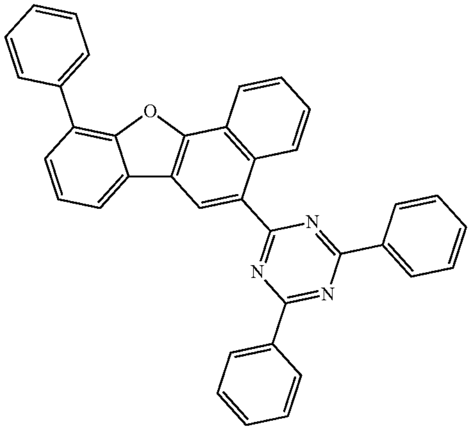
-continued
C5
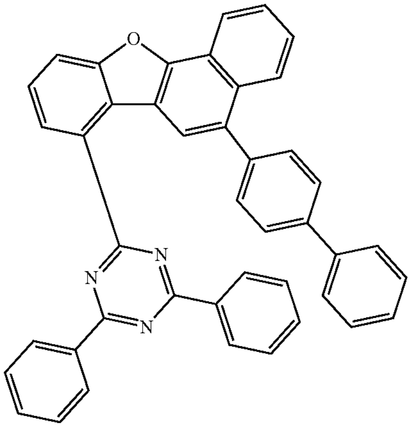
C6
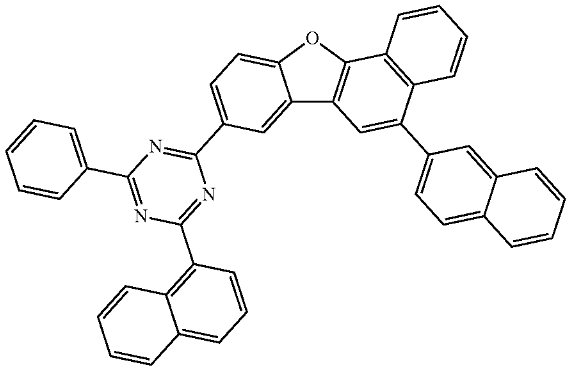
C7
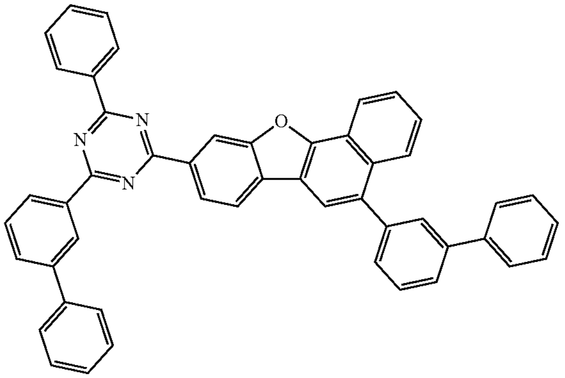
C8
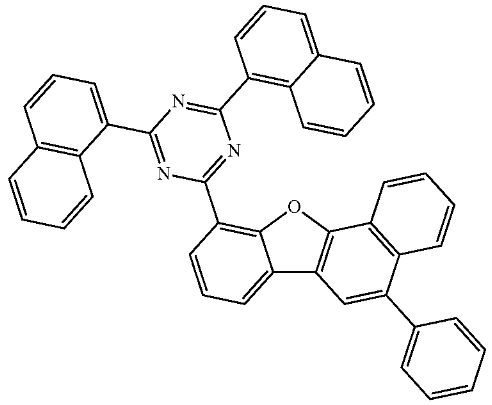

-continued
C9
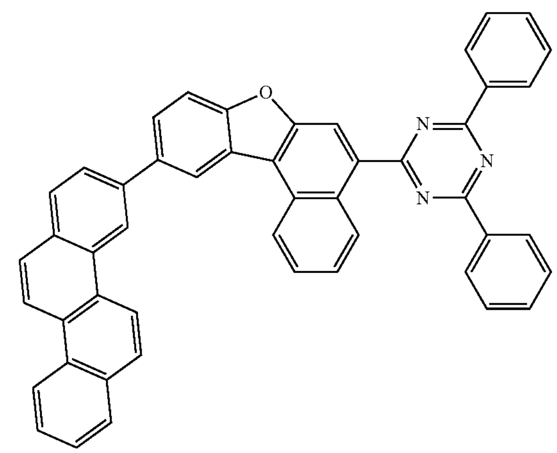
C10
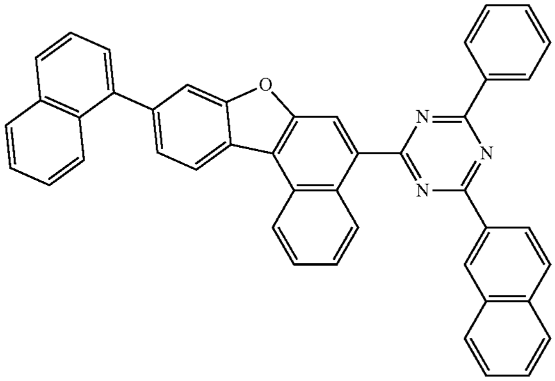
C11
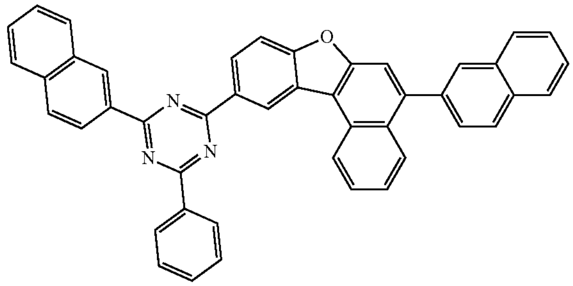
C12
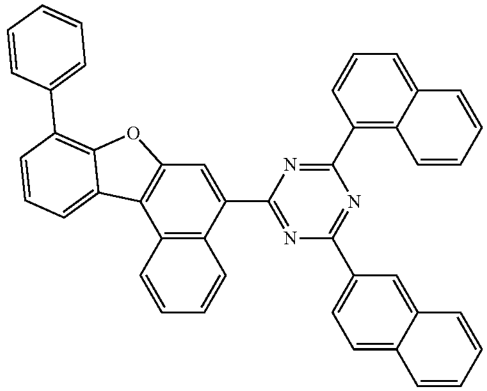
-continued
C13
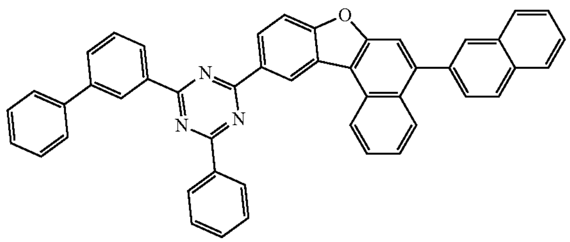
C14
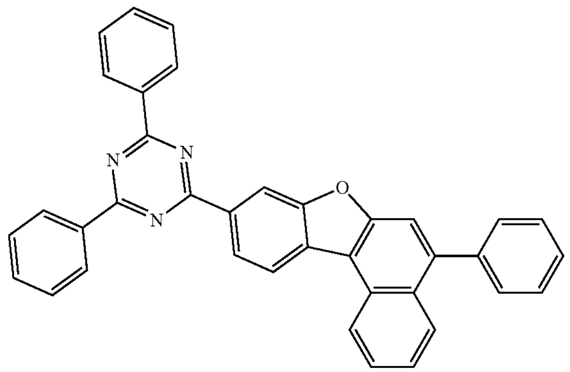
C15
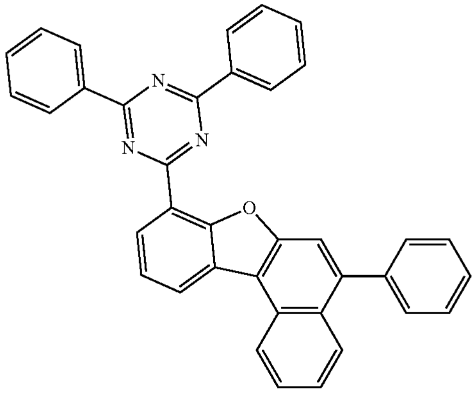
C16
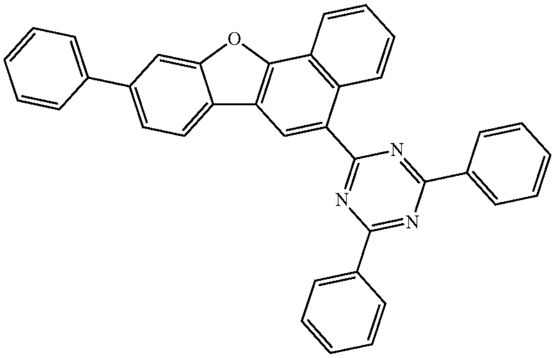

C17
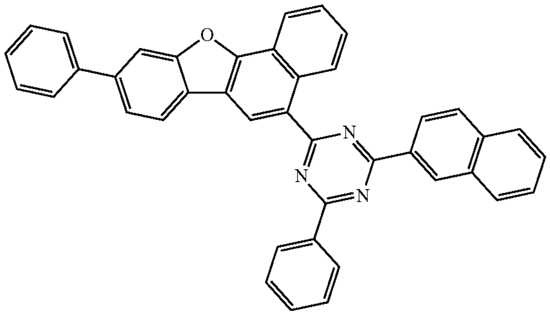
C18
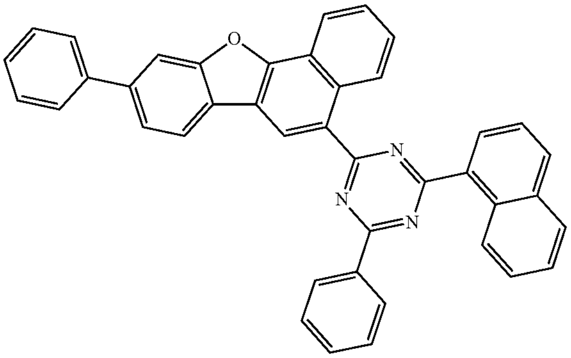
C19
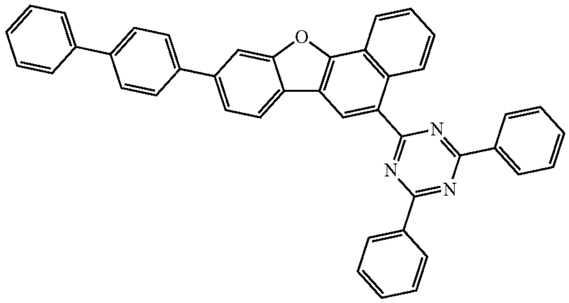
C20
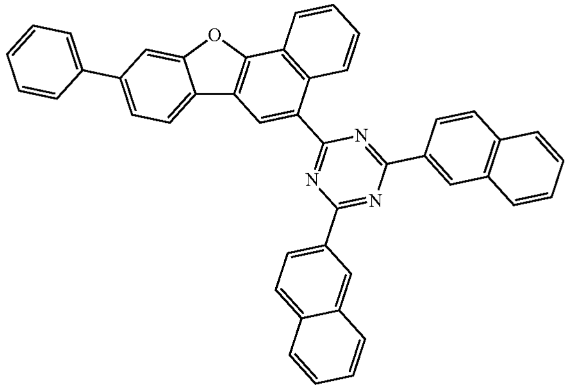
C21
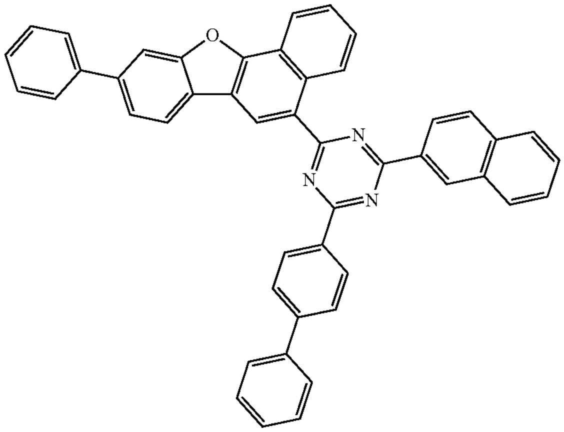
C22
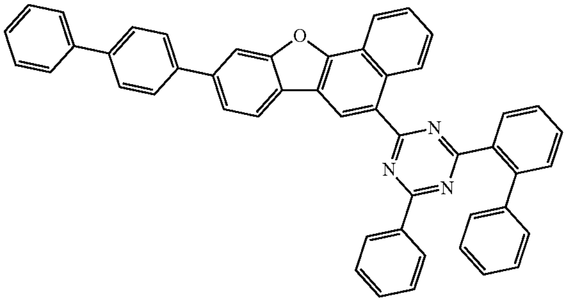
C23
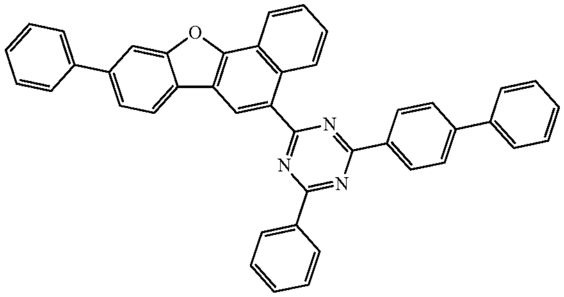
C24
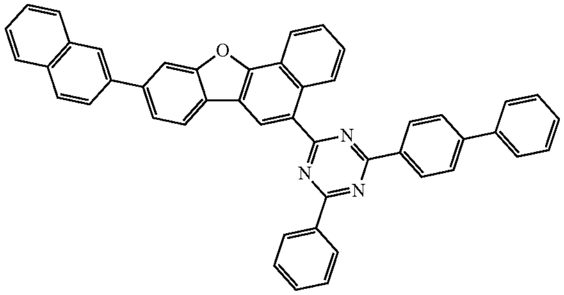

-continued
C25
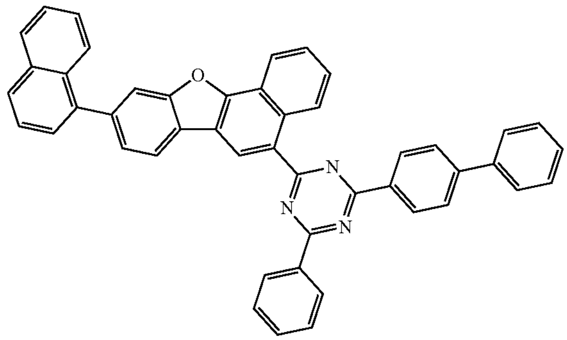
C26
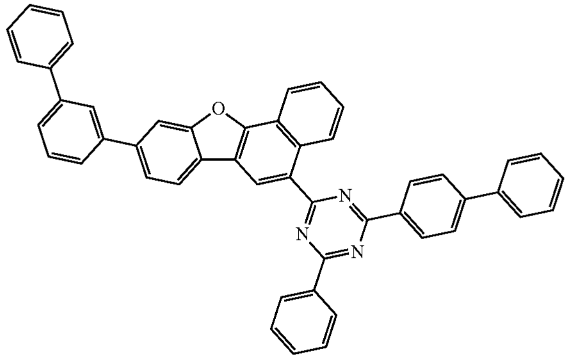
C27
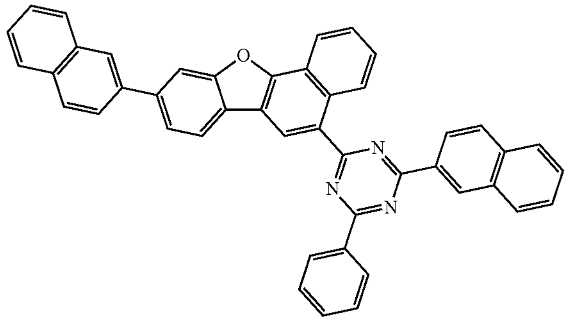
C28
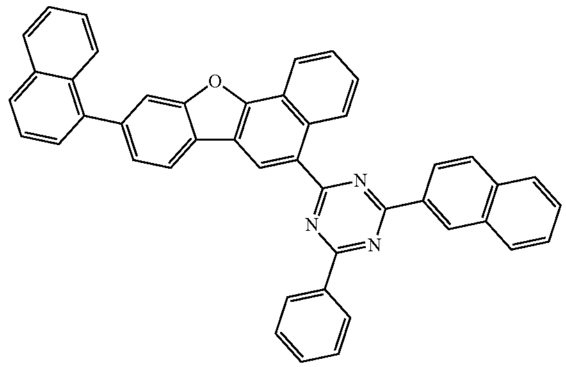
-continued
C29
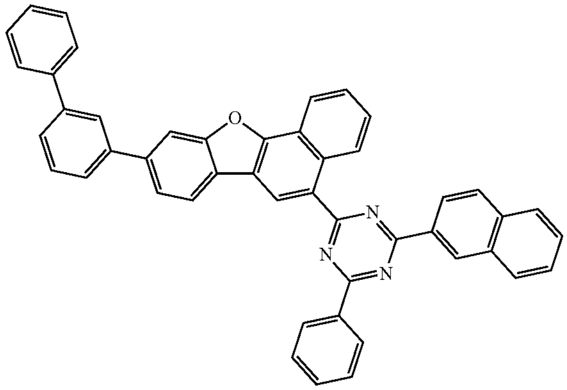
C30
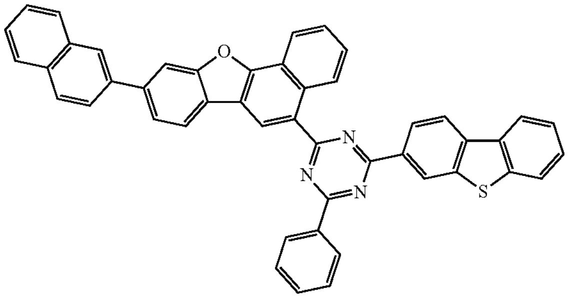
C31
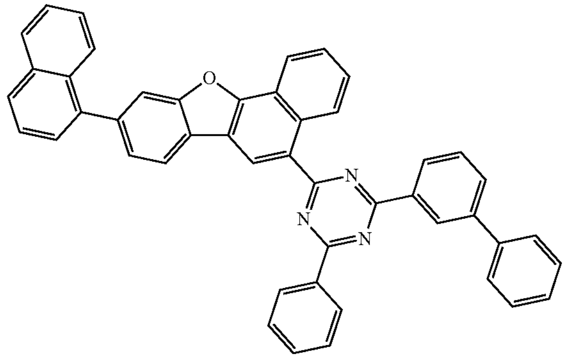
C32
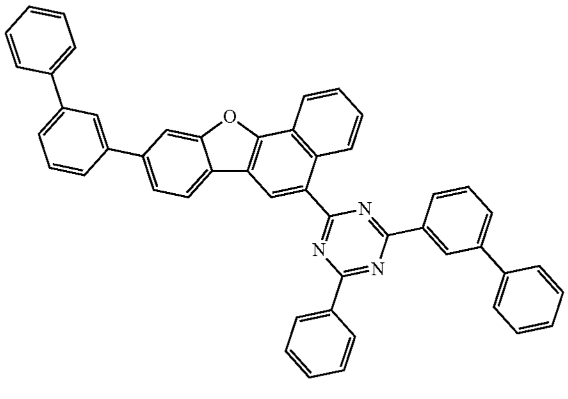

-continued
C33
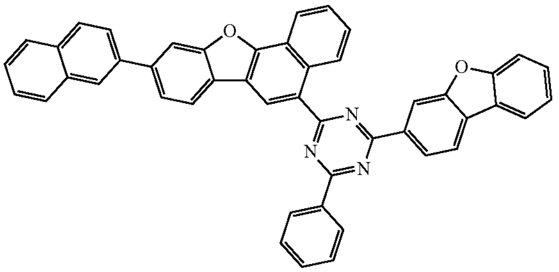
C34
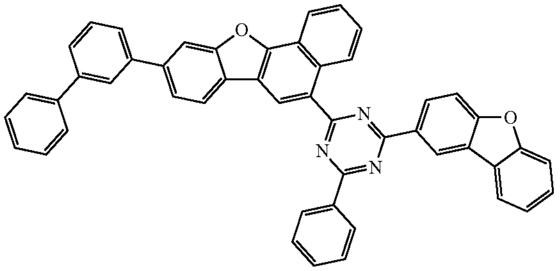
C35
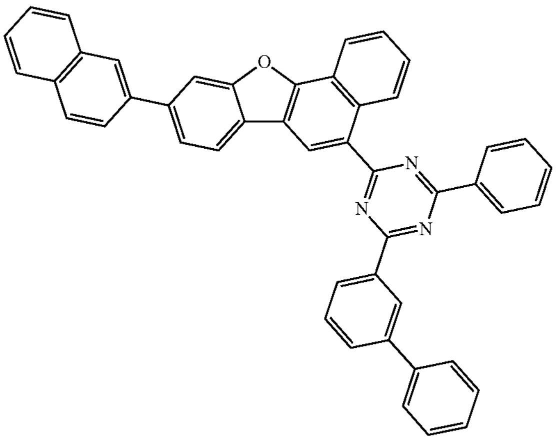
C36
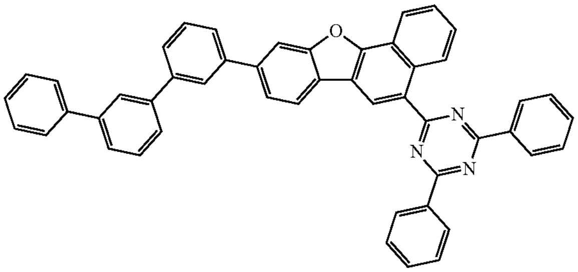
-continued
C37
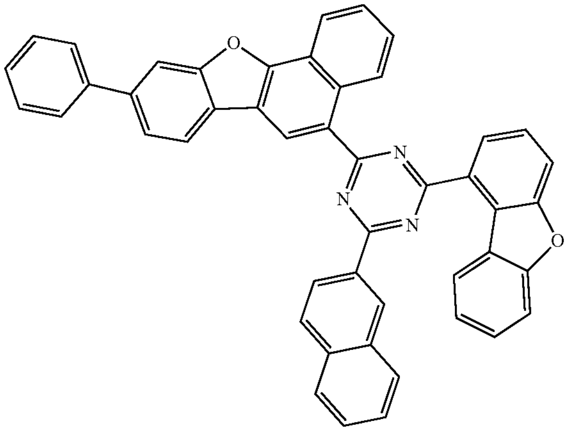
C38
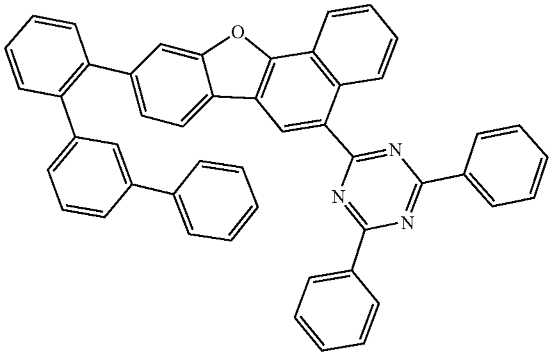
C39
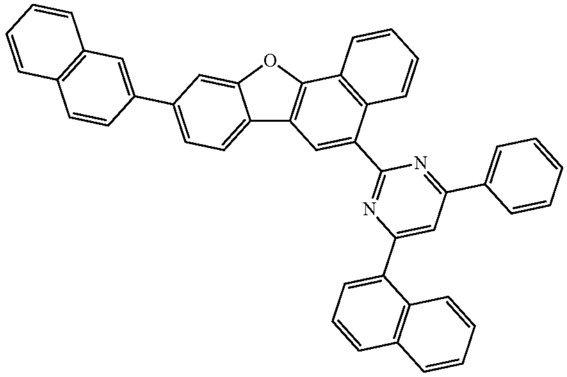
C40
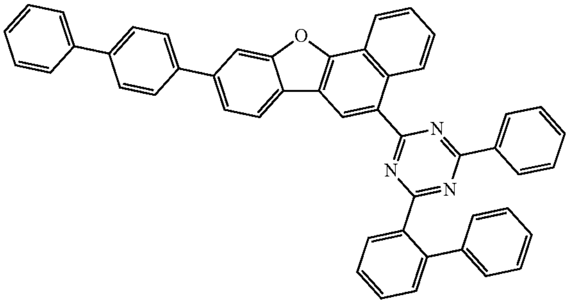

-continued
C41
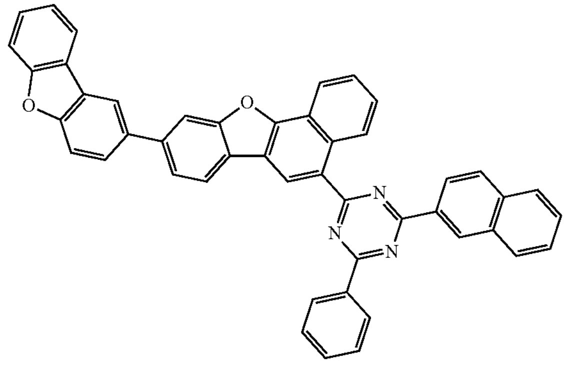
C42
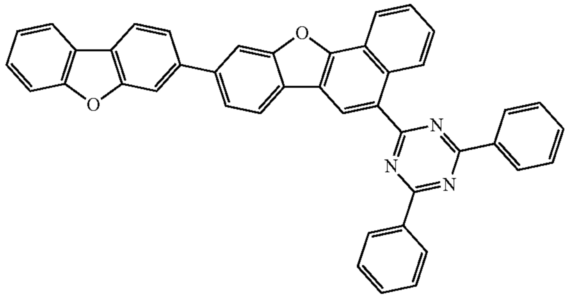
C43
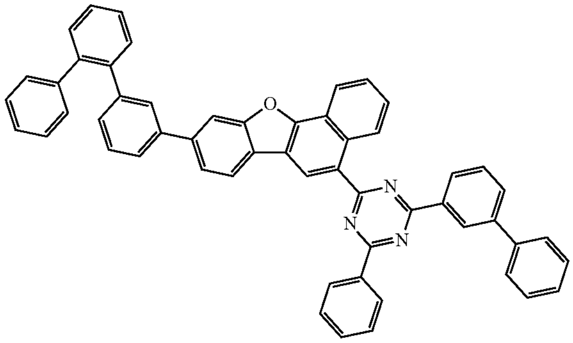
C44
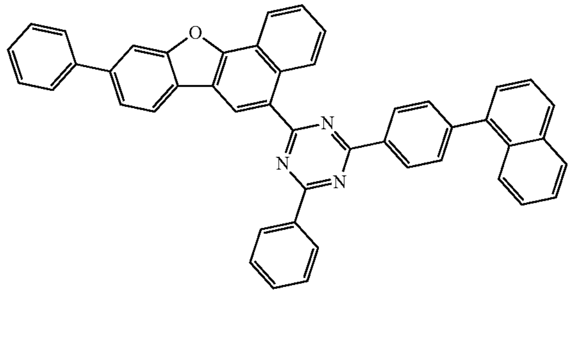
-continued
C45
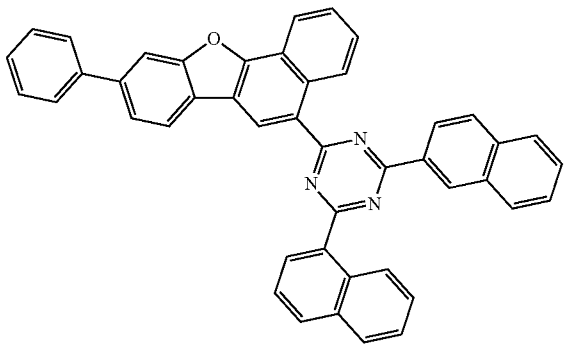
C46
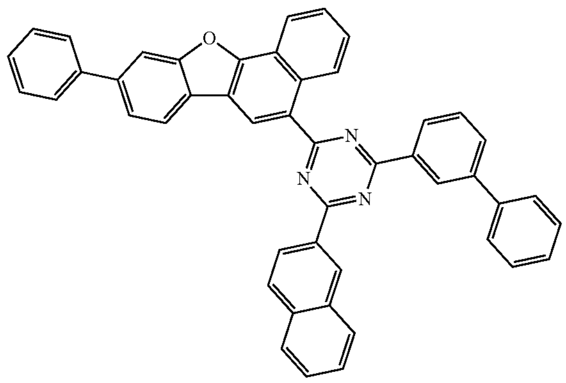
C47
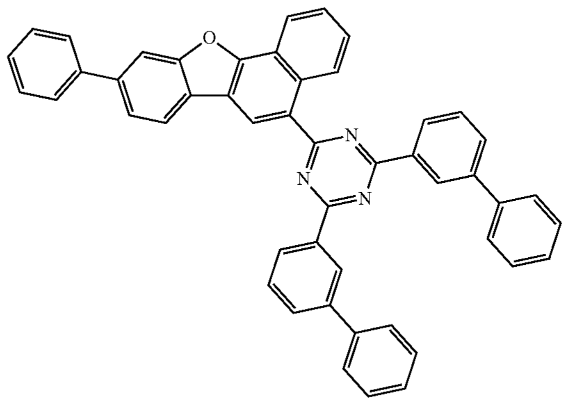
C48
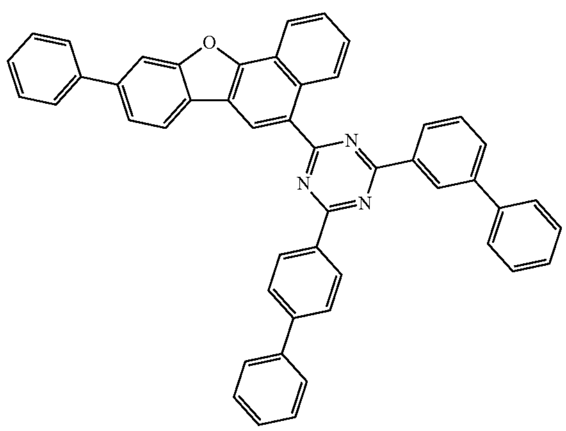

C49
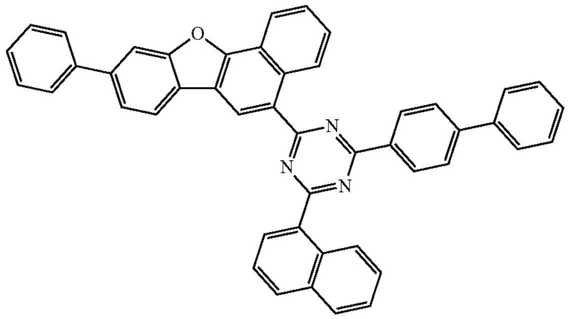
C50
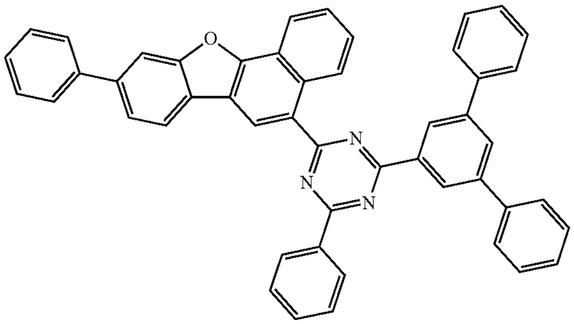
C51
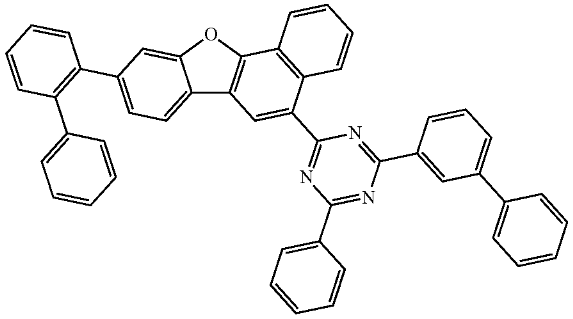
C52
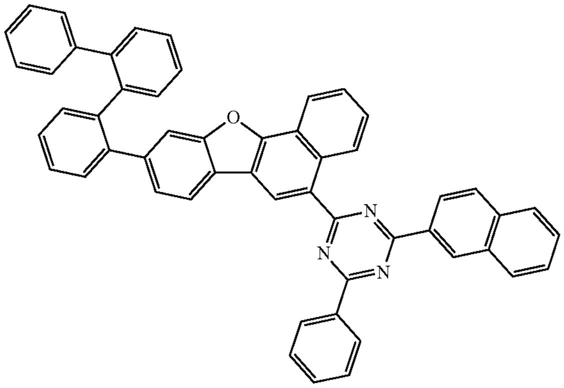
C53
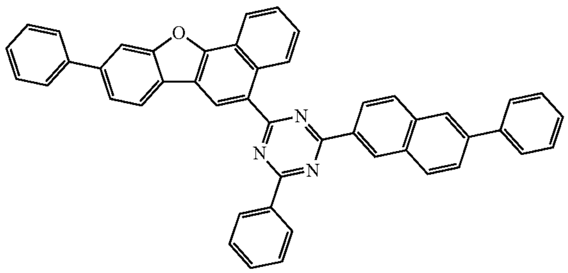
C54
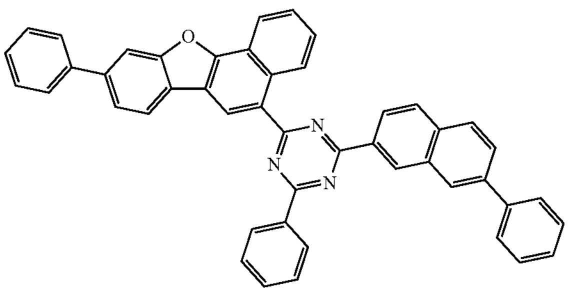
C55
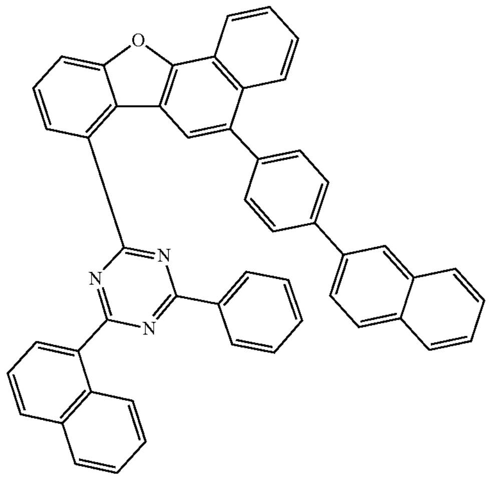
C56
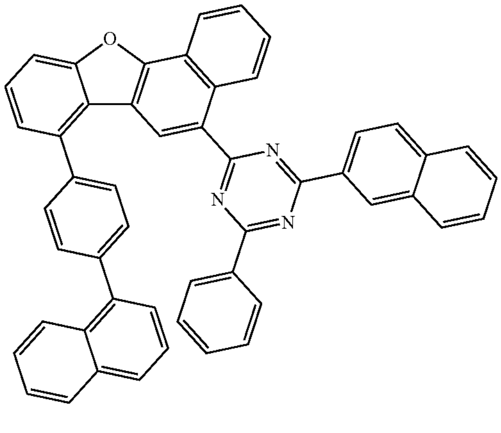

-continued
C57
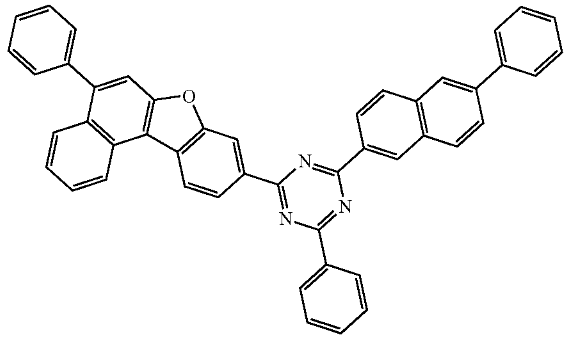
C58
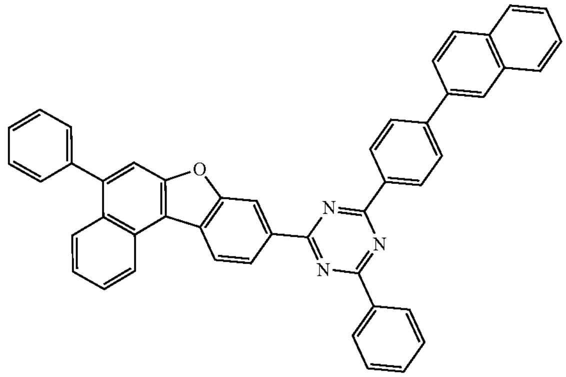
C59
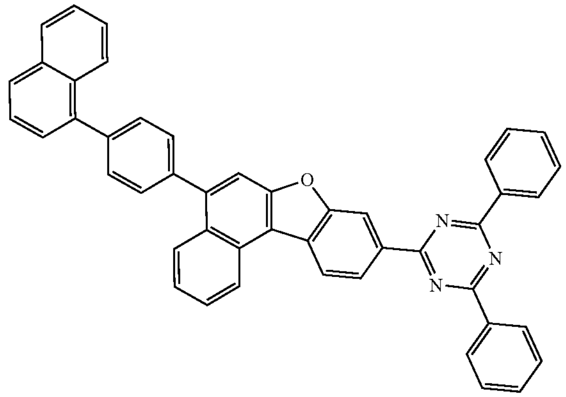
C60
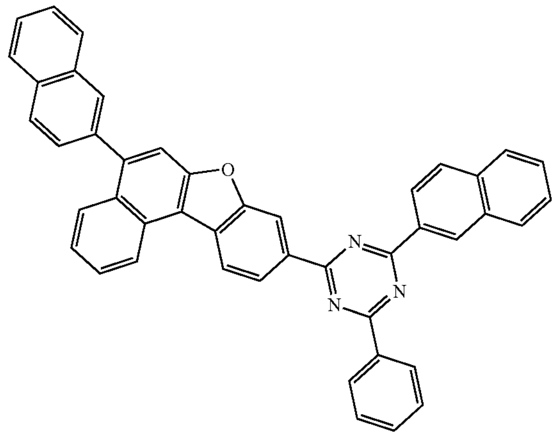
-continued
C61
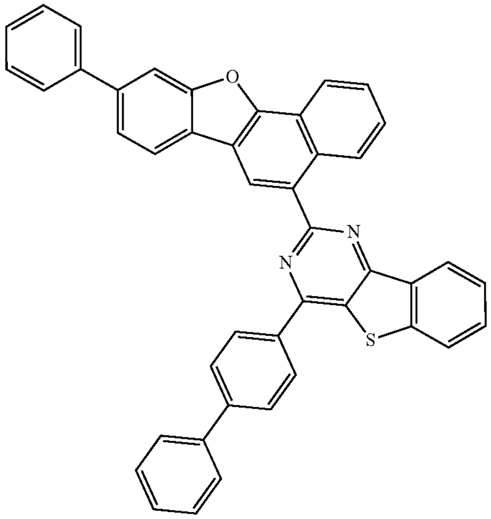
C62
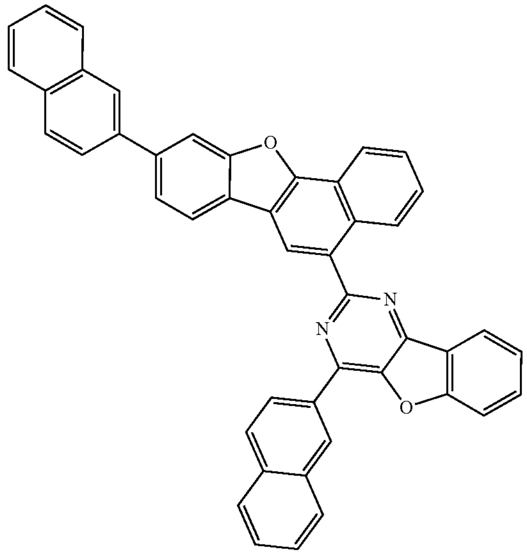
C63
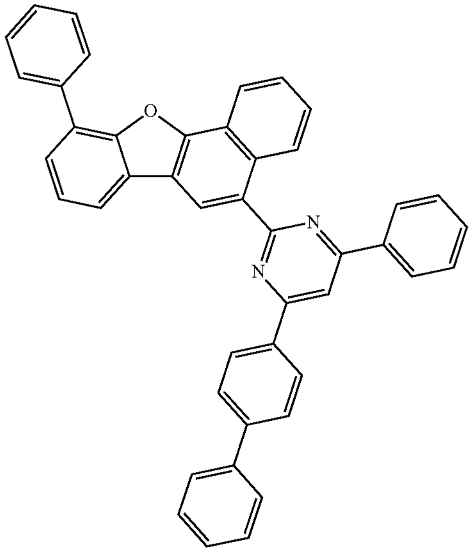

-continued
C64
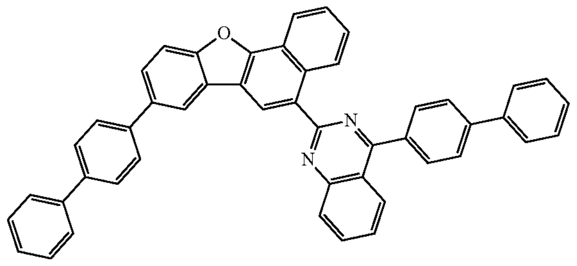
C65
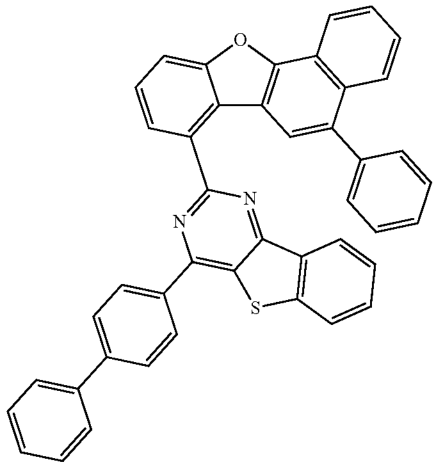
C66
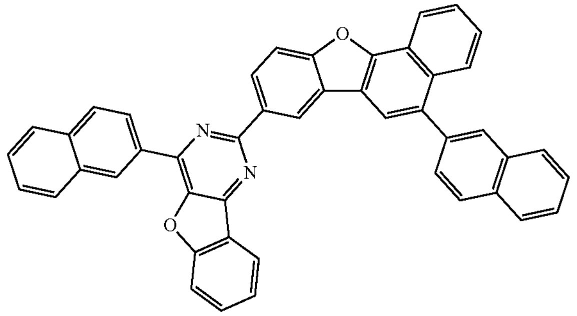
C67
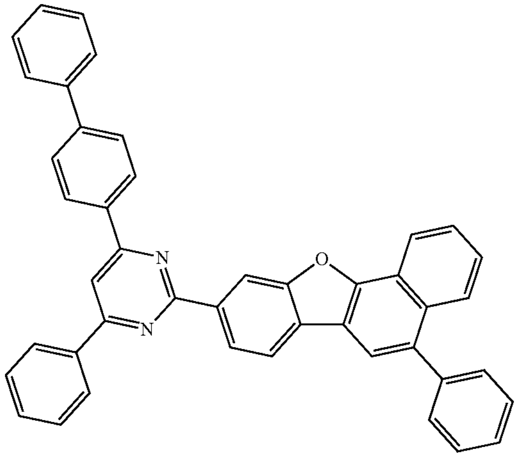
-continued
C68
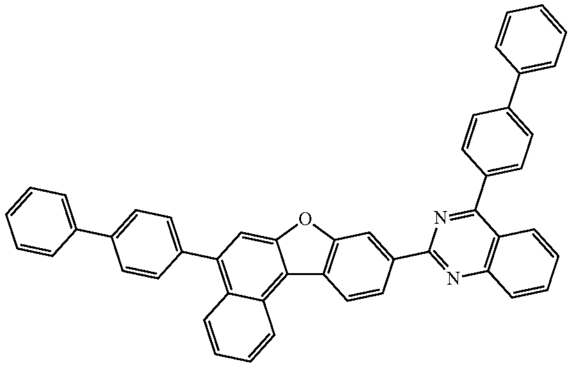
C69
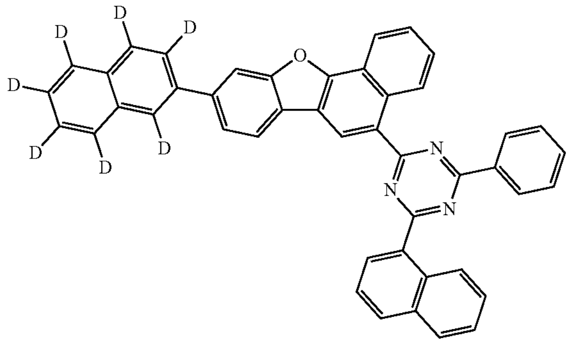
C70
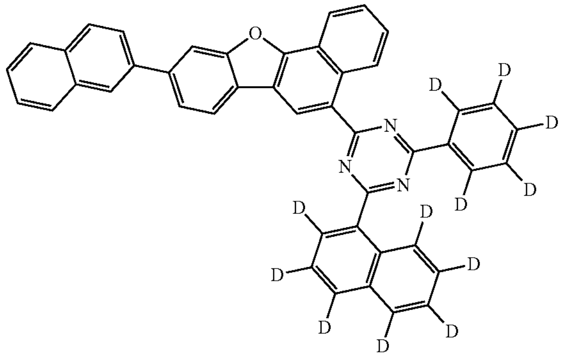
C71
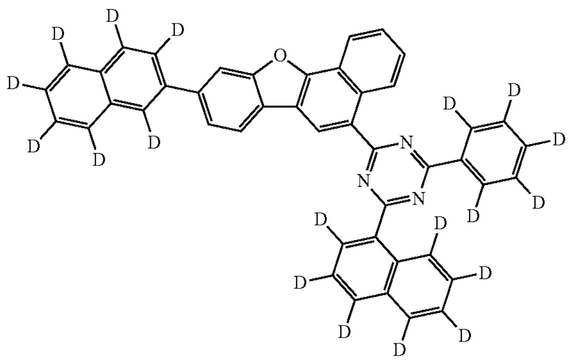

-continued
C72
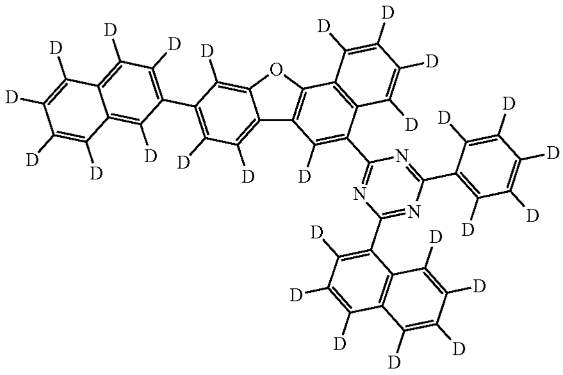
C73
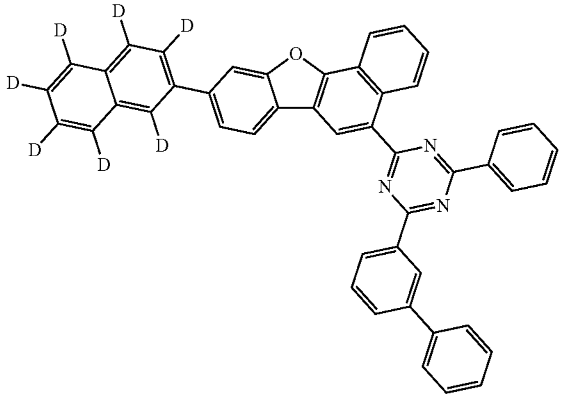
C74
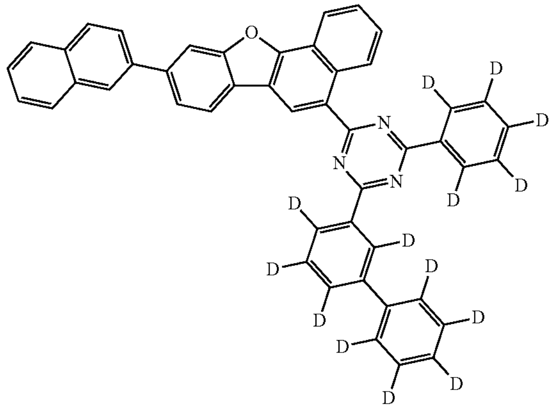
-continued
C75
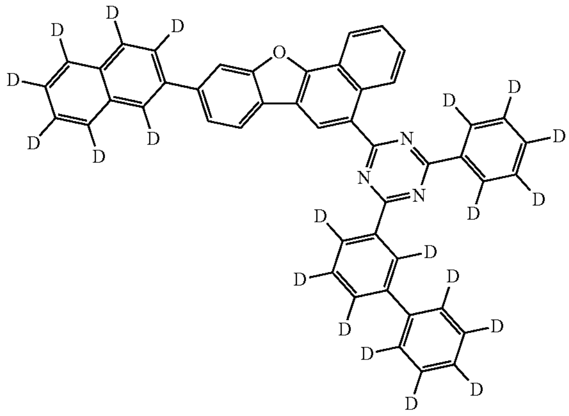
C76
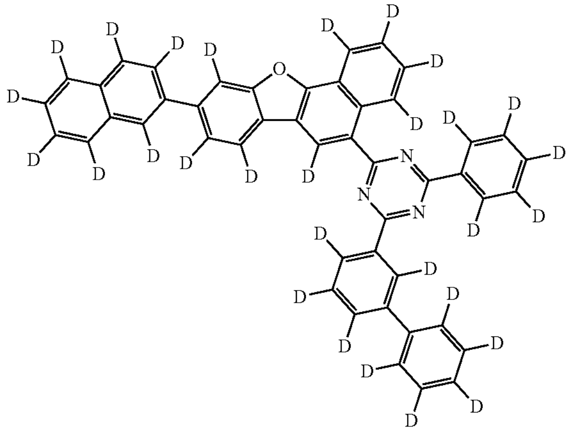
C77
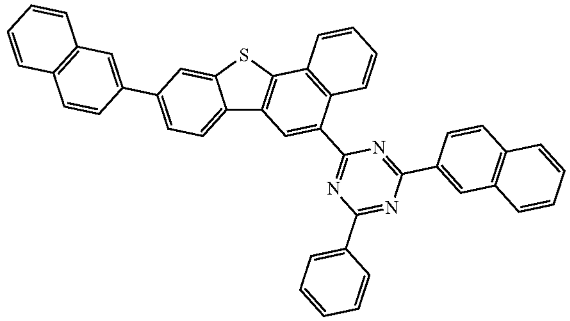

-continued

C78

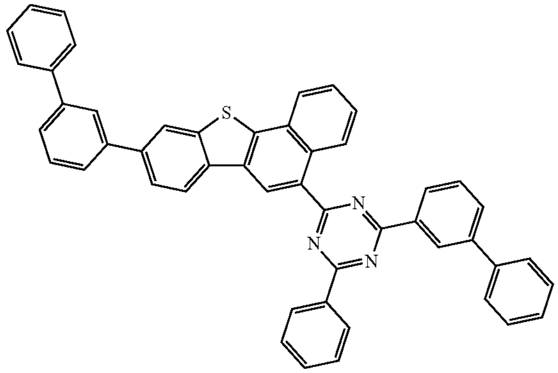

C79

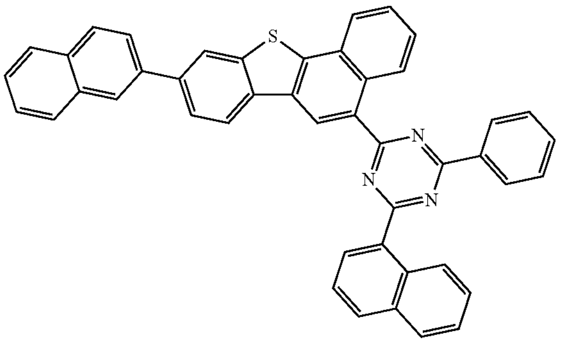

-continued

C80

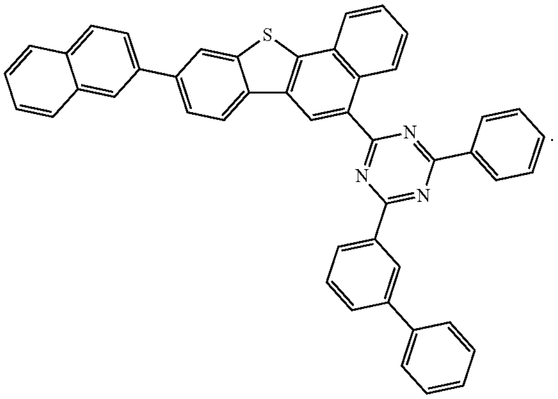

11. The composition of claim 1, wherein a molar ratio of the heterocyclic compound represented by Chemical Formula A, the heterocyclic compound represented by Chemical Formula B, and the heterocyclic compound represented by Chemical Formula C is 0.1 to 3:0.1 to 2.5:0.1 to 2.

12. An organic light emitting device comprising:

a first electrode;

a second electrode provided to face the first electrode; and an organic material layer having one or more layers provided between the first electrode and the second electrode, wherein one or more layers of the organic material layer comprise the composition according to claim 1.

13. The organic light emitting device of claim 12, wherein the organic material layer further comprises a light emitting layer (emission layer), and the light emitting layer comprises the composition for an organic light emitting device.

* * * * *